US006476263B1

(12) United States Patent
Wu et al.

(10) Patent No.: US 6,476,263 B1
(45) Date of Patent: Nov. 5, 2002

(54) COMPOUNDS FOR INHIBITING β-AMYLOID PEPTIDE RELEASE AND/OR ITS SYNTHESIS

(75) Inventors: Jing Wu, San Mateo, CA (US); Jay S. Tung, Belmont, CA (US); Eugene D. Thorsett, Moss Beach, CA (US); Jon K. Reel, Carmel, IN (US); Warren J. Porter, Indianapolis, IN (US); Jeffrey S. Nissen, Indianapolis, IN (US); Thomas E. Mabry, Indianapolis, IN (US); Lee H. Latimer, Oakland, CA (US); Varghese John, San Francisco, CA (US); Beverly K. Folmer, Newark, DE (US); James J. Droste, Indianapolis, IN (US); Thomas C. Britton, Carmel, IN (US); James E. Audia, Indianapolis, IN (US)

(73) Assignees: Elan Pharmaceuticals, Inc., South San Francisco, CA (US); Eli Lilly Company, Indianapolis, IN (US)

( * ) Notice: Subject to any disclaimer, the term of this patent is extended or adjusted under 35 U.S.C. 154(b) by 0 days.

(21) Appl. No.: 09/826,412

(22) Filed: Apr. 3, 2001

Related U.S. Application Data

(63) Continuation of application No. 09/164,448, filed on Sep. 30, 1998, now Pat. No. 6,211,235, which is a continuation-in-part of application No. 08/976,289, filed on Nov. 21, 1997, now Pat. No. 6,191,166.
(60) Provisional application No. 60/108,166, filed on Nov. 22, 1996, provisional application No. 60/064,859, filed on Feb. 28, 1997, provisional application No. 60/108,161, filed on Feb. 28, 1997, and provisional application No. 60/098,558, filed on Feb. 28, 1997.

(51) Int. Cl.⁷ .............................................. C07C 233/00
(52) U.S. Cl. ..................... 564/152; 564/153; 564/159; 564/160; 564/161; 564/41; 560/41; 562/450
(58) Field of Search ...................... 564/152, 153, 564/159, 160, 161; 560/41; 562/450

(56) References Cited

U.S. PATENT DOCUMENTS

| 4,410,520 A | 10/1983 | Watthey |
| 4,473,575 A | 9/1984 | Watthey |
| 5,015,639 A | 5/1991 | Berger et al. |
| 5,206,235 A | 4/1993 | Fisher et al. |
| 5,247,080 A | 9/1993 | Berger et al. |
| 5,486,541 A | 1/1996 | Sterling et al. |
| 5,502,048 A | 3/1996 | Chapdelaire et al. |
| 5,519,061 A | 5/1996 | Youdim et al. |
| 5,532,415 A | 7/1996 | Youdim et al. |
| 5,656,626 A | 8/1997 | Chapdelaine et al. |
| 5,672,598 A | 9/1997 | De et al. |

FOREIGN PATENT DOCUMENTS

| EP | 0652009 A1 | 5/1995 |
| EP | 0732399 A2 | 9/1996 |
| EP | 0 778 266 | 6/1997 |
| WO | WO 95/09838 | 4/1995 |
| WO | WO 95/13084 | 5/1995 |
| WO | WO 96/20725 | 7/1996 |
| WO | WO 96/20949 | 7/1996 |
| WO | WO 96/22966 | 8/1996 |
| WO | WO 96/39194 | 12/1996 |
| WO | WO 97/30072 | 8/1997 |

OTHER PUBLICATIONS

Wagner, B. M. et al, J. Med. Chem (1994) 37(12) 1833–40.*
Lum, et al., Selective Inhibition of the Chymotrypsin–like Activity of the 20S Proteasome by 5–Methoxy–1–Indanone Dipeptide Benzamides, Biorg, and Med. Chem Lets. 8: 209–214 (1998).
Wolfe, et al., *A Substrate–Based Difluoro Ketone Selectively Inhibits Alzheimer's γSecretase Activity*, J. Med. Chem., 41:6–9 (1998).
Smith, et al., *β–APP Processing as a Therapeutic Target for Alzheimer's Disease*, Current Pharmaceutical Design, 3:439–445 (1997).
Cordell, *β–Amyloid Formation as a Potential Therapeutic Target for Alzheimer's Disease*, Annu. Rev. Pharmacol. Toxicol. 34:69–89 (1994).
Jhu, J., et al., J. Org. Chem. 60 6389–96 (1995).
Papadopoulos, et al., Tetrahedon, 47(4/5):563–572 (1991).
Waldmann, et al., Tetrahedron Letters, 37(48):8725–8728 (1996).
Adams, et al., Potent and Selective Inhibitors of the Proteasome: Dipeptidyl Boronic Acids, Biorg. and Med. Chem. Lets. 8:333–338 (1998).

* cited by examiner

Primary Examiner—Paul J. Killos
(74) Attorney, Agent, or Firm—Burns, Doane, Swecker & Mathis LLP

(57) ABSTRACT

Disclosed are compounds which inhibit β-amyloid peptide release and/or its synthesis, and, accordingly, have utility in treating Alzheimer's disease. Also disclosed are pharmaceutical compositions comprising a compound which inhibits β-amyloid peptide release and/or its synthesis.

28 Claims, No Drawings

US 6,476,263 B1

COMPOUNDS FOR INHIBITING β-AMYLOID PEPTIDE RELEASE AND/OR ITS SYNTHESIS

CROSS-REFERENCE TO RELATED APPLICATIONS

This application is a continuation of application number 09/164,448, filed on Sep. 30, 1998, now U.S. Pat. No. 6,211,235 is a continuation-in-part of U.S. Ser. No. 08/976,289, filed Nov. 21, 1997, now U.S. Pat. No. 6,191,166 which application claims the benefit of U.S. Provisional Application Ser. No. 60/108,166 filed Nov. 22, 1996; 60/064,859 filed Feb. 28, 1997; 60/108,161, filed Feb. 28, 1997; and 60/098,558, filed Feb. 28, 1997.

BACKGROUND OF THE INVENTION

Field of the Invention

This invention relates to compounds and pharmaceutical compositions comprising such compounds which inhibit cellular β-amyloid peptide release and/or its synthesis, and, accordingly, have utility in treating Alzheimer's disease.

Reference

The following publications, patents and patent applications are cited in this application as superscript numbers:

[1] Glenner, et al., "Alzheimer's Disease: Initial Report of the Purification and Characterization of a Novel Cerebrovascular Amyloid Protein", *Biochem. Biophys. Res. Commun.*, 120:885–890 (1984).

[2] Glenner, et al., "Polypeptide Marker for Alzheimer's Disease and its Use for Diagnosis", U.S. Pat. No. 4,666,829 issued May 19, 1987.

[3] Selkoe, "The Molecular Pathology of Alzheimer's Disease", *Neuron*, 6:487–498 (1991).

[4] Goate, et al., "Segregation of a Missense Mutation in the Amyloid Precursor Protein Gene with Familial Alzheimer's Disease", *Nature*, 349:704–706 (1990).

[5] Chartier-Harlan, et al., "Early-Onset Alzheimer's Disease Caused by Mutations at Codon 717 of the β-Amyloid Precursor Proteing Gene", *Nature*, 353:844–846 (1989).

[6] Murrell, et al., "A Mutation in the Amyloid Precursor Protein Associated with Hereditary Alzheimer's Disease", *Science*, 254:97–99 (1991).

[7] Mullan, et al., "A Pathogenic Mutation for Probable Alzheimer's Disease in the APP Gene at the N-Terminus of β-Amyloid, *Nature Genet.*, 1:345–347 (1992).

[8] Schenk, et al., "Methods and Compositions for the Detection of Soluble β-Amyloid Peptide", International Patent Application Publication No. WO 94/10569, published May 11, 1994.

[9] Selkoe, "Amyloid Protein and Alzheimer's Disease", *Scientific American*, pp. 2–8, November, 1991.

[10] Losse, et al., Tetrahedron, 27:1423–1434 (1971).

[11] Citron, et al., "Mutation of the β-Amyloid Precursor Protein in Familial Alzheimer's Disease Increases P-Protein Production, *Nature*, 360:672–674 (1992).

[12] Hansen, et al., "Reexamination and Further Development of a Precise and Rapid Dye Method for Measuring Cell Growth/Cell Kill", *J. Immun. Meth.*, 119:203–210 (1989).

[13] P. Seubert, *Nature* (1992) 359:325–327

[14] Johnson-Wood et al., *PNAS USA* (1997) 94:1550–1555

[15] *Tetrahedron Letters*, 34(48), 7685 (1993))

All of the above publications, patents and patent applications are herein incorporated by reference in their entirety to the same extent as if each individual publication, patent or patent application was specifically and individually indicated to be incorporated by reference in its entirety.

State of the Art

Alzheimer's Disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in races and ethnic groups worldwide and presents a major present and future public health problem. The disease is currently estimated to affect about two to three million individuals in the United States alone. AD is at present incurable. No treatment that effectively prevents AD or reverses its symptoms and course is currently known.

The brains of individuals with AD exhibit characteristic lesions termed senile (or amyloid) plaques, amyloid angiopathy (amyloid deposits in blood vessels) and neurofibrillary tangles. Large numbers of these lesions, particularly amyloid plaques and neurofibrillary tangles, are generally found in several areas of the human brain important for memory and cognitive function in patients with AD. Smaller numbers of these lesions in a more restrictive anatomical distribution are also found in the brains of most aged humans who do not have clinical AD. Amyloid plaques and amyloid angiopathy also characterize the brains of individuals with Trisomy 21 (Down's Syndrome) and Hereditary Cerebral Hemorrhage with Amyloidosis of the Dutch Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the amyloid plaques and vascular amyloid deposits (amyloid angiopathy) characteristic of AD and the other disorders mentioned above is an approximately 4.2 kilodalton (kD) protein of about 39–43 amino acids designated the β-amyloid peptide (βAP) or sometimes Aβ, AβP or β/A4. β-Amyloid peptide was first purified and a partial amino acid sequence was provided by Glenner, et al.[1] The isolation procedure and the sequence data for the first 28 amino acids are described in U.S. Pat. No. 4,666,829[2].

Molecular biological and protein chemical analyses have shown that the β-amyloid peptide is a small fragment of a much larger precursor protein (APP), that is normally produced by cells in many tissues of various animals, including humans. Knowledge of the structure of the gene encoding the APP has demonstrated that β-amyloid peptide arises as a peptide fragment that is cleaved from APP by protease enzyme(s). The precise biochemical mechanism by which the β-amyloid peptide fragment is cleaved from APP and subsequently deposited as amyloid plaques in the cerebral tissue and in the walls of the cerebral and meningeal blood vessels is currently unknown.

Several lines of evidence indicate that progressive cerebral deposition of β-amyloid peptide plays a seminal role in the pathogenesis of AD and can precede cognitive symptoms by years or decades. See, for example, Selkoe[3]. The most important line of evidence is the discovery that missense DNA mutations at amino acid 717 of the 770-amino acid isoform of APP can be found in affected members but not unaffected members of several families with a genetically determined (familial) form of AD (Goate, et al.[4]; Chartier-Harlan, et al.[5]; and Murrell, et al.[6]) and is referred to as the Swedish variant. A double mutation changing lysine$^{595}$-methionine$^{596}$ to asparagine$^{595}$-leucine$^{596}$ (with reference to the 695 isoform) found in a Swedish family was reported in 1992 (Mullan, et al.[7]). Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the β-amyloid peptide deposition disease, HCHWA-D, and a change from alanine to glycine at amino acid 692 appears to cause a phenotype that resembles AD is some patients but HCHWA-D in others. The discovery of these and other mutations in APP in genetically based cases of AD prove that alteration of APP and subsequent deposition of its β-amyloid peptide fragment can cause AD.

Despite the progress which has been made in understanding the underlying mechanisms of AD and other β-amyloid peptide related diseases, there remains a need to develop methods and compositions for treatment of the disease(s). Ideally, the treatment methods would advantageously be based on drugs which are capable of inhibiting β-amyloid peptide release and/or its synthesis in vivo.

SUMMARY OF THE INVENTION

This invention is directed to the discovery of a class of compounds which inhibit β-amyloid peptide release and/or its synthesis and, therefore, are useful in the prevention of AD in patients susceptible to AD and/or in the treatment of patients with AD in order to inhibit further deterioration in their condition. The class of compounds having the described properties are selected from the generic formulas I–IV below:

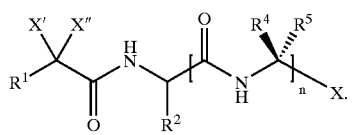

I wherein $R^1$ is selected from the group consisting of:
(a) aryl group substituted with from 1 to 3 substituents selected from the group consisting of hydroxy, acyl, acyloxy, alkyl, alkoxy, alkenyl, alkynyl, amino, aminoacyl, alkaryl, aryl, aryloxy, carboxyl, carboxylalkyl, carboxylamido, cyano, halo, nitro, heteroaryl, and trihalomethyl provided that at least one of said substituents is selected from acyl, acyloxy, alkenyl, alkynyl, aminoacyl, alkaryl, aryloxy, carboxyl, carboxylalkyl, carboxylamido, fluoro and heteroaryl,
(b) a heteroaryl group substituted with 1 to 3 substituents selected from the group consisting hydroxy, acyl, acyloxy, alkyl, alkoxy, alkenyl, alkynyl, amino, aminoacyl, alkaryl, aryl, aryloxy, carboxyl, carboxylalkyl, carboxylamido, cyano, halo, nitro, heteroaryl, and trihalomethyl provided that at least one of said substituents is selected from acyl, acyloxy, alkenyl, alkynyl, aminoacyl, alkaryl, aryloxy, carboxyl, carboxylalkyl, carboxylamido, fluoro and heteroaryl,
(c) cycloalkenyl,
(d) substituted alkyl provided that the substituent is not aryl and/or heteroaryl groups,
(e) substituted alkenyl provided that the substituent is not aralkenyl or heteroaralkenyl,
(f) substituted alkynyl provided that the substituent is not aralkynyl or heteroaralkynyl, and
(h) heterocyclic;

$R^2$ is selected from the group consisting of alkyl, substituted alkyl, alkenyl, substituted alkenyl, alkynyl, substituted alkynyl, cycloalkyl, aryl, heteroaryl and heterocyclic;
each $R^4$ is independently selected from the group consisting of hydrogen, alkyl, alkenyl, alkynyl, aryl, cycloalkyl, cycloalkenyl, heteroaryl, heterocyclic, substituted alkyl, substituted alkenyl and substituted alkynyl;
each $R^5$ is selected from hydrogen and methyl or together with $R^4$ forms a cycloalkyl group of from 3 to 6 carbon atoms;
X is —C(O)Y or —C(S)Y where Y is selected from the group consisting of
(a) alkyl or cycloalkyl,
(b) substituted alkyl with the proviso that the substitution on said substituted alkyl do not include α-haloalkyl, α-diazoalkyl, α-OC(O)alkyl or α-OC(O)aryl groups,
(c) alkoxy or thioalkoxy,
(d) substituted alkoxy or substituted thioalkoxy,
(e) hydroxy,
(f) aryl,
(g) heteroaryl,
(h) heterocyclic,
(i) —NR'R" where R' and R" are independently selected from hydrogen, alkyl, substituted alkyl, alkenyl, substituted alkenyl, alkynyl, substituted alkynyl, cycloalkyl, aryl, heteroaryl, heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl, alkoxy or carboxyalkyl groups,
(j) —NHSO$_2$—$R^8$ where $R^8$ is selected from alkyl, substituted alkyl, alkenyl, substituted alkenyl, cycloalkyl, aryl, heteroaryl and heterocyclic,
(k) —NR$^9$NR$^{10}$R$^{10}$ where $R^9$ is hydrogen or alkyl, and each $R^{10}$ is independently selected from hydrogen, alkyl, substituted alkyl, alkenyl, substituted alkenyl, cycloalkyl, aryl, heteroaryl, heterocyclic, and
(l) —ONR$^9$[C(O)O]$_z$R$^{10}$ where z is zero or one, $R^9$ and $R^{10}$ are as defined above;
X can also be —CR$^6$R$^6$Y' where each $R^6$ is independently selected from the group consisting of hydrogen, alkyl, cycloalkyl, aryl, heteroaryl and heterocyclic and Y' is selected from the group consisting of hydroxyl, amino, thiol, alkoxy, substituted alkoxy, phthalimido, —OC(O)R$^7$, —SSR$^7$, —SSC(O)R$^7$ where $R^7$ is selected from the group consisting of alkyl, substituted alkyl, cycloalkyl, aryl, heteroaryl and heterocyclic,
X' is hydrogen, hydroxy or fluoro;
X" is hydrogen, hydroxy or fluoro, or X' and X" together form an
oxo group, and
n is an integer equal to 1 or 2;
with the proviso excluding the following known compound:
when $R^1$ is o-fluorophenyl, $R^2$ is 3,4-dichlorophenyl or ethyl, $R^4$ and $R^5$ are hydrogen, X' and X" are hydrogen, then X is not —C(O)OCH$_3$;

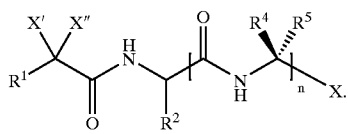

II wherein $R^1$ is selected from the group consisting of alkyl, alkenyl, alkynyl, cycloalkyl, cycloalkenyl, substituted alkyl, substituted alkenyl, substituted alkynyl, aryl, heteroaryl and heterocyclic;

$R^2$ is selected from the group consisting of (a) substituted alkyl provided that such substituted alkyl groups do not include aryl or heteroaryl substituted alkyl or a side-chain of a naturally occurring amino acid, (b) substituted alkenyl provided that such substituted alkenyl groups do not include aryl or heteroaryl substituted alkenyl, (c) substituted alkynyl provided that such substituted alkynyl groups do not include aryl or heteroaryl substituted alkynyl, (d) heterocyclic, (e) aryl group substituted with from 1 to 3 substituents selected from the group consisting of hydroxy, acyl, acyloxy, alkyl, alkoxy, alkenyl, alkynyl, amino, aminoacyl, alkaryl, aryl, aryloxy, carboxyl, carboxylalkyl, carboxylamido, cyano, halo, nitro, heteroaryl, and trihalomethyl provided that at least one of said substituents is selected from acyl, acyloxy, alkenyl, alkynyl, aminoacyl, alkaryl, aryloxy, carboxyl, carboxylalkyl, carboxylamido, and heteroaryl, and (f) a heteroaryl group substituted with 1 to 3 substituents selected from the group consisting of alkyl, alkoxy, aryl, alkaryl, aryloxy, halo, nitro, heteroaryl, thioalkoxy, thioaryloxy provided that if there is an alkyl substituent on the substituted heteroaryl group then there is at least one other substituent which is not alkyl;

each $R^4$ is independently selected from the group consisting of hydrogen, alkyl, alkenyl, alkynyl, aryl, cycloalkyl, cycloalkenyl, heteroaryl, heterocyclic, substituted alkyl, substituted alkenyl and substituted alkynyl;

each $R^5$ is selected from hydrogen and methyl or together with $R^4$ forms a cycloalkyl group of from 3 to 6 carbon atoms;

X is —C(O)Y or —C(S)Y where Y is selected from the group consisting of (a) alkyl or cycloalkyl, (b) substituted alkyl with the proviso that the substitution on said substituted alkyl do not include α-haloalkyl, α-diazoalkyl, α-OC(O)alkyl or αOC(O)aryl groups, (c) alkoxy or thioalkoxy, (d) substituted alkoxy or substituted thioalkoxy, (e) hydroxy, (f) aryl, (g) heteroaryl, (h) heterocyclic, (i) —NR'R" where R' and R" are independently selected from hydrogen, alkyl, substituted alkyl, alkenyl, substituted alkenyl, alkynyl, substituted alkynyl, cycloalkyl, aryl, heteroaryl, heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl, alkoxy or carboxyalkyl groups, (j) —NHS$^2$—R$^8$ where R$^8$ is selected from alkyl, substituted alkyl, alkenyl, substituted alkenyl, cycloalkyl, aryl, heteroaryl and heterocyclic, (k) —NR$^9$NR$^{10}$N$^{10}$ where R$^9$ is hydrogen or alkyl, and each R$^{10}$ is independently selected from hydrogen, alkyl, substituted alkyl, alkenyl, substituted alkenyl, cycloalkyl, aryl, heteroaryl, heterocyclic, and (l) —ONR$^9$[C(O)O]$_z$R$^{10}$ where z is zero or one, R$^9$ and R$^{10}$ are as defined above;

X can also be —CR$^6$R$^6$Y' where each R$^6$ is independently selected from the group consisting of hydrogen, alkyl, alkoxy, substituted alkoxy, cycloalkyl, aryl, heteroaryl and heterocyclic and Y' is selected from the group consisting of hydroxyl, amino, thiol, alkoxy, phthalimido, —OC(O)R$^7$, —SSR$^7$, —SSC(O)R$^7$ where R$^7$ is selected from the group consisting of alkyl, substituted alkyl, cycloalkyl, aryl, heteroaryl and heterocyclic, X' is hydrogen, hydroxy or fluoro;

X' is hydrogen, hydroxy or fluoro, or X' and X" together form an oxo group, and n is an integer equal to 1 or 2;

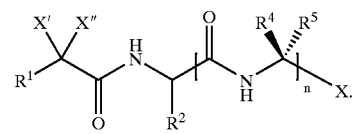

III wherein $R^1$ is selected from the group consisting of alkyl, alkenyl, alkynyl, cycloalkyl, cycloalkenyl, substituted alkyl, substituted alkenyl, substituted alkynyl, aryl, heteroaryl and heterocyclic;

$R^2$ is selected from the group consisting of alkyl, substituted alkyl, alkenyl, substituted alkenyl, alkynyl, substituted alkynyl, cycloalkyl, aryl, heteroaryl and heterocyclic;

$R^4$ is selected from the group consisting of hydrogen, alkyl, alkenyl, alkynyl, aryl, cycloalkyl, cycloalkenyl, heteroaryl, heterocyclic, substituted alkyl, substituted alkenyl and substituted alkynyl provided that at least one $R^4$ is selected to be:

(a) substituted alkyl provided that such substituted alkyl groups do not include aryl or heteroaryl substituted alkyl or a side-chain of a naturally occurring amino acid, (b) substituted alkenyl provided that such substituted alkenyl groups do not include aryl or heteroaryl substituted alkenyl, (c) substituted alkynyl provided that such substituted alkynyl groups do not include aryl or heteroaryl substituted alkynyl, (d) heterocyclic, (e) aryl group substituted with from 1 to 3 substituents selected from the group consisting of hydroxy, acyl, acyloxy, alkyl, alkoxy, alkenyl, alkynyl, amino, aminoacyl, alkaryl, aryl, aryloxy, carboxyl, carboxylalkyl, carboxylamido, cyano, halo, nitro, heteroaryl, and trihalomethyl provided that at least one of said substituents is selected from acyl, acyloxy, alkenyl, alkynyl, aminoacyl, alkaryl, aryloxy, carboxyl, carboxylalkyl, carboxylamido, and heteroaryl, and (f) a heteroaryl group substituted with 1 to 3 substituents selected from the group consisting of alkyl, alkoxy, aryl, alkaryl, aryloxy, halo, nitro, heteroaryl, thioalkoxy, thioaryloxy provided that if there is an alkyl substituent on the substituted heteroaryl group then there is at least one other substituent which is not alkyl;

each $R^5$ is selected from hydrogen and methyl or together with $R^4$ forms a cycloalkyl group of from 3 to 6 carbon atoms;

X is —C(O)Y or —C(S)Y where Y is selected from the group consisting of (a) alkyl or cycloalkyl, (b) substituted alkyl with the proviso that the substitution on said substituted alkyl do not include α-haloalkyl, α-diazoalkyl, α-OC(O)alkyl or β-OC(O)aryl groups, (c) alkoxy or thioalkoxy, (d) substituted alkoxy or substituted thioalkoxy, (e) hydroxy, (f) aryl, (g) heteroaryl, (h) heterocyclic, (i) —NR' R" where R' and R" are independently selected from hydrogen, alkyl, substituted alkyl, alkenyl, substituted alkenyl, alkynyl, substituted alkynyl, cycloalkyl, aryl, heteroaryl, heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl, alkoxy or carboxyalkyl groups, (j) —NHSO$_2$—R$^8$ where R$^8$ is selected from alkyl, substituted alkyl, alkenyl, substituted alkenyl, cycloalkyl, aryl, heteroaryl and heterocyclic, (k) —NR$^9$NR$^{10}$R$^{10}$ where R$^9$ is hydrogen or alkyl, and each R$^{10}$ is independently selected from hydrogen, alkyl, substituted alkyl, alkenyl, substituted alkenyl, cycloalkyl, aryl, heteroaryl, heterocyclic, and (l) —ONR$^9$[C(O)O]$_z$R$^{10}$ where z is zero or one, R$^9$ and R$^{10}$ are as defined above;

X can also be —CR$^6$R$^6$Y' where each R$^6$ is independently selected from the group consisting of hydrogen, alkyl, alkoxy, substituted alkoxy, cycloalkyl, aryl, heteroaryl and heterocyclic and Y' is selected from the group consisting of hydroxyl, amino, thiol, alkoxy, phthalimido, —OC(O)R$^7$, —SSR$^7$, —SSC(O)R$^7$ where R$^7$ is selected from the group consisting of alkyl, substituted alkyl, cycloalkyl, aryl, heteroaryl and heterocyclic, X' is hydrogen, hydroxy or fluoro;

X" is hydrogen, hydroxy or fluoro, or X' and X" together form an oxo group, and n is an integer equal to 1 or 2; and

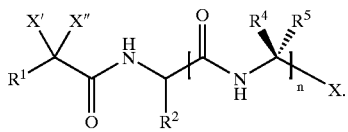

IV wherein R$^1$ is selected from the group consisting of alkyl, alkenyl, alkynyl, cycloalkyl, cycloalkenyl, substituted alkyl, substituted alkenyl, substituted alkynyl, aryl, heteroaryl and heterocyclic;

R$^2$ is selected from the group consisting of alkyl, substituted alkyl, alkenyl, substituted alkenyl, alkynyl, substituted alkynyl, cycloalkyl, aryl, heteroaryl and heterocyclic;

each R$^4$ is independently selected from the group consisting of hydrogen, alkyl, alkenyl, alkynyl, aryl, cycloalkyl, cycloalkenyl, heteroaryl, heterocyclic, substituted alkyl, substituted alkenyl and substituted alkynyl;

each R$^5$ is selected from hydrogen and methyl or together with R$^4$ forms a cycloalkyl group of from 3 to 6 carbon atoms;

X is selected from the group consisting of (a) —C(O)-alkyl, (b) —C(O)-substituted alkoxy or substituted thioalkoxy provided that the substituted alkoxy groups do not include benzyl and phenethyl, (c) —C(O)-aryl wherein the aryl group is substituted with from 1 to 3 substituents selected from the group consisting of hydroxy, acyl, acyloxy, alkyl, alkoxy, alkenyl, alkynyl, amino, aminoacyl, alkaryl, aryl, aryloxy, carboxyl, carboxylalkyl, carboxylamido, cyano, halo, nitro, heteroaryl, and trihalomethyl, (d) —C(O)-heteroaryl wherein the heteroaryl group is substituted with 1 to 3 substituents selected from the group consisting of alkyl, alkoxy, aryl, alkaryl, aryloxy, halo, nitro, heteroaryl, thioalkoxy and thioaryloxy (e) —C(O)-NR' R" where R' and R" are independently selected from hydrogen, alkyl, substituted alkyl, cycloalkyl, aryl, heteroaryl, heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl or alkoxy groups, and X can also be —CR$^6$R$^6$Y' where each R$^6$ is independently selected from the group consisting of hydrogen, alkyl, cycloalkyl, aryl, heteroaryl and heterocyclic and Y' is selected from the group consisting of amino, thiol, alkoxy, phthalimido, —OC(O)R$^7$, —SSR$^7$, —SSC(O)R$^7$ where R$^7$ is selected from the group consisting of alkyl, substituted alkyl, cycloalkyl, aryl, heteroaryl and heterocyclic, provided that R' and R" are not both independently selected from hydrogen, alkyl, phenyl, benzyl and phenethyl;

X' is hydrogen, hydroxy or fluoro;

X" is hydrogen, hydroxy or fluoro, or X' and X" together form an oxo group, and n is an integer equal to 1 or 2;

with the proviso that:

when R$^1$ is iso-propyl, R$^2$ is phenyl, R$^4$ is methyl, R$^5$ is hydrogen, X' and X" are hydrogen, n is 2, and the second R$^4$ at the carboxy terminus is methyl, then X is not —C(O)NH-pNO$_2$—φ;

with the additional provisos that in compounds selected from formulas I–IV:

A. when R$^1$ is phenyl, R$^2$ is methyl, R$^4$ is —CH(OH)CH$_3$ derived from D-threonine, R$^5$ is hydrogen, X' and X" are hydrogen, and n is 1, then X is not —C(O)OH or —C(O)OCH$_3$;

B. when R$^1$ is 3-nitrophenyl, R$^2$ is methyl, R$^4$ is —CH(OH)CH$_3$, R$^5$ is hydrogen, X' and X" are hydrogen, and n is 1, then X is not —C(O)NH$_2$ or —CH$_2$OH;

C. when R$^1$ is 3,5-difluorophenyl, R$^2$ is methyl, R$^4$ is phenyl derived from D-phenylglycine, R$^5$ is hydrogen, X' and X" are hydrogen, and n is 1, then X is not —CHOHφ or —CH$_2$OH;

D. when R$_1$ is N-(2-pyrrolidinonyl), R$_2$ is methyl, R$_4$ is benzyl, R$^5$ is hydrogen, X' and X" are hydrogen, and n is 1, then X is not —C(O)OCH$_3$;

E. when R$^1$ is 3,5-difluorophenyl, R$^2$ is methyl derived from D-alanine, R$^4$ is phenyl derived from D-phenylglycine, R$^5$ is hydrogen, X' and X" are hydrogen, and n is 1, then X is not —C(O)NH-benzyl;

F. when R$^1$ is 3,5-difluorophenyl, R$^2$ is methyl, R$^4$ is hydrogen, R$^5$ is hydrogen, X' and X" are hydrogen, and n is 1, then X is not —CH$_2$OH;

G. when R$^1$ is 3,5-difluorophenyl, R$^2$ is methyl, R$^4$ is 4-phenylphenyl, R$^5$ is hydrogen, X' and X" are hydrogen, and n is 1, then X is not —C(O)NHC(CH$_3$)$_3$; and H. when R$^1$ is 3,5-difluorophenyl, R$^2$ is methyl, R$^4$ is phenyl derived from D-phenylglycine, R$^5$ is hydrogen, X' and X" are hydrogen, and n is 1, then X is not —C(O)NHCH(CH$_3$)φ.

Preferably, the compounds of this invention are derived from L-amino acids.

The compounds described above are useful for inhibiting β-amyloid peptide release and/or its synthesis in a cell when administered to such a cell in an amount effective in inhibiting the cellular release and/or synthesis of β-amyloid peptide.

Because the in vivo generation of β-amyloid peptide is associated with the pathogenesis of AD[8,9], the compounds of this invention can also be employed in conjunction with a pharmaceutical composition to prophylactically and/or therapeutically prevent and/or treat AD. When employed for prophylactic methods for preventing the onset of AD in a patient at risk for developing AD, a pharmaceutical composition comprising a pharmaceutically inert carrier and an effective amount of a compound or a mixture of compounds of this invention above is administered to the patient.

When employed for therapeutic methods for treating a patient with AD in order to inhibit further deterioration in the condition of that patient, a pharmaceutical composition comprising a pharmaceutically inert carrier and an effective amount of a compound or a mixture of compounds of this invention above is administered to the patient.

Compounds suitable for use in the claimed methods include, by way of example only, the following:

N-[N-(3,5-difluorophenylacetyl)-L-alaninyl]-(S)-2-aminohexanoate methyl ester

N-[N-(3,5-difluorophenylacetyl)-L-alaninyl]-L-histidine methyl ester

N-benzyl-N'-[N-(3,5-difluorophenylacetyl)-L-alaninyl]-(S)-2-aminohexanamide

N-2-(N,N-dimethylamino)ethyl-N'-[N-(3,5-difluorophenylacetyl)-L-alaninyl]-(S)-2-aminohexanamide N-(2-methoxyethyl)-N'-[N-(3,5-difluorophenylacetyl)-L-alaninyl]-(S)-2-aminohexanamide N-2-(N,N-dimethylamino)ethyl-N'-[N-(3,5-difluorophenylacetyl)-L-alaninyl]-L-phenylalaninamide N-(4-pyridyl)methyl-N'-[N-(3,5-difluorophenylacetyl)-L-alaninyl]-L-phenylalaninamide N-(3-pyridyl)methyl-N'-[N-(3,5-difluorophenylacetyl)-L-alaninyl]-L-phenylalaninamide N-(4-pyridyl)methyl-N'-[N-(3,5-difluorophenylacetyl)-L-alaninyl]-(S)-2-aminohexanamide N-[N-(3,5-difluorophenylacetyl)-L-alaninyl]-(S)-2-aminohexanoate tert-butyl ester N-[N-(3,5-difluorophenylacetyl)-L-alaninyl]-L-4-[3-(N,N-dimethylamino)propoxy]phenylalanine methyl ester N-[N-(3,5-difluorophenylacetyl)-L-alaninyl]-L-4-[(tert-butyloxycarbonyl)methoxy]phenylalanine methyl ester N-[N-(3,5-difluorophenylacetyl)-L-alaninyl]-L-tyrosine methyl ester N-[N-(3,5-difluorophenylacetyl)-L-alaninyl]-L-4-(carboxymethoxy)phenylalanine methyl ester N-[N-(3,5-difluorophenylacetyl)-L-alaninyl]-L-4-(2-morpholinoethoxy)phenylalanine methyl ester N-[N-(3,5-difluorophenylacetyl)-L-alaninyl]-(S)-2-amino-6-(N,N-dimethylamino)hexanoate methyl ester N-[N-(3,5-difluorophenylacetyl)-L-alaninyl]-(S)-2-amino-3-(2-pyridyl)propionate methyl ester N-[N-(3,5-difluorophenylacetyl)-L-alaninyl]-(S)-2-amino-3-(3-pyridyl)propionate methyl ester N-[N-(3,5-difluorophenylacetyl)-L-alaninyl]-(S)-2-amino-3-(4-pyridyl)propionate methyl ester N-[N-(3,5-difluorophenylacetyl)-L-alaninyl]-2-amino-3-methoxypropionate methyl ester N-[N-(3,5-difluorophenylacetyl)-L-alaninyl]-2-amino-3-morpholinopropionate methyl ester N-(2-methoxyethyl)-N'-[N-(3,5-difluorophenylacetyl)-L-alaninyl]-L-4-(2-morpholinoethoxy)phenylalaninamide N-(2-methoxyethyl)-N'-[N-(3,5-difluorophenylacetyl)-L-alaninyl]-2-amino-3-methoxypropionamide N-[N-(3,5-difluorophenylacetyl)-L-alaninyl]glycine methyl ester N-(2-methoxyethyl)-N'-[N-(3,5-difluorophenylacetyl)-L-alaninyl]-2-amino-3-(4-pyridyl)propionamide N-(2-methoxyethyl)-N'-[N-(3,5-difluorophenylacetyl)-L-alaninyl]-2-amino-3-(2-pyridyl)propionamide N-[N-(3,5-difluorophenylacetyl)-L-alaninyl]-(S)-2-amino-3-(thiazol-4-yl)propionate methyl ester N-(3-methoxybenzyl)-N'-[N-(3,5-difluorophenylacetyl)-L-alaninyl]-L-phenylalaninamide N-[N-(3,5-difluorophenylacetyl)-L-alaninyl]-(S)-2-amino-3-(1-naphthyl)propionate methyl ester N-[N-(3,5-difluorophenylacetyl)-L-alaninyl]-(S)-2-amino-3-(2-naphthyl)propionate methyl ester N-[N-(3,5-difluorophenylacetyl)-L-alaninyl]-(S)-2-amino-3-(2-thienyl)propionate methyl ester N-[N-(3,5-difluorophenylacetyl)-L-alaninyl]-L-phenylalanine benzyl ester N-[N-(3,5-difluorophenylacetyl)-L-alaninyl]-L-phenylalanine 3-bromo-propyl ester N-[N-(3,5-difluorophenylacetyl)-L-alaninyl]-L-phenylalanine 3-iodopropyl ester N-[N-(3,5-difluorophenylacetyl)-L-alaninyl]-L-leucine tert-butyl ester N'-[N-(3,5-difluorophenylacetyl)-L-alaninyl]-2-amino-2-(2-pyridyl)acetamide N'-[N-(3,5-difluorophenylacetyl)-L-alaninyl]-2-amino-2-(3-pyridyl)acetamide N-[N-(3,5-difluorophenylacetyl)-L-alaninyl]-N$_ε$-(tert-butoxycarbonyl)-L-lysine methyl ester methyl N-[N-(3,5-difluorophenylacetyl)-L-alaninyl]-(S)-2-amino-4-phenylbutanoate N-[N-(3,5-difluorophenylacetyl)-L-alaninyl]glycine 2-phenylethyl ester N-[N-(3,5-difluorophenylacetyl)-L-alaninyl]glycine 3-phenylpropyl ester
N'-[N-(3,5-difluorophenylacetyl)-L-alaninyl]-2-amino-2-(4-pyridyl)acetamide
N-[N-(3,5-difluorophenylacetyl)-L-alaninyl]-2-amino-2-(3-pyridyl)acetate ethyl ester
N-methyl-N'-[N-(3,5-difluorophenylacetyl)-L-alaninyl]-(S)-2-aminohexanamide
N,N-dimethyl-N'-[N-(3,5-difluorophenylacetyl)-L-alaninyl]-(S)-2-aminohexanamide
N'-[N-(3,5-difluorophenylacetyl)-L-alaninyl]-(S)-2-aminohexanamide
N-[N-(3,5-difluorophenylacetyl)-L-alaninyl]-2-amino-2-(3-methoxyphenyl)acetate methyl ester
N-[N-(3,5-difluorophenylacetyl)-L-alaninyl]-2-amino-2-(4-methoxyphenyl)acetate methyl ester
N-[N-(3,5-difluorophenylacetyl)-L-alaninyl]-2-amino-2-(2-pyridyl)acetate ethyl ester
N-[N-(3,5-difluorophenylacetyl)-L-alaninyl]-2-amino-2-(4-pyridyl)acetate ethyl ester
N-[N-(cyclohex-1-enylacetyl)-L-alaninyl]-L-phenylalanine methyl ester
N-[N-(3,5-difluorophenylacetyl)-L-alaninyl]-1-aminocyclopropane-1-carboxylate methyl ester
N-2-(N,N-dimethylamino)ethyl-N-methyl-N'-[N-(3,5-difluorophenylacetyl)-L-alaninyl]-L-alaninamide
N-[N-(3,5-difluorophenylacetyl)-L-alaninyl]glycine benzyl ester
N-hydroxy-N'-[N-(3-nitrophenylacetyl)-L-alaninyl]-D,L-threoninamide
N-[N-(3,5-difluorophenylacetyl)-L-alaninyl]-L-alanine ethyl ester
N'-[N-(3,5-difluorophenylacetyl)-L-alaninyl]-L-alaninamide
N-methoxy-N-methyl-N'-[N-(isovaleryl)-L-phenylglycinyl]-L-alaninamide
N-iso-butyl-N'-[N-(3,5-difluorophenylacetyl)-L-alaninyl]-L-alaninamide
N,N-di-n-propyl-N'-[N-(3,5-difluorophenylacetyl)-L-alaninyl]-L-alaninamide
N'-[N-(3,5-difluorophenylacetyl)-L-alaninyl]-L-valinamide
N-(4-nitrophenyl)-N'-[N-(3,5-difluorophenylacetyl)-L-alaninyl]-L-alaninamide
N-[N-(3,5-difluorophenylacetyl)-L-alaninyl]-L-phenylalanine methyl ester
N'-[N-(3,5-difluorophenylacetyl)-L-alaninyl]-L-phenylalaninamide
N-(2-methoxyethyl)-N'-[N-(3,5-difluorophenylacetyl)-L-alaninyl]-L-phenylalaninamide
N-(4-nitrobenzyl)-N'-[N-(3,5-difluorophenylacetyl)-L-alaninyl]-L-alaninamide
N-(4-nitrophenyl)-N'-[N-[N-(isovaleryl)-L-phenylglycinyl]-L-alaninyl]-L-alaninamide
N-(4-nitrophenyl)-N'-[N-(3,5-difluorophenylacetyl)-L-alaninyl]-L-phenylalaninamide
N-benzyl-N-methyl-N'-[N-(3,5-difluorophenylacetyl)-L-alaninyl]-L-alaninamide
N-(3,5-difluorobenzyl)-N'-[N-(3,5-difluorophenylacetyl)-L-alaninyl]-L-alaninamide
N-(3-nitrobenzyl)-N'-[N-(3,5-difluorophenylacetyl)-L-alaninyl]-L-alaninamide
N-benzyl-N'-[N-(3,5-difluorophenylacetyl)-L-alaninyl]-L-alaninamide
N-(4-nitrobenzyl)-N'-[N-(3,5-difluorophenylacetyl)-L-alaninyl]-L-phenylalaninamide
N-[N-(3,5-difluorophenylacetyl)-L-alaninyl]-L-tryptophan methyl ester
N-(4-methoxybenzyl)-N'-[N-(3,5-difluorophenylacetyl)-L-alaninyl]-L-alaninamide
N-[N-[N-(3,5-difluorophenylacetyl)-L-alaninyl]-L-phenylalaninyl]-L-phenylglycine methyl ester
N-[N-(3,5-difluorophenylacetyl)-L-alaninyl]-L-phenylglycine methyl ester
N-[N-[N-(3,5-difluorophenylacetyl)-L-alaninyl]-L-alaninyl]-L-phenylglycine methyl ester
N-(2-phenylethyl)-N'-[N-(3,5-difluorophenylacetyl)-L-alaninyl]-L-alaninamide
N'-[N-(3,5-difluorophenylacetyl)-L-alaninyl]-L-tryptophanamide
N-[N-(3,5-difluorophenylacetyl)-L-alaninyl]-(S)-2-amino-3-cyclohexylpropionate methyl ester
N-(2-methoxyethyl)-N'-[N-(3,5-difluorophenylacetyl)-L-alaninyl]-(S)-2-amino-3-(4-nitrophenyl)propionamide
N-[(R)-α-methylbenzyl]-N'-[N-(3,5-difluorophenylacetyl)-L-alaninyl]-L-alaninamide
N-[(S)-α-methylbenzyl]-N'-[N-(3,5-difluorophenylacetyl)-L-alaninyl]-L-alaninamide
N-(4-fluorobenzyl)-N'-[N-(3,5-difluorophenylacetyl)-L-alaninyl]-L-alaninamide
N-(4-pyridylmethyl)-N'-[N-(3,5-difluorophenylacetyl)-L-alaninyl]-L-alaninamide
N-(4-trifluoromethylbenzyl)-N'-[N-(3,5-difluorophenylacetyl)-L-alaninyl]-L-alaninamide
N-[N-(3,5-difluorophenylacetyl)-L-alaninyl]-2-amino-2-phenylpropionate ethyl ester
N-[N-(3,5-difluorophenylacetyl)-L-alaninyl]-L-phenylalanine tert-butyl ester
N-[N-(3,5-difluorophenylacetyl)-L-alaninyl]-2-amino-2-methylpropionate methyl ester
N-[N-(3,5-difluorophenylacetyl)-L-alaninyl]-2-amino-2-cyclohexylacetate ethyl ester
N-(2-methoxyethyl)-N'-[N-(3,5-difluorophenylacetyl)-L-alaninyl]-L-phenylglycinamide
N-2-(N,N-dimethylamino)ethyl-N'-[N-(3,5-difluorophenylacetyl)-L-alaninyl]-L-phenylglycinamide
N-(2-pyridylmethyl)-N'-[N-(3,5-difluorophenylacetyl)-L-alaninyl]-L-phenylglycinamide
N-[N-(3,5-difluorophenylacetyl)-L-alaninyl]-2-amino-2-(4-fluorophenyl)acetate ethyl ester
N-[N-(3,5-difluorophenylacetyl)-L-alaninyl]-2-amino-2-(2-fluorophenyl)acetate ethyl ester
N-[N-(3,5-difluorophenylacetyl)-L-phenylglycinyl]-L-alanine ethyl ester
N-[N-(3,5-difluorophenylacetyl)-L-alaninyl]-2-amino-3-phthalimidopropionate ethyl ester
N-[N-(3,5-difluorophenylacetyl)-L-alaninyl]-L-phenylglycine neopentyl ester
N-tert-butyl-N'-[N-(3,5-difluorophenylacetyl)-L-alaninyl]-L-phenylglycinamide
N-[N-(3,5-difluorophenylacetyl)-L-alaninyl]-L-phenylglycine tert-butyl ester
N'-[N-(3,5-difluorophenylacetyl)-L-alaninyl]-L-phenylglycinamide 4-[N-[N-(3-nitrophenylacetyl)-L-alaninyl]-L-valinyl]morpholine N-[N-(3,5-difluorophenylacetyl)-L-alaninyl]-(S)-2-aminopentanoate methyl ester 4-[N-[N-(3-nitrophenylacetyl)-L-alaninyl]-(S)-2-amino-3-tert-butoxybutyryl]morpholine 4-[N-[N-(3-nitrophenylacetyl)-L-alaninyl]-L-isoleucinyl]morpholine N-[N-(3,5-difluorophenylacetyl)-L-alaninyl]-L-leucine methyl ester N-2-methoxyethyl-N'-[N-(3,5-difluorophenylacetyl)-L-alaninyl]-L-alaninamide N-2-(N,N-dimethylamino)ethyl-N'-[N-(3,5-difluorophenylacetyl)-L-alaninyl]-L-alaninamide N-cyclohexyl-N'-[N-(3,5-difluorophenylacetyl)-L-alaninyl]-L-alaninamide N-neopentyl-N'-[N-(3,5-difluorophenylacetyl)-L-alaninyl]-L-alaninamide N-tetrahydrofurfuryl-N'-[N-(3,5-difluorophenylacetyl)-L-alaninyl]-L-alaninamide N-2-pyridylmethyl-N'-[N-(3,5-difluorophenylacetyl)-L-alaninyl]-L-alaninamide 3-[N-[N-(3,5-difluorophenylacetyl)-L-alaninyl]-L-alaninyl]thiazolidine N-[N-(3,5-difluorophenylacetyl)-L-alaninyl]-(S)-2-aminobutanoate methyl ester N-(R)-sec-butyl-N'-[N-(3,5-difluorophenylacetyl)-L-alaninyl]-L-alaninamide 1-[N-[N-(3,5-difluorophenylacetyl)-L-alaninyl]pyrrolidine N-(S)-sec-butyl-N'-[N-(3,5-difluorophenylacetyl)-L-alaninyl]-L-alaninamide N-[N-(3,5-difluorophenylacetyl)-L-alaninyl]-L-valine methyl ester N-2-fluoroethyl-N'-[N-(3,5-difluorophenylacetyl)-L-alaninyl]-L-alaninamide N-[(S)-6-methyl-3-oxohept-2-yl]-N'-(3,5-difluorophenylacetyl)-L-alaninamide N-4-nitrobenzyl-N'-[N-(3,5-difluorophenylacetyl)-L-alaninyl]-(S)-2-aminobutyramide N-4-nitrobenzyl-N'-[N-(3,5-difluorophenylacetyl)-L-alaninyl]-(S)-2-aminopentanamide N-[N-(3,5-difluorophenylacetyl)-L-alaninyl]-2-amino-2-(3-fluorophenyl)acetate methyl ester N'-[N-(3,5-difluorophenylacetyl)-L-alaninyl]-(S)-2-amino-2-(2-thienyl)acetamide N-[N-(3,5-difluorophenylacetyl)-L-alaninyl]-2-amino-2-(5-chlorobenzothiophen-2-yl)acetate methyl ester N-[N-(3,5-difluorophenylacetyl)-L-alaninyl]-2-amino-2-(benzothiophen-2-yl)acetate ethyl ester N-[N-(3,5-difluorophenylacetyl)-L-alaninyl]-2-amino-2-(benzothiophen-3-yl)acetate methyl ester N-[N-(3,5-difluorophenylacetyl)-L-alaninyl]-2-amino-2-(2-thienyl)acetate methyl ester N-[N-(3,5-difluorophenylacetyl)-L-alaninyl]-2-amino-2-(benzothiophen-5-yl)acetate ethyl ester N-[N-(3,5-difluorophenylacetyl)-L-alaninyl]-(S)-2-amino-2-(2-thienyl)acetate methyl ester N-[N-(3,5-difluorophenylacetyl)-L-alaninyl]-(S)-2-amino-2-(2-thienyl)acetate tert-butyl ester N-[N-(3,5-difluorophenylacetyl)-L-alaninyl]-(S)-2-amino-2-(2-thienyl)acetic acid N-[N-(3,5-difluorophenylacetyl)-L-alaninyl]-2-amino-2-(1H-tetrazol-5-yl)acetate methyl ester N-[N-(3,5-difluorophenylacetyl)-L-alaninyl]-(S)-2-amino-2-(6-methoxy-2-naphthyl)acetate methyl ester N-[N-(3,5-difluorophenylacetyl)-L-alaninyl]-2-amino-2-(3-trifluoromethylphenyl)acetate methyl ester N-[N-(3,5-difluorophenylacetyl)-L-alaninyl]-2-amino-2-(4,5,6,7-tetrahydrobenzothiophen-2-yl)acetate methyl ester N-[N-(3,5-difluorophenylacetyl)-L-alaninyl]-2-amino-2-(thieno[2,3-b]thiophen-2-yl)acetate methyl ester N-[N-(3,5-difuorophenylacetyl)-L-alaninyl]-2-amino-2-(2-methylthiazol-4-yl)acetate methyl ester N-[N-(3,5-difluorophenylacetyl)-L-alaninyl]-(S)-2-aminohex-4-enoate methyl ester N-tert-butyl-N'-[N-(3,5-Difluorophenylacetyl)-L-alaninyl]-(S)-2-amino-2-(4-phenylphenyl)acetamide N-[N-(3,5-difluorophenylacetyl)-(S)-2-aminobutanoyl]-L-phenylglycine tert-Butyl Ester N-[N-(3,5-difluorophenylacetyl)-L-valinyl]-L-phenylglycine tert-butyl ester N-[N-(3,5-difluorophenylacetyl)-L-methioninyl]-L-phenylglycine methyl ester N-[N-(3,5-difluorophenylacetyl)-L-valinyl]-L-phenylglycine methyl ester N-[N-(3,5-difluorophenylacetyl)-2-aminobutanoyl]-L-phenylglycine methyl ester N-[N-(3,5-difluorophenylacetyl)-L-leucinyl]-L-phenylglycine methyl ester N-[N-(3,5-difluorophenylacetyl)-L-phenylalaninyl]-L-phenylglycine methyl ester N-[N-(3,5-difluorophenylacetyl)glycinyl]-L-phenylglycine methyl ester N-[N-(3,5-difluorophenylacetyl)-L-phenylglycinyl]-L-phenylglycine methyl ester N-cyclohexyl-N'-[N-(3,5-difluorophenylacetyl)-L-alaninyl]-L-phenylglycinamide N-[N-(3,5-difluorophenylacetyl)-L-alaninyl]-L-lysine methyl ester N-[N-(3,5-difluorophenylacetyl)-L-alaninyl]-L-glutamide N-[(S)-3-hydroxy-6-methylhept-2-yl]-N'-(3,5-difluorophenylacetyl)-L-alaninamide N-[(S)-2-hydroxy-1-phenyleth-1-yl]-N'-(3,5-difluorophenylacetyl)-L-alaninamide N-[N-(3,5-difluorophenyl-α-fluoroacetyl)-L-alaniny]-L-phenylglycine tert-butyl ester N-[N-(3,5-difluorophenylacetyl)-2-(S)-aminocyclohexylacetyl]-L-phenylglycine methyl ester N-[(1R,2S)-1-hydroxy-1-phenylprop-2-yl]-N'-(3,5-difluorophenylacetyl)-L-alaninamide N-[(1R,2S)-1-hydroxy-1,2-diphenyleth-2-yl]-N'-(3,5-difluorophenylacetyl)-L-alaninamide N-[(1S,2R)-1-hydroxy-1-phenylprop-2-yl]-N'-(3,5-difluorophenylacetyl)-L-alaninamide N-2-methoxyethyl-N'-[N-(3,5-difluorophenylacetyl)-L-alaninyl]-glycinamide N-[(S)-α-hydroxy-α-phenyl-iso-propyl]-N'-(3,5-difluorophenylacetyl)-L-alaninamide N-[(S)-2-hydroxy-1,2-diphenylethyl]-N'-(3,5-difluorophenylacetyl)-L-alaninamide N-[(S)-1-hydroxyhex-2-yl]-N'-(3,5-difluorophenylacetyl)-L-alaninamide N-[α-hydroxy-α'-(4-hydroxyphenyl)-iso-propyl]-N'-(3,5-difluorophenylacetyl)-L-alaninamide N-2-pyridylmethyl-N'-[N-(3,5-difluorophenylacetyl)-L-alaninyl]-L-phenylalaninamide N-[α-hydroxy-α'-pyrid-2-yl-iso-propyl]-N'-(3,5-difluorophenylacetyl)-L-alaninamide N-[α-hydroxy-α'-pyrid-4-yl-iso-propyl]-N'-(3,5-difluorophenylacetyl)-L-alaninamide N-[(S)-1-hydroxy-4-methylpent-2-yl]-N'-(3,5-difluorophenylacetyl)-L-alaninamide N-[α-methoxy-prop-2-yl]-N'-(3,5-difluorophenylacetyl)-L-alaninamide N-[1-hydroxy-3-methyl-but-2-yl]-N'-(3,5-difluorophenylacetyl)-L-alaninamide N-[N-(3,5-difluorophenylacetyl)-L-alaninyl]-2-amino-2-(6-aminopyrid-2-yl)acetate methyl ester N-[1-hydroxy-prop-2-yl]-N'-(3,5-difluorophenylacetyl)-L-alaninamide N-[(S)-2-methoxy-1-phenyleth-1-yl]-N'-(3,5-difluorophenylacetyl)-L-alaninamide N-[(S)-1-methoxy-2-phenyl-prop-2-yl]-N'-(3,5-difluorophenylacetyl)-L-alaninamide N-[(S)-1-acetoxyhex-2-yl]-N'-(3,5-difluorophenylacetyl)-L-alaninamide N-[(S)-1-(tert-butylcarbonyloxy)-hex-2-yl]-N'-(3,5-difluorophenylacetyl)-L-alaninamide N-[2-hydroxy-1-(thien-2-yl)ethyl]-N'-(3,5-difluorophenylacetyl)-L-alaninamide N-[(S)-2-hydroxy-2-methyl-1-phenylprop-1-yl]-N'-(3,5-difluorophenylacetyl)-L-alaninamide N-[N-(3,5-difluorophenylacetyl)-L-(thien-2-yl)glycinyl]-L-phenylalanine tert-butyl ester N-[N-(3,5-difluorophenylacetyl)-L-phenylglycinyl]-L-phenylglycinol N-[N-(3,5-difluorophenylacetyl)-D,L-phenylglycinyl]-D,L-phenylglycinamide N-[N-(3,5-difluorophenylacetyl)-D,L-valinyl]-D,L-phenylglycinamide N-[N-(3,5-difluorophenylacetyl)-L-norleucinyl]-L-phenylglycine methyl ester N-[N-(3,5-difluorophenylacetyl)-L-norvalinyl]-L-phenylglycine methyl ester N-[N-(3,5-difluorophenylacetyl)-L-tert-leucinyl]-L-phenylglycine methyl ester N-[N-(3,5-difluorophenylacetyl)-L-isoleucinyl]-L-phenylglycine methyl ester N-[N-(3,5-difluorophenylacetyl)-L-cyclohexylalaninyl]-L-phenylglycine methyl ester N-[N-(3,5-difluorophenylacetyl)-(S)-2-amino-2-(cyclopropyl)acetyl]-L-phenylglycine methyl ester N-[N-(3,5-difluorophenylacetyl)-(S)-2-amino-2-(thien-3-yl)acetyl]-L-phenylglycine methyl ester N-[N-(3,5-difluorophenylacetyl)-(S)-2-amino-2-(thien-2-yl)acetyl]-L-phenylglycine methyl ester N-[N-(3,5-difluorophenylacetyl)-L-(4-fluorophenyl)glycinyl]-L-phenylglycine methyl ester N-[N-(3,5-difluorophenylacetyl)-D-(4-fluorophenyl)glycinyl]-L-phenylglycine methyl ester N-[N-(3,5-difluorophenylacetyl)-L-(4-methoxyphenyl)glycinyl]-L-phenylglycine methyl ester N-[N-(3,5-difluorophenylacetyl)-L-phenylglycinyl]-L-phenylglycine tert-butyl ester N-tert-butyl-N'-[N-(3,5-difluorophenylacetyl)-L-alaninyl]-L-(5-bromothien-2-yl)glycinamide N-tert-butyl-N'-[N-(3,5-difluorophenylacetyl)-L-alaninyl]-D-(5-bromothien-2-yl)glycinamide N-tert-butyl-N'-[N-(3,5-difluorophenylacetyl)-L-alaninyl]-L-(4-bromothien-2-yl)glycinamide N-tert-butyl-N'-[N-(3,5-difluorophenylacetyl)-L-alaninyl]-L-(thien-2-yl)glycinamide N-tert-butyl-N'-[N-(3,5-difluorophenylacetyl)-L-alaninyl]-D-(thien-2-yl)glycinamide N-tert-butyl-N'-[N-(3,5-difluorophenylacetyl)-L-alaninyl]-L-(thien-3-yl)glycinamide N-tert-butyl-N'-[N-(3,5-difluorophenylacetyl)-L-alaninyl]-D-(thien-3-yl)glycinamide N-tert-butyl-N'-[N-(3,5-difluorophenylacetyl)-L-alaninyl]-D-phenylglycinamide N-tert-butyl-N'-[N-(3,5-difluorophenylacetyl)-L-alaninyl]-L-phenylglycinamide N-tert-butyl-N'-[N-(3,5-difluorophenylacetyl)-L-alaninyl]-D,L-(5-chlorothien-2-yl)glycinamide N-Cyclohexyl-N'-[N-(3,5-difluorophenylacetyl)-L-alaninyl]-D-4-(phenyl)phenylglycinamide N-tert-butyl-N'-[N-(3,5-difluorophenylacetyl)-L-alaninyl]-L-3-(phenoxy)phenylglycinamide N-(S)-(−)-α-methylbenzyl-N'-[N-(3,5-difluorophenylacetyl)-L-alaniny]-D,L-phenylglycinamide N-tert-butyl-N'-[N-(3,5-difluorophenylacetyl)-L-alaninyl]-L-3-(phenyl)phenylglycinamide N-tert-butyl-N'-[N-(3,5-difluorophenylacetyl)-L-alaninyl]-L-4-(ethyl)phenylglycinamide N-tert-butyl-N'-[N-(3,5-difluorophenylacetyl)-L-alaninyl]-L-2-(phenyl)phenylglycinamide N-tert-butyl-N'-[N-(3,5-difluorophenylacetyl)-L-alaninyl]-L-2-(benzyl)phenylglycinamide N-tert-butyl-N'-[N-(3,5-difluorophenylacetyl)-L-alaninyl]-D,L-4-bromophenylglycinamide N-tert-butyl-N'-[N-(3,5-difluorophenylacetyl)-L-alaninyl]-L-4-(cyclohexyl)phenylglycinamide N-tert-butyl-N'-[N-(3,5-difluorophenylacetyl)-L-alaninyl]-L-4-(4-ethylphenyl)phenylglycinamide N-tert-butyl-N'-[N-(3,5-difluorophenylacetyl)-L-alaninyl]-D,L-4-(tert-butyl)phenylglycinamide N-tert-butyl-N'-[N-(3,5-difluorophenylacetyl)-L-alaninyl]-D,L-3-(4-chlorophenoxy)phenylglycinamide N-cyclohexyl-N'-[N-(3,5-difluorophenylacetyl)-L-alaninyl]-L-4-(phenyl)phenylglycinamide N-[N-(3,5-difluorophenyl-α-hydroxyacetyl)-L-alaninyl]-L-phenylglycine tert-butyl ester N-tert-butyl-N'-[N-(3,5-difluorophenyl-α,α-difluoroacetyl)-L-alaninyl]-L-phenylglycinamide N-[N-(3,5-difluorophenylacetyl)-L-alaninyl]-D-phenylglycine tert-butyl ester N-[(S)-1-oxo-1-phenylprop-2-yl]-N'-(3,5-difluorophenylacetyl)-L-alaninamide N-[N-(3,5-difluorophenylacetyl)-L-alaninyl]-D,L-(pyrid-3-yl)glycine tert-butyl ester

[N-[N-(3,5-difluorophenylacetyl)-L-alaninyl]-D,L-phenylglycinyl]morpholine

N-[N-(3,5-difluorophenylacetyl)-L-alaninyl]-D,L-(2-methoxy)phenylglycine methyl ester N-[N-(3,5-difluorophenylacetyl)-L-alaninyl]-D,L-phenylglycine N-tert-butoxycarbonyl(hydroxyl amine) ester N-neopentyl-N'-[N-(3,5-difluorophenylacetyl)-L-alaninyl]-D,L-phenylglycinamide N-tetrahydrofurfuryl-N'-[N-(3,5-difluorophenylacetyl)-L-alaninyl]-D,L-phenylglycinamide N-methoxy-N'-[N-(3,5-difluorophenylacetyl)-L-alaninyl]-D,L-phenylglycinamide

[N-[N-(3,5-difluorophenylacetyl)-L-alaninyl]-D,L-phenylglycinyl]azetidine

N-iso-butyl-N'-[N-(3,5-difluorophenylacetyl)-L-alaninyl]-D,L-phenylglycinamide

N-cyclopropanemethyl-N'-[N-(3,5-difluorophenylacetyl)-L-alaninyl]-D,L-phenylglycinamide N-methoxy-N-methyl-N'-[N-(3,5-difluorophenylacetyl)-L-alaninyl]-D,L-phenylglycinamide N-2-methylprop-2-enyl-N'-[N-(3,5-difluorophenylacetyl)-L-alaninyl]-D,L-phenylglycinamide N-(pyrid-3-yl)methyl-N'-[N-(3,5-difluorophenylacetyl)-L-alaninyl]-D,L-phenylglycinamide N-(pyrid-4-yl)methyl-N'-[N-(3,5-difluorophenylacetyl)-L-alaninyl]-D,L-phenylglycinamide N-furfuryl-N'-[N-(3,5-difluorophenylacetyl)-L-alaninyl]-D,L-phenylglycinamide N-cyclopentyl-N'-[N-(3,5-difluorophenylacetyl)-L-alaninyl]-D,L-phenylglycinamide N-1-benzylpiperidin-4-yl-N'-[N-(3,5-difluorophenylacetyl)-L-alaninyl]-D,L-phenylglycinamide N,N-dimethyl-N'-[N-(3,5-difluorophenylacetyl)-L-alaninyl]-D,L-phenylglycinamide N-2,2,6,6-tetramethylpiperidin-4-yl-N'-[N-(3,5-difluorophenylacetyl)-L-alaninyl]-D,L-phenylglycinamide N-2-methylcyclohexyl-N'-[N-(3,5-difluorophenylacetyl)-L-alaninyl]-D,L-phenylglycinamide N-4-methylcyclohexyl-N'-[N-(3,5-difluorophenylacetyl)-L-alaninyl]-D,L-phenylglycinamide N-1-ethoxycarbonylpiperidin-4-yl-N'-[N-(3,5-difluorophenylacetyl)-L-alaninyl]-D,L-phenylglycinamide N-methyl-N'-[N-(3,5-difluorophenylacetyl)-L-alaninyl]-L-phenylglycinamide N-tert-butoxy-N'-[N-(3,5-difluorophenylacetyl)-L-alaninyl]-D,L-phenylglycinamide N-[N-(3,5-difluorophenylacetyl)-L-alaninyl]-D,L-phenylglycine N-tert-butyl(hydroxylamine) ester N-[N-(3,5-difluorophenylacetyl)-L-alaninyl]-L-phenylglycine hydrazide N-(1-ethoxyethen-1-yl)-[N'-(3,5-difluorophenylacetyl)-L-alaninyl]-L-phenylglycine hydrazide N-4-(phenyl)butyl-N'-[N-(3,5-difluorophenylacetyl)-L-alaninyl]-L-phenylglycinamide N-3-(4-iodophenoxy)propyl-N'-[N-(3,5-difluorophenylacetyl)-L-alaninyl]-L-phenylglycinamide N-6-(amino)hexyl-N'-[N-(3,5-difluorophenylacetyl)-L-alaninyl]-D,L-phenylglycinamide Hydrochloride N-1-(phthalimido)pent-2-yl-N'-(3,5-difluorophenylacetyl)-L-alaninamide N-[N-(3,5-difluorophenylacetyl)-L-(3,5-difluorophenyl)glycinyl]-L-(3,5-difluorophenyl)glycine methyl ester N-[N-(3,5-difluorophenylacetyl)-L-alaninyl]-L-norleucine N-[N-(3,5-difluorophenylacetyl)-L-alaninyl]-L-4-fluorophenylglycine iso-propyl ester N-(isopropyl) N'-[N-(3,5-difluorophenylacetyl)-L-alaninyl]-L-phenylglycinamide N-[N-(3,5-difluorophenylacetyl)-L-alaninyl]-L-phenylglycine iso-butyl ester N-[N-(3,5-difluorophenylacetyl)-L-alaninyl]-D-phenylglycine methyl ester N-[N-(3,5-difluorophenylacetyl)-L-alaninyl]-2-amino-2-(5-chlorobenzothiophen-3-yl)acetate methyl ester N-[N-(3,5-difluorophenylacetyl)-L-alaninyl]-(S-2-amino-3-(thiazol-4-yl)propionate tert-butyl ester N-[N-(3,5-difluorophenylacetyl)-L-alaninyl]-L-phenylglycinamide tert-butyl ester N-[N-(3,5-difluorophenylacetyl)-L-alaninyl]-D-(thien-2-yl)glycinamide N-[N-(3-fluorophenylacetyl)-L-alaninyl]-D-phenylglycinamide N-[N-(4-fluorophenylacetyl)-L-alaninyl]-D-phenylglycinamide N-[N-(3,5-difluorophenylacetyl)-L-alaninyl]-D-phenylglycine N-[N-(3,5-difluorophenylacetyl)-L-alaninyl]-D-phenylglycinamide N'-[N-(3,5-difluorophenylacetyl)-L-alaninyl]-(S)-2-amino-2-(2-furanyl)acetamide N'-[N-(3,5-difluorophenylacetyl)-D-alaninyl]-D-phenylglycinamide N'-[N-(3,4-difluorophenylacetyl)-D-alaninyl]-D-phenylglycinamide N'-[N-(3,5-difluorophenylacetyl)-L-alaninyl]-L-phenylalanin-N-methylsulfonamide N"-methyl-N"-phenyl-N'-[N-(3,5-difluorophenylacetyl)-L-alaninyl]-glycinamide N"-methyl-N"-phenyl-N'-[N-(3,5-difluorophenylacetyl)-L-alaninyl]-L-alaninamide N'-[N-(3,5-difluorophenylacetyl)-L-methioninyl]-L-phenylglycinamide N"-methyl-N"-benzyl-N'-[N-(3,5-difluorophenylacetyl)-L-alaninyl]-glycinamide N"-4-fluorobenzyl-N'-[N-(3,5-difluorophenylacetyl)-L-alaninyl]-L-phenylglycinamide N'-[N-(3,5-difluorophenylacetyl)-L-alaninyl]-L-(4-fluoro)phenylglycine neopentyl ester N-[N-(2,3,4,5,6-pentafluorophenylacetyl)-L-alaninyl]-L-(pyrid-3-yl)glycine methyl ester N-[N-(3,5-difluorophenylacetyl)-L-alaninyl]-L-(pyrid-3-yl)glycine tert-butyl ester N-[N-(3,5-difluorophenylacetyl)-L-(O-benzyl)serinyl]-L-phenylglycine methyl ester N-[N-(3,5-difluorophenylacetyl)-L-(O-benzyl)threoninyl]-L-phenylglycine methyl ester N-[N-(3,5-difluorophenylacetyl)-L-threoninyl]-L-phenylglycine methyl ester N-[N-(3,5-difluorophenylacetyl)-L-serinyl]-L-phenylglycine methyl ester N"-4-methylphenyl-N'-[N-(3,5-difluorophenylacetyl)-L-alaninyl]-L-phenylglycinamide N"-tetrahydrofurfuryl-N'-[N-(3,5-difluorophenylacetyl)-L-alaninyl]-L-phenylglycinamide N'-[N-(3,5-difluorophenylacetyl)-L-alaninyl]-L-4-fluorophenyl-glycinamide N'-[N-(3,5-difluorophenylacetyl)-L-methionyl]-L-phenylglycinamide N-[N-(3,5-difluorophenylacetyl)-2-aminobutanoyl]-L-phenylglycinamide N'-[N-(3,5-difluorophenylacetyl)-L-phenylglycinyl]-L-phenylglycinamide N-[N-(3,5-difluorophenylacetyl)-L-valinyl]-L-phenylglycinamide N-[(R)-α-methylbenzyl]-N'-[N-(3,5-difluorophenylacetyl)-L-alaninyl]-L-phenylglycinamide N-[1-phenyl-2-oxo-3-methylbutan-1-yl]-N'-(3,5-difluorophenylacetyl)-L-alaninamide N-[1-phenyl-2-oxo-propan-1-yl]-N'-(3,5-difluorophenylacetyl)-L-alaninamide N-[1-phenyl-2-oxo-pentan-1-yl]-N'-(3,5-difluorophenylacetyl)-L-alaninamide N-[1-phenyl-2-oxo-2-phenyl-ethan-1-yl]-N'-(3,5-difluorophenyl-acetyl)-L-alaninamide N-[1-phenyl-2-oxo-butan-1-yl]-N'-(3,5-difluorophenyl-acetyl)-L-alaninamide N-[1-phenyl-2-oxo-4-methylpentan-1-yl]-N'-(3,5-difluorophenyl-acetyl)-L-alaninamide N'-[N-(3,5-difluorophenylacetyl)-L-alaninyl]-L-α-hydroxyphenylalanine methyl ester N"-[4-((2-hydroxy-4-azido)-phenyl)-NHC(O)-)butyl]-N'-[N-(3,5-difluorophenylacetyl)-L-alaninyl]-L-phenylglycinamide N-[(S)-1-phenyl-2-oxo-2-phenyl-ethan-1-yl]-N'-(3,5-difluorophenyl-acetyl)-L-alaninamide N'-[N-(3,5-difluorophenylacetyl)-L-alaninyl]-L-4-fluorophenylglycine tert-butyl ester N'-[N-(3,5-difluorophenylacetyl)-L-alaninyl]-L-4-phenylphenylglycine tert-butyl ester N"-tert-butyl-N'-[N-(3,5-difluorophenylacetyl)-L-alaninyl]-L-4-n-butylphenylglycinamide N"-tert-butyl-N'-[N-(3,5-difluorophenylacetyl)-L-alaninyl]-D,L-4-(phenylacetenyl)phenylglycinamide N'-[N-(3,5-difluorophenylacetyl)-L-alaninyl]-D,L-phenylglycinthioamide N-[1,3-diphenyl-2-oxo-propan-1-yl]-N'-(3,5-difluorophenylacetyl)-L-alaninamide N-[1-phenyl-2-oxo-2-cyclopentylethan-1-yl]-N'-(3,5-difluorophenylacetyl)-L-alaninamide N-[1-phenyl-2-oxo-hexan-1-yl]-N'-(3,5-difluorophenylacetyl)-L-alaninamide N-[1-phenyl-2-oxo-3-methylpentan-1-yl]-N'-(3,5-difluorophenylacetyl)-L-alaninamide N"-n-hexyl-6-biotinamidyl-N'-[N-(3,5-difluorophenylacetyl)-L-alaninyl]-D,L-phenylglycinthioamide N'-[N-(3,5-difluorophenylacetyl)-L-methioninyl]-L-methionine N'-[N-(2-tert-BOC-amino)propionyl)-L-alaninyl]-L-phenylglycine methyl ester N"-tert-butyl N'-[N-(3,5-difluorophenylacetyl)-L-alaninyl]-L-2-fluorophenylglycinamide N'-[N-(3,5-difluorophenylacetyl)-L-alaninyl]-D,L-2-phenylglycine methyl ester N-[(S)-1-phenyl-2-oxo-3-phenylpropan-1-yl]-N'-(3,5-difluorophenylacetyl)-L-alaninamide N'-[N-(3,5-difluorophenylacetyl)-D,L-thien-3-ylglycinyl]-D,L-2-phenylglycine N'-[N-(3,5-difluorophenylacetyl)-D,L-thien-3-ylglycinyl]-D,L-2-phenylglycine tert-butyl ester N'-[N-(3,5-difluorophenylacetyl)-L-thien-3-ylglycinyl]-L-2-phenylglycine N'-[N-(3,5-difluorophenylacetyl)-L-thien-3-ylglycinyl]-L-2-phenylglycine tert-butyl ester N-[2-hydroxy-1-(S)phenyleth-1-yl]-N'-[(3,5-difluorophenylacetyl)-L-phenylglycinyl]-L-alaninamide N-[2-hydroxyeth-1-yl]-N'-[(3,5-difluorophenylacetyl)-L-alaninyl]-L-phenylglycinamide N'-[N-(3,5-difluorophenyl-2-oxo-acetyl)-L-alaninyl]-L-2-phenylglycinetert-butyl ester

[N-(3-aminoproprionyl)-L-alaninyl]-L-phenylglycine tert-butyl ester

[N-(3-tert-butoxycarbonylamino)propionyl)-L-alaninyl]-L-phenylglycine tert-butyl ester N-cyclohexyl-N-methyl-N'-[N-(3,5-difluorophenylacetyl)-L-alaniny]-D,L-phenylglycinamide N-cyclohexyl-N-methyl-N'-[N-(3,5-difluorophenyl-α-hydroxyacetyl)-L-alaninyl]-D,L-phenylglycinamide N-cyclohexyl-N'-[N-3,5-difluorophenyl-α-hydroxyacetyl)-L-alaninyl]-D,L-phenylglycinamide.

The pharmaceutical compositions described above comprise a pharmaceutically inert carrier and a compound of this invention.

In the compounds above, X" is preferably hydrogen and X' is preferably hydrogen or fluoro.

Preferred $R^1$ substituted aryl groups include, for example, monosubsti-tuted phenyls (preferably 3 or 5 substituents); disubstituted phenyls (preferably 3,5 substituents); and trisubstituted phenyls (preferably 3,4,5 substituents). Preferably, the substituted phenyl groups do not include more than 3 substituents.

Examples of substituted phenyls include, for instance, 4-fluorophenyl, 4-chlorophenyl, 4-bromophenyl, 4-nitrophenyl, 4-methylphenyl, 3-methoxyphenyl, 3-nitrophenyl, 3-fluorophenyl, 3-chlorophenyl, 3-bromophenyl, 3-thiomethoxyphenyl, 3-methylphenyl, 3-trifluoromethylphenyl, 2-hydroxyphenyl, 2-methylphenyl, 2-fluorophenyl, 2-chlorophenyl, 3,4-difluorophenyl, 2,3,4,5,6-pentafluorophenyl, 3,4-dibromophenyl, 3,4-dichlorophenyl, 3,4-methylene-dioxyphenyl, 3,5-difluorophenyl, 3,5-dichlorophenyl, 2,4-dichlorophenyl, and 2,5-difluorophenyl.

Preferred $R^1$ alkaryl groups include, by way of example, benzyl, 2-phenylethyl, 3-phenyl-n-propyl, and the like.

Preferred $R^1$ alkyl, substituted alkyl, alkenyl, cycloalkyl and cycloalkenyl groups include, by way of example, iso-propyl, n-propyl, n-butyl, iso-butyl, sec-butyl, tert-butyl, —$CH_2CH=CH_2$, —$CH_2CH=CH(CH_2)_4CH_3$, cyclopropyl, cyclobutyl, cyclohexyl, cyclopentyl, cyclohex-1-enyl, —$CH_2$-cyclopropyl, —$CH_2$-cyclobutyl, —$CH_2$-cyclohexyl, —$CH_2$-cyclopentyl, —$CH_2CH_2$-cyclopropyl, —$CH_2CH_2$-cyclobutyl, —$CH_2CH_2$-cyclohexyl, —$CH_2CH_2$-cyclopentyl, aminomethyl, N-tert-butoxycarbonylaminomethyl, and the like.

Preferred $R^1$ heteroaryls and substituted heteroaryls include, by way of example, pyrid-2-yl, pyrid-3-yl, pyrid-4-yl, fluoropyridyls (including 5-fluoropyrid-3-yl), chloropyridyls (including 5-chloropyrid-3-yl), thien-2-yl, thien-3-yl, benzothiazol-4-yl, 2-phenylbenzoxazol-5-yl, furan-2-yl, benzofuran-2-yl, thionaphthen-2-yl, 2-chlorothiophen-5-yl, 3-methylisoxazol-5-yl, 2-(thiophenyl)thiophen-5-yl, 6-methoxythionaphthen-2-yl, 3-phenyl-1,2,4-thiooxadiazol-5-yl, 2-phenyloxazol-4-yl, and the like.

Preferably $R^2$ is selected from the group consisting of hydrogen, alkyl, substituted alkyl, cycloalkyl, aryl, heteroaryl and heterocyclic. Particularly preferred $R^2$ substituents include, by way of example, methyl, ethyl, n-propyl, iso-propyl, n-butyl, iso-butyl, sec-butyl, phenyl, 4-fluorophenyl, 3,5-difluoro-phenyl, 4-methoxyphenyl, benzyl, cyclopropyl, cyclohexyl, cyclopentyl, cycloheptyl, thien-2-yl, thien-3-yl, —CH$_2$CH$_2$SCH$_3$, —CH$_2$OCH$_2\phi$, —CH(CH$_3$)OCH$_2\phi$, —CH(OH)CH$_3$, —CH$_2$OH and the like. As noted below, $R^2$ (as well as $R^4$) is preferably the side chain of an L-amino acid.

Preferred $R^4$ substituents include, for example, hydrogen, methyl, ethyl, iso-propyl, n-propyl, n-butyl, sec-butyl, iso-butyl, cyclopentyl, cyclohexyl, allyl, iso-but-2-enyl, 3-methylpentyl, —CH$_2$-cyclopropyl, —CH$_2$-cyclohexyl, —CH$_2$-indol-3-yl, phenyl, p-(phenyl)phenyl, m-(phenyl)phenyl o-fluorophenyl, m-fluorophenyl, p-fluorophenyl, p-bromophenyl, m-methoxyphenyl, p-methoxyphenyl, phenethyl, benzyl, m-hydroxybenzyl, p-hydroxybenzyl, p-nitrobenzyl, m-trifluoromethylphenyl,p-(CH$_3$)$_2$NCH$_2$CH$_2$CH$_2$O-benzyl, p-(CH$_3$)$_3$COC(O)CH$_2$O-benzyl, p-phenylphenyl, 3,5-difluorophenyl, p-(HOOCCH$_2$O)-benzyl, 2-aminopyrid-6-yl, 4-(N-morpholino-CH$_2$CH$_2$O)-benzyl, —CH$_2$CH$_2$C(O)NH$_2$, —CH$_2$-imidazol-4-yl, —CH$_2$—(3-tetrahydrofuranyl), —CH$_2$-thien-2-yl, —CH$_2$-thiazol-4-yl, —CH$_2$(1-methyl)cyclopropyl, —CH$_2$-thien-3-yl, thien-3-yl, thien-2-yl, —CH$_2$—C(O)O-t-butyl, —CH$_2$—C(CH$_3$)$_3$, —CH$_2$CH(CH$_2$CH$_3$)$_2$, 2-methylcyclopentyl,-cyclohex-2-enyl, —CH[CH(CH$_3$)$_2$]COOCH$_3$, —(CH$_2$)$_2$SCH$_3$, —CH$_2$CH$_2$N(CH$_3$)$_2$, —CH$_2$C(CH$_3$)=CH$_2$, —CH$_2$CH=CHCH$_3$ (cis and trans), —CH$_2$OH, —CH(OH)CH$_3$, —CH(O-t-butyl)CH$_3$, —CH$_2$OCH$_3$, —(CH$_2$)$_4$NH-Boc, —(CH$_2$)$_4$NH$_2$, —CH$_2$)$_4$N(CH$_3$)$_2$, —CH$_2$-pyridyl (e.g., 2-pyridyl, 3-pyridyl and 4-pyridyl), pyridyl (2-pyridyl, 3-pyridyl and 4-pyridyl), —CH$_2$-naphthyl (e.g., 1-naphthyl and 2-naphthyl), —CH$_2$—(N-morpholino), p-(N-morpholino-CH$_2$CH$_2$O)-benzyl, benzo[b]thiophen-2-yl, benzo[b]thiophen-3-yl, 5-chlorobenzo[b]thiophen-2-yl, 4,5,6,7-tetrahydrobenzo[b]thiophen-2-yl, benzo[b]thiophen-3-yl, tetrazol-5-yl, 5-chlorobenzo[b]thiophen-3-yl, benzo[b]thiophen-5-yl, 6-methoxynaphth-2-yl, —CH$_2$—N-phthalimidyl, 2-methylthiazol-4-yl, and thieno[2,3-b]thiophen-2-yl, 5-bromothien-2-yl, 4-bromothien-2-yl, 5-chlorothien-2-yl, 3-phenoxyphenyl, 2-phenoxyphenyl, 4-ethylphenyl, 2-benzylphenyl, (4-ethylphenyl)phenyl, 4-tert-butylphenyl, 4-n-butylphenyl, o-(4-chlorophenoxy)phenyl, furan-2-yl, 4-phenylacetylenylphenyl and the like.

Preferably, $R^5$ is hydrogen. However, in another embodiment, $R^4$ and $R^5$ are fused to form a cycloalkyl group including, for example, cyclopropyl, cyclobutyl, and the like.

One preferred X substituent is —C(O)Y. Preferably Y is hydroxy, alkoxy or substituted alkoxy such as methoxy, ethoxy, n-propoxy, iso-propoxy, n-butoxy, iso-butoxy, tert-butoxy, neo-pentoxy, benzyloxy, 2-phenylethoxy, 3-phenyl-n-propoxy, 3-iodo-n-propoxy, 4-bromo-n-butoxy, —ONHC(O)OC(CH$_3$)$_3$, —ONHC(CH$_3$)$_3$ and the like. Another preferred Y group is —NR'R" where R' and R" are as defined above. Such preferred Y groups include, by way of example, amino (—NH$_2$), —NH(iso-butyl), —NH(sec-butyl), N-methylamino, N,N-dimethylamino, N-benzylamino, N-morpholino, azetidino, N-thiomorpholino, N-piperidinyl, N-hexamethyleneimino, N-heptamethylene-imino, N-pyrrolidinyl, —NH-methallyl, —NHCH$_2$—(faran-2-yl), —NHCH$_2$-cyclopropyl, —NH(tert-butyl), —NH(p-methylphenyl), —NHOCH$_3$, —NHCH$_2$(p-fluorophenyl), —NHCH$_2$CH$_2$OCH$_3$, —NH-cyclopentyl, —NH-cyclohexyl, —NHCH$_2$CH$_2$N(CH$_3$)$_2$, —NHCH$_2$C(CH$_3$)$_3$, —NHCH$_2$—(pyrid-2-yl), —NHCH$_2$-(pyrid-3-yl), —NHCH$_2$-(pyrid-4-yl), N-thiazolindinyl, —N(CH$_2$CH$_2$CH$_3$)$_2$, —N[CH$_2$CH(CH$_3$)$_2$]$_2$, —NHOH, —NH(p-NO$_2$-$\phi$), —NHCH$_2$(p-NO$_2$-$\phi$), —NHCH$_2$(m-NO$_2$-$\phi$), —N(CH$_3$)OCH$_3$, —N(CH$_3$)CH$_2$-$\phi$, —NHCH$_2$—(3,5-difluorophenyl), —NHCH$_2$CH$_2$F, —NHCH$_2$(p-CH$_3$O—$\phi$), —NHCH$_2$(m—CH$_3$O—$\phi$), —NHCH$_2$p-CF$_3$—$\phi$), —N(CH$_3$)CH$_2$CH$_2$OCH$_3$, —NHCH$_2$CH$_2\phi$, —NHCH(CH$_3$)$\phi$, —NHCH$_2$—(p-F-$\phi$), —N(CH$_3$)CH$_2$CH$_2$N(CH$_3$)$_2$—NHCH$_2$—(tetrahydrofuran-2-yl), —NHCH$_2$(p-trifluoromethylphenyl), —NHCH$_2$C(CH$_3$)=CH$_2$, —NH-[(p-benzyl)pyrid-4-yl], —NH-[(2,6-dimethyl)pyrid-4-yl], —NH—(2-methylcyclohexyl), —NH—(4-methylcyclohexyl), —NH-[N-ethoxycarbonyl]-piperidin-4-yl, —NHOC(CH$_3$)$_3$, —NHCH$_2$CH$_2$CH$_2$—$\phi$, —C(O)NH(CH$_2$)$_3$O-(p-CH$_3$)$\phi$, —C(O)NH(CH$_2$)$_6$NH$_2$, —NH—(tetrahydrofuran-2-yl), —N(CH$_3$)$\phi$, —NH(CH$_2$)$_4$NHC(O)-(2-hydroxy-4-azido)-phenyl, —NH(CH$_2$)$_6$—(biotinamidyl), and the like.

Another preferred Y group is an alkyl group such as methyl, ethyl, iso-propyl, n-propyl, iso-butyl, n-butyl, sec-butyl, tert-butyl, —CH$_2$CH$_2$CH(CH$_3$)$_2$, —CH$_2$-pyridy-2-yl, —CH$_2$-pyridy-3-yl, —CH$_2$-pyridy-4-yl, —CH$_2$-fur-2-yl, and the like; a substituted alkyl group such as benzyl; a cycloalkyl group such as cyclopentyl; and an aryl group such as phenyl.

Still another preferred Y group is —NHSO$_2$—R where R is selected from alkyl, substituted alkyl, alkenyl, substituted alkenyl, cycloalkyl, aryl, heteroaryl and heterocyclic. Such groups are exemplified by NH—SO$_2$—CH$_3$.

Preferred Y' groups include a substituted alkyl group such as —CH$_2$OH, —CH(OH)CH$_2$CH$_2$CH(CH$_3$)$_2$, —CH(OH)$\phi$, —CH(OH)CH$_2$C(O)OCH$_3$, —C(OH)(CH$_3$)$_2$, —CH$_2$OCH$_3$, —CH$_2$OC(O)OCH$_3$, —CH$_2$OC(O)C(CH$_3$)$_3$, and the like.

Preferred compounds for use in the methods of this invention include those set forth in the tables below:

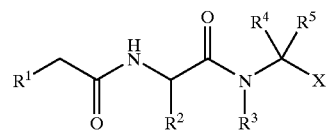

| R$^1$ | R$^2$ | R$^3$ | R$^4$ | R$^5$ | X |
|---|---|---|---|---|---|
| t-butyl | —CH$_3$ | H | $\phi$ | H | —C(O)NH$_2$ |
| thien-2-yl | —CH$_3$ | H | $\phi$ | H | —C(O)NH$_2$ |
| n-butyl | —CH$_3$ | H | $\phi$ | H | —C(O)NH$_2$ |
| 3,5-di-F-$\phi$- | —CH$_3$ | H | —CH$_2$CH$_2$CH$_3$ | H | —C(O)OCH$_3$ |
| 3,5-di-F-$\phi$- | —CH$_3$ | H | —CH$_2$-imidazol-4-yl | H | —C(O)OCH$_3$ |

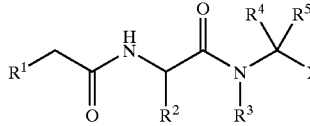

| R¹ | R² | R³ | R⁴ | R⁵ | X |
|---|---|---|---|---|---|
| 3,5-di-F-φ- | —CH₃ | H | —CH₂CH₂CH₂CH₃ | H | —C(O)NHCH₂-φ |
| 3,5-di-F-φ- | —CH₃ | H | —(CH₂)₃CH₃ | H | —C(O)NHCH₂CH₂N(CH₃)₂ |
| 3,5-di-F-φ- | —CH₃ | H | —(CH₂)₃CH₃ | H | —C(O)NHCH₂CH₂OCH₃ |
| 3,5-di-F-φ- | —CH₃ | H | —CH₂-φ | H | —C(O)NHCH₂CH₂N(CH₃)₂ |
| 3,5-di-F-φ- | —CH₃ | H | —CH₂-φ | H | —C(O)NHCH₂—(pyrid-4-yl) |
| 3,5-di-F-φ- | —CH₃ | H | —CH₂-φ | H | —C(O)NHCH₂—(pyrid-3-yl) |
| 3,5-di-F-φ- | —CH₃ | H | —(CH₂)₃CH₃ | H | —C(O)NHCH₂-pyrid-4-yl |
| 3,5-di-F-φ- | —CH₃ | H | —CH₂CH₂CH₂CH₃ | H | —C(O)OC(CH₃)₃ |
| 3,5-di-F-φ- | —CH₃ | H | p-(CH₃)₂NCH₂CH₂O-benzyl- | H | —C(O)OCH₃ |
| 3,5-di-F-φ- | —CH₃ | H | p-(CH₃)₃COC(O)CH₂O-benzyl- | H | —C(O)OCH₃ |
| 3,5-di-F-φ- | —CH₃ | H | p-hydroxybenzyl- | H | —C(O)OCH₃ |
| 3,5-di-F-φ- | —CH₃ | H | p-HOOCCH₂O-benzyl | H | —C(O)OCH₃ |
| 3,5-di-F-φ- | —CH₃ | H | p-(N-morpholino-CH₂CH₂O-benzyl- | H | —C(O)OCH₃ |
| 3,5-di-F-φ- | —CH₃ | H | —(CH₂)₄—N(CH₃)₂ | H | —C(O)OCH₃ |
| 3,5-di-F-φ- | —CH₃ | H | —CH₂—(pyrid-2-yl) | H | —C(O)OCH₃ |
| 3,5-di-F-φ- | —CH₃ | H | —CH₂—(pyrid-3-yl) | H | —C(O)OCH₃ |
| 3,5-di-F-φ- | —CH₃ | H | —CH₂—(pyrid-4-yl) | H | —C(O)OCH₃ |
| 3,5-di-F-φ- | —CH₃ | H | —CH₂OCH₃ | H | —C(O)OCH₃ |
| 3,5-di-F-φ- | —CH₃ | H | —CH₂—(N-morpholino) | H | —C(O)OCH₃ |
| 3,5-di-F-φ- | —CH₃ | H | p-(N-morpholino-CH₂CH₂—O)-benzyl- | H | —C(O)NHCH₂CH₂OCH₃ |
| 3,5-di-F-φ- | —CH₃ | H | —CH₂OCH₃ | H | —C(O)NHCH₂CH₂OCH₃ |
| 3,5-di-F-φ- | —CH₃ | H | H | H | —C(O)OCH₃ |
| 3,5-di-F-φ- | —CH₃ | H | —CH₂-pyrid-4-yl | H | —C(O)NHCH₂CH₂OCH₃ |
| 3,5-di-F-φ- | —CH₃ | H | —CH₂-pyrid-2-yl | H | —C(O)NHCH₂CH₂OCH₃ |
| 3,5-di-F-φ- | —CH₃ | H | —CH₂-thiazol-4-yl | H | —C(O)OCH₃ |
| 3,5-di-F-φ- | —CH₃ | H | —CH₂-φ | H | —C(O)NHCH₂—(m-CH₃O-φ) |
| 3,5-di-F-φ- | —CH₃ | H | —CH₂-1-naphthyl | H | —C(O)OCH₃ |
| 3,5-di-F-φ- | —CH₃ | H | —CH₂-2-naphthyl | H | —C(O)OCH₃ |
| 3,5-di-F-φ- | —CH₃ | H | —CH₂-thien-2-yl | H | —C(O)OCH₃ |
| 3,5-di-F-φ- | —CH₃ | H | —CH₂-φ | H | —C(O)OCH₂-φ |
| 3,5-di-F-φ- | —CH₃ | H | —CH₂-φ | H | —C(O)OCH₂CH₂CH₂Br |
| 3,5-di-F-φ- | —CH₃ | H | —CH₂-φ | H | —C(O)OCH₂CH₂CH₂I |
| 3,5-di-F-φ- | —CH₃ | H | —CH₂CH(CH₃)₂ | H | —C(O)OC(CH₃)₃ |
| 3,5-di-F-φ- | —CH₃ | H | pyrid-2-yl | H | —C(O)NH₂ |
| 3,5-di-F-φ- | —CH₃ | H | pyrid-3-yl | H | —C(O)NH₂ |
| 3,5-di-F-φ- | —CH₃ | H | —(CH₂)₄—NHC(O)OC(CH₃)₃ | H | —C(O)OCH₃ |
| 3,5-di-F-φ- | —CH₃ | H | —CH₂CH₂-φ | H | —C(O)OCH₃ |
| 3,5-di-F-φ- | —CH₃ | H | H | H | —C(O)OCH₂CH₂φ |
| 3,5-di-F-φ- | —CH₃ | H | H | H | —C(O)OCH₂CH₂CH₂φ |
| 3,5-di-F-φ- | —CH₃ | H | pyrid-4-yl | H | —C(O)NH₂ |
| 3,5-di-F-φ- | —CH₃ | H | pyrid-3-yl | H | —C(O)OCH₂CH₃ |
| 3,5-di-F-φ- | —CH₃ | H | —CH₂CH₂CH₂CH₃ | H | —C(O)NHCH₃ |
| 3,5-di-F-φ- | —CH₃ | H | —CH₂CH₂CH₂CH₃ | H | —C(O)N(CH₃)₂ |
| 3,5-di-F-φ- | —CH₃ | H | —CH₂CH₂CH₂CH₃ | H | —C(O)NH₂ |
| 3,5-di-F-φ- | —CH₃ | H | m-CH₃O-φ- | H | —C(O)OCH₃ |
| 3,5-di-F-φ- | —CH₃ | H | p-CH₃O-φ- | H | —C(O)OCH₃ |
| 3,5-di-F-φ- | —CH₃ | H | pyrid-2-yl | H | —C(O)OCH₂CH₃ |
| 3,5-di-F-φ- | —CH₃ | H | pyrid-4-yl | H | —C(O)OCH₂CH₃ |
| cyclohex-1-enyl | —CH₃ | H | —CH₂-φ | H | —C(O)OCH₃ |
| 3,5-di-F-φ- | —CH₃ | H | R⁴/R⁵ = -cyclopropyl | | —C(O)OCH₃ |
| 3,5-di-F-φ- | —CH₃ | H | —CH₃ | H | —C(O)N(CH₃)CH₂—CH₂N(CH₃)₂ |
| 3,5-di-F-φ- | —CH₃ | H | H | H | —C(O)OCH₂-φ |
| 3-NO₂-φ- | —CH₃ | H | —CH(OH)CH₃ | H | —C(O)NHOH |
| 3,5-di-F-φ- | —CH₃ | H | —CH₃ | H | —C(O)OCH₂CH₃ |
| 3,5-di-F-φ- | —CH₃ | H | —CH₃ | H | —C(O)NH₂ |
| (CH₃)₂CH— | -φ | H | —CH₃ | H | —C(O)N(CH₃)—OCH₃ |
| 3,5-di-F-φ- | —CH₃ | H | —CH₃ | H | —C(O)NHCH₂CH(CH₃)₂ |
| 3,5-di-F-φ- | —CH₃ | H | —CH₃ | H | —C(O)N(CH₂CH₂CH₃)₂ |
| 3,5-di-F-φ- | —CH₃ | H | —CH(CH₃)₂ | H | —C(O)NH₂ |
| 3,5-di-F-φ- | —CH₃ | H | —CH₃ | H | —C(O)NH—(p-NO₂-φ) |
| 3,5-di-F-φ- | —CH₃ | H | —CH₂-φ | H | —C(O)OCH₃ |
| 3,5-di-F-φ- | —CH₃ | H | —CH₂-φ | H | —C(O)NH₂ |
| 3,5-di-F-φ- | —CH₃ | H | —CH₂-φ | H | —C(O)NHCH₂CH₂OCH₃ |
| 3,5-di-F-φ- | —CH₃ | H | —CH₃ | H | —C(O)NHCH₂—(p-NO₂-φ) |

-continued

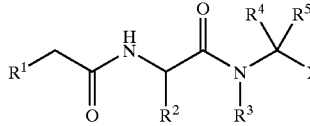

| R¹ | R² | R³ | R⁴ | R⁵ | X |
|---|---|---|---|---|---|
| 3,5-di-F-φ- | —CH₃ | H | —CH₂-φ | H | —C(O)NH—(p-NO₂-φ) |
| 3,5-di-F-φ- | —CH₃ | H | —CH₃ | H | —C(O)N(CH₃)CH₂-φ |
| 3,5-di-F-φ- | —CH₃ | H | —CH₃ | H | —C(O)NHCH₂—(3,5-di-F-φ) |
| 3,5-di-F-φ- | —CH₃ | H | —CH₃ | H | —C(O)NHCH₂—(m-NO₂-φ) |
| 3,5-di-F-φ- | —CH₃ | H | —CH₃ | H | —C(O)NHCH₂-φ |
| 3,5-di-F-φ- | —CH₃ | H | —CH₂-φ | H | —C(O)NHCH₂-(p-NO₂-φ) |
| 3,5-di-F-φ- | —CH₃ | H | —CH₂-indol-3-yl | H | —C(O)OCH₃ |
| 3,5-di-F-φ- | —CH₃ | H | —CH₃ | H | —C(O)NHCH₂—(p-OCH₃-φ) |
| 3,5-di-F-φ- | —CH₃ | H | -φ | H | —C(O)OCH₃ |
| 3,5-di-F-φ- | —CH₃ | H | —CH₃ | H | —C(O)NHCH₂CH₂-φ |
| 3,5-di-F-φ- | —CH₃ | H | —CH₂-indol-3-yl | H | —C(O)NH₂ |
| 3,5-di-F-φ- | —CH₃ | H | —CH₂-cyclohexyl | H | —C(O)OCH₃ |
| 3,5-di-F-φ- | —CH₃ | H | p-NO₂-benzyl- | H | —C(O)NHCH₂CH₂OCH₃ |
| 3,5-di-F-φ- | —CH₃ | H | —CH₃ | H | —C(O)NHCH(CH₃)φ |
| 3,5-di-F-φ- | —CH₃ | H | —CH₃ | H | —C(O)NHCH(CH₃)φ |
| 3,5-di-F-φ- | —CH₃ | H | —CH₃ | H | —C(O)NHCH₂—(p-F-φ) |
| 3,5-di-F-φ- | —CH₃ | H | —CH₃ | H | —C(O)NHCH₂—(pyrid-4-yl) |
| 3,5-di-F-φ- | —CH₃ | H | —CH₃ | H | —C(O)NHCH₂—(p-F₃C-φ) |
| 3,5-di-F-φ- | —CH₃ | H | -φ | —CH₃ | —C(O)OCH₂CH₃ |
| 3,5-di-F-φ- | —CH₃ | H | —CH₂-φ | H | —C(O)OC(CH₃)₃ |
| 3,5-di-F-φ- | —CH₃ | H | —CH₃ | —CH₃ | —C(O)OCH₃ |
| 3,5-di-F-φ- | —CH₃ | H | cyclohexyl | H | —C(O)OCH₂CH₃ |
| 3,5-di-F-φ- | —CH₃ | H | -φ | H | —C(O)NHCH₂CH₂OCH₃ |
| 3,5-di-F-φ- | —CH₃ | H | -φ | H | —C(O)NHCH₂CH₂N(CH₃)₂ |
| 3,5-di-F-φ- | —CH₃ | H | -φ | H | —C(O)NHCH₂—(pyrid-2-yl) |
| 3,5-di-F-φ- | —CH₃ | H | p-F-φ | H | —C(O)OCH₂CH₃ |
| 3,5-di-F-φ- | —CH₃ | H | o-F-φ | H | —C(O)OCH₂CH₃ |
| 3,5-di-F-φ- | -φ | H | —CH₃ | H | —C(O)OCH₂CH₃ |
| 3,5-di-F-φ- | —CH₃ | H | —CH₂—N-phthalimidyl | H | —C(O)OCH₂CH₃ |
| 3,5-di-F-φ- | —CH₃ | H | -φ | H | —C(O)OCH₂C(CH₃)₃ |
| 3,5-di-F-φ- | —CH₃ | H | -φ | H | —C(O)NHC(CH₃)₃ |
| 3,5-di-F-φ- | —CH₃ | H | -φ | H | —C(O)OC(CH₃)₃ |
| 3,5-di-F-φ- | —CH₃ | H | -φ | H | —C(O)OC(CH₃)₃ |
| 3,5-di-F-φ- | —CH₃ | H | -φ | H | —C(O)NH₂ |
| 3-NO₂-φ- | —CH₃ | H | —CH(CH₃)₂ | H | —C(O)—N-morpholino |
| 3-NO₂-φ- | —CH₃ | H | —CHCH₃<br>\|<br>O-t-butyl | H | —C(O)—N-morpholino |
| 3-NO₂-φ- | —CH₃ | H | —CH(CH₃)CH₂CH₃ | H | —C(O)—N-morpholino |
| 3,5-di-F-φ- | —CH₃ | H | —CH₂CH(CH₃)₂ | H | —C(O)OCH₃ |
| 3,5-di-F-φ- | —CH₃ | H | —CH₃ | H | —C(O)NHCH₂CH₂OCH₃ |
| 3,5-di-F-φ- | —CH₃ | H | —CH₃ | H | —C(O)NHCH₂CH₂N(CH₃)₂ |
| 3,5-di-F-φ- | —CH₃ | H | —CH₃ | H | —C(O)NH-cyclohexyl |
| 3,5-di-F-φ- | —CH₃ | H | —CH₃ | H | —C(O)NHCH₂C(CH₃)₃ |
| 3,5-di-F-φ- | —CH₃ | H | —CH₃ | H | —C(O)NHCH₂—(tetra-hydrofuran-2-yl) |
| 3,5-di-F-φ- | —CH₃ | H | —CH₃ | H | C(O)NHCH₂—(pyrid-2-yl) |
| 3,5-di-F-φ- | —CH₃ | H | —CH₃ | H | —C(O)—(N-thiazolidinyl) |
| 3,5-di-F-φ- | —CH₃ | H | —CH₂CH₃ | H | —C(O)OCH₃ |
| 3,5-di-F-φ- | —CH₃ | H | —CH₂CH₂CH₃ | H | —C(O)OCH₃ |
| 3,5-di-F-φ- | —CH₃ | H | —CH₃ | H | —C(O)NHCH(CH₃)CH₂CH₃ |
| 3,5-di-F-φ- | —CH₃ | H | —CH₃ | H | —C(O)—(N-pyrrolidinyl) |
| 3,5-di-F-φ- | —CH₃ | H | —CH₃ | H | —C(O)NHCH(CH₃)CH₂CH₃ |
| 3,5-di-F-φ- | —CH₃ | H | —CH(CH₃)₂ | H | —C(O)OCH₃ |
| 3,5-di-F-φ- | —CH₃ | H | —CH₃ | H | —C(O)NHCH₂CH₂—F |
| 3,5-di-F-φ- | —CH₃ | H | —CH₃ | H | —C(O)CH₂CH₂CH(CH₃)₂ |
| 3,5-di-F-φ- | —CH₃ | H | —CH₂CH₃ | H | —C(O)NHCH₂—(p-NO₂-φ) |
| 3,5-di-F-φ- | —CH₃ | H | —CH₂CH₂CH₃ | H | —C(O)NHCH₂—(p-NO₂-φ) |
| 3,5-di-F-φ- | —CH₃ | H | m-F-φ- | H | —C(O)OCH₃ |
| 3,5-di-F-φ- | —CH₃ | H | thien-2-yl | H | —C(O)NH₂ |
| 3,5-di-F-φ- | —CH₃ | H | thien-2-yl | H | —C(O)NH₂ |
| 3,5-di-F-φ- | —CH₃ | H | 5-chlorobenzo[b]thiophen-2-yl | H | —C(O)OCH₃ |
| 3,5-di-F-φ- | —CH₃ | H | benzo[b]thiophen-6-yl | H | —C(O)OCH₂CH₃ |
| 3,5-di-F-φ- | —CH₃ | H | benzo[b]thiophen-2-yl | H | —C(O)OCH₂CH₃ |
| 3,5-di-F-φ- | —CH₃ | H | benzo[b]thiophen-3-yl | H | —C(O)OCH₃ |
| 3,5-di-F-φ- | —CH₃ | H | thien-2-yl | H | —C(O)OCH₃ |
| 3,5-di-F-φ- | —CH₃ | H | benzo[b]thiophen-5-yl | H | —C(O)OCH₂CH₃ |

-continued

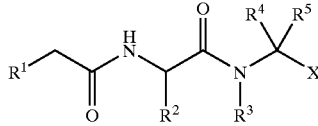

| R¹ | R² | R³ | R⁴ | R⁵ | X |
|---|---|---|---|---|---|
| 3,5-di-F-φ- | —CH₃ | H | thien-2-yl | H | —C(O)OCH₃ |
| 3,5-di-F-φ- | —CH₃ | H | thien-2-yl | H | —C(O)OC(CH₃)₃ |
| 3,5-di-F-φ- | —CH₃ | H | thien-2-yl | H | —C(O)OH |
| 3,5-di-F-φ- | —CH₃ | H | tetrazol-5-yl | H | —C(O)OCH₃ |
| 3,5-di-F-φ- | —CH₃ | H | 2-aminopyrid-6-yl | H | —C(O)OCH₃ |
| 3,5-di-F-φ- | —CH₃ | H | 6-methoxynaphth-2-yl | H | —C(O)OCH₃ |
| 3,5-di-F-φ- | —CH₃ | H | m-CF₃-φ- | H | —C(O)OCH₃ |
| 3,5-di-F-φ- | —CH₃ | H | 4,5,6,7'-tetrahydro-benzo[b]thiophen-2-yl | H | —C(O)OCH₃ |
| 3,5-di-F-φ- | —CH₃ | H | thieno[2,3-b]thiophen-2-yl | H | —C(O)OCH₃ |
| 3,5-di-F-φ- | —CH₃ | H | 2-methylthiazol-4-yl | H | —C(O)OCH₃ |
| 3,5-di-F-φ- | —CH₃ | H | —CH₂CH=CHCH₃ (trans) | H | —C(O)OCH₃ |
| 3,5-di-F-φ- | —CH₃ | H | (p-φ)-φ | H | —C(O)NHC(CH₃)₃ |
| 3,5-di-F-φ- | —CH₂CH₃ | H | -φ | H | —C(O)OC(CH₃)₃ |
| 3,5-di-F-φ- | —CH(CH₃)₂ | H | -φ | H | —C(O)OC(CH₃)₃ |
| 3,5-di-F-φ- | —CH₂CH₂SCH₃ | H | -φ | H | —C(O)OCH₃ |
| 3,5-di-F-φ- | —CH(CH₃)₂ | H | -φ | H | —C(O)OCH₃ |
| 3,5-di-F-φ- | —CH₂CH₃ | H | -φ | H | —C(O)OCH₃ |
| 3,5-di-F-φ- | —CH₂CH(CH₃)₂ | H | -φ | H | —C(O)OCH₃ |
| 3,5-di-F-φ- | —CH₂φ | H | -φ | H | —C(O)OCH₃ |
| 3,5-di-F-φ- | —H | H | -φ | H | —C(O)OCH₃ |
| 3,5-di-F-φ- | -φ | H | -φ | H | —C(O)OCH₃ |
| 3,5-di-F-φ- | —CH₃ | H | -φ | H | —C(O)NH-cyclohexyl |
| 3,5-di-F-φ- | —CH₃ | H | —(CH₂)₄NH₂ | H | —C(O)OCH₃ |
| 3,5-di-F-φ- | —CH₃ | H | —CH₂CH₂C(O)NH₂ | H | —C(O)NH₂ |
| 3,5-di-F-φ- | —CH₃ | H | H | H | —C(O)NHCH₂CH₂OCH₃ |
| 3,5-di-F-φ- | -cyclohexyl | H | -φ | H | —C(O)OCH₃ |
| 3,5-di-F-φ- | —CH₃ | H | —CH₂-φ | H | —C(O)NHCH₂-pyrid-2-yl |
| 3,5-di-F-φ- | -thien-2-yl | H | -φ | H | —C(O)OC(CH₃)₃ |
| 3,5-di-F-φ- | φ | H | -φ | H | —C(O)NH₂ |
| 3,5-di-F-φ- | —CH(CH₃)₂ | H | -φ | H | —C(O)NH₂ |
| 3,5-di-F-φ- | —(CH₂)₃CH₃ | H | -φ | H | —C(O)OCH₃ |
| 3,5-di-F-φ- | —(CH₂)₂CH₃ | H | -φ | H | —C(O)OCH₃ |
| 3,5-di-F-φ- | —C(CH₂)₃ | H | -φ | H | —C(O)OCH₃ |
| 3,5-di-F-φ- | —C(CH₃)CH₂CH₃ | H | -φ | H | —C(O)OCH₃ |
| 3,5-di-F-φ- | —CH₂-cyclohexyl | H | -φ | H | —C(O)OCH₃ |
| 3,5-di-F-φ- | -cyclopropyl | H | -φ | H | —C(O)OCH₃ |
| 3,5-di-F-φ- | -thien-3-yl | H | -φ | H | —C(O)OCH₃ |
| 3,5-di-F-φ- | -thien-2-yl | H | -φ | H | —C(O)OCH₃ |
| 3,5-di-F-φ- | p-F-φ | H | -φ | H | —C(O)OCH₃ |
| 3,5-di-F-φ- | p-OCH₃-φ | H | -φ | H | —C(O)OCH₃ |
| 3,5-di-F-φ- | -φ | H | -φ | H | —C(O)OC(CH₃)₃ |
| 3,5-di-F-φ- | —CH₃ | H | 5-bromothien-2-yl | H | —C(O)NHC(CH₃)₃ |
| 3,5-di-F-φ- | —CH₃ | H | 4-bromothien-2-yl | H | —C(O)NHC(CH₃)₃ |
| 3,5-di-F-φ- | —CH₃ | H | thien-2-yl | H | —C(O)NHC(CH₃)₃ |
| 3,5-di-F-φ- | —CH₃ | H | thien-3-yl | H | —C(O)NHC(CH₃)₃ |
| 3,5-di-F-φ- | —CH₃ | H | -φ | H | —C(O)NHC(CH₃)₃ |
| 3,5-di-F-φ- | —CH₃ | H | 5-chlorothien-2-yl | H | —C(O)NHC(CH₃)₃ |
| 3,5-di-F-φ- | —CH₃ | H | (p-φ)-φ- | H | —C(O)NH-cyclohexyl |
| 3,5-di-F-φ- | —CH₃ | H | (m-phenoxy)-φ- | H | —C(O)NHC(CH₃)₃ |
| 3,5-di-F-φ- | —CH₃ | H | -φ | H | —C(O)NH-cyclohexyl |
| 3,5-di-F-φ- | —CH₃ | H | (m-φ)-φ- | H | —C(O)NHC(CH₃)₃ |
| 3,5-di-F-φ- | —CH₃ | H | (p-CH₃CH₂)-φ- | H | —C(O)NHC(CH₃)₃ |
| 3,5-di-F-φ- | —CH₃ | H | (o-φ)-φ- | H | —C(O)NHC(CH₃)₃ |
| 3,5-di-F-φ- | —CH₃ | H | (o-benzyl)-φ | H | —C(O)NHC(CH₃)₃ |
| 3,5-di-F-φ- | —CH₃ | H | (p-Br)-φ- | H | —C(O)NHC(CH₃)₃ |
| 3,5-di-F-φ- | —CH₃ | H | (p-cyclohexyl)-φ- | H | —C(O)NHC(CH₃)₃ |
| 3,5-di-F-φ- | —CH₃ | H | p-(p-CH₃CH₂φ)-φ- | H | —C(O)NHC(CH₃)₃ |
| 3,5-di-F-φ- | —CH₃ | H | (p-tert-butyl)-φ- | H | —C(O)NHC(CH₃)₃ |
| 3,5-di-F-φ- | —CH₃ | H | m-(4-Cl-phenoxy)-φ- | H | —C(O)NHC(CH₃)₃ |
| 3,5-di-F-φ- | —CH₃ | H | (p-φ)-φ- | H | —C(O)NH-cyclohexyl |
| 3,5-di-F-φ- | —CH₃ | H | -φ | H | —C(O)OC(CH₃)₃ |
| 3,5-di-F-φ- | —CH₃ | H | —CH₃ | H | —C(O)-φ |
| 3,5-di-F-φ- | —CH₃ | H | pyrid-3-yl | H | —C(O)OC(CH₃)₃ |
| 3,5-di-F-φ- | —CH₃ | H | -φ | H | —C(O)-morpholino |
| 3,5-di-F-φ- | —CH₃ | H | (o-methoxy)-φ | H | —C(O)OCH₃ |
| 3,5-di-F-φ- | —CH₃ | H | -φ | H | —C(O)ONHC(O)OC(CH₃)₃ |
| 3,5-di-F-φ- | —CH₃ | H | -φ | H | —C(O)NHCH₂C(CH₃)₃ |
| 3,5-di-F-φ- | —CH₃ | H | -φ | H | —C(O)NHCH(CH₃)₂ |

-continued

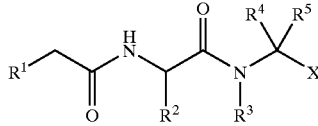

| R¹ | R² | R³ | R⁴ | R⁵ | X |
|---|---|---|---|---|---|
| 3,5-di-F-φ- | —CH₃ | H | -φ | H | —C(O)NHCH₂-furan-2-yl |
| 3,5-di-F-φ- | —CH₃ | H | -φ | H | —C(O)NHOCH₃ |
| 3,5-di-F-φ- | —CH₃ | H | -φ | H | —C(O)-azetidine |
| 3,5-di-F-φ- | —CH₃ | H | -φ | H | —C(O)-cyclobutylamide |
| 3,5-di-F-φ- | —CH₃ | H | -φ | H | —C(O)NHCH₂CH(CH₃)₂ |
| 3,5-di-F-φ- | —CH₃ | H | -φ | H | —C(O)NHCH₂-cyclopropyl |
| 3,5-di-F-φ- | —CH₃ | H | -φ | H | —C(O)N(CH₃)OCH₃ |
| 3,5-di-F-φ- | —CH₃ | H | -φ | H | —C(O)NHCH₂C(CH₃)=CH₂ |
| 3,5-di-F-φ- | —CH₃ | H | -φ | H | —C(O)NHCH₂-pyrid-3-yl |
| 3,5-di-F-φ- | —CH₃ | H | -φ | H | —C(O)NHCH₂-pyrid-4-yl |
| 3,5-di-F-φ- | —CH₃ | H | -φ | H | —C(O)NHCH₂-fur-2-yl |
| 3,5-di-F-φ- | —CH₃ | H | -φ | H | C(O)NH-cyclopentyl |
| 3,5-di-F-φ- | —CH₃ | H | -φ | H | —C(O)NH—[(p-benzyl)-pyrid-4-yl] |
| 3,5-di-F-φ- | —CH₃ | H | -φ | H | —C(O)N(CH₃)₂ |
| 3,5-di-F-φ- | —CH₃ | H | -φ | H | —C(O)NH—[2,6-dimethylpyrid-4-yl] |
| 3,5-di-F-φ- | —CH₃ | H | -φ | H | —C(O)NH—(2-methylcyclohexyl) |
| 3,5-di-F-φ- | —CH₃ | H | -φ | H | —C(O)NH—(4-methylcyclohexyl) |
| 3,5-di-F-φ- | —CH₃ | H | -φ | H | —C(O)NH—[N-ethoxycarbonyl]-piperidin-4-yl |
| 3,5-di-F-φ- | —CH₃ | H | -φ | H | —C(O)NHCH₃ |
| 3,5-di-F-φ- | —CH₃ | H | -φ | H | —C(O)NHOC(CH₃)₃ |
| 3,5-di-F-φ- | —CH₃ | H | -φ | H | —C(O)ONHC(CH₃)₃ |
| 3,5-di-F-φ- | —CH₃ | H | -φ | H | —C(O)NHNH₂ |
| 3,5-di-F-φ- | —CH₃ | H | -φ | H | —C(O)NHN=C(CH₃)OCH₂CH₃ |
| 3,5-di-F-φ- | —CH₃ | H | -φ | H | —C(O)NH(CH₂)₄-φ |
| 3,5-di-F-φ- | —CH₃ | H | -φ | H | —C(O)NH(CH₂)₃O—(p-I)φ |
| 3,5-di-F-φ- | —CH₃ | H | -φ | H | —C(O)NH(CH₂)₆NH₂ |
| 3,5-di-F-φ- | 3,5-di-F-φ- | H | 3,5-di-F-φ- | H | —C(O)OCH₃ |
| 3,5-di-F-φ- | —CH₃ | H | —CH₂CH₂CH₂CH₃ | H | —C(O)OH |
| 3,5-di-F-φ- | thien-2-yl | H | -φ | H | —C(O)OC(CH₃)₃ |
| 3,5-di-F-φ- | —CH₃ | H | p-F-φ | H | —C(O)OCH(CH₃)₂ |
| 3,5-di-F-φ- | —CH₃ | H | -φ | H | —C(O)OCH₂CH(CH₃)₂ |
| 3,5-di-F-φ- | —CH₃ | H | -φ | H | —C(O)OCH₃ |
| 3,5-di-F-φ- | —CH₃ | H | 5-chlorobenzo[b]thiophen-3-yl | H | —C(O)OCH₃ |
| 3,5-di-F-φ- | —CH₃ | H | —CH₂-thiazol-4-yl | H | —C(O)OC(CH₃)₃ |
| 3,5-di-F-φ- | —CH₃ | H | -φ | H | —C(O)NHC(CH₃)₃ |
| 3,5-di-F-φ- | —CH₃ | H | thien-2-yl | H | —C(O)NH₂ |
| 3-F-φ- | —CH₃ | H | -φ | H | —C(O)NH₂ |
| 4-F-φ- | —CH₃ | H | -φ | H | —C(O)NH₂ |
| 3,5-di-F-φ- | —CH₃ | H | -φ | H | —COOH |
| 3,5-di-F-φ- | —CH₃ | H | furan-2-yl | H | —C(O)NH₂ |
| 3,4-di-F-φ- | —CH₃ | H | -φ | H | —C(O)NH₂ |
| 3,5-di-F-φ- | —CH₃ | H | —CH₂-φ | H | —C(O)NH—SO₂—CH₃ |
| 3,5-di-F-φ- | —CH₃ | H | H | H | —C(O)N(CH₃)φ |
| 3,5-di-F-φ- | —CH₃ | H | —CH₃ | H | —C(O)N(CH₃)φ |
| 3,5-di-F-φ- | —CH₂CH₂SCH₃ | H | -φ | H | —C(O)NH₂ |
| 3,5-di-F-φ- | —CH₃ | H | H | H | —C(O)N(CH₃)CH₂φ |
| 3,5-di-F-φ- | —CH₃ | H | -φ | H | —C(O)NHCH₂(p-F-φ) |
| 3,5-di-F-φ- | —CH₃ | H | 4-fluorophenyl | H | —C(O)OCH₂C(CH₃)₃ |
| 2,3,4,5,6-penta-F-φ- | —CH₃ | H | -pyrid-3-yl | H | —C(O)OCH₃ |
| 3,5-di-F-φ- | —CH₂OCH₂-φ | H | -φ | H | —C(O)OCH₃ |
| 3,5-di-F-φ- | —CH(CH₃)OCH₂-φ | H | -φ | H | —C(O)OCH₃ |
| 3,5-di-F-φ- | —CH(OH)CH₃ | H | -φ | H | —C(O)OCH₃ |
| 3,5-di-F-φ- | —CH₂OH | H | -φ | H | —C(O)OCH₃ |
| 3,5-di-F-φ- | —CH₃ | H | -φ | H | —C(O)NH—(4-methylphenyl) |
| 3,5-di-F-φ- | —CH₃ | H | -φ | H | —C(O)NH-tetrahydrofurfuryl |
| 3,5-di-F-φ- | —CH₃ | H | 4-fluoro-φ | H | —C(O)NH₂ |
| 3,5-di-F-φ- | —CH₂CH₂SCH₃ | H | -φ | H | —C(O)NH₂ |
| 3,5-di-F-φ- | —CH₂CH₃ | H | -φ | H | —C(O)NH₂ |
| 3,5-di-F-φ- | -φ | H | -φ | H | —C(O)NH₂ |

-continued

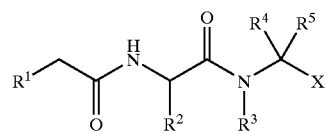

| R¹ | R² | R³ | R⁴ | R⁵ | X |
|---|---|---|---|---|---|
| 3,5-di-F-φ- | —CH(CH₃)₂ | H | -φ | H | —C(O)NH₂ |
| 3,5-di-F-φ- | —CH₃ | H | -φ | H | —C(O)NHCH(CH₃)φ |
| 3,5-di-F-φ- | —CH₃ | H | -φ | H | —C(O)CH(CH₃)₂ |
| 3,5-di-F-φ- | —CH₃ | H | -φ | H | —C(O)CH₃ |
| 3,5-di-F-φ- | —CH₃ | H | -φ | H | —C(O)CH₂CH₂CH₃ |
| 3,5-di-F-φ- | —CH₃ | H | -φ | H | —C(O)-φ |
| 3,5-di-F-φ- | —CH₃ | H | -φ | H | —C(O)CH₂CH₃ |
| 3,5-di-F-φ- | —CH₃ | H | -φ | H | —C(O)CH₂CH(CH₃)₂ |
| 3,5-di-F-φ- | —CH₃ | H | -φ | H | —C(O)OCH₃ |
| 3,5-di-F-φ- | —CH₃ | H | -φ | H | —C(O)NH(CH₂)₄NHC(O)—(2-hydroxy-φ-azido)-phenyl |
| 3,5-di-F-φ- | —CH₃ | H | 4-fluoro-φ | H | —C(O)OC(CH₃)₃ |
| 3,5-di-F-φ- | —CH₃ | H | 4-φ-φ- | H | —C(O)OC(CH₃)₃ |
| 3,5-di-F-φ- | —CH₃ | H | 4-n-butylphenyl | H | —C(O)NHC(CH₃)₃ |
| 3,5-di-F-φ- | —CH₃ | H | 4-phenylacetylenylphenyl | H | —C(O)NHC(CH₃)₃ |
| 3,5-di-F-φ- | —CH₃ | H | -φ | H | —C(S)NH₂ |
| 3,5-di-F-φ- | —CH₃ | H | -φ | H | —C(O)CH₂-φ |
| 3,5-di-F-φ- | —CH₃ | H | -φ | H | —C(O)-cyclopentyl |
| 3,5-di-F-φ- | —CH₃ | H | -φ | H | —C(O)-n-butyl |
| 3,5-di-F-φ- | —CH₃ | H | -φ | H | —C(O)CH(CH₃)CH₂CH₃ |
| 3,5-di-F-φ- | —CH₃ | H | -φ | H | —C(S)NH(CH₂)₆—(biotinamidyl) |
| 3,5-di-F-φ- | —CH₂CH₂SCH₃ | H | —CH₂CH₂SCH₃ | H | —C(O)OH |
| t-BOC—NH—CH₂— | —CH₃ | H | -φ | H | —C(O)OCH₃ |
| 3,5-di-F-φ- | —CH₃ | H | 2-F-φ- | H | —C(O)NHC(CH₃)₃ |
| 3,5-di-F-φ- | —CH₃ | H | -φ | H | —C(O)OCH₃ |
| 3,5-di-F-φ- | thien-3-yl | H | -φ | H | —C(O)OH |
| 3,5-di-F-φ- | thien-3-yl | H | -φ | H | —C(O)OC(CH₃)₃ |
| H₂N—CH₂— | —CH₃ | H | -φ | H | —C(O)OC(CH₃)₃ |
| (CH₃)₃COC(O)NHCH₂ | —CH₃ | H | -φ | H | —C(O)OC(CH₃)₃ |
| 3,5-di-F-φ- | —CH₃ | H | -φ | H | —C(O)N(CH₃)cyclohexyl |

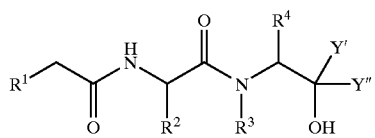

| R¹ | R² | R³ | R⁴ | Y' | Y'' |
|---|---|---|---|---|---|
| 3,5-di-F-φ- | —CH₃ | H | —CH₃ | —CH₂CH₂CH(CH₃)₂ | H |
| 3,5-di-F-φ- | —CH₃ | H | -φ | H | H |
| 3,5-di-F-φ- | —CH₃ | H | —CH₂φ | H | H |
| 3,5-di-F-φ- | —CH₃ | H | —CH₃ | -φ | H |
| 3,5-di-F-φ- | —CH₃ | H | —CH₃ | -φ | H |
| 3,5-di-F-φ- | —CH₃ | H | -φ | -φ | H |
| 3,5-di-F-φ- | —CH₃ | H | —(CH₂)₃CH₃ | H | H |
| 3,5-di-F-φ- | —CH₃ | H | —CH₂-(p-hydroxyphenyl) | H | H |
| 3,5-di-F-φ- | —CH₃ | H | —CH₂-2-pyridyl | H | H |
| 3,5-di-F-φ- | —CH₃ | H | —CH₂-4-pyridyl | H | H |
| 3,5-di-F-φ- | —CH₃ | H | —CH₂CH(CH₃)₂ | H | H |
| 3,5-di-F-φ- | —CH₃ | H | —CH(CH₃)₂ | H | H |
| 3,5-di-F-φ- | —CH₃ | H | —CH₃ | H | H |
| 3,5-di-F-φ- | —CH₃ | H | thien-2-yl | H | H |
| 3,5-di-F-φ- | —CH₃ | H | -φ | —CH₃ | —CH₃ |
| 3,5-di-F-φ- | -φ | H | -φ | H | H |

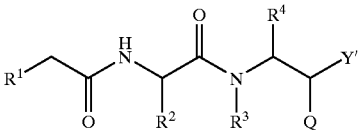

| R¹ | R² | R³ | R⁴ | Q | Y' |
|---|---|---|---|---|---|
| 3,5-di-F-φ- | —CH₃ | H | —CH₃ | —OCH₃ | H |
| 3,5-di-F-φ- | —CH₃ | H | -φ | —OCH₃ | H |
| 3,5-di-F-φ- | —CH₃ | H | —CH₂φ | —OCH₃ | H |
| 3,5-di-F-φ- | —CH₃ | H | —CH₂CH₂CH₂CH₃ | —OC(O)CH₃ | H |
| 3,5-di-F-φ- | —CH₃ | H | —CH₂CH₂CH₂CH₃ | —OC(O)C(CH₃)₃ | H |
| 3,5-di-F-φ- | —CH₃ | H | —CH₂CH₂CH₃ | -phthalimido | H |

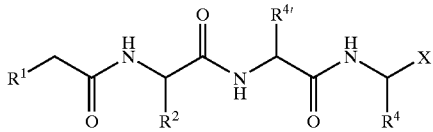

| R¹ | R² | R⁴' | R⁴ | X |
|---|---|---|---|---|
| (CH₃)₂CH | -φ | —CH₃ | —CH₃ | —C(O)NH(p-NO₂-φ) |
| 3,5-di-F-φ- | —CH₃ | —CH₂-φ | -φ | —C(O)OCH₃ |
| 3,5-di-F-φ- | —CH₃ | —CH₃ | -φ | —C(O)OCH₃ |
| 3,5-di-F-φ- | -φ | —CH₃ | -φ | —CH₂OH |
| 3,5-di-F-φ- | —CH₃ | -φ | H | —CH₂OH |

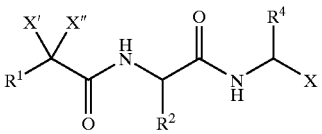

| R¹ | X' | X" | R² | R⁴ | X |
|---|---|---|---|---|---|
| 3,5-di-F-φ- | —F | H | —CH₃ | -φ | —C(O)OC(CH₃)₃ |
| 3,5-di-F-φ- | —OH | H | —CH₃ | -φ | —C(O)OC(CH₃)₃ |
| 3,5-di-F-φ- | —F | F | —CH₃ | -φ | —C(O)NHC(CH₃)₃ |
| 3,5-di-F-φ- | X'/X"=O | | —CH₃ | -φ | —C(O)OC(CH₃)₃ |
| 3,5-di-F-φ- | —OH | H | —CH₃ | -φ | —C(O)N(CH₃)cyclohexyl |
| 3,5-di-F-φ- | —OH | H | —CH₃ | -φ | —C(O)NHcyclohexyl |

DETAILED DESCRIPTION OF THE INVENTION

As above, this invention relates to methods for inhibiting β-amyloid peptide release and/or its synthesis, and, accordingly, have utility in treating Alzheimer's disease. However, prior to describing this invention in further detail, the following terms will first be defined.

Definitions

The term "β-amyloid peptide" refers to a 39–43 amino acid peptide having a molecular weight of about 4.2 kD, which peptide is substantially homologous to the form of the protein described by Glenner, et al.[1] including mutations and post-translational modifications of the normal β-amyloid peptide. In whatever form, the β-amyloid peptide is an approximate 39–43 amino acid fragment of a large membrane-spanning glycoprotein, referred to as the β-amyloid precursor protein (APP). Its 43-amino acid sequence is:

```
1
  Asp Ala Glu Phe Arg His Asp Ser Gly Tyr
11
  Glu Val His His Gln Lys Leu Val Phe Phe
21
  Ala Glu Asp Val Gly Ser Asn Lys Gly Ala
31
  Ile Ile Gly Leu Met Val Gly Gly Val Val
41
  Ile Ala Thr (SEQ ID NO: 1)
``` or a sequence which is substantially homologous thereto.

"Alkyl" refers to monovalent alkyl groups preferably having from 1 to 10 carbon atoms and more preferably 1 to 6 carbon atoms. This term is exemplified by groups such as methyl, ethyl, n-propyl, iso-propyl, n-butyl, iso-butyl, n-hexyl, and the like.

"Substituted alkyl" refers to an alkyl group, preferably of from 1 to 10 carbon atoms, having from 1 to 3 substituents selected from the group consisting of alkoxy, substituted alkoxy, aryloxy, heteroaryloxy, heterocyclyloxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, aryl, heteroaryl, heterocyclic, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic.

"Alkylene" refers to divalent alkylene groups preferably having from 1 to 10 carbon atoms and more preferably 1 to 6 carbon atoms. This term is exemplified by groups such as methylene (—CH₂—), ethylene (—CH₂CH₂—), the propylene isomers (e.g., —CH₂CH₂CH₂— and —CH(CH₃)CH₂—), and the like.

"Alkaryl" refers to -alkylene-aryl groups preferably having from 1 to 10 carbon atoms in the alkylene moiety and from 6 to 10 carbon atoms in the aryl moiety. Such alkaryl groups are exemplified by benzyl, phenethyl and the like.

"Alkoxy" refers to the group "alkyl-O-". Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O-" where substituted alkyl is as defined above.

"Alkylalkoxy" refers to the group "-alkylene-O-alkyl" where alkylene and alkyl are as defined above. Such groups include, by way of example, methylenemethoxy (—CH₂OCH₃), ethylenemethoxy (—CH₂CH₂OCH₃), n-propylene-iso-propoxy (—CH₂CH₂CH₂OCH(CH₃)₂), methylene-t-butoxy (—CH₂—O—C(CH₃)₃) and the like.

"Alkylthioalkoxy" refers to the group "-alkylene-S-alkyl" wherein alkylene and alkyl are as defined above. Such groups include, by way of example, methylthiomethoxy (—CH₂SCH₃), ethylthiomethoxy (—CH₂CH₂SCH₃), n-propyl-iso-thiopropoxy (—CH₂CH₂CH₂SCH(CH₃)₂), methylthio-t-butoxy (—CH₂SC(CH₃)₃) and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH₂), n-propenyl (—CH₂CH=CH₂), iso-propenyl (—C(CH₃)=CH₂), but-2-enyl (—CH₂CH=CHCH₃), and the like.

"Substituted alkenyl" refers to an alkenyl group as defined above having from 1 to 3 substituents selected from the group consisting of alkoxy, substituted alkoxy, acyl, acylamino, amino, aminoacyl, aminocarboxy esters, cyano, halogen, hydroxyl, carboxyl, carboxylalkyl, cycloalkyl, oxyacyl, oxyacylamino, thiol, thioalkoxy, substituted thioalkoxy, aryl, heteroaryl, heterocyclic, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH$_2$C≡CH) and the like.

"Substituted alkynyl" refers to an alkynyl group as defined above having from 1 to 3 substituents selected from the group consisting of alkoxy, substituted alkoxy, acyl, acylamino, amino, aminoacyl, aminocarboxy esters, cyano, halogen, hydroxyl, carboxyl, carboxylalkyl, cycloalkyl, oxyacyl, oxyacylamino, thiol, thioalkoxy, substituted thioalkyoxy, aryl, heteroaryl, heterocyclic, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic.

"Acyl" refers to the groups alkyl-C(O)—, substituted alkyl-C(O)—, cycloalkyl-C(O)—, aryl-C(O)—, heteroaryl-C(O)— and heterocyclic-C(O)— where alkyl, substituted alkyl, cycloalkyl, aryl, heteroayl and heterocyclic are as defined herein.

"Acylamino" refers to the group —C(O)NRR where each R is independently hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Aminoacyl" refers to the group —NRC(O)R where each R is independently hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Oxyacyl" refers to the groups —OC(O)-alkyl, —OC(O)-aryl, —C(O)O— heteroaryl-, and —C(O)O-heterocyclic where alkyl, ary, heteroaryl and heterocyclic are as defined herein.

"Oxyacylamino" refers to the groups —OC(O)NR-alkyl, —OC(O)NR— substituted alkyl, —OC(O)NR-aryl, —OC(O)NR-heteroaryl-, and —OC(O)NR— heterocyclic where R is hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Aminocarboxy esters" refers to the groups —NRC(O)O-alkyl, —NRC(O)O-substituted alkyl, —NRC(O)O-aryl, —NRC(O)O-heteroaryl, and —NRC(O)O-heterocyclic where R is hydrogen, alkyl, substituted alkyl, cycloalkyl, aryl, heteroaryl, and heterocyclic and where each of alkyl, substituted alkyl, cycloalkyl, aryl, heteroaryl and heterocyclic are as defined herein.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 5 and preferably 1 to 3 substituents selected from the group consisting of hydroxy, biotinamidyl, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, azido, carboxyl, carboxylalkyl, acylamino, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic, and the like. Preferred substituents include alkyl, alkoxy, halo, cyano, nitro, trihalomethyl, and thioalkoxy.

"Aryloxy" refers to the group aryl-O— wherein the aryl group is as defined above including optionally substituted aryl groups as also defined above.

The term "carboxy terminal R$^4$ group" refers to that R$^4$ group in compounds of formula I which, when n is two, is closest to the X group.

"Carboxyalkyl" refers to the groups —C(O)O-alkyl and —C(O)O-substituted alkyl where alkyl and substituted alkyl are as defined above.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 8 carbon atoms having a single cyclic ring and at least one point of internal unsaturation which can be optionally substituted with from 1 to 3 alkyl groups. Examples of suitable cycloalkenyl groups include, for instance, cyclobut-2-enyl, cyclopent-3-enyl, cyclooct-3-enyl and the like.

"Halo" or "halogen" refers to fluoro, chloro, bromo and iodo and preferably is either chloro or bromo.

"Heteroaryl" refers to a monovalent aromatic group of from 2 to 10 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, aminoacyl, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl, heteroaryl and heterocyclic and the like. Preferred substituents include alkyl, alkoxy, halo, cyano, nitro, trihalomethyl, and thioalkoxy.

Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heteroaryloxy" refers to the group heteroaryl-O— wherein the heteroaryl group is as defined above including optionally substituted heteroaryl groups as also defined above.

"Heterocycle" or "heterocyclic" refers to a monovalent (i.e., one point of attachment) saturated or unsaturated group having a single ring or multiple condensed rings, from 1 to 8 carbon atoms and from 1 to 4 hetero atoms selected from nitrogen, sulfur or oxygen within the ring.

Unless otherwise constrained by the definition for the heterocyclic substituent, such heterocyclic groups can be optionally substituted with 1 to 4 substituents selected from the group consisting of hydroxy, acyl, alkyl, alkoxy, alkenyl, alkynyl, substituted alkyl, substituted alkoxy, substituted alkenyl, substituted alkynyl, amino, aminoacyl, aminocarboxy esters, alkaryl, aryl, aryloxy, carboxyl, carboxylalkyl, aminoacyl, cyano, halo, nitro, heteroaryl, heterocyclic, oxyacyl, oxyacylamino, thioalkoxy, substituted thioalkoxy, trihalomethyl, mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, aryl,- heteroaryl and heterocyclic, and the like. Such heterocyclic groups can have a single ring or multiple condensed rings. Preferred heteroaryls include morpholino, piperidinyl, and the like.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, piperidinyl, pyrrolidine, tetrahydrofuranyl, and the like.

"Heterocyclyloxy" refers to the group heterocyclyl-O— wherein the heterocyclic group is as defined above including optionally substituted heterocyclic groups as also defined above.

"Oxyacyl" refers to the groups —OC(O)-alkyl, —OC(O)-aryl, —C(O)O— heteroaryl-, and —C(O)O-heterocyclic where alkyl, aryl, heteroaryl and heterocyclic are as defined herein.

"Oxyacylamino" refers to the groups —OC(O)NH-alkyl, —OC(O)NH— substituted alkyl, —OC(O)NH-aryl, —OC(O)NH-heteroaryl-, and —OC(O)NH— heterocyclic where alkyl, aryl, heteroaryl and heterocyclic are as defined herein.

"Thiol" refers to the group —SH.

"Thioalkoxy" refers to the group —S-alkyl.

"Substituted thioalkoxy" refers to the group —S-substituted alkyl.

"Thioaryloxy" refers to the group aryl-S— wherein the aryl group is as defined above including optionally substituted aryl groups also defined above.

"Thioheteroaryloxy" refers to the group heteroaryl-S— wherein the heteroaryl group is as defined above including optionally substituted aryl groups as also defined above.

"Residues of naturally occurring amino acids" refer to the residues of those 20 α-amino acids found in nature which are incorporated into protein by specific recognition of the charged tRNA molecule with its cognate mRNA codon in humans.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of the invention are readily prepared via several divergent synthetic routes with the particular route selected relative to the ease of compound preparation, commercial availability of starting materials, etc.

A first synthetic method involves conventional coupling of an acetic acid derivative with a primary amine of an esterified amino acid as shown in reaction (1) below:

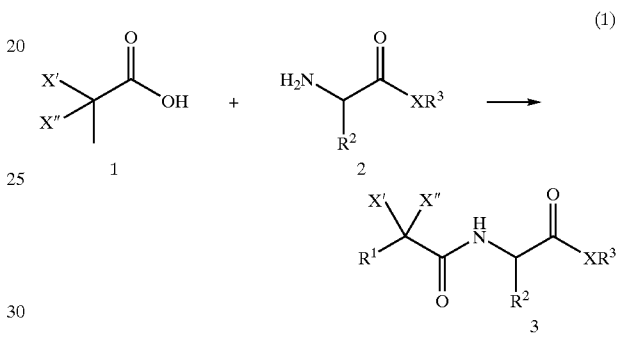

wherein $R^1$, $R^2$, $R^3$, X' and X" are as defined above, and X is either oxygen or —NH—.

Reaction (1) merely involves coupling of a suitable acid derivative 1 with the primary amine of amino acid ester 2 under conditions which provide for the N-acetyl derivative 3S. This reaction is conventionally conducted for peptide synthesis and synthetic methods used therein can also be employed to prepare the N-acetyl amino acid esters 3 of this invention. For example, well known coupling reagents such as carbodiimides with or without the use of well known additives such as N-hydroxysuccinimide, 1-hydroxybenzotriazole, etc. can be used to facilitate coupling. The reaction is conventionally conducted in an inert aprotic diluent such as dimethylformamide, dichloromethane, chloroform, acetonitrile, tetrahydrofuran and the like. Alternatively, the acid halide of compound 1 can be employed in reaction (1) and, when so employed, it is typically employed in the presence of a suitable base to scavenge the acid generated during the reaction. Suitable bases include, by way of example, triethylamine, diisopropylethylamine, N-methylmorpholine and the like.

Reaction (1) is preferably conducted at from about 0° C. to about 60° C. until reaction completion which typically occurs within 1 to about 24 hours. Upon reaction completion, N-acetyl amino acid ester 3 is recovered by conventional methods including precipitation, chromatography, filtration and the like or alternatively is hydrolyzed to the corresponding acid without purification and/or isolation other than conventional work-up (e.g., aqueous extraction, etc.). Alternatively, the synthesis described above in reaction (1) can be conducted on the amino acid ($XR^3$=OH) and subsequent to N-acetyl formation as described above.

In any event, if an N-acetyl amino acid ester is formed, it is converted to the corresponding acid prior to the coupling step with another amino acid ester/amide, HNHCR⁴R⁵C(O)Y. Coupling is accomplished using well known peptide coupling chemistry with well known coupling reagents such as carbodiimides with or without the use of well known additives such as N-hydroxysuccinimide, 1-hydroxybenzotriazole, etc. which can be used to facilitate coupling. The reaction is conventionally conducted in an inert aprotic polar diluent such as dimethylformamide, dichloromethane, chloroform, acetonitrile, tetrahydrofuran and the like.

Such coupling yields compounds of formula I where n is 1. The synthesis of compounds of formula I where n is 2 is accomplished via a second coupling reaction. Specifically, in the first coupling reaction, HNHCR⁴R⁵C(O)Y is selected to be an amino acid ester. That is to say that Y is —O-alkyl. After coupling, the ester is hydrolyzed via conventional conditions well known in the art to provide for the corresponding carboxylic acid which can now be used to couple a second amino acid ester/amide.

In reaction (1), each of the reagents (compound 1 and amino acid ester 2) are well known in the art with a plurality of each being commercially available.

Alternatively, the compounds of formula I can be prepared by first forming the dipeptide ester and then N-acylating these esters. That is to say that the amino acid ester or amide HNHCR⁴R⁵C(O)Y is coupled to the N-blocked amino acid BlockNHCHR²COOH via conventional coupling conditions to provide for the dipeptide BlockNHCHR²C(O)N(H)CR⁴R⁵C(O)Y. The blocking group is then removed via conventional conditions to provide for the free amine which is then N-acylated in the manner described above to provide for the compounds of formula I.

After coupling and N-acylation (in whatever order) is complete, the resulting esters and amides can be derivatized via conventional chemistry to provide for derivatives of the synthesized compounds. For example, conventional reduction of a terminal ester group with lithium borohydride leads to the terminal —CH₂OH group. Alternatively, an ester group can be converted to a primary amide [—C(O)NH₂] by reaction with ammonia in methanol with a catalytic amount of sodium cyanide while heating.

Similarly, reactive functionality which is blocked on, for example, R², can be deblocked and then derivatized. For example, the a BOC protected amino group (e.g., lysine side chain) can be deblocked after synthesis and the amino group acylated or otherwised derivatized.

Additionally, a terminal ester can be subjected to transesterification techniques to provide for other esters. Numerous techniques are known in the art to effect transesterification and each technique merely replaces one ester group with a different ester group derived from the corresponding alcohol or thioalcohol and, in some cases, a catalyst such as titanium (IV) iso-propoxide is used to facilitate reaction completion. In one technique, the alcohol or thioalcohol is first treated with sodium hydride in a suitable diluent such as toluene to form the corresponding sodium alkoxide or thioalkoxide which is then employed to effect transesterification. The efficiency of this technique makes it particularly useful with high boiling and/or expensive alcohols or thioalcohols.

In another transesterification technique, the ester to be transesterified is placed in a large excess of the alcohol or thioalcohol which effects transesterification. A catalytic amount of sodium hydride is then added and the reaction proceeds quickly under conventional conditions to provide the desired transesterified product. Because this protocol requires the use of a large excess of alcohol or thioalcohol, this procedure is particularly useful when the alcohol or thioalcohol is inexpensive.

Transesterification provides a facile means to provide for a multiplicity of different ester substituents on the compounds of formula I above. In all cases, the alcohols and thioalcohols employed to effect transesterification are well known in the art with a significant number being commercially available.

Other methods for preparing the esters of this invention include, by way of example, first hydrolyzing the ester to the free acid followed by O-alkylation with a halo-R³ group in the presence of a base such as potassium carbonate. Alternatively, for esterification procedures for alcohols containing an ester group can be achieved by using the methods of Losse, et al.[11].

The compounds described herein can also be prepared by use of polymer supported forms of carbodiimide peptide coupling reagents. A polymer supported form of EDC, for example, has been described (*Tetrahedron Letters*, 34(48), 7685 (1993))[10]. Additionally, a new carbodiimide coupling reagent, PEPC, and its corresponding polymer supported forms have been discovered and are very useful for the preparation of the compounds of the present invention.

Polymers suitable for use in making a polymer supported coupling reagent are either commercially available or may be prepared by methods well known to the artisan skilled in the polymer arts. A suitable polymer must possess pendant sidechains bearing moieties reactive with the terminal amine of the carbodiimide. Such reactive moieties include chloro, bromo, iodo and methanesulfonyl. Preferably, the reactive moiety is a chloromethyl group. Additionally, the polymer's backbone must be inert to both the carbodiimide and reaction conditions under which the ultimate polymer bound coupling reagents will be used.

Certain hydroxymethylated resins may be converted into chloromethylated resins useful for the preparation of polymer supported coupling reagents. Examples of these hydroxylated resins include the 4-hydroxymethylphenylacetamidomethyl resin (Pam Resin) and 4-benzyloxybenzyl alcohol resin (Wang Resin) available from Advanced Chemtech of Louisville, Ky., USA (see Advanced Chemtech 1993–1994 catalog, page 115). The hydroxymethyl groups of these resins may be converted into the desired chloromethyl groups by any of a number of methods well known to the skilled artisan.

Preferred resins are the chloromethylated styrene/divinylbenzene resins because of their ready commercial availability. As the name suggests, these resins are already chloromethylated and require no chemical modification prior to use. These resins are commercially known as Merrifield's resins and are available from Aldrich Chemical Company of Milwaukee, Wis., USA (see Aldrich 1994–1995 catalog, page 899). Methods for the preparation of PEPC and its polymer supported forms are outlined in the following scheme.

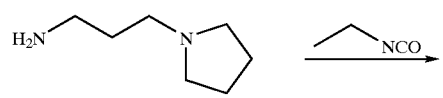

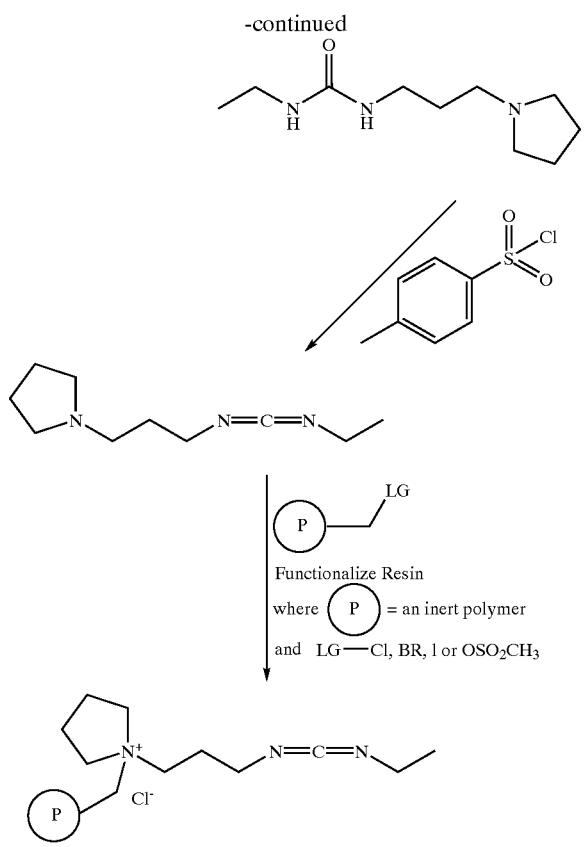

Such methods are describe more fully in U.S. patent application Ser. No. 60/019,790 filed Jun. 14, 1996 which application is incorporated herein by reference in its entirety. Briefly PEPC is prepared by first reacting ethyl isocyanate with 1-(3-aminopropyl)pyrrolidine. The resulting urea is treated with 4-toluenesulfonyl chloride to provide PEPC. The polymer supported form is prepared by reaction of PEPC with an appropriate resin under standard conditions to give the desired reagent.

The carboxylic acid coupling reactions employing these reagents are performed at about ambient temperature to about 45° C., for from about 3 to 120 hours. Typically, the product may be isolated by washing the reaction with $CHCl_3$ and concentrating the remaining organics under reduced pressure. As discussed supra, isolation of products from reactions where a polymer bound reagent has been used is greatly simplified, requiring only filtration of the reaction mixture and then concentration of the filtrate under reduced pressure.

Still other methods for the preparation of esters are provided in the examples below.

Compounds where X is —$CR^6R^6Y'$ are readily prepared by coupling, e.g., an amino alcohol $H_2NCR^4R^5CR^6R^6OH$, to the carboxyl group of $R^1ZCX'X''C(O)NHCHR^2C(O)OH$ under standard coupling conditions well known in peptide coupling chemistry which can use well known coupling reagents such as carbodiimides with or without the use of well known additives such as N-hydroxysuccinimide, 1-hydroxybenzotriazole, etc. If necessary, well known blocking groups on Y' can be employed to protect the group during coupling. Such blocking groups are particularly desirable when Y' is an amino group.

The reaction is conventionally conducted in an inert aprotic polar diluent such as dimethylformamide, dichloromethane, chloroform, acetonitrile, tetrahydrofuran and the like. Upon reaction completion, any blocking groups on Y' are selectively removed to provide for the desired compound.

When Y' is —OH or —SH, post-synthetic conversion of these groups to the corresponding esters (i.e., —$OC(O)R^7$), disulfides (i.e., —$SSR^7$) and —$SSC(O)R^7$ groups is accomplished using well known chemistry. For example, ester synthesis requires only reaction with a suitable acid such as acetic acid ($R^7$=methyl), acid halide (e.g., acid chloride) or acid anhydride under suitable esterification conditions.

When one of $R^6$ is hydrogen, post-synthetic oxidation of the —$CHR^6OH$ group leads to the ketone derivatives. Alternatively, such ketones can be prepared by coupling the suitable aminoketone HCl salt with the terminal carboxyl group of the amino acid as illustrated in Example 168 below.

In these synthetic methods, the starting materials can contain a chiral center (e.g., alanine) and, when a racemic starting material is employed, the resulting product is a mixture of R,S enatiomers. Alternatively, a chiral isomer of the starting material can be employed and, if the reaction protocol employed does not racemize this starting material, a chiral product is obtained. Such reaction protocols can involve inversion of the chiral center during synthesis.

Accordingly, unless otherwise indicated, the products of this invention are a mixture of R,S enatiomers or diasteriomers. Preferably, however, when a chiral product is desired, the chiral product corresponds to the L-amino acid derivative. Alternatively, chiral products can be obtained via purification techniques which separate enatiomers from a R,S mixture to provide for one or the other stereoisomer. Such techniques are well known in the art.

Pharmaceutical Formulations

When employed as pharmaceuticals, the compounds of formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of formula I above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 560 mg quantities.

FORMULATION EXAMPLE 9

A subcutaneous formulation may be prepared as follows:

| Ingredient | Quantity |
|---|---|
| Active Ingredient | 5.0 mg |
| corn oil | 1 ml |

FORMULATION EXAMPLE 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*, Mace Publishing Company, Philadelphia, Pa., 17th ed. (1985).

Utility

The compounds and pharmaceutical compositions of the invention are useful in inhibiting β-amyloid peptide release and/or its synthesis, and, accordingly, have utility in treating Alzheimer's disease in mammals including humans.

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount of compound administered to the patient will vary depending upon what is being administered, the purpose of the administration, such as prophylaxis or therapy, the state of the patient, the manner of administration, and the like. In therapeutic applications, compositions are administered to a patient already suffering from AD in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of AD in the patient, the age, weight and general condition of the patient, and the like. Preferably, for use as therapeutics, the compounds described herein are administered at dosages ranging from about 1 to about 500 mg/kg/day.

In prophylactic applications, compositions are administered to a patient at risk of developing AD (determined for example by genetic screening or familial trait) in an amount sufficient to inhibit the onset of symptoms of the disease. An amount adequate to accomplish this is defined as "prophylactically effective dose."

Amounts effective for this use will depend on the judgment of the attending clinician depending upon factors such as the age, weight and general condition of the patient, and the like. Preferably, for use as prophylactics, the compounds described herein are administered at dosages ranging from about 1 to about 500 mg/kg/day.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | | |
|---|---|---|
| BOC | = | tert-butoxycarbonyl |
| BOP | = | benzotriazol-1-yloxy-tris(dimethylamino)phosphonium hexafluorophosphate |
| bd | = | broad doublet |
| bs | = | broad singlet |
| c | = | concentration (g/mL) |
| CDI | = | 1,1'-carbonyldiimidazole |
| d | = | doublet |
| dd | = | doublet of doublets |
| DCM | = | dichloromethane |
| DEAD | = | diethyl azodicarboxylate |
| DMF | = | dimethylformamide |
| DMSO | = | dimethylsulfoxide |
| EDC | = | 1-(3-dimethylaminopropyl)-3-ethylcarbodiimide hydrochloride |
| EEDQ | = | 2-ethoxy-1-ethoxycarbonyl-1,2-dihydroquinoline |
| eq. | = | equivalents |
| EtOAc | = | ethyl acetate |
| EtOH | = | ethanol |
| g | = | grams |
| L | = | liter |
| m | = | multiplet |
| max | = | maximum |
| MeOH | = | methanol |
| meq | = | milliequivalent |
| mg | = | milligram |
| mL | = | milliliter |
| mm | = | millimeter |
| mmol | = | millimole |
| N/A | = | not available |
| N | = | normal |
| ng | = | nanogram |
| nm | = | nanometers |
| OD | = | optical density |
| φ | = | phenyl |
| PEPC | = | 1-(3-(1-pyrrolidinyl)propyl)-3-ethylcarbodiimide |

| | | |
|---|---|---|
| psi | = | pounds per square inch |
| q | = | quartet |
| quint. | = | quintet |
| rpm | = | rotations per minute |
| s | = | singlet |
| t | = | triplet |
| TFA | = | trifluoroacetic acid |
| THF | = | tetrahydrofuran |
| tlc | = | thin layer chromatography |
| μL | = | microliter |
| UV | = | ultraviolet |

In the examples below, all temperatures are in degrees Celcius (unless otherwise indicated) and each of the compounds set forth in these examples was prepared by one of the following general procedures, unless otherwise indicated.

Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Fluka" indicates that the compound or reagent is commercially available from Fluka Chemical Corp., 980 South 2nd Street, Ronkonkoma N.Y. 11779 USA; the term "Lancaster" indicates that the compound or reagent is commercially available from Lancaster Synthesis, Inc., P.O. Box 100 Windham, N.H. 03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa.; the term "Bachem" indicates that the compound or reagent is commercially available from Bachem Biosciences Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 0HW United Kingdom; and the term "TCI" indicates that the compound or reagent is commercially available from TCI America, 9211 North Harborgate Street, Portland Ore. 97203; the term "Alfa" indicates that the compound or reagent is commercially available from Johnson Matthey Catalog Company, Inc. 30 Bond Street, Ward Hill, Mass. 01835-0747; the term "Novabiochem" indicates that the compound or reagent is commercially available from Calbiochem-Novabiochem Corp. 10933 North Torrey Pines Road, P.O. Box 12087, La Jolla Calif. 92039-2087; the term "Oakwood" indicates that the compound or reagent is commercially available from Oakwood, Columbia, S.C.; the term "Advanced Chemtech" indicates that the compound or reagent is commercially available from Advanced Chemtech, Louisville, Ky.; the term "Pfaltz & Bauer" indicates that the compound or reagent is commercially available from Pfaltz & Bauer, Waterbury, Conn., USA; and the term "Rieke Metals, Inc" indicates that the compound or reagent is commercially available from Rieke Metals, Inc., 6133 Heide Lane, Lincoln, Nebr., USA.

The following General Procedures A'–K' and Examples A1–A81 illustrate the synthesis of N-(aryl/heteroarylacetyl) amino acid esters which can be hydrolyzed to provide for N-(aryl/heteroarylacetyl)amino acid starting materials of this invention. Other N-(aryl/heteroarylacetyl)amino acid esters can be prepared using these procedures from commerically available or known starting materials.

GENERAL PROCEDURE A'

Coupling of $R^1C(X')(X'')C(O)Cl$ with $H_2NCH(R^2)C(O)XR^3$

To a stirred solution of (D,L)-alanine iso-butyl ester hydrochloride (from Example B below) (4.6 mmol) in 5 mL of pyridine was added 4.6 mmol of an acid chloride. Precipitation occurred immediately. The mixture was stirred for 3.5 h, diluted with 100 mL of diethyl ether, washed with 10% HCl three times, brine once, 20% potassium carbonate once and brine once. The solution was dried over magnesium sulfate, filtered, and evaporated at reduced pressure to yield the product. Other amino acid esters may also be employed in this procedure.

GENERAL PROCEDURE B'

Coupling of $R^1C(X')(X'')C(O)OH$ with $H_2NCH(R^2)C(O)XR^3$

A solution of the acid (3.3 mmol) and CDI in 20 mL THF was stirred for 2 h. L-alanine iso-butyl ester hydrochloride (from Example B below) (3.6 mmol) was added, followed by 1.5 mL (10.8 mmol) of triethylamine. The reaction mixture was stirred overnight. The reaction mixture was diluted with 100 mL of diethyl ether, washed with 10% HCl three times, brine once, 20% potassium carbonate once and brine once. The solution was dried over magnesium sulfate, filtered, and evaporated at reduced pressure to yield the product. Other amino acid esters may also be employed in this procedure.

GENERAL PROCEDURE C'

Esterification of $R^1C(X')(X'')C(O)NHCH(R^2)C(O)OH$ with $HOR^3$

To a stirred solution of phenylacetylvaline (1.6470 g, 7.0 mmol) in 20 mL THF was added CDI (1.05 g, 6.5 mmol) and the mixture was stirred for 1.5 h. 2-Methylbutanol (0.53 g, 6 mmol) was added the mixture, followed by addition of NaH (0.16 g, 6.5 mmol). Bubbling occurred immediately. The reaction mixture was stirred overnight. The reaction mixture was diluted with 100 mL of diethyl ether, washed with 10% HCl three times, brine once, 20% potassium carbonate once and brine once. The solution was dried over magnesium sulfate, filtered, and evaporated at reduced pressure to yield the product. Other N-acyl amino acids and alcohols may also be employed in this procedure.

GENERAL PROCEDURE D'

Ester Hydrolysis to the Free Acid

Ester hydrolysis to the free acid was conducted by conventional methods. Below are two examples of such conventional de-esterification methods.

To the ester in a 1:1 mixture of $CH_3OH/H_2O$ was added 2–5 equivalents of $K_2CO_3$. The mixture was heated to about 50° C. for about 0.5 to 1.5 hours until tlc showed complete reaction. The reaction was cooled to room temperature and the methanol was removed at reduced pressure. The pH of the remaining aqueous solution was adjusted to about 2, and ethyl acetate was added to extract the product. The organic phase was then washed with saturated aqueous NaCl and dried over $MgSO_4$. The solution was stripped free of solvent at reduced pressure to yield the product.

The amino acid ester was dissolved in dioxane/water (4:1) to which was added LiOH (~2 eq.) that was dissolved in water such that the total solvent after addition was about 2:1 dioxane:water. The reaction mixture was stirred until reaction completion and the dioxane was removed under reduced pressure. The residue was diluted with EtOAc, the layers were separated and the aqueous layer acidified to pH 2. The aqueous layer was back extracted with EtOAc, the combined organics were dried over $Na_2SO_4$ and the solvent was removed under reduced pressure after filtration. The residue was purified by conventional methods (e.g., recrystallization).

The following exemplifies this later example. The methyl ester of 3-$NO_2$ phenylacetyl alanine 9.27 g (0.0348 mols) was dissolved in 60 mL dioxane and 15 mL of $H_2O$ and adding LiOH (3.06 g, 0.0731 mol) that has been dissolved in 15 mL of $H_2O$. After stirring for 4 hours, the dioxane was removed under reduced pressure and the residue diluted with EtOAc, the layers were separated and the aqueous layer acidified to pH 2. The aqueous layer was back extracted with EtOAc (4×100 mL), the combined organics were dried over $Na_2SO_4$ and the solvent was removed under reduced pressure after filtration. The residue was recrystallized from EtOAc/isooctane giving 7.5 g (85%) of 3-nitrophenylacetyl alanine. $C_{11}H_{12}N_2O_5$ requires C=52.38, H=4.80, and N=11.11. Analysis found C=52.54, H=4.85, and N=11.08. $[\alpha]_{23}$=−29.9 @ 589 nm.

GENERAL PROCEDURE E'

Low Temperature BOP Coupling of Acid and Alcohol

A solution of methylene chloride containing the carboxylic acid (100M %) and N-methyl morpholine (150 M %) was cooled to −20° C. under nitrogen. BOP (105 M %) was added in one portion and the reaction mixture was maintained at −20° C. for 15 minutes. The corresponding alcohol (120 M %) was added and the reaction mixture was allowed to warm to room temperature and stirred for 12 hours. The reaction mixture was then poured into water and extracted with ethyl acetate (3×). The combined ethyl acetate portions were backwashed with saturated aqueous citric acid (2×), saturated aqueous sodium bicarbonate (2×), brine (1×), dried over anhydrous magnesium sulfate or sodium sulfate and the solvent removed under reduced pressure to yield the crude product.

GENERAL PROCEDURE F'

EDC Coupling of Acid and Amine

The acid derivative was dissolved in methylene chloride. The amine (1 eq.), N-methylmorpholine (5 eq.), and hydroxybenzotriazole monohydrate (1.2 eq.) were added in sequence. The reaction was cooled to about 0° C. and then 1.2 eq. of 1-(3-dimethylaminopropyl)-3-ethylcarbodiimide hydrochloride was added. The solution was allowed to stir overnight and come to room temperature under $N_2$ pressure. The reaction mix was worked up by washing the solution with saturated, aqueous $Na_2CO_3$, 0.1M citric acid, and brine before drying with $Na_2SO_4$ and removal of solvents to yield crude product. Pure products were obtained by flash chromatography in an appropriate solvent.

GENERAL PROCEDURE G'

EDC Coupling of Acid and Amine

A round bottom flask was charged with carboxylic acid (1.0 eq.), hydroxybenzotriazole hydrate (1.1 eq.) and amine (1.0 eq.) in THF under nitrogen atmosphere. An appropriate amount (1.1 eq. for free amines and 2.2 eq. for hydrochloride amine salts) of base, such as Hunig's base was added to the well stirred mixture followed by EDC (1.1 eq.). After stirring from 4 to 17 hours at room temperature the solvent was removed at reduced pressure, the residue taken up in EtOAc (or similar solvent)/water. The organic layer was washed with saturated aqueous sodium bicarbonate solution, IN HCl, brine and dried over anhydrous sodium sulfate. In some cases, the isolated product was analytically pure at this stage while, in other cases, purification via chromatography and/or recrystallization was required prior to biological evaluation.

GENERAL PROCEDURE H'

Coupling of $R^1C(X')(X'')C(O)Cl$ with $H_2NCH(R^2)C(O)XR^3$

An excess of oxalyl chloride in dichloromethane was added to the acid derivative together with one drop of DMF. The resulting mixture was stirred for about 2 hours or until bubbling ceases. The solvent was then removed under reduced pressure and rediluted with dry methylene chloride. To the resulting solution was added about 1.1 eq. of the appropriate amino acid ester and triethylamine (1.1 eq. in methylene chloride). The system was stirred at room temperature for 2 hours and then the solvent was removed under reduced pressure. The residue was dissolved in ethyl acetate, washed with 1N HCl followed by 1N NaOH. The organic layer was dried over anhydrous soldium sulfate, filtered and the solvent removed under reduced pressure to provide for the desired product.

GENERAL PROCEDURE I'

P-EPC Coupling

P-EPC coupling employs an amino acid ester and a substituted acetic acid compound. The acetic acid derivative is well known in the art and is typically commercially available. The amino acid ester is prepared by conventional methods from the known and typically commercially available N-B OC amino acid as described in GENERAL PROCEDURE J' below.

Specifically, the appropriate amino ester free base (0.0346 mmols) and substituted phenylacetic acid (0.069 mmols) were dissolved in 2.0 mL $CHCl_3$ (EtOH free), treated with 150 mg of P-EPC (0.87 meq./g) and the reaction was mixed for 4 days at 23° C. The reaction was filtered through a plug of cotton, rinsed with 2.0 mL of $CHCl_3$ and the filtrate evaporated under a stream of nitrogen. The purity of each sample was determined by $^1H$ NMR and ranged from 50% to >95%. Between 8.0 and 15.0 mg of final product was obtained from each reaction and was tested without additional purification.

GENERAL PROCEDURE J'

Synthesis of Amino Acid Esters From the Corresponding N-BOC Amino Acid

A. Esterification of the Acid.

The N-BOC amino acid was dissolved in dioxane and treated with an excess of alcohol (~1.5 eq.) and catalytic DMAP (100 mg) at 0° C. Stirring was continued until reaction completion whereupon the product was recovered by conventional methods.

B. Removal of N-BOC Group.

The N-BOC protected amino acid was dissolved in methylene chloride (0.05M) and treated with 10 eq. of TFA at room temperature under a nitrogen atmosphere. The reaction was monitored by tlc until starting material was consumed usually within 1–5 hours. An additional 10 eq. of TFA was added to the reaction if the starting material was still present after 5 hours. The reaction was carefully neutralized with Na₂CO₃, separated, the organic layer washed with brine and dried over anhydrous Na₂SO₄. The crude amine was then used without purification.

Specific exemplification of these procedures are as follows:

1. Racemic (+/−)-N-BOC-α-amino butyric acid (Aldrich) (9.29 g, 0.0457 mol) was dissolved in 100 mL of dioxane and treated with iso-butyl alcohol (6.26 mL, 0.0686 mol), EDC (8.72 g, 0.0457) and catalytic DMAP (100 mg) at 0° C. After stirring for 17 hours, the organics were evaporated at reduced pressure, the residue diluted with EtOAc washed with NaHCO₃, brine and dried over Na₂SO₄. Evaporation yields 8.42 g (71%) of an oil. $C_{13}H_{25}NO_4$ requires: C=60.21, H=9.72, and N=5.40. Anal found: C=59.91, H=9.89, and N=5.67.

The above N-BOC amino acid ester (8.00 g, 0.032 mol) was deprotected as above giving 3.12 g (61%) of the free base as a colorless oil which solidifies upon standing.

2. L-N-BOC-alanine (Aldrich) (8.97 g, 0.047 mol) was dissolved in 100 mL of $CH_2Cl_2$, iso-butyl alcohol (21.9 mL, 0.238 mol) and treated with DMAP (100 mg) and EDC (10.0 g, 0.52 mol) at 0° C. The mixture was stirred for 17 hours, diluted with $H_2O$, washed with 1.0 N HCl, NaHCO₃, then brine and the organics were dried over Na₂SO₄. Filtration and evaporation yields 11.8 g (quantitative) of L-N-BOC alanine iso-butyl ester which is contaminated with a small amount of solvent. A sample was vacuum dried for analytical analysis. $C_{12}H_{23}NO_4$ requires: C=58.79, H=9.38, and N=5.71. Anal found: C=58.73, H=9.55, and N=5.96.

The above N-BOC amino acid ester (11.8 g, 0.0481 mol) was deprotected as above. The free base was converted to the corresponding HCl salt using saturated HCl (g)/EtOAc to give L-N-alanine iso-butyl ester hydrochloride. Obtained 4.2 g (48%) of a colorless solid. $C_7H_{15}NO_2$. HCl requires: C=46.28, H=8.88, and N=7.71. Anal found: C=46.01, H=8.85, and N=7.68.

GENERAL PROCEDURE K'

Methyl Ester Formation from Amino Acids

The amino acid (amino acid or amino acid hydrochloride) is suspended in methanol and chilled to 0° C. HCl gas is bubbled through this solution for 5 minutes. The reaction is allowed to warm to room temperature then stirred for 4 hours. The solvents are then removed at reduced pressure to afford the desired amino acid methyl ester hydrochloride. This product is usually used without further purification.

Example A'

Synthesis of Free and Polymer Bound PEPC
N-ethyl-N'-3-(1-pyrrolidinyl)propylurea To a solution of 27.7 g (0.39 mol) ethyl isocyanate in 250 mL chloroform was added 50 g (0.39 mol), 3-(1-pyrrolidinyl)propylamine dropwise with cooling. Once the addition was complete, the cooling bath was removed and the reaction mixture stirred at room temperature for 4 hours. The reaction mixture was then concentrated under reduced pressure to give 74.5 g (96.4%) of the desired urea as a clear oil.

1-(3-(1-Pyrrolidinyl)propyl)-3-ethylcarbodiimide (P-FPC)

To a solution of 31.0 g (0.156 mol) N-ethyl-N'-3-(1-pyrrolidinyl)propyl-urea in 500 mL dichloromethane was added 62.6 g (0.62 mol) triethylamine and the solution was cooled to 0° C. To this solution were then added 59.17 g (0.31 mol) 4-toluenesulfonyl chloride in 400 mL dichloromethane dropwise at such a rate as to maintain the reaction at 0–5° C. After the addition was complete, the reaction mixture was warmed to room temperature and then heated to reflux for 4 hours. After cooling to room temperature, the reaction mixture was washed with saturated aqueous potassium carbonate (3×150 mL). The aqueous phases were combined and extracted with dichloromethane. All organic phases were combined and concentrated under reduced pressure. The resultant orange slurry was suspended in 250 mL diethyl ether and the solution decanted off from the solid. The slurry/decantation process was repeated 3 more times. The ether solutions were combined and concentrated under reduced pressure to give 18.9 g (67%) of the desired product as a crude orange oil. A portion of the oil was distilled under vacuum to give a colorless oil distilling at 78–82° C. (0.4 mm Hg).

Preparation of a Polymer Supported Form of 1-(3-(1-Pyrrolidinyl)propyl)-3-ethylcarbodiimide (P-EPC)

A suspension of 8.75 g (48.3 mmol), 1-(3-(1-pyrrolidinyl)propyl)-3-ethylcarbodiimide and 24.17 g (24.17 mmol) Merrifield's resin (2% cross-linked, 200–400 mesh, chloromethylated styrene/divinylbenzene copolymer, 1 meq. Cl/g) in dimethylformamide was heated at 100° C. for 2 days. The reaction was cooled and filtered and the resulting resin washed sequentially with 1L DMF, 1L THF and 1L diethyl ether. The remaining resin was then dried under vacuum for 18 hours.

Example B'

Preparation of Alanine iso-Butyl Ester Hydrochloride

A mixture of 35.64 g (0.4 mol) of (D,L)-alanine (Aldrich) (or L-alanine (Aldrich)); 44 mL (0.6 mol) of thionyl chloride (Aldrich) and 200 mL of isobutanol was refluxed for 1.5 hours and the volatiles were removed completely on a rotavapor of 90° C. under reduced pressure to give (D,L)-alanine iso-butyl ester hydrochloride (or L-alanine iso-butyl ester hydrochloride), which was pure enough to be used for further transformations.

Example C'

Preparation of 3,5-Dichlorophenylacetic Acid

To a solution of 3.5 g of 3,5-dichlorobenzyl alcohol (Aldrich) in 75 mL of dichloromethane at 0° C. was added 1.8 mL of methane sulfonylchloride followed by 3.5 mL of triethylamine added dropwise. After 2 hours the solution was diluted to 150 mL with dichloromethane, washed with 3N HCl, saturated aqueous NaHCO₃ dried with Na₂SO₄ and the solvents removed to yield the desired 3,5-dichlorobenzyl methanesulfonate as a yellow oil that was used without purification.

The crude sulfonate was dissolved in 50 mL of DMF at 0° C. and then 3 g of KCN was added. After 2 hours an additional 50 mL of DMF was added and the solution was stirred for 16 hours. The red solution was diluted with 1 L of $H_2O$ and acidified to pH 3 with 3N HCl. The aqueous solution was extracted with dichloromethane. The combined organics were washed with 3N HCl, dried with Na₂SO₄ and the solvents removed at reduced pressure to yield crude 3,5-dichlorophenylacetonitrile which was used without purification.

The nitrile was added to a mixture of 40 mL of concentrated sulfuric acid and 50 mL $H_2O$ and heated to reflux for 48 hours, cooled to room temperature and stirred for 48 hours. The reaction was diluted into 1 L of crushed ice, warmed to toom temperature and extracted with 2×200 mL of dichloromethane and 2×200 mL of ethylacetate. Both sets of organics were combined and washed with saturated aqueous $NaHCO_3$. The $NaHCO_3$ fractions were combined and acidified to pH 1 with 3N HCl. The white solid was too fine to filter and was extracted out with 2×200 mL of dichloromethane. The combined organics were dried with $Na_2SO_4$ and the solvents removed at reduced presure to yield crude 3,5-dichlorophenylacetic acid as a white solid. The solid was slurried with hexane and filtered to get 1.75 g of white solid.

NMR ($CDCl_3$): (in ppm), 3.61 (s, 2H), 7.19 (s, 1H), 7.30 (s, 1H)

Example D'

Synthesis of N-(3-Chlorophenylacetyl)alanine

The title compound was prepared using L-alanine (Nova Biochem) and 3-chlorophenyl acetic acid (Aldrich) by following General Procedures F' or G', followed by hydrolysis using General Procedure D'.

Example A1

Synthesis of N-(Phenylacetyl)-D,L-alanine iso-Butyl Ester

Following General Procedure A' above and using phenylacetyl chloride (Aldrich) and D,L-alanine iso-butyl ester hydrochloride (from Example B' above), the title compound was prepared. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=7.23–7.36 (m, 5H), 6.18 (d, 1H), 4.58 (t, J=7.3 Hz, 1H), 3.87 (m, 2H), 3.57 (s, 2H), 1.90 (m, 1H), 1.34 (d, J=7.2 Hz, 3H), 0.89 (d, J=6.8 Hz, 6H). $^{13}$C-nmr ($CDCl_3$): δ=172.7, 170.3, 134.5, 129.2, 128.8, 127.2, 71.3, 48.1, 43.4, 27.5, 18.8, 18.3. $C_{15}H_{21}NO_3$ (MW=263.34; Mass Spectroscopy ($MH^+$=264)).

Example A2

Synthesis of N-(3-Phenylpropionyl)-D,L-alanine iso-Butyl Ester

Following General Procedure A' above and using 3-phenylpropionyl chloride (Aldrich) and D,L-alanine iso-butyl ester hydrochloride (from Example B' above), the title compound was prepared as a solid having a melting point of from 51°–54° C. The reaction was monitored by tlc on silica gel and purification was by extraction with $Et_2O$ followed by washes with aqueous $K_2CO_3$ and aqueous HCl. NMR data was as follows:

$^1$H-nmr ($CDCl_3$): δ=7.25 (m, 2H), 7.19 (m, 3H), 6.28 (d, J=7.2 Hz, 1H), 4.58 (quint., J=7.2 Hz, 1H), 3.89 (m, 2H), 2.95 (t, J=7.7 Hz, 2H), 2.50 (m, 2H), 1.92 (m, 1H), 1.33 (d, J=7.1 Hz, 3H), 0.91 (d, J=6.7 Hz, 6H). $^{13}$C-nmr ($CDCl_3$): δ=173.0, 171.5, 140.6, 128.3, 128.1, 126.0, 71.2, 47.8, 37.9, 31.4, 27.5, 18.79, 18.77, 18.3. $C_{16}H_{23}NO_3$ (MW=277.37, Mass Spectroscopy ($MH^+$278)).

Example A3

Synthesis of N-(3-Methylpentanoyl)-L-alanine iso-Butyl Ester

Following General Procedure B' and using 3-methylpentanoic acid (Aldrich) and L-alanine iso-butyl ester hydrochloride (from Example B' above), the title compound was prepared as an oil. The reaction was monitored by tlc on silica gel and purification was by extraction with $ET_2O$ followed by washes with aqueous $K_2CO_3$ and aqueous HCl.

NMR data was as follows:

$^1$H-nmr ($CDCl_3$): δ=6.08 (d, J=5.9 Hz, 1H), 4.62 (quint., J=7.3 Hz, 1H), 3.92 (m, 2H), 2.22 (m, 1H), 1.84–2.00 (m, 3H), 1.40 (d, J=7.2 Hz, 3H), 1.35 (m, 1H), 1.20 (m, 1H), 0.85–0.96 (m, 12H). $^{13}$C-nmr ($CDCl_3$): δ=173.3, 172.1, 71.4, 47.9, 43.9, 32.3, 29.38, 29.35, 27.6, 19.10, 19.06, 18.93, 18.91, 18.72, 18.67, 11.3. $C_{13}H_{25}NO_3$ (MW=243.35, Mass Spectroscopy ($MH^+$244)).

Example A4

Synthesis of N-[(4-Chlorophenyl)acetyl]-L-alanine iso-Butyl Ester

Following General Procedure B' and using 4-chlorophenylacetic acid (Aldrich) and L-alanine iso-butyl ester hydrochloride (from Example B' above), the title compound was prepared as a solid having a melting point of 111°–113° C. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=7.30 (d, J=8.2 Hz, 2H), 7.21 (d, J=8.3 Hz, 2H), 6.18 (d, J=5.5 Hz, 1H), 4.57 (quint., J=7.2 Hz, 1H), 3.88 (m, 2H), 3.53 (s, 2H), 1.91 (m, 1H), 1.36 (d, J=7.1 Hz, 3H), 0.90 (d, J=6.8 Hz, 6H). $^{13}$C-nmr ($CDCl_3$): δ=172.8, 169.8, 133.1, 133.0, 130.6, 128.9, 71.4, 48.2, 42.6, 27.6, 18.85, 18.82, 18.4. $C_{15}H_{20}NO_3Cl$ (MW=297.78, Mass Spectroscopy ($MH^+$298)).

Example A5

Synthesis of N-[(3,4-Dichlorophenyl)acetyl]-L-alanine iso-Butyl Ester

Following General Procedure B' and using 3,4-dichlorophenylacetic acid (Aldrich) and L-alanine iso-butyl ester hydrochloride (from Example B' above), the title compound was prepared as a solid having a melting point of 81°–83° C. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=0.90 (d, J=6.8 Hz, 6H), 1.38 (d, J=7.1 Hz, 3H), 1.91 (m, 1H), 3.50 (s, 2H), 3.90 (m, 2H), 4.57 (quint., J=7.1 Hz, 1H), 6.31 (d, J=4.9 Hz, 1H), 7.12 (m, 1H), 7.38 (m, 2H). $^{13}$C-nmr ($CDCl_3$): δ=18.4, 18.8, 18.9, 27.6, 42.2, 48.3, 71.5, 128.6, 130.6, 131.2, 131.3, 132.6, 134.7, 169.2, 172.8. $C_{15}H_{19}NO_3Cl_2$ (MW=332.23, Mass Spectroscopy ($MH^+$332)).

Example A6

Synthesis of N-[(4-Methylphenyl)acetyl]-D,L-alanine iso-Butyl Ester

Following General Procedure B' and using 4-methylphenylacetic acid (Aldrich) and D,L-alanine iso-butyl ester hydrochloride (from Example B' above), the title compound was prepared as a solid having a melting point of 102°–104° C. The reaction was monitored by tlc on silica gel (Rf=0.6 in 33% ethyl acetate/hexanes) and purification was by extraction with $Et_2O$ followed by washes with aqueous $K_2CO_3$ and aqueous HCl.

NMR data was as follows:

$^1$H-nmr (CDCl$_3$): δ=0.90 (d, J=6.7 Hz, 6H), 1.35 (d, J=7.2 Hz, 3H), 1.91 (m, 1H), 2.34 (s, 3H), 3.55 (s, 2H), 3.88 (m, 2H), 4.58 (m, 1H), 6.05 (bd, 1H), 7.16 (s, 4H). $^{13}$C-nmr (CDCl$_3$): δ=18.5, 18.85, 18.87, 21.0, 27.6, 43.1, 48.1, 71.3, 129.2, 129.6, 131.3, 136.9, 170.6, 172.8. C$_{16}$H$_{23}$NO$_3$ (MW=277.37, Mass Spectroscopy (MH$^+$278)).

Example A7

Synthesis of N-[(3-Pyridyl)acetyl]-D,L-alanine iso-Butyl Ester

Following General Procedure F' and using 3-pyridylacetic acid hydrochloride (Aldrich) and D,L-alanine iso-butyl ester hydrochloride (from Example B' above), the title compound was prepared as a solid having a melting point of 62°–64° C. The reaction was monitored by tlc on silica gel (Rf=0.48 10% methanol/dichloromethane) and purification was by silica gel chromatography.

NMR data was as follows:

$^1$H-nmr (CDCl$_3$): δ=8.40 (d, J=2.8, 2H); 7.6 (m, 1H): 7.16 (m, 2H); 4.5 (quint., J=7.2, 7.2, 1H); 3.8 (m, 2H); 3.48 (s, 2H); 1.8 (m, 1H); 1.30 (d, J=7.2, 3H); 0.81 (d, J=6.7, 6H). $^{13}$C-nmr (CDCl$_3$): δ=173.4, 170.1, 150.6, 148.8, 137.4, 131.4, 124.1, 71.9, 48.9, 40.6, 28.1, 19.5, 19.4, 18.6. C$_{14}$H$_{20}$N$_2$O$_3$ (MW=264, Mass Spectroscopy (MH$^+$265)).

Example A8

Synthesis of N-[(1-Naphthyl)acetyl]-L-alanine iso-Butyl Ester

Following General Procedure B' and using 1-naphthylacetic acid (Aldrich) and L-alanine iso-butyl ester hydrochloride (from Example B' above), the title compound was prepared as a solid having a melting point of 69°–73° C. The reaction was monitored by tlc on silica gel and purification was by extraction with ET$_2$O followed by washes with aqueous K$_2$CO$_3$ and aqueous HCl.

NMR data was as follows:

$^1$H-nmr (CDCl$_3$): δ=0.83 (m, 6H), 1.25 (d, J=7.1 Hz, 3H), 1.81 (m, 1H), 3.79 (m, 2H), 4.04 (2s, 2H), 4.57 (quint., J=7.3 Hz, 1H), 5.99 (d, J=7.1 Hz, 1H), 7.44 (m, 2H), 7.53 (m, 2H), 7.85 (m, 2H), 7.98 (m, 1H). $^{13}$C-nmr (CDCl$_3$): δ=18.2, 18.81, 18.83, 27.5, 41.5, 48.2, 71.3, 123.7, 125.6, 126.1, 126.6, 128.2, 128.5, 128.7, 130.7, 132.0, 133.9, 170.3, 172.5. C$_{19}$H$_{23}$NO$_3$ (MW=313.40, Mass Spectroscopy (MH$^+$314)).

Example A9

Synthesis of N-[(2-Naphthyl)acetyl]-L-alanine iso-Butyl Ester

Following General Procedure B' and using 2-naphthylacetic acid (Aldrich) and L-alanine iso-butyl ester hydrochloride (from Example B' above), the title compound was prepared as a solid having a melting point of 128°–129° C. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.86 (m, 6H), 1.35 (d, J=7.1 Hz, 3H), 1.78 (m, 1H), 3.76 (s, 2H), 3.87 (m, 2H), 4.62 (quint., J=7.2 Hz, 1H), 6.13 (d, J=7.1 Hz, 1H), 7.41 (m, 1H), 7.48 (m, 2H), 7.74 (s, 1H), 7.83 (m, 3H). $^{13}$C-nmr (CDCl$_3$): δ=18.4, 18.82, 18.85, 27.6, 43.7, 48.2, 71.4, 125.9, 126.3, 127.2, 127.6, 127.7, 128.2, 128.7, 132.0, 132.5, 133.5, 170.3, 172.8. C$_{19}$H$_{23}$NO$_3$ (MW=313.40, Mass Spectroscopy (MH$^+$314)).

Example A10

Synthesis of N-(4-phenylbutanoyl)-L-alanine iso-Butyl Ester

Following General Procedure B' and using 4-phenylbutanoic acid (Aldrich) and L-alanine iso-butyl ester hydrochloride (from Example B' above), the title compound was prepared as an oil. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=0.92 (d, J=6.7 Hz, 6H), 1.38 (d, J=7.1 Hz, 3H), 1.96 (m, 3H), 2.21 (t, J=7.1 Hz, 2H), 2.64 (t, J=7.3 Hz, 2H), 3.90 (m, 2H), 4.59 (quint., J=7.2 Hz, 1H), 6.31 (d, 1H), 7.16 (m, 3H), 7.24 (m, 2H). $^{13}$C-nmr (CDCl$_3$): δ=18.3, 18.75, 18.78, 26.8, 27.5, 34.9, 35.3, 47.8, 71.2, 125.7, 128.2, 128.3, 141.3, 172.1, 173.0. C$_{17}$H$_{25}$NO$_3$ (MW=291.39, Mass Spectroscopy (MH$^+$292)).

Example A11

Synthesis of N-(5-phenylpentanoyl)-L-alanine iso-Butyl Ester

Following General Procedure B' and using 5-phenylpentanoic acid (Aldrich) and L-alanine iso-butyl ester hydrochloride (from Example B' above), the title compound was prepared as an oil. The reaction was monitored by tlc on silica gel and purification was by extraction with Et$_2$O followed by washes with aqueous K$_2$CO$_3$ and aqueous HCl.

NMR data was as follows:

$^1$H-nmr (CDCl$_3$): δ=7.23 (m, 2H), 7.17 (m, 3H), 6.30 (d, 1H), 4.59 (quint., J=7.3 Hz, 1H), 3.91 (m, 2H), 2.61 (t, J=7.2 Hz, 2H), 2.22 (t, J=7.2 Hz, 2H), 1.93 (m, 1H), 1.66 (m, 4H), 1.38 (d, J=7.2 Hz, 3H), 0.92 (d, J=6.7 Hz, 6H). $^{13}$C-nmr (CDCl$_3$): δ=173.1, 172.3, 142.0, 128.2, 128.1, 125.6, 71.2, 47.8, 36.1, 35.5, 30.8, 27.5, 25.0, 18.80, 18.77, 18.4. C$_{18}$H$_{27}$NO$_3$ (MW=305.39, Mass Spectroscopy (MH$^+$306)).

Example A12

Synthesis of N-[(4-pyridyl)acetyl]-D,L-alanine iso-Butyl Ester

Following General Procedure F' and using 4-pyridylacetic acid hydrochloride (Aldrich) and (D,L)-alanine iso-butyl ester hydrochloride (from Example B' above), the title compound was prepared as a solid having a melting point of 64–66° C. The reaction was monitored by tlc on silica gel (Rf=0.43 10% methanol/dichloromethane) and purification was by silica gel chromatography.

NMR data was as follows:

$^1$H-nmr (CDCl$_3$): δ=8.51 (dd, J=1.6, 2.8, 1.6, 2H); 7.23 (dd, J=4.3, 1.6, 4.4, 2H); 6.71 (d, J=6.8, 1H); 4.56 (quint., J=7.3, 7.2, 1H); 3.88 (m, 2H); 3.53 (s, 2H); 1.89 (m, 1H); 1.36 (d, J=7.2, 3H); 0.88 (d, J=6.7, 6H). $^{13}$C-nmr (CDCl$_3$): δ=173.5, 169.3, 150.5, 144.4, 125.1, 72.1, 48.9, 43.0, 28.2, 19.5,19.5,18.9. C$_{14}$H$_{20}$N$_2$O$_3$ (MW=264, Mass Spectroscopy (MH$^+$265)).

Example A13

Synthesis of N-(phenylacetyl)-L-alanine iso-Butyl Ester

Following General Procedure B' and using phenylacetyl chloride (Aldrich) and L-alanine iso-butyl ester hydrochloride (from Example B' above), the title compound was prepared as a solid having a melting point of 45°–47° C. The reaction was monitored by tlc on silica gel and purification was by extraction with $Et_2O$ followed by washes with aqueous $K_2CO_3$ and aqueous HCl.

NMR data was as follows:

$^1$H-nmr ($CDCl_3$): δ=7.24–7.39 (m, 5H), 6.14 (d, 1H), 4.58 (t, J=7.3 Hz, 1H), 3.88 (m, 2H), 3.58 (s, 2H), 1.90 (m, 1H), 1.35 (d, J=7.2 Hz, 3H), 0.89 (d, J=6.7 Hz, 6H). $^{13}$C-nmr ($CDCl_3$): δ=172.8, 170.4, 134.5, 129.3, 128.9, 127.2, 71.3, 48.1, 43.5, 27.5, 18.9, 18.8, 18.4. $C_{15}H_{21}NO_3$ (MW=263.34, Mass Spectroscopy ($MH^+$264)).

Example A14

Synthesis of 2-[(3,4-dichlorophenyl)acetamido]butyric Acid iso-Butyl Ester

Following General Procedure I' above and using 3,4-dichlorophenylacetic acid (Aldrich) and iso-butyl 2-aminobutyrate (prepared following General Procedure J' above) the title compound was prepared. The reaction was monitored by tlc on silica gel and purification was by filtration as described in the general procedure.

NMR data was as follows:

$^1$H-nmr ($CDCl_3$): δ=7.36 (m, 3H), 6.03 (bd, 1H), 4.54 (m, 1H), 3.87 (m, 2H), 3.49 (s, 2H), 1.93 (m, 2H), 1.72 (m, 1H), 0.88 (d, 6H), 0.80 (t, 3H).

Example A15

Synthesis of 2-[(3-methoxyphenyl)acetamido]butyric Acid iso-Butyl Ester

Following General Procedure I' above and using 3-methoxyphenylacetic acid (Aldrich) and iso-butyl 2-aminobutyrate (prepared frollowing General Procedure J' above), the title compound was prepared. The reaction was monitored by tlc on silica gel and purification was by filtration as described in the general procedure.

NMR data was as follows:

$^1$H-nmr ($CDCl_3$): δ=6.75 (m, 4H), 5.93 (bd, 1H), 4.51 (m, 1H), 3.83 (m, 2H), 3.75 (s, 2H), 3.52 (s, 2H), 1.82 (m, 2H), 1.60 (m, 1H), 0.84 (d, 6H), 0.74 (t, 3H). $C_{17}H_{25}NO_4$ (MW=307.39, Mass Spectroscopy ($MH^+$309)).

Example A16

Synthesis of 2-[(4-nitrophenyl)acetamido]butyric Acid iso-Butyl Ester

Following General Procedure I' above and using 4-nitrophenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr ($CDCl_3$): δ=8.16 (d, 2H), 7.44 (d, 2H), 6.04 (bd, 1H), 4.55 (m, 1H), 3.86 (m, 2H), 3.66 (s, 2H), 1.86 (m, 2H), 1.67 (m, 1H), 0.85 (d, 6H), 0.81 (t, 3H). $C_{16}H_{22}N_2O_5$ (MW=322.36, Mass Spectroscopy ($MH^+$323)).

Example A17

Synthesis of 2-[(3,4-Methylenedioxyphenyl)acetamido]butyric Acid iso-Butyl Ester Following General Procedure I' above and using 3,4-(methylenedioxy)-phenyl acetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr ($CDCl_3$): δ=6.72 (m, 3H), 5.92 (bd, 1H), 4.54 (m, 1H), 3.86 (m, 2H), 3.66 (s, 2H), 1.86 (m, 2H), 1.66 (m, 1H), 0.89 (d, 6H), 0.79 (t, 3H).

Example A18

Synthesis of 2-[(Thien-3-yl)acetamido]butyric Acid iso-Butyl Ester

Following General Procedure I' above and using 3-thiopheneacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr ($CDCl_3$): δ=7.37 (m, 1H), 7.16 (m, 1H), 7.04 (m, 1H), 6.05 (bd, 1H), 4.57 (m, 1H), 3.66 (s, 2H), 1.93 (m, 2H), 1.67 (m, 1H), 0.91 (d, 6H), 0.86 (t. 3H).

Example A19

Synthesis of 2-[(4-Chlorophenyl)acetamido]butyric Acid iso-Butyl Ester

Following General Procedure I' above and using 4-chlorophenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr ($CDCl_3$): δ=7.22 (m, 2H), 7.11 (m, 2H), 5.80 (m, 1H), 4.44 (m, 1H), 3.78 (m, 2H), 3.43 (s, 2H), 1.77 (m, 2H), 1.56 (m, 1H), 0.83 (d, 6H), 0.71 (t, 3H).

Example A20

Synthesis of 2-[(3-Nitrophenyl)acetamido]butyric Acid iso-Butyl Ester

Following General Procedure I' above and using 3-nitrophenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr ($CDCl_3$): δ=8.15 (m, 2H), 7.65 (m, 1H), 6.08 (m, 1H), 4.46 (m, 1H), 3.92 (m, 2H), 3.68 (s, 2H), 1.91 (m, 2H), 1.75 (m, 1H), 0.98 (d, 6H), 0.71 (t, 3H).

Example A21

Synthesis of 2-[(2-Hydroxyphenyl)acetamido]butyric Acid iso-Butyl Ester

Following General Procedure I' above and using 2-hydroxyphenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.14 (m, 1H), 7.01 (m, 1H), 6.93 (m, 1H), 6.79 (m, 1H), 6.46 (m, 1H), 4.51 (m, 1H), 3.87 (m, 2H), 3.57 (s, 2H), 2.01 (m, 2H), 1.75 (m, 1H), 0.89 (d, 6H), 0.85 (t, 3H).

Example A22

Synthesis of 2-[(2-Naphthyl)acetamido]butyric Acid iso-Butyl Ester

Following General Procedure I' above and using 2-naphthylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.83 (m, 7H), 5.95 (m, 1H), 4.58 (m, 1H), 3.84 (m, 2H), 3.75 (s, 2H), 1.89 (m, 2H), 1.63 (m, 1H), 0.91 (d, 6H), 0.81 (t, 3H). C$_{20}$H$_{25}$NO$_3$ (MW 327.42, Mass Spectroscopy (MH$^+$328)).

Example A23

Synthesis of 2-[(2,4-Dichlorophenyl)acetamido]butyric Acid iso-Butyl Ester

Following General Procedure I' above and using 2,4-dichlorophenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.49 (m, 1H), 7.22 (m, 2H), 5.98 (m, 1H), 4.52 (m, 1H), 3.86 (m, 2H), 3.61 (s, 2H), 1.84 (m, 2H), 1.6 2 (m, 1H), 0 .87 (d, 6H), 0.80 (t, 3H), Example A24

Synthesis of 2-[(4-Bromophenyl)acetamido]butyric Acid iso-Butyl Ester

Following General Procedure I' above and using 4-bromophenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.43 (d, 2H), 7.19 (d, 2H), 5.85 (m, 1H), 4.51 (m, 1H), 3.81 (m, 2H), 3.47 (s, 2H), 1.84 (m, 2H), 1.61 (m, 1H), 0.84 (d, 6H), 0.76 (t, 3H), C$_{16}$H$_{22}$NO$_3$Br (MW=356.26, Mass Spectroscopy (MH$^+$358)).

Example A25

Synthesis of 2-[(3-Chlorophenyl)acetamido]butyric Acid iso-Butyl Ester

Following General Procedure I' above and using 3-chlorophenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.25 (m, 3H), 7.12 (m, 1H), 5.80 (m, 1H), 4.52 (m, 1H), 3.86 (m, 2H), 3.50 (s, 2H), 1.87 (m, 2H), 1.67 (m, 1H), 0.88 (d, 6H), 0.77 (t, 3H). C$_{16}$H$_{22}$NO$_3$Cl (MW=311.81 Mass Spectroscopy (MH$^+$313)).

Example A26

Synthesis of 2-[(3-Fluorophenyl)acetamido]butyric Acid iso-Butyl Ester

Following General Procedure I' above and using 3-fluorophenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.31 (m, 1H), 7.01 (m, 3H), 5.95 (m, 1H), 4.54 (m, 1H), 3.84 (m, 2H), 3.54 (s, 2H), 1.88 (m, 2H), 1.65 (m, 1H), 0.87 (d, 6H), 0.81 (t, 3H). C$_{16}$H$_{22}$NO$_3$F (MW=295.35 Mass Spectroscopy (MH$^+$296)).

Example A27

Synthesis of 2-[(Benzothiazol-4-yl)acetamido]butyric Acid iso-Butyl Ester

Following General Procedure I' above and using 4-benzothiazol-4-yl acetic acid (Chemservice) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.82 (m, 1H), 7.51–7.21 (m, 4H), 5.84 (m, 1H), 4.51 (m, 1H), 3.90 (s, 2H), 3.79 (m, 2H), 1.78 (m, 2H), 1.58 (m, 1H), 0.80 (d, 6H), 0.66 (t, 3H).

Example A28

Synthesis of 2-[(2-Methylphenyl)acetamido]butyric Acid iso-Butyl Ester

Following General Procedure I' above and using 2-methylphenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.18 (m, 4H), 5.79 (m, 1H), 4.54 (m, 1H), 3.85 (m, 2H), 3.59 (s, 2H), 3.29 (s, 3H), 1.81 (m, 2H), 1.59 (m, 1H), 0.87 (d, 6H), 0.77 (t, 3H), C$_{17}$H$_{25}$NO$_3$ (MW=291.39 Mass Spectroscopy (M$^+$291)).

Example A29

Synthesis of 2-[(2-Fluorophenyl)acetamido]butyric Acid iso-Butyl Ester

Following General Procedure I' above and using 2-fluorophenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.28 (m, 1H), 7.09 (m, 3H), 6.03 (m, 1H), 4.54 (m, 1H), 3.87 (m, 2H), 3.57 (s, 2H), 1.89 (m, 2H), 1.64 (m, 1H), 0.88 (d, 6H), 0.80 (t, 3H).

Example A30

Synthesis of 2-[(4-Fluorophenyl)acetamido]butyric Acid iso-Butyl Ester

Following General Procedure I' above and using 4-fluorophenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.20 (m, 2H), 6.97 (m, 2H), 5.87 (m, 1H), 4.492 (m, 1H), 3.83 (m, 2H), 3.48 (s, 2H), 1.86 (m, 2H), 1.60 (m, 1H), 0.87 (d, 6H), 0.78 (t, 3H). $C_{16}H_{22}NO_3F$ (MW=295.35 Mass Spectroscopy (M$^+$296)).

Example A31

Synthesis of 2-[(3-Bromophenyl)acetamido]butyric Acid iso-Butyl Ester

Following General Procedure I' above and using 3-bromophenylacetic acid (Aldrich) and iso-butyl 2-aminobutyrate (prepared following General Procedure J' above), the title compound was prepared. The reaction was monitored by tlc on silica gel and purification was by filtration as described in the general procedure. NMR data was as follows:

$^1$H-nmr (CDCl$_3$): δ=7.45 (m, 2H), 7.23 (m, 2H), 5.95 (m, 1H), 4.55 (m, 1H), 3.84 (m, 2H), 3.55 (s, 2H), 1.89 (m, 2H), 1.68 (m, 1H), 0.91 (d, 6H), 0.81 (t, 3H). $C_{16}H_{22}NO_3Br$ (MW=356.26 Mass Spectroscopy (M$^+$357)).

Example A32

Synthesis of 2-[(3-trifluoromethylphenyl)acetamido]butyric Acid iso-Butyl Ester

Following General Procedure I' above and using 3-trifluoromethylphenylacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.52 (m, 1H), 7.47 (m, 2H), 6.01 (m, 1H), 4.56 (m, 1H), 3.86 (m, 2H), 3.61 (s, 2H), 1.84 (m, 2H), 1.62 (m, 1H), 0.87 (d, 6H), 0.80 (t, 3H), $C_{17}H_{22}NO_3F_3$ (MW=345.36 Mass Spectroscopy (MH$^+$345)).

Example A33

Synthesis of 2-[(2-Thienyl)acetamido]butyric Acid iso-Butyl Ester

Following General Procedure I' above and using 2-thiopheneacetic acid (Aldrich) and iso-butyl 2-aminobutyrate (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=6.89 (m, 3H), 6.07 (bd, 1H), 4.50 (m, 1H), 3.82 (m, 2H), 3.71 (s, 2H), 1.85 (m, 2H), 1.62 (m, 1H), 0.81 (d, 6H), 0.75 (t, 3H). $C_{14}H_{21}NO_3S$ (MW=283.39, Mass Spectroscopy (MH$^+$284)).

Example A34

Synthesis of 2-(Phenylacetamido)butyric Acid iso-Butyl Ester

Following General Procedure H' above and using phenylacetic acid (Aldrich) and iso-butyl 2-aminobutyrate (prepared following General Procedure J' above), the title compound was prepared. The reaction was monitored by tlc on silica gel and purification was by chromatography on silica gel using 9:1 toluene:EtOAc as the eluant.

NMR data was as follows:

$^1$H-nmr (CDCl$_3$): δ=7.17–7.28 (m, 5H), 6.23 (bd, 1H), 4.51 (m, 1H), 3.86 (m, 2H), 3.54 (s, 2H), 1.87 (m, 2H), 1.62 (m, 1H), 0.87 (d, 6H), 0.78 (t, 3H). $C_{16}H_{23}NO_3$ (MW=277.36, Mass Spectroscopy (MH$^+$277)).

Example A35

Synthesis of N-(Phenylacetyl)valine 2-Methylbutyl Ester

Step A. Preparation of N-(Phenylacetyl) Valine

To a stirred solution of 5.15 g (44 mmol) of valine (Bachem) in 50 mL (100 mmol) of 2N NaOH cooled to 0° C. was added dropwise 5.3 mL (40 mmol) of phenylacetyl chloride (Aldrich). A colorless oil precipitated. The reaction mixture was allowed to warm to room temperature and stirred for 18 hours, washed with 50 mL diethyl ether, acidified to pH 2–3 with aqueous HCl. The white precipitate formed was filtered off, washed thoroughly with water, followed by diethyl ether to give 7.1 g (30 mmol, 69% yield) of the title compound.

NMR data was as follows:

$^1$H-nmr (DMSO-d$_6$): δ=12.63 (s, 1H), 8.25 (d, J=8.6 Hz, 1H), 7.27 (m, 5H), 4.15 (m, 1H), 3.56 (d, J=13.8 Hz, 1H), 3.47 (d, J=13.8 Hz, 1H), 2.05 (m, 1H), 0.87 (d, J=6.8, Hz, 3H), 0.84 (d, J=6.8 Hz, 3). $^{13}$C-nmr (DMSO-d$_6$): δ=173.2, 170.4, 136.6, 129.0, 128.2, 126.3, 57.1, 41.9, 30.0, 19.2, 18.0 $C_{13}H_{17}NO_3$ (MW=235.29; Mass Spectroscopy (MH$^{+=}$236)).

Step B. Synthesis of N-(Phenylacetyl)valine 2-Methylbutyl Ester

Following General Procedure C' and using the N-(phenylacetyl) valine prepared in Step A above and 2-methylbutan-1-ol (Aldrich), the title compound was prepared as a diastereomeric mixture. The reaction was monitored by tlc on silica gel and purification was by filtration as described in the general procedure.

NMR data was as follows:

$^1$H-nmr (CDCl$_3$): δ=7.25–7.40 (m, 5H), 5.95 (d, 1H), 4.56 (m, 1H), 3.84–4.00 (m, 2H), 3.61 (s, 2H), 2.10 (m, 1H), 1.68 (m, 1H), 1.38 (m, 1H), 1.15 (m 1H), 0.82–0.94 (m, 9H), 0.76 (d, 3H). $^{13}$C-nmr (CDCl$_3$): δ=171.84, 171.81, 170.7, 134.6, 129.31, 129.27, 128.9, 127.3, 69.8, 57.0, 43.7, 33.9, 31.3, 25.9, 25.8, 18.9, 17.4, 16.34, 16.27, 11.12, 11.07. $C_{18}H_{27}NO_3$ (MW=305.42, Mass Spectroscopy (MH 306)).

Example A36

Synthesis of N-(Phenylacetyl)-L-methionine iso-Butyl Ester

L-Methionine (0.129 g, 0.869 mmols) (Aldrich) was taken-up in dioxane (5.0 mL) and treated with a saturated solution of sodium bicarbonate (5.0 mL) followed by phenylacetyl chloride (Aldrich) (0.114 mL, 0.822 mmols). After stirring for 17 hours at room temperature the mixture was diluted with ethyl acetate, the layers separated and the aqueous layer acidified to pH 2 with 5N HCl. The crude product was extracted into ethyl acetate, dried over sodium sulfate, vacuum dried and used without further purification.

N-phenylacetyl-L-methionine (0.1285 g, 0.447 mmol) was dissolved in 3.0 mL dioxane and iso-butyl alcohol (0.2 mL) and treated with EDC (0.094 g, 0.492 mmol), and catalytic DMAP (0.015 g). After stirring for 17 hours at 23°

C., the mixture was evaporated at reduced pressure to an oil, the residue was diluted in EtOAc and washed with 0.1 N HCl and saturated sodium bicarbonate. Chromatography on silica gel using 98:2 CHCl$_3$/MeOH as eluant provided the pure product.

NMR data was as follows:

$^1$H-nmr (CDCl$_3$): δ=7.4–7.23 (m, 5H), 6.14 (bd, 1H), 4.70 (m, 1H), 3.89 (d, 2H), 3.62 (s, 2H), 2.43 (m, 2H), 2.12 (m, 1H), 1.93 (m, 2H), 0.94 (d, 6H). C$_{17}$H$_{25}$NO$_3$S (MW=323.17, Mass Spectroscopy (M$^+$323).

Example A37

Synthesis of N-(Phenylacetyl)-L-leucine iso-Butyl Ester

L-Leucine (Aldrich) (0.114 g, 0.869 mmols) was taken-up in dioxane (5.0 mL) and treated with a saturated solution of sodium bicarbonate (5.0 mL) followed by phenylacetyl chloride (Aldrich) (0.114 mL, 0.822 mmols). After stirring for 17 hours at room temperature the mixture was diluted with ethyl acetate, the layers separated and the aqueous layer acidified to pH 2 with 5N HCl. The crude product was extracted into ethyl acetate, dried over sodium sulfate, vacuum dried and used without further purification.

N-Phenylacetyl-L-leucine (0.0081 g, 0.038 mmol) was dissolved in 2.0 mL CHCl$_3$ (EtOH free) and iso-butyl alcohol (0.055 mL) and treated with P-EPC (100 mg, 0.87 milliequivalents). The mixture was rotated for 4 days, filtered through a plug of cotton and the filtrate evaporated at reduced pressure to an oil which was sufficiently pure for testing.

NMR data was as follows:

$^1$H-nmr (CDCl): δ=7.22 (m, 5H), 5.57 (d, 1H), 4.35 (m, 1H), 3.35 (m, 3H), 1.35 (m, 4H), 0.68 (m, 9H). C$_{18}$H$_{27}$NO$_3$ (MW=305.40, Mass Spectroscopy (M$^+$305)).

Example A38

Synthesis of N-[(3-Chlorophenyl)acetyl]alanine 3-Methylbut-2-enyl ester

Following General Procedure C' above and using N-(3-chlorophenylacetyl alanine (from Example D' above) and 3-methylbut-2-en-1-ol (Aldrich), the title compound can be prepared. The reaction was monitored by tlc on silica gel and purification was by liquid chromatography using 30% EtOAc/hexane as the eluant.

NMR data was as follows:

$^1$H-nmr (CDCl$_3$): δ=7.39–7.16 (m, 4H), 6.06 (bd, 1H), 5.38–5.29 (m, 1H), 4.63 (d, J=9Hz, 2H), 3.56 (s, 2H), 1.79 (s, 3H), 1.7 (s, 3H), 1.39 (d, J=9Hz, 3H).

Example A39

Synthesis of N-[(3-Chlorophenyl)acetyl]alanine Cyclopropylmethyl Ester

Following General Procedure C' above, and using N-(3-chlorophenylacetyl alanine (from Example D' above) and cyclopropylmethanol (Aldrich), the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.2–7.1 (m, 4H), 6.09 (bs, 1H), 4.6 (dq, J=9 Hz, 1H), 3.96 (dd, J=9Hz, 2H), 3.59 (s, 2H), 1.2 (d, J=9Hz, 3H), 1.2–1.0 (m, 1H), 0.603–0.503 (m, 2H), 0.300–0.203 (m, 2H).

Example A40

Synthesis of N-[(3-Chlorophenyl)acetyl]alanine 2-Thienylmethyl Ester

Following General Procedure C' above, and using N-(3-chlorophenylacetyl alanine (from Example D' above) and 2-thiophenemethanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.37–6.97 (m, 7H), 5.97 (q, J=14 Hz, 2H), 4.6 (dq, J=9 Hz, 1H), 3.76 (s, 2H), 1.38 (d, J=9Hz, 3H).

Example A41

Synthesis of N-[(3-Chlorophenyl)acetyl]alanine (1-Methylcyclopropyl)methyl Ester Following General Procedure C' above, and using N-(3-chlorophenylacetyl alanine (from Example D' above) and (1-methylcyclopropyl)methanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=8.6 (bd, J=9 Hz, 1H), 3.86 (q, J=14 Hz, 2H), 3.4 (s, 2H), 2.29 (q, J=9 Hz, 1H), 1.3 (d, J=9Hz, 3H), 1.03 (s, 3H), 0.5–0.4 (m, 2H), 0.4–0.28 (m, 2H).

Example A42

Synthesis of N-[(3-Chlorophenyl)acetyl]alanine 3-Thienylmethyl Ester

Following General Procedure C' above, and using N-(3-chlorophenylacetyl alanine (from Example D' above) and 3-thiophenemethanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=8.03 (bd, J=9 Hz, 1H), 7.56–7.5 (m, 1H), 7.47 (bs, 1H), 7.4–7.17 (m, 4H), 7.06 (d, J=9 Hz, 1H), 5.1 (s, 2H), 4.3 (dq, 1H), 1.3 (d, J=9 Hz, 3H).

Example A43

Synthesis of N-[(3-Chlorophenyl)acetyl]alanine 2-Methylcyclopentyl Ester

Following General Procedure C' above, and using N-(3-chlorophenylacetyl alanine (from Example D' above) and 2-methylcyclopentanol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.39–7.16 (m, 4H), 6.3 (bd, 1H), 4.79–4.7 (m, 1H), 4.6–4.25 (m, J=9 Hz, 1H), 3.577 (s, 2H), 2.09–1.8 (m, 2H), 1.74–1.6 (m, 2H), 1.39 (dd, J=9 Hz, 3H), 1.2 (dt, J=9 Hz, 1H), 0.979 (dd, J=9 Hz, 2H). C$_{17}$H$_{22}$NO$_3$Cl (MW=323.82, Mass Spectroscopy (MH$^+$323).

Example A44

Synthesis of N-[(3-Chlorophenyl)acetyl]alanine 2-Methylprop-2-enyl Ester

Following General Procedure C' above, and using N-(3-chlorophenylacetyl alanine (from Example D' above) and 2-methylprop-2-en-1-ol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=7.39–7.16 (m, 4H), 6.03 (bs, 1H), 4.77 (s, 2H), 4.7–4.29 (m, 3H), 2.59 (s, 2H), 1.73 (s, 3H), 1.43 (d, J=9 Hz, 3H). C$_{15}$H$_{18}$NO$_3$Cl (MW=295.76, Mass Spectroscopy (MH$^+$295)).

Example A45

Synthesis of N-[(3-Chlorophenyl)acetyl]alanine Cyclohex-2-enyl Ester

Following General Procedure C' above, and using N-(3-chlorophenylacetyl) alanine (from Example D' above) and cyclohex-2-en-1-ol (Aldrich) the title compound can be prepared. The reaction was monitored by tlc on silica gel and purification was by liquid chromatography using 3:7 EtOAc:hexane as the eluant.

NMR data was as follows:

$^1$H-nmr (CDCl$_3$): δ=8.6 (bd, J=9 Hz, 1H), 7.4–7.2 (m, 4H), 6.0–5.8 (m, 1H), 5.7–5.5 (m, 1H), 5.1 (bs, 1H), 4.13–4.29 (m, 1H), 3.5 (s, 2H), 2.1–1.9 (m, 2H), 1.8–1.69 (m, 1H), 1.69–1.49 (m, 4H), 1.3 (dd, J=9 Hz, 3H). C$_{17}$H$_{20}$NO$_3$Cl (MW=321.8, Mass Spectroscopy (MH$^+$321.2)).

Example A46

Synthesis of N-[(2-Phenylbenzoxazol-5-yl)acetyl]alanine iso-Butyl Ester

Following General Procedure I' above, and using 5-(2-phenylbenzoxazol)-yl-acetic acid (CAS# 62143-69-5) and alanine iso-butyl ester (prepared following General Procedure J' above), the title compound was prepared.

NMR data was as follows:

$^1$H-nmr (CDCl$_3$): δ=8.24 (m, 3H), 7.68 (m, 1H), 7.51 (m, 5H), 6.04 (m, 1H), 4.58 (m, 1H), 3.85 (m, 2H), 3.68 (s, 2H), 1.9 (m, 1H), 1.35 (d, 3H), 0.87 (d, 6H). C$_{22}$H$_{24}$N$_2$O$_4$ (MW=380, Mass Spectroscopy (MH$^+$381)).

Example 47

Synthesis of N-[(3-Methylthiophenyl)acetyl]alanine iso-Butyl Ester

Following General Procedure I' above, and using 3-methylthiophenylacetic acid (CAS# 18698-73-2) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.14 (m, 2H), 7.01 (m, 1H), 4.56 (m, 1H), 3.88 (m, 2H), 3.54 (s, 2H), 2.46 (s, 3H), 1.89 (m, 1H), 1.35 (d, 3H), 0.85 (d, 6H). C$_{16}$H$_{23}$NO$_3$S (MW=309, Mass Spectroscopy (MH$^+$310)).

Example A48

Synthesis of N-4-[(2-Furyl)acetyl]alanine iso-Butyl Ester

Following General Procedure I' above, and using 2-furylacetic acid (CAS# 2745-26-8) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.36 (m, 1H), 6.34 (m, 1H), 6.21 (m, 1H), 4.56 (m, 1H), 3.91 (m, 2H), 3.61 (s, 2H), 1.92 (m, 1H), 1.38 (d, 3H), 0.89 (d, 6H). C$_{13}$H$_{19}$NO$_4$ (MW=253, Mass Spectroscopy (MH$^+$254)).

Example A49

Synthesis of N-[(Benzofuran-2-yl)acetyl]alanine iso-Butyl Ester

Following General Procedure I' above, and using benzofuran-2-ylacetic acid (Maybridge) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.51 (m, 1H), 7.44 (m, 1H), 7.25 (m, 2H), 6.67 (s, 1H), 4.60 (m, 1H), 3.87 (m, 2H), 3.77 (s, 2H), 1.88 (m, 1H), 1.38 (d, 3H), 0.87 (d, 6H). C$_{17}$H$_{21}$NO$_4$ (MW=303, Mass Spectroscopy (MH$^+$304)).

Example A50

Synthesis of N-[(Benzothiophen-3-yl)acetyl]alanine iso-Butyl Ester

Following General Procedure I' above, and using thianaphthen-3-ylacetic acid (Lancaster) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.89 (m, 1H), 7.76 (m, 1H), 7.38 (m, 3H), 6.07 (m, 1H), 4.57 (m, 1H), 3.92 (m, 2H), 3.82 (s, 4H), 1.84 (m, 1H), 1.32 (d, 3H), 0.85 (d, 6H). C$_{17}$H$_{21}$NO$_3$S (MW=319, Mass Spectroscopy (MH$^+$320)).

Example A51

Synthesis of N-[(2-Chloro-5-thienyl)acetyl]alanine iso-Butyl Ester

Following General Procedure I' above, and using 5-chloro-2-thienyl)acetic acid (CAS# 13669-19-7) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=6.77 (m, 1H), 6.68 (d, 1H), 6.31 (bm, 1H), 4.59 (m, 1H), 3.91 (m, 2H), 3.38 (s, 2H), 1.90 (m, 1H), 1.39 (d, 3H), 0.89 (d, 6H). C$_{13}$H$_{18}$NO$_3$SCl (MW=303, Mass Spectroscopy (MH$^+$303)).

Example A52

Synthesis of N-[(3-Methylisoxazol-5-yl)acetyl]alanine iso-Butyl Ester

Following General Procedure I' above, and using (3-methyl-isoxazol-5-yl)acetic acid (CAS# 19668-85-0) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=6.07 (s, 2H), 4.56 (m, 1H), 3.92 (m, 2H), 3.68 (s, 2H), 2.29 (s, 3H), 1.94 (m, 1H), 1.89 (d, 3H), 0.91 (d, 6H). C$_{13}$H$_{20}$N$_2$O$_4$ (MW=268, Mass Spectroscopy (MH$^+$269)).

Example A53

Synthesis of N-[(2-Phenylthiothienyl)acetyl]alanine iso-Butyl Ester

Following General Procedure I' above, and using (2-phenyl-thiothienyl)acetic acid and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.21–7.11 (m, 6H), 6.92 (d, 1H), 4.56(m, 1H), 3.87 (m, 2H), 3.72 (s, 2H), 1.94 (m, 1H), 1.38 (d, 3H), 0.89 (d, 6H). C$_{19}$H$_{23}$NO$_3$S$_2$ (MW=377, Mass Spectroscopy (MH$^+$378)).

Example A54

Synthesis of N-[(6-Methoxybenzothiophen-2-yl)acetyl]alanine iso-Butyl Ester

Following General Procedure I' above, and using (6-methoxythianaphthen-2-yl)acetic acid and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.59 (d, 1H), 7.33 (d, 1H), 7.16 (s, 1H), 7.03 (dd, 1H), 4.56 (m, 1H), 3.87(s, 3H), 3.84 (m, 2H), 3.76 (s, 2H), 1.85 (m, 1H), 1.30 (d, 3H), 0.86 (d, 6H). C$_{18}$H$_{23}$NO$_4$S (MW=349, Mass Spectroscopy (MH$^+$350)).

Example A55

Synthesis of N-[(3-Phenyl-1,2,4-thiadiazol-5-yl)acetyl]alanine iso-Butyl Ester

Following General Procedure I' above, and using (3-phenyl-1,2,4-thiadiazol-5-yl)acetic acid (CAS# 90771-06-5) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.47 (m, 5H), 4.66 (m, 1H), 4.16 (s, 2H), 3.91 (m, 2H), 1.93 (m, 1H), 1.48 (d, 3H), 0.93 (d, 6H). C$_{17}$H$_{21}$N$_3$O$_3$S (MW=347, Mass Spectroscopy (MH$^+$348)).

Example A56

Synthesis of N-[2-Phenyloxazol-4-yl)acetyl]alanine iso-Butyl Ester

Following General Procedure I' above, and using (2-phenyloxazol-4-yl)acetic acid (CAS# 22086-89-1) and alanine iso-butyl ester (prepared following General Procedure J' above), the title compound was prepared. The reaction was monitored by tlc on silica gel and purification was by filtration as described in the general procedure.

NMR data was as follows:

Example A57

Synthesis of N-[(3-Methylphenyl)acetyl]alanine iso-Butyl Ester

Following General Procedure I' above, and using 3-methylphenylacetic acid (Aldrich) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.21 (m, 1H), 7.07 (m, 3H), 4.54 (m, 1H), 3.83 (m, 2H), 3.52 (s, 2H), 2.35 (s, 3H), 1.87 (m, 1H), 1.32 (d, 3H), 0.88 (d, 6H). C$_{16}$H$_{23}$NO$_3$ (MW=277, Mass Spectroscopy (MH$^+$278)).

Example A58

Synthesis of N-[(2,5-Difluorophenyl)acetyl]alanine iso-Butyl Ester

Following General Procedure I' above, and using 2,5-difluorophenylacetic acid (Aldrich) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.08–6.94 (m, 3H), 4.57 (m, 1H), 3.91 (m, 2H), 3.56 (s, 2H), 1.92 (m, 1H), 1.41 (d, 3H), 0.91 (d, 6H). C$_{15}$H$_{19}$NO$_3$F$_2$ (MW 299, Mass Spectroscopy (MH$^+$ 300)).

Example A59

Synthesis of N-[(3,5-Difluorophenyl)acetyl]alanine iso-Butyl Ester

Following General Procedure I' above, and using 3,5-difluorophenylacetic acid (Aldrich) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=6.81 (m, 2H), 6.74 (m, 1H), 6.06 (m, 1H), 4.57 (m, 1H), 3.92 (m, 2H), 3.51 (s, 2H), 1.94 (m, 1H), 1.36 (d, 3H), 0.87 (d, 6H). C$_{15}$H$_{19}$NO$_3$F$_2$ (MW=299, Mass Spectroscopy (MH$^+$300)).

Example A60

Synthesis of N-[(3-Thienyl)acetyl]alanine iso-Butyl Ester

Following General Procedure I' above, and using 3-thiopheneacetic acid (Aldrich) and alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.33 (m, 1H), 7.14 (m, 1H), 7.01 (m, 1H), 6.09 (m, 1H), 4.58 (m, 1H), 3.88 (m, 2H), 3.60 (s, 2H), 1.91 (m, 1H), 1.37 (d, 3H), 0.92 (d, 6H). Optical Rotation: [α]$_{23}$–52 (c 1 MeOH) @ 589 nm. C$_{13}$H$_{19}$NO$_3$S (MW=269, Mass Spectroscopy (MH$^+$269)).

Example A61

Synthesis of N-[(4-Methylphenyl)acetyl]-L-alanine iso-Butyl Ester

Following General Procedure I' above, and using 4-methylphenylacetic acid (Aldrich) and L-alanine iso-butyl ester (prepared following General Procedure J' above), the title compound was prepared. The reaction was monitored by tlc on silica gel and purification was by filtration as described in the general procedure.

NMR data was as follows:

$^1$H-nmr (CDCl$_3$): δ=7.11 (s, 4H), 5.93 (m, 1H), 4.58 (m, 1H), 3.88 (m, 2H), 3.54 (s, 2H), 2.33 (s, 3H), 1.89 (m, 1H), 1.32 (d, 3H), 0.89 (d, 6H). C$_{16}$H$_{23}$NO$_3$ (MW=277.35, Mass Spectroscopy (MH$^+$278)).

Example A62

Synthesis of N-(Phenylacetyl)-L-alanine S-1-(Methoxycarbonyl) iso-Butyl Ester

Following General Procedure K' and using (S)-(+)-2-hydroxy-2-methylbutyric acid (Aldrich) in place of the amino acid, methyl (S)-(+)-2-hydroxy-2-methylbutyrate was prepared.

Methyl (S)-(+)-2-hydroxy-2-methylbutyrate was then coupled with carbobenzyloxy-L-alanine (Aldrich) using General Procedure E' to provide carbobenzyloxy-L-alanine S-1-(methoxycarbonyl) iso-butyl ester.

Carbobenzyloxy-L-alanine S-1-(methoxycarbonyl) iso-butyl ester (1.0 g) was then dissolved in 20 mL of methanol and 6N HCl (0.5 mL) and 10% palladium on carbon (0.1 g) were added. This reaction mixture was hydrogenated at 40 psi of hydrogen on a Parr apparatus for 5 hours at room temperature and then filtered through a pad of Celite. The filtrate was concentrated at reduced pressure to provide L-alanine S-1-(methoxycarbonyl) iso-butyl ester hydrochloride (98% yield).

L-Alanine S-1-(methoxycarbonyl) iso-butyl ester hydrochloride was then coupled to phenylacetic acid using General Procedure G' to provide the title compound.

NMR data was as follows:

$^1$H-nmr (CDCl$_3$): δ=7.35–7.20 (m, 5H), 6.22 (bd, 1H), 4.83 (d, 1H), 4.65 (p, 1H), 3.68 (s, 3H), 3.55 (s, 2H), 2.21 (m, 1H), 1.40 (d, 3H), 0.97 (d, 3H), 0.93 (d, 3H). $^{13}$C-nmr (CDCl$_3$): δ=173.25, 171.18, 170.22, 135.11, 129.94, 129.50, 127.88, 52.67, 48.49, 43.98, 30.53, 19.21, 18.75, 17.58.

Example A63

Synthesis of N-[(3-Nitrophenyl)acetyl]-L-alanine iso-Butyl Ester

Following General Procedure H' above and using 3-nitrophenylacetic acid (Aldrich) and L-alanine iso-butyl ester hydrochloride (from Example B' above), the title compound was prepared. The reaction was monitored by tlc on silica gel and purification was by recrystallization from butyl chloride.

NMR data was as follows: $^1$H-nmr (CDCl$_3$): δ=8.17 (m, 2H), 7.68 (d, 1H), 7.52 (t, 1H), 6.18 (m, 1H), 4.48 (m, 1H), 3.94 (m, 2H), 3.67 (s, 2H), 1.93 (m, 1H), 1.42 (d, 3H), 0.91 (d, 3H). Optical Rotation: [α]$_{23}$–49 (c 5, MeOH).

Example A64

Synthesis of N-[(3,5-Difluorophenyl)acetyl]alanine Ethyl Ester

Following General Procedure G' and using 3,5-difluorophenylacetic acid (Aldrich) and alanine ethyl ester (Aldrich), the title compound was prepared as a solid with a melting point of 93°–95° C. The reaction was monitored by tlc on silica gel (Rf=0.8 in EtOAC) and purification was by chromatography on silica gel using EtOAc as the eluant followed by recrystallization from 1-chlorobutane.

NMR data was as follows: $^1$H-nmr (DMSO-d$_6$): δ=1.30 (d, 3H); 3.52 (s, 2H). C$_{13}$H$_{15}$NO$_3$F$_2$ (MW=271.26, Mass Spectroscopy (MH$^+$271)).

Example A65

Synthesis of N-[(3-Nitrophenyl)acetyl]methionine Ethyl Ester

Following General Procedure G' above and using 3-nitrophenylacetic acid (Aldrich) and methionine ethyl ester hydrochloride (Aldrich), the title compound was prepared. The reaction was monitored by tlc on silica gel and purification was by recrystallization from butyl chloride.

NMR data was as follows:

$^1$H-nmr (CDCl$_3$): δ=8.18 (s, 1H), 8.15 (d, 1H), 7.66 (d, 1H), 7.48 (t, 1H), 6.30 (m, 1H), 4.67 (m, 1H), 4.21 (t, 2H), 3.67 (s, 2H), 2.47 (t, 2H), 2.12 (m, 2 H), 2.08 (s, 3H), 1.27 (t, 3H). Optical Rotation: [α]$_{23}$–30 (c 5, MeOH).

Example A66

Synthesis of N-[(3-Chlorophenyl)acetyl]alanine iso-Butyl Ester

Following General Procedure G' above and using 3-chlorophenylacetic acid (Aldrich) and alanine iso-butyl ester (prepared following General Procedure J' above), the title compound was prepared. The reaction was monitored by tlc on silica gel.

NMR data was as follows:

$^1$H-nmr (CDCl$_3$): δ=7.29 (m, 3H), 7.18 (m, 1H), 6.0 (m, 1H), 4.56 (m, 1H), 3.89 (m, 2H), 3.53 (s, 2H), 1.91 (m, 1H), 1.39 (d, 3 H), 0.91 (d, 3H). Optical Rotation: [α]$_{23}$–45 (c 5, MeOH). C$_{15}$H$_{20}$NO$_3$Cl (MW=297.78, Mass Spectroscopy (MH$^+$297)).

Example A67

Synthesis of N-[(3-Chlorophenyl)acetyl]alanine 2-(N,N-dimethylamino)ethyl Ester

Following General Procedure C' above, and using N-(3-chlorophenyl-acetyl)alanine (from Example D' above) and 2-(N,N-dimethyl amino) ethanol (Aldrich), the title compound can be prepared. The reaction was monitored by tlc on silica gel and purification was by liquid chromatography using 0.1: 2:0.79 NH$_4$OH:EtOH:CHCl$_3$ as the eluant.

NMR data was as follows:

$^1$H-nmr (CDCl$_3$): 7.37 (s, 1H), 7.33–7.2 (m, 3H), 4.675–4.6 (m, 1H), 4.5–4.37 (m, 1H), 4.25–4.13 (m, 1H), 3.6 (d, J=7 Hz, 2H), 2.86 (bs, 2H), 2.3 (s, 6H), 1.23 (d, J=9Hz, 3H). C$_{15}$H$_{21}$N$_2$O$_3$Cl (MW=313.799, Mass Spectroscopy (M$^+$313)).

Example A68

Synthesis of 2-[(3,5-Dichlorophenyl)acetamido]hexanoic Acid Methyl Ester

Following General Procedure F' above, an using 3,5-dichlorphenylacetic acid (from Example C' above) and L-norleucine methyl ester hydrochloride (Bachem), the title compound was prepared as a solid having a melting point of 77°–78° C. The reaction was monitored by tlc on silica gel (Rf=0.70 in 40% EtOAC/hexanes) and purification was by flash chromatography on silica gel using 40% EtOAc/hexanes as the eluant.

NMR data was as follows:

$^1$H-nmr (CDCl$_3$): δ=7.20 (s), 7.18 (s), 6.6 (m), 4.55 (m), 3.7 (s), 3.5 (s), 3.4 (s), 2.0 (s), 1.8 (m), 1.6 (m), 1.2 (m), 0.8 (t). $^{13}$C-nmr (CDCl$_3$): δ=173.54, 169.67, 138.43, 135.72, 128.33, 128.07, 78.04, 77.62, 77.19, 53.04, 52.90, 43.14, 32.57, 27.87, 22.81, 14.41.

Example A69

Synthesis of N-[(3,5-Diclorophenyl)acetyl]-L-alanine iso-Butyl Ester

Following General Procedure F' above, and using 3,5-dichlorophenylacetic acid (from Example C' above) and L-alanine iso-butyl ester hydrochloride (from Example B' above), the title compound was prepared as a solid having a melting point of 115°–116° C. The reaction was monitored by tlc on silica gel (Rf=0.40 in 3% methanol/dichloromethane) and purification was by flash chromatography on silica gel using 3% methanol/dichloromethane as the eluant.

NMR data was as follows:

$^1$H-nmr (CDCl$_3$): δ=7.27 (d, J=2 Hz, 1H), 7.19 (s, 2H), 6.22 (d, J=6 Hz, 1H), 4.59 (quint., J=7 Hz, 1H), 3.9 (q, J=4 Hz, 2H), 3.5 (s, 2H), 1.9 (m, 1H), 1.4 (d, J=7 Hz, 3H), 0.91 (d, J=7 Hz, 6H). $^{13}$C-nmr (CDCl$_3$): δ=173.45, 169.37, 138.31, 135.75, 128.39, 128.11, 78.04, 77.61, 77.19, 72.19, 54.03, 48.97, 43.12, 28.24, 19.52, 19.49, 19.09. C$_{15}$H$_{19}$NO$_3$Cl$_2$ (MW=331.9, Mass Spectroscopy (MH$^+$ 332)).

Example A70

Synthesis of N-(Cyclohexylacetyl)-L-alanine iso-Butyl Ester

Following General Procedure B' above, and using cyclohexylacetic acid (Aldrich) and L-alanine iso-butyl ester hydrochloride (from Example B' above), the title compound was prepared as a solid having a melting point of 92° C.–93° C. The reaction was monitored by tlc on silica gel (Rf=0.39 in 1:3 EtOAc:hexane) and purification was by extraction with Et$_2$O followed by washes with aqueous K$_2$CO$_3$ and aqueous HCl.

NMR data was as follows:

$^1$H-nmr (CDCl$_3$): δ=0.93 (d, J=6.7 Hz, 6H), 0.85–1.01 (m, 2H), 1.05–1.35 (m, 3H), 1.40 (d, J=7.1 Hz, 3H), 1.60–1.85 (m, 6H), 1.95 (m, 1H), 2.06 (d, J=7.0 Hz, 2H), 3.92 (m, 2H), 4.61 (m, 1H), 6.08 (bd, 1H). $^{13}$C-nmr (CDCl$_3$): δ=18.7, 18.9, 26.0, 26.1, 27.6, 33.0, 35.3, 44.6, 47.9, 71.4, 171.8, 173.3. C$_{15}$H$_{27}$NO$_3$ (MW=269.39, Mass Spectroscopy (MH$^+$270)).

Example A71

Synthesis of N-(Cyclopentylacetyl)-L-alanine iso-Butyl Ester

Following General Procedure B' above, and using cyclopentylacetic acid (Aldrich) and L-alanine iso-butyl ester hydrochloride (from Example B' above), the title compound was prepared as a solid having a melting point of 62° C.–64° C. The reaction was monitored by tlc on silica gel (Rf=0.37 in 1:3 EtOAc:hexane) and purification was by extraction with Et$_2$O followed by washes with aqueous K$_2$CO$_3$ and aqueous HCl.

NMR data was as follows:

$^1$H-nmr (CDCl$_3$): δ=0.87 (d, J=6.8 Hz, 6H), 1.01–1.17 (m, 2H), 1.34 (d, J=7.2 Hz, 3H), 1.40–1.62 (m, 4H), 1.70–1.83 (m, 2H), 1.89 (m, 1H), 2.15 (m, 2H), 3.86 (m, 2H), 4.55 (m, 1H), 6.30 (d, J=7.1 Hz, 1H). $^{13}$C-nmr (CDCl$_3$): δ=18.4, 18.78, 18.80, 24.8 (very high), 27.5, 32.27, 32.32, 36.9, 42.5, 47.7, 71.2, 172.2, 173.2. Elemental Analysis-Calc (%): C, 65.85; H, 9.87; N, 5.49; Found (%): C, 66.01; H, 10.08; N, 5.49. C$_{14}$H$_{25}$NO$_3$ (MW=255.36, Mass Spectroscopy (MH$^+$256)).

Example A72

Synthesis of N-[(Cyclohex-1-enyl)acetyl]-L-alanine iso-Butyl Ester

Following General Procedure B' above, and using cyclohex-1-enyl acetic acid (Alfa) and L-alanine iso-butyl ester hydrochloride (from Example B' above), the title compound was prepared as a solid having a melting point of 49° C.–51° C. The reaction was monitored by tlc on silica gel (Rf=0.40 in 1:3 EtOAc:hexane) and purification was by extraction with Et$_2$O followed by washes with aqueous K$_2$CO$_3$ and aqueous HCl.

NMR data was as follows:

$^1$H-nmr (CDCl$_3$): δ 0.91 (d, J=4.5 Hz, 3H), 0.93 (d, J=6.7 Hz, 3H), 1.40 (d, J=7.2 Hz, 3H), 1.52–1.70 (m, 4H), 1.97 (m, 3H), 2.06 (bs, 2H), 2.89 (s, 2H), 3.92 (m, 2H), 4.59 (m, 1H), 5.65 (s, 1H), 6.33 (d, J=6.6 Hz, 1H). $^{13}$C-nmr (CDCl$_3$): δ=18.7, 18.91, 18.93, 21.9, 22.7, 25.3, 27.6, 28.3, 46.1, 47.9, 71.4, 127.1, 132.5, 170.6, 173.1. Elemental Analysis-Calc (%): C, 67.38; H, 9.42; N, 5.24; Found (%): C, 67.34; H, 9.54; N, 5.16. C$_{15}$H$_{25}$NO$_3$ (MW=267.37, Mass Spectroscopy (MH$^+$268)).

Example A73

Synthesis of N-[(3-Chlorophenyl)acetyl]alanine 3-methylbut-2-enyl Thioester

Following General Procedure C' above, and using N-[(3-chlorophenyl)acetyl]alanine and 3-methyl-2-butene thioester (TCI), the title compound can be prepared. The reaction was monitored by tlc on silica gel and purification was by liquid chromatography using 3:7 EtOAc:Hexane as the eluant.

NMR data was as follows:

$^1$H-nmr (DMSO-d$_6$): δ=5.2–5.075 (m, 1H), 4.37 (dq, J=9 Hz, 1H), 3.56 (s), 3.43 (d, J=12 Hz, 2H), 1.266 (d, J=12 Hz, 6H), 1.3 (d, J=9 Hz, 3H). C$_{16}$H$_{20}$NO$_2$ClS (MW=325.86, Mass Spectroscopy (M$^+$325)).

Example A74

Synthesis of N-[(2-Phenyl)-2-fluoroacetyl]alanine Ethyl Ester

Following General Procedure F' above, and using α-fluorophenyl acetic acid (Aldrich) and alanine ethyl ester (Aldrich), the title compound was prepared. The reaction was monitored by tlc on silica gel (Rf=0.75 in 1:1 EtOAc:hexane) and purification was by chromatography on silica gel using 1:2 ethyl acetate/hexanes as the eluent.

NMR data was as follows:

$^1$H-nmr (DMSO-d$_6$): δ=1.14 (q, 3H), 1.34 (d, 3H), 4.07 (m, 2H), 4.33 (m, 1H), 5.84 (d, 1H), 6.01 (d, 1H), 7.40–7.55 (m, 5H), 8.87 (m, 1H). Cl$_3$H$_{16}$NO$_3$F (MW=253.27, Mass Spectroscopy (MH$^+$253)).

Example A75

Synthesis of N-(3,5-Difluorophenylacetyl)-L-phenylglycine Methyl Ester

Following General Procedure F above, and using 3,5-difluorophenylacetic acid (Aldrich) and L-phenylglycine methyl ester hydrochloride (Bachem), the title compound was prepared.

NMR data was as follows:

$^1$H-nmr (CDCl$_3$): δ=7.4–7.3 (m, 5H), 6.9–6.7 (m, 3H), 6.55 (d 1H, 7.1 Hz), 5.56 (d 1H 7 Hz), 3.72 (s 3H), 3.57 (s 2H). $^{13}$C-nmr (CDCl$_3$): δ=197.6, 177.6, 171.8, 169.3, 136.7, 129.6, 129.3, 127.8, 113.0, 112.9, 112.7, 111.4, 103.8, 103.5, 65.1, 57.2, 53.5, 45.1, 43.3, 43.3 C$_{17}$H$_{15}$NO$_3$F$_2$ (MW=319.31, Mass Spectroscopy (MH +320)).

Example A76

Synthesis of N-(3,5-Difluorophenylacetyl)-L-phenylglycine iso-Butyl Ester

The 3,5-difluorophenylacetic acid (Aldrich) was EDC coupled to L-phenylglycine methyl ester hydrochloride (Bachem) via General Procedure F above.

The resulting compound was placed in a large excess of the desired alcohol. A catalytic amount of dry NaH was added, and the reaction was followed by tlc until the presence of starting material was no longer detected. The reaction was quenched with a few milliliters of 1 N HCl, and after a few minutes of stirring saturated aqueous NaHCO$_3$ was added. The volume of the reaction mixture was reduced on a rotary evaporator until the excess alcohol was removed and then the remaining residue was taken up in ethyl acetate and additional water was added. The organic phase was washed with saturated aqueous NaCl and dried over MgSO$_4$. The solution was stripped free of solvent on a rotary evaporator, and the crude product residue was then further purified by chromatography.

NMR data was as follows:

$^1$H-nmr (CDCl$_3$): δ=7.35–7.3 (m 5H), 6.8–6.7 (m 3H), 6.60 (d 1H, 7 Hz), 5.55 (d 1H 7.1 Hz), 3.9 (m 2H), 3.60 (s 2H), 1.85 (m 1H 7 Hz), 0.8 (q 6H 7 Hz), $^{13}$C-nmr (CDCl$_3$): δ=171.3, 169.3, 165.4, 138.5, 137.0, 129.5, 129.2, 127.6, 113.1, 113.0, 112.8, 112.7, 103.8, 103.5, 103.2, 75.5, 57.2, 43.4, 43.3, 28.2, 19.3 C$_{20}$H$_{21}$NO$_3$F$_2$ (MW=361.39, Mass Spectroscopy (MH +362)).

Example A77

Synthesis of N-(Cyclopentylacetyl)-L-phenylglycine Methyl Eester

Following General Procedure D' above, and using cyclopentylacetic acid (Aldrich) with L-phenylglycine methyl ester hydrochloride (Bachem) the title compound was prepared.

NMR data was as follows:

$^1$H-nmr (CDCl$_3$): δ=7.35 (s, 5H), 6.44 (bd, 1H), 5.6 (d, 1H), 3.72 (s, 3H), 2.24 (bs, 3H), 1.9–1.4 (m, 6H), 1.2–1.05 (m, 2H). $^{13}$C-nmr (CDCl$_3$): δ=172.3, 171.7, 136.7, 129.0, 128.6, 127.3, 56.2, 52.7, 42.5, 36.9, 32.40, 32.38, 24.8.

Example A78

Synthesis of N-(Cyclopentylacetyl)-L-alanine Methyl Ester

Following General Procedure D' above, and using cyclopentylacetic acid (Aldrich) with L-alanine methyl ester hydrochloride (Sigma) the title compound was prepared.

NMR data was as follows:

$^1$H-nmr (CDCl$_3$): δ=6.38 (d, 1H), 4.50 (m, 1H), 3.65 (s, 3H), 2.13 (bs, 3H), 1.80–1.00 (m (includes d at 1.30, 3H), 11H). $^{13}$C-nmr (CDCl$_3$): δ=173.7, 172.5, 52.1, 47.6, 42.3, 36.8, 32.15, 32.14, 18.0 C$_{11}$H$_{19}$NO$_3$ (MW=213.28, Mass Spectroscopy (MH$^+$214)).

Example A79

Synthesis of N-(Cyclopropylacetyl)-L-phenylglycine Methyl Ester

Following General Procedure D' above, and using cyclopropylacetic acid (Aldrich) with L-phenylglycine methyl ester hydrochloride (Bachem), the title compound was prepared.

NMR data was as follows: $^1$H-nmr (CDCl$_3$): δ=7.35 (m, 5H), 6.97 (bd, J=7.2 Hz, 1H), 5.59 (d, J=7.8 Hz, 1H), 3.71 (s, 3H), 2.17 (m, 2H), 1.05–0.95 (m, 1H) 0.62 (m, 2H), (m, 2H). $^{13}$C-nmr(CDCl$_3$): δ=171.9, 174.6, 136.6, 129.0, 128.5, 127.2, 56.1, 52.7, 41.0, 6.9, 4.37, 4.33.

Example A80

Synthesis of N-(Cyclopropylacetyl)-L-alanine Methyl Ester

Following General Procedure D' above, and using cyclopropylacetic acid (Aldrich) with L-alanine methyl ester hydrochloride (Sigma), the title compound was prepared.

NMR data was as follows: $^1$H-nmr (CDCl$_3$): δ=6.60 (d, 1H), 4.55 (m, 1H), 3.69 (s, 3H), 2.10 (m, 2H), 1.34 (d, 3H), 0.95 (m, 1H), 0.58 (m, 2H), 0.15 (m, 2H). $^{13}$C-nmr (CDCl$_3$): δ=173.7, 172.3, 52.3, 47.7, 41.0, 18.2, 6.7, 4.27, 4.22.

Example A81

Synthesis of N-[(3-Nitrophenyl)acetyl]-L-methionine iso-Butyl Ester

Following General Procedure H' above, and using nitrophenylacetic acid (Aldrich) and L-methionine (Aldrich), the title compound was prepared as a tan oil. The reaction was monitored by tlc on silica gel.

NMR data was as follows:

$^1$H-nmr (CDCl$_3$): δ=8.16 (m, 2H), 7.67 (d, 1H), 7.32 (t, 1H), 6.31 (bd, 1H), 4.69 (m, 1H), 3.90 (d, 2H), 3.68 (s, 2H), 2.47 (t, 2H), 2.15 (m, 1H), 2.02 (s, 3H), 1.90 (m, 2H), 0.91 (d, 6H). C$_{17}$H$_{24}$N$_2$O$_5$S (MW=368.4, Mass Spectroscopy (MH$^+$368)).

The following General Procedures A"–B" and Examples B1–B2 illustrate the synthesis of N-(aryl/heteroarylacetyl) amino acid starting materials useful in this invention. Other N-(aryl/heteroarylacetyl)amino acids can be prepared using these procedures from commerically available or known starting materials.

GENERAL PROCEDURE A"

Acid Chloride Preparation 3,5-Difluorophenylacetic acid (30 g, 0.174 mol) (Aldrich) was dissolved in dichloromethane and this solution was cooled to 0° C. DMF (0.5 mL, catalytic) was added followed by the dropwise addition of oxalyl chloride (18 mL, 0.20 mol) over a 5 minute period. The reaction was stirred for 3 h and then rotoevaporated at reduced pressure to a residue which was placed on a high vacuum pump for 1 h to afford 3,5-difluorophenylacetyl chloride as a thin yellow oil. Other acid chlorides can be prepared in a similar manner.

GENERAL PROCEDURE B"

Schotten-Bauman Procedure 3,5-Difluorophenylacetyl chloride (from General Procedure A") was added dropwise to a 0° C. solution of L-alanine (Aldrich) (16.7 g, 0.187 mol) in 2 N sodium hydroxide (215 mL, 0.43 mol). The reaction was stirred for 1 h at 0° C. and then overnight at room temperature. The reaction was diluted with water (100 mL), then extracted with ethyl acetate (3×150 mL). The organic layer was then washed with brine (200 mL), dried over $MgSO_4$, and rotoevaporated at reduced pressure to a residue. Recrystallization of the residue from ethyl acetate/hexanes afforded the desired product (34.5 g, 82% yield). Other acid chlorides may be used in this procedure to provide for intermediates useful in this invention.

Example B1

Synthesis of N-(Phenylacetyl)-L-alanine

Following General Procedure B" above, title compound was prepared from phenylacetyl chloride (Aldrich) and L-alanine (Aldrich) as a solid having a melting point of 102–104° C.

NMR data was as follows:

$^1$H-nmr ($CDCl_3$): δ=9.14 (br s, 1H), 7.21–7.40 (m, 5H), 6.20 (d, J=7.0 Hz, 1H), 4.55 (m, 1H), 3.61 (s, 2H), 1.37 (d, J 7.1 Hz, 3H). $^{13}$C-nmr ($CDCl_3$): δ=176.0, 171.8, 134.0, 129.4, 127.5, 48.3, 43.2, 17.9.

Example B2

Synthesis of N-(3,5-Difluorophenylacetyl)-L-alanine

Following General Procedure B" above, the title compound was prepared from 3,5-difluorophenylacetyl chloride (from General Procedure A" above) and L-alanine (Aldrich).

NMR data was as follows:

$^1$H-nmr ($CD_3OD$): δ=8.32 (br s, 0.3H), 6.71 (m, 2H), 6.60 (m, 1H), 4.74 (br s, 1.7H), 4.16(m, 1H), 3.36(s, 2H), 1.19(d,J=7.3Hz, 3H). $^{13}$C-nmr ($CD_3OD$): δ=175.9, 172.4, 164.4 (dd, J=13.0, 245.3 Hz), 141.1, 113.1 (dd, J=7.8, 17.1 Hz), 102.9 (t, J=25.7 Hz), 49.5, 42.7, 17.5.

The following General Procedures A'''–C''' and Examples C1–C8 illustrate the synthesis of dipeptide ester starting materials useful in this invention. Other dipeptide esters can be prepared using these procedures from commerically available or known starting materials.

GENERAL PROCEDURE A'''

EDC Coupling Procedure

A round bottom flask containing a magnetic stir bar under an atmosphere of nitrogen at 0° C. or room temperature was charged with THF, carboxylic acid (1.0 eq), an amine or amine hydrochloride (1.1 eq.), 1-hydroxybenzotriazole hydrate (1.15–1.2 eq.), N,N-diisopropylethylamine (2.2–2.9 eq.), followed by 1-(3-dimethylaminopropyl)-3-ethylcarbodiimide hydrochloride (EDC) (1.15–1.2 eq.). The cooling bath was removed and the mixture allowed to warm to room temperature with stirring for 10–20 hours. The mixture was diluted with EtOAc and washed with 0.5 N aqueous HCl (2×), dilute aqueous $NaHCO_3$ (1×), brine (1×) and dried over either $Na_2SO_4$ or $MgSO_4$. The drying agent was removed by filtration and the filtrate concentrated in vacuo. The residue was either used without further purification or purified using standard procedures, such as flash chromatography on silica gel and/or recrystallization.

GENERAL PROCEDURE B'''

Removal of the N-tert-Boc Protecting Group

The N-tert-Boc-amine was dissolved in a suitable dry solvent (such as 1,4-dioxane or ethyl acetate) and the solution was cooled in an ice bath. Gaseous HCl was introduced into the solution until the mixture was saturated with HCl. The mixture was then stirred until the reaction was complete. The resulting mixture was concentrated under reduced pressure to yield the amine hydrochloride. The amine hydrochloride was used without purification or was triturated using, for example, diethyl ether and the resulting solid was collected by filtration.

GENERAL PROCEDURE C'''

EEDQ Coupling Procedure

A round bottom flask containing a magnetic stir bar under as atmosphere of nitrogen at room temperature was charged with THF, a carboxylic acid (1 eq.), an amine hydrochloride (1.1 eq.), and 2-ethoxy-1-ethoxycarbonyl-1,2-dihydroquinoline (EEDQ) (1.1 eq). The reaction mixture was allowed to stir for 15 minutes and then 4-methylmorpholine (1.1 eq) was added and stirring was continued at room temperature for 15–20 hours. The reaction mixture was concentrated in vacuo and the resulting residue was partitioned between ethyl acetate and water. The organic phase was separated and washed with saturated aqueous $NH_4Cl$ (2×), saturated aqueous $NaHCO_3$ (2×), followed by brine (1×). The organic phase was then dried over $Na_2SO_4$ and the drying agent was removed by filtration and the filtrate concentrated in vacuo. The residue was either used without further purification or purified using standard procedures, such as flash chromatography on silica gel and/or recrystallization.

Example C1

Synthesis of N-(L-Methionine) L-phenylglycine Methl Ester Hydrochloride

Following General Procedure A''' and using N-(tert-butoxycarbonyl)-L-methionine (Sigma) and L-phenylglycine methyl ester hydrochloride (Bachem), the Boc-protected dipeptide was prepared as a crude solid or foam. The resulting crude dipeptide was deprotected using General Procedure B''' to afford the title compound as a crude solid or foam.

Example C2

Synthesis of N-(2-Aminobutanoyl)-L-phenylglycine Methl Ester Hydrochloride

Following General Procedure A''' and using N-(tert-butoxycarbonyl)-2-aminobutyric acid (Sigma) and L-phenylglycine methyl ester hydrochloride (Bachem), the Boc-protected dipeptide was prepared as a crude solid or foam. The resulting crude dipeptide was deprotected using General Procedure B''' to afford the title compound as a crude solid or foam.

Example C3

Synthesis of N-(L-Leucine)-L-phenylglycine Methl Ester Hydrochloride

Following General Procedure A''' and using N-(tert-butoxycarbonyl)-L-leucine (Sigma) and L-phenylglycine methyl ester hydrochloride (Bachem), the Boc-protected dipeptide was prepared as a crude solid or foam. The resulting crude dipeptide was deprotected using General Procedure B''' to afford the title compound as a crude solid or foam.

Example C4

Synthesis of N-(L-Phenylalanine)-L-phenylglycine Methl Ester Hydrochloride

Following General Procedure A''' and using N-(tert-butoxycarbonyl)-L-phenylalanine (Sigma) and L-phenylglycine methyl ester hydrochloride (Bachem), the Boc-protected dipeptide was prepared as a crude solid or foam. The resulting crude dipeptide was deprotected using General Procedure B''' to afford the title compound as a crude solid or foam.

Example C5

Synthesis of N-(Glycine)-L-phenylglycine Methl Ester Hydrochloride

Following General Procedure A''' and using N-(tert-butoxycarbonyl)glycine (Sigma) and L-phenylglycine methyl ester hydrochloride (Bachem), the Boc-protected dipeptide was prepared as a crude solid or foam. The resulting crude dipeptide was deprotected using General Procedure B''' to afford the title compound as a crude solid or foam.

Example C6

Synthesis of N-(L-Phenylglycine)-L-phenylglycine Methl Ester Hydrochloride

Following General Procedure C''' and using N-(tert-butoxycarbonyl)-L-phenylalanine (Sigma) and L-phenylglycine methyl ester hydrochloride (Bachem), the Boc-protected dipeptide was prepared as a crude solid or foam. The resulting crude dipeptide was deprotected using General Procedure B''' to afford the title compound as a crude solid or foam.

Example C7

Synthesis of N-(L-Valine)-L-phenylglycine Methl Ester Hydrochloride

Following General Procedure A''' and using N-(tert-butoxycarbonyl)-L-valine (Sigma) and L-phenylglycine methyl ester hydrochloride (Bachem), the Boc-protected dipeptide was prepared as a crude solid or foam. The resulting crude dipeptide was deprotected using General Procedure B''' to afford the title compound as a crude solid or foam.

Example C8

Synthesis of N-[(S)-2-Aminocyclohexylacetyl)-L-phenylglycine Methl Ester Hydrochloride Following General Procedure A''' and using N-(tert-butoxycarbonyl)-(S)-aminocyclohexylacetic acid (e.g., Boc-L-cyclohexylglycine) and L-phenylglycine methyl ester hydrochloride (Bachem), the Boc-protected dipeptide was prepared as a crude solid or foam. The resulting crude dipeptide was deprotected using General Procedure B''' to afford the title compound as a crude solid or foam.

The following Examples D1–D4 illustrate the synthesis of various intermediates useful as starting materials for this invention. Similar intermediates can be prepared using these procedures and commerically available or known starting materials.

Example D1

Synthesis of 3,5-Difluorophenyl-α-fluoroacetic Acid

Methyl 3,5-difluoromandelate was prepared following General Procedure G below and using commmerically available 3,5-difluoromandelic acid. The resultant α-hydroxy methyl ester was fluorinated according to the general procedure described in W. J. Middleton, et al., $Org. Synth. Col. Vol. VI$, 835. Specifically, a solution of diethylaminosulfur trifluoride (1.1 eq) in $CH_2Cl_2$ was cooled to 0° C. and treated with methyl 3,5-difluoromandelate (1.0 eq) as a solution in $CH_2Cl_2$. After 10 min. the cooling bath was removed and the reaction was stirred at ambient temperature for 30 min. The reaction was monitored by tlc (Rf=0.65, 1:1 ethyl acetate/hexanes). The mixture was then poured onto ice and the layers separated. The organic phase was washed with saturated aqueous $NaHCO_3$ and brine. The organic layer was dried over $Na_2SO_4$, filtered, and concentrated in vacuo. The product was purified by LC2000 chromatograpy (180 mL/min) using 10% EtoAc/hexanes as the eluent. The resulting methyl 3,5-difluorophenyl-α-fluoroacetate was hydrolyzed by dissolving the ester in 70% aqueous dioxane and treating with lithium hydroxide (2.0 eq.). No starting material remained by tlc after 2 h. The dioxane was removed via rotary evaporation. The aqueous mixture was first washed with ethyl acetate and then acidified with 0.01 N HCl. The aqueous layer was extracted with ethyl acetate. The organic phase was washed with brine, dried over $Na_2SO_4$, filtered, and concentrated. The crude solid was recrystallized from ethyl acetate/hexanes affording 3,5-difluorophenyl-α-fluoroacetic acid as a white solid having a melting point of 90–110° C. $C_8H_5F_3O_2$ (MW=190.1); mass spectroscopy: 190.1.

Example D2

Synthesis of (S)-2-Hydroxy-2-methyl-1-phenylprop-1-ylamine (S)-2-Hydroxy-2-methyl-1-phenylprop-1-ylamine was prepared by adding 5.0 equivalents of methyl magnesium bromide to a solution of L-phenylglycine methyl ester hydrochloride in THF at 0° C. The reaction mixture was stirred for 1 hour and then quenched with sodium bicarbonate. After standard work-up conditions, the residue was purified by silica gel chromatography using 10% MeOH/$CHCl_3$ as the eluent.

Example D3

Synthesis of Methyl (S)-2-Amino-2-(6-methoxy-2-naphthyl)acetate (S)-2-(tert-Butoxycarbonylamino)-2-(6-methoxy-2-naphthyl)acetic acid was prepared from 2-(6-methoxy-2-naphthyl)acetic acid according to the general method described by D. A. Evans, et al., $J. Amer. Chem. Soc.$, (1990), 112, 4011–4030. Briefly, (S)-3-(6-methoxy-2-naphthylacetyl)-4-benzyl-2-ozazolidinone was converted to (S)-3-[(S)-6-methoxy-2-naphthyl-α-azidoacetyl)-4-benzyl-2-ozazolidinone via standard enolate azidation procedures using potassium 1,1,1,3,3,3-hexamethyldisilazane and trimethylsilyl azide at −78° C. Treatment of the azide derivative with 3 equivalents of lithium hydroxide in THF then provided (S)-2-azido-2-(6-methoxy-2-naphthyl)acetic acid. Reduction of this intermediate, as its sodium salt, in 1:1 1,4-dioxane/water (0.05 M) with 1 atm of hydrogen, 10% Pd/C at 25° C. afforded (S)-2-azido-2-(6-methoxy-2-naphthyl)acetic acid, which was then converted, without isolation, to its N-Boc derivative on treatment with 1.4 equivalents of di-tert-butyl dicarbonate and 0.47 equivalents of sodium carbonate. The product was isolated by the acidification to pH 2 with 1 N NaHSO$_4$ and extraction with three portions of ethyl acetate. The product was recrystallized from ethyl acetate/hexanes to afford a white solid, m.p.=176° C. (shrink); 197–199° C. (dec).

NMR data was as follows:

$^1$HMR (DMSO-d$_6$): δ=12.78 (s, 1H), 7.84–7.77 (m, 3H), 7.62 (d, J=8 Hz, 1H), 7.49 (d, J=8 Hz, 1H), 7.31 (d, J=2 Hz, 1H), 7.17 (dd, J=9, 2 Hz, 1H), 5.22 (d, J=8 Hz, 1H), 3.87 (s, 3H), 1.39 (s, 9H).

(S)-2-(tert-Butoxycarbonylamino)-2-(6-methoxy-2-naphthyl)acetic acid was then converted into the methyl ester using General Procedure G below. The methyl ester was then dissolved in CH$_2$Cl$_2$ and this solution cooled to 0° C. Trifluoroacetic acid (50 molar eq.) was added and the reaction was allowed to warm to room temperature and stirring was continued for 2 hrs. The reaction mixture was then concentrated and the residue extracted into CH$_2$Cl$_2$ and washed with sodium bicarbonate solution. The organic layer was dried over Na$_2$SO$_4$, filtered and concentrated to yield methyl (S)-2-amino-2-(6-methoxy-2-naphthyl)acetate.

Example D4

Synthesis of Methyl 2-Amino-2-(thieno[2,3-b]thiophen-2-yl)acetate

To a 3.75 mole equivalents of sodium hydride (oil free) was added DMF and the resulting mixture was cooled to 0° C. A solution of methyl thieno[2,3-b]thiophene-2-carboxylate (1 mole eq.) and methyl methylsulfinyl methyl sulfide (1.1 mole eq.) in DMF was then added dropwise and the reaction mixture was stirred at 0° C. for 30 min and then allowed to warm to room temperature and stirring was continued for 3 h. The reaction was then quenched with methanol and the product extracted into EtOAc. The organic extracts were washed with water followed by brine, and then dried over Na$_2$SO$_4$, filtered and concentrated to give a gummy brown oil. The residue was slurried in diethyl ether and the resulting solid collected. The solid was then dissolved in hot ethyl acetate and decolorizing carbon was added. The mixture was then filtered and solvent removed to give a solid, which was used without further purification.

Acetic anhydride (10 mole eq.) and acetic acid (1.8 mole eq.) were mixed together and heated to 70° C. for 15 min. and then cooled to 65° C. The solid sulfone from above was added in portions and the reaction was allowed to stir at 70° C. for 30 min. and then cooled and concentrated. The resulting solid was taken up in ethyl acetate and washed with sodium bicarbonate solution, followed by 1 N NaS$_2$O$_3$ solution. The solution was then dried over MgSO$_4$, filtered and concentrated to give methyl 2-keto-2-(thieno[2,3-b]thiophen-2-yl)thioacetate as a solid, which was used without further purification.

To the 2-keto compound (0.0165 moles) (4.0 g) was added 270 mL of methanol and 16.5 mL of 1 N NaOH. The reaction was allowed to stir for 6 h at room temperature and then methoxyamine (1.38 g, 0.0165 moles) was added and stirring was continued for 18 h. The reaction mixture was then concentrated and the residue dissolved in ethyl acetate and washed with water. The aqueous layer was then acidified with in HCl and the oily product was extracted into ethyl acetate and washed with brine. The organic layer was dried over MgSO$_4$, filtered and concentrated to give 4.0 g of 2-(hydroxyimino)-2-(thieno[2,3-b]thiophen-2-yl)acetic acid as a yellow solid.

The methyl ester was then prepared using General Procedure G below and the oxime was reduced to an amino group using General Procedure R below to afford methyl 2-amino-2-(thieno[2,3-b]thiophen-2-yl)acetate.

Example D5

Synthesis of N-Methyl-N'BOC-Leucinamide

A solution of 0.9968 g (4 mmol) of N-BOC-leucine (Bachem) and 1.2323 g (7.6 mmol) of CDI in 40 mL of THF was stirred for 1 hour, and then 0.5402 g (8 mmol) of methylamine hydrochloride (Aldrich) and 0.8092 g (8 mmol) of N-methylmorpholine were added. The mixture was stirred for 16 hours, evaporated at reduced pressure to dryness, and the residue was washed thproughly with water, 1N NaOH, water, followed by diethyl ether to yield 0.886 g (3.09 mmol, 70%) of the title compound.

Example D6

Synthesis of N-BOC-Norleucine amide

To a stirred mixture of 3.47 g (15 mmol) of BOC-norleucine (Bachem), 3.44 g (22.5 mmol) of 1-hydroxybenzotriazole monohydrate and 50 mL of dichloromethane at 0° C. was added 3.45 g (1.2 mmol) of EDC. The resulting mixture was stirred at 0° C. for 1 hour and then ammonia gas was bubbled through the mixture for 10 min. The cooling bath was allowed to warm to room temperature and the mixture stirred for 18 hours. The mixture was evaporated at reduced pressure to dryness, triturated with 20% Na$_2$CO$_3$. The resulting solid was collected by filtration and washed with water to yield 2.69 g (11.7 mmol, 78%) of the title compound.

Example D7

Synthesis of N-[N-(3,5-Difluorophenylacetyl)-L-alaninyl]-L-alanine

The title compound was prepared by dissolving 1.98 g (0.006 mols) of N-[N-(3,5-difluorophenylacetyl)-L-alaninyl]-L-alanine ethyl ester (from Example 85 below) in 60 mL dioxane and 15 mL of H$_2$O and adding LiOH (0.25 g, 0.006 mol) that has been dissolved in 15 mL of H$_2$O. After stirring for 3 hours, the dioxane was removed under reduced pressure and the residue diluted with EtOAc, the layers were separated and the aqueous layer acidified to pH 2. The aqueous layer was back extracted with EtOAc (4×100 ml), and the combined organics were dried over Na$_2$SO$_4$ and the solvent was removed under reduced pressure after filtration. The residue was recrystallized from EtOAc/isooctane giving 1.7 g (90%). C$_{14}$H$_{16}$F$_2$N$_2$O$_4$ requires C, 53.50 H, 5.13 N, 8.91. Anal found C, 53.30 H, 5.26 N, 8.98.

Example D8

Synthesis of m-Nitrophenylacetyl-L-alanine 2,4,5-Trichlorophenyl Ester m-Nitrophenylacetyl-L-alanine (1 eq.) and 2,4,5-tricholophenol (1.3 eq.) were stirred in dicholomethane. A 1.0 M solution of 1,3-dicyclohexylcarbodiimide in dichloromethane (1.2 eq.) was added and the mixture was stirred at ambient temperature for 16 hours. The resulting mixture was filtered and the filtrate was concentrated under reduced pressure. The resulting oil was purified by silica gel chromatography using 1:2 ethyl acetate/hexanes as the eluant to provide the title compound as a pink solid. For $C_{17}H_{13}Cl_3N_2O_5$: Calc. 47.30% C, 3.04% H, 6.49% N. Found 47.57% C, 3.18% H, 6.47% N.

Example D9

Synthesis of D,L-α-Methylphenylglycine Ethyl Ester

The title was prepared using the procedures described in J. J. Fitt and H. W. Gschwend, *J. Org. Chem.*, 42, No. 15, 2639 (1977). More specifically, D,L-phenylglycine (Aldrich) was stirred in dimethylformamide dimethylacetal and the mixture was heated at reflux under an atmosphere of dry nitrogen for 4 hours. After cooling, the mixture was concentrated under reduced pressure to provide a yellow oily solid. The mixture was slurried in diethyl ether and filtered through Celite. The filtrate was concentrated to an orange oil which was purified by vacuum distillation to provide a yellow oil which solidified. The yellow solid was stirred in dry THF at −20° C. under dry nitrogen. Lithium bis(trimethylsilyl)amide (1.05 eq, 1.0M solution in THF) was added dropwise. The resulting mixture was allowed to warm to −10° C. and stirring was continued for 1 hour at that temperature. Methyl iodide (1.05 eq) was added and the mixture was allowed to warm ambient temperature with stirring. After 14 hours, the mixture was concentrated. The residue was partitioned between aqueous potassium carbonate and chloroform. The organic portion was dried (sodium sulfate) and concentrated under reduced pressure. The product was purified by silica gel chromatography to yield a yellow oil. The yellow oil was stirred in absolute ethanol. Dry zinc chloride (4 eq.) was added and the mixture was heated at reflux. After 14 hours, the mixture was concentrated under reduced pressure to provide a yellow oil. The oil was partitioned between aqueous potassium carbonate and chloroform. The organic portion was dried (sodium sulfate) and concentrated under reduced pressure. The title compound was purified by silica gel chromatography.

Example D10

Synthesis of D,L-Phthalimidoalanine Ethyl Ester Hydrochloride

N-(Diphenylmethylene)glycine ethyl ester (1 eq.) (Aldrich) was stirred in dry THF at −78° C. under an atmosphere of dry nitrogen. Lithium bis(trimethylsiyl)amide (1.02 eq, 1.0 M solution in THF) was added dropwise. The resulting mixture was stirred 1 hour at −78° C. A THF solution of N-(bromomethyl)phthalimide (1.1 eq) (Aldrich) was added and the mixture was allowed to warm to ambient temperature and then stirring was continued for 1 hour. Hydrochloric acid (600 mL, 2N) was added and the mixture was stirred for 20 minutes. The THF was removed on a rotoevaporator. The resulting aqueous mixture was washed with diethyl ether, and then concentrated (to 100 mL) to yield a thick slurry. A white solid was collected, washed with cold water and dried in a vacuum oven to yield the title compound which was used without further purification.

Example D11

Synthesis of N-(3-Nitrophenylacetyl)-L-alanine

The title compound was prepared by dissolving 9.27 g (0.0348 mols) of the N-(3-nitrophenylacetyl)-L-alanine methyl ester in 60 mL of dioxane and 15 mL of $H_2O$ and adding LiOH (3.06 g, 0.0731 mol) that has been dissolved in 15 mL of $H_2O$. After stirring for 4 hours, the dioxane was removed under reduced pressure and the residue diluted with EtOAc, the layers were separated and the aqueous layer acidified to pH 2. The aqueous layer was back extracted with EtOAc (4×100 ml), the combined organics were dried over $Na_2SO_4$ and the solvent was removed under reduced pressure after filtration. The residue was recrystallized from EtOAc/isooctane giving 7.5 g (85%). $C_{11}H_{12}N_2O_5$ requires C, 52.38 H, 4.80 N, 11.11. Anal found C, 52.54 H, 4.85 N, 11.08. $[\alpha]_{23}$=−29.9 @ 589 nm.

Example D12

Synthesis of Methyl 2-Amino-2-(3-fluorophenyl) acetate Hydrochloride

Potassium cyanide (6.3, 0.1 mol) and ammonium carbonate (15.7 g, 0.2 mol) were dissolved in 50 mL of water (in a well ventilated fume hood). 3-Fluorobenzaldehyde (5.0 g, 0.04mol) was dissolved in 50 mL of EtOH and added to the reaction. After stirring at reflux under nitrogen atmosphere for 17 hours, the reaction was cooled to 23° C., the pH adjusted to 2.0 by the addition of 5 N HCl and cooled to 5° C. The resulting hydantoin was collected, rinsed with cold water and vacuum dried giving 3.59 of an off-white solid. The hydantoin was hydrolyzed at reflux using 1 N NaOH giving 2-amino-2-(3-fluorophenyl)acetic acid which was esterified via Procedure H in methanol to give the title compound.

Example D13

Synthesis of N-[N-(S)-2-Aminobutanoyl]-L-phenylglycine tert-Butyl Ester

A mixture of N-[N-(benzyloxycarbonyl)-(S)-2-aminobutanoyl]-L-phenylglycine tert-butyl ester (4.13 g) (prepared from N-(benzyloxycarbonyl)-(S)-2-aminobutanoic acid (Novabiochem) and L-phenylglycine tert-butyl ester hydrochloride (Novabiochem) using General Procedure D) and 20% Pd(OH)$_2$/C (0.360 g) in EtOH (200 mL) was shaken in a Parr Apparatus under a hydrogen atmosphere (40 psi) for 4 hours. The solids were removed by filtration through a plug of Celite, while rinsing with EtOH. The filtrate was concentrated to an off-white oil, which was used without further purification. $^1$H-NMR in CDCl$_3$ revealed that ~10% trans-esterification to the ethyl occurred during this reaction. The ethyl ester was removed by flash chromatography after subsequent reaction of this compound.

Example D14

Synthesis of N-[N-L-Valinyl]-L-phenylglycine tert-Butyl Ester

A mixture of N-[N-(benzyloxycarbonyl)-L-valinyl]-L-phenylglycine tert-butyl ester (4.63 g) (prepared from N-(benzyloxycarbonyl)-L-valine (Aldrich) and L-phenylglycine tert-butyl ester hydrochloride (Novabiochem) using General Procedure D) and 20% Pd(OH)$_2$/C (0.360 g) in EtOH (200 mL) was shaken in a Parr Apparatus under a hydrogen atmosphere (40 psi) for 4 hours. The solids were removed by filtration through a plug of Celite, while rinsing with EtOH. The filtrate was concentrated to an off-white solid, which was used without further purification. $^1$H-NMR in CDCl$_3$ revealed that ~1% trans-esterification to the ethyl occurred during this reaction. The ethyl ester was removed by flash chromatography after subsequent reaction of this compound.

Example D15

Synthesis of (S)-Phenylglycinol Methyl Ether (S)-(+)-2-phenylglycinol (1 eq.) (Aldrich) was stirred in dry THF under an atmosphere of dry nitrogen. Sodium hydride (1 eq.) was added and the resulting mixture was stirred for 1 hour at ambient temperature. A THF solution of iodomethane (1 eq.) was added and the mixture was stirred for 1 hour. The mixture was concentrated to provide a residue which was taken up in water and extracted with chloroform. The organic extracts were concentrated under reduced pressure to yield the title compound as an oil which was purified by silica gel chromatography to yield a crude product which was used without further purification.

Example D16

Synthesis of (S)-2-Hydroxy-2-methyl-1-phenylprop-1-ylamine

To a stirred, cooled (0° C.) suspension of 5.6 g (27.8 mmol) of L-phenylglycine methyl ester hydrochloride (Aldrich) in 200 mL of dry THF was added methylmagnesium bromide (46.3 mL, 138.9 mmol, 3.0 M in diethyl ether). During the addition, the internal temperature increased to 24° C. Stirring was continued for 1 hour, after which the reaction was carefully quenched by addition of saturated sodium bicarbonate solution. The reaction mixture was partitioned between ethyl acetate and aqueous sodium bicarbonate solution, back extracting the aqueous layer with 3 volumes of ethyl acetate. The combined organics were dried over anhydrous sodium sulfate and concentrated under reduced pressure. The product was purified by flash chromatography on silica gel, eluting with 10% methanol in chloroform (neutralized with ammonium hydroxide) to afford 1.96 g to the title compound.

Example D17

Synthesis of 5-Chloro-2-thiophenecarboxaldehyde

A solution of 2-chlorothiophene (Aldrich; 1 molar eq.) in THF was cooled to −78° C. and treated with n-butyl]ithium (1.6M in hexanes; 1.1 molar eq.) in a dropwise manner. The resultant yellow solution was stirred at −78° C. for 40 minutes. Dimethylformamide (1.1 molar eq.) was added dropwise and the reaction stirred and additional 30 minutes. The mixture was diluted with methylene chloride and washed with 10% acetic acid, 1 M potassium carbonate, and brine. The organic phase was dried over $Na_2SO_4$, filtered, and concentrated. The residue was purified by HPLC eluting with 15% ethyl acetate/hexanes to afford the title compound.

Example D18

Synthesis of (S)-(−)-α-Methylbenzylisocyanide

Prepared according to the general procedure of Wolber, E. K. A.; Rüchardt, C. *Chem. Ber.* 1991, 124, 1667. To a suspension of 1,1'-carbonyidiimidazole (1.6 molar eq.; Aldrich) in acetonitrile at 0° C. was treated with methanesulfonic acid (3.2 molar eq.; Aldrich) in a dropwise fashion. A very thick suspension results. S-(−)-α-Methylbenzyl formamide (1 molar eq.; from Example D19 below) was added as a solution in acetonitrile via cannulation. The mixture was stirred overnight at ambient temperature. The suspension was filtered, washing with acetonitrile. The filtrate was concentrated and purified via flash chromatography eluting with 30% ethyl acetate/hexanes. The oil was further purified via bulb-to-bulb distillation (80° C., 0.04 mm Hg) giving a pale yellow oil in 51% yield. Calcd for $C_9H_9N$: C, 82.41; H, 6.92; N, 10.68. Found: C, 82.56; H, 6.82; N, 10.71.

Example D19

Synthesis of (S)-(−)-α-Methylbenzyl Formamide (S)-(−)-α-Methylbenzylamine (1 molar eq., Aldrich) was treated with ethyl formate (80 molar eq.; Aldrich). A precipitate formed immediately. The suspension was heated to reflux (55° C.) for 3 hours. The precipitate went into solution upon heating. The solution was cooled to ambient temperature and concentrated via rotary evaporation. The resultant solid was used without purification.

Example D20

Synthesis of 3-(Phenyl)benzaldehyde

A solution of 3-bromobiphenyl (Aldrich; 1 molar eq.) in dry THF was cooled to −78° C. and treated with tert-butyl]ithium (Aldrich; 1.7 M in hexanes, 2 molar eq.) in a dropwise manner. The reaction was allowed to stir at −78° C. for 40 minutes. Dimethylformamide (Aldrich; 2.5 molar eq.) was added and stirring continued an additional 20 minutes. The mixture was partitioned in a separatory funnel between methylene chloride and water. The organic layer was dried over $Na_2SO_4$, filtered, and concentrated. The residue was purified via HPLC eluting with 5% ethyl acetate/hexanes. The desired aldehyde was obtained in 71% yield.

Example D21

Synthesis of 4-(Cyclohexyl)benzaldehyde

18-Crown-6 (Aldrich; 4 molar eq.) and pyridinium chlorochromate (Aldrich; 4 molar eq.) were added together in chloroform and stirred for 20 minutes. 4-Cyclohexylbenzylalcohol (from Example D22 below; 1 molar eq.) was added and stirring continued for 3 hours. Ether was added and the mixture filtered through a plug of silica eluting with ether. The solvent was removed via rotary evaporation. The residue was dissolved in ether and washed with water. The organic layer was dried over $Na_2SO_4$, filtered, and concentrated.

Example D22

Synthesis of 4-(Cyclohexyl)benzyl Alcohol

To a solution of 4-cyclohexylbenzoic acid (Aldrich; 1 molar eq.) in toluene was added diiso-butylaluminum hydride (Aldrich; 1 M in toluene; 4 molar eq.) over a 2 hour period. After addition was complete, the reaction was heated to 60° C. for 1 hour. The reaction was cooled to 5° C. and quenched with saturated aqueous ammonium chloride. The layers were separated and the aqueous layer extracted with ethyl acetate. The combined organics were filtered to remove salts and concentrated.

Example D23

Synthesis of 3,5-Difluorophenyl-α,α-difluoroacetic Acid

A solution of ethyl 3,5-difluorophenyl-α,α-difluoroacetate (from Example D24 below; 1 molar eq.) in 50% aqueous ethanol was treated with lithium hydroxide (1.5 molar eq.). The solution was stirred for 3 hours at ambient temperature then concentrated via rotary evaporation. The residue was taken up in water; a small amount of 1 N NaOH was added to make basic. The aqueous mixture was extracted with ether. The aqueous layer was acidified to pH 3 with 1 N HCl. The acid was extracted thrice with methylene chloride. The combined methylene chloride extracts were dried over $Na_2SO_4$, filtered, and concentrated.

Example D24

Synthesis of Ethyl 3,5-Difluorophenyl-α,α-difluoroacetate

Ethyl 3,5-difluorophenyl-α-ketoacetate (Rieke Metals, Inc. #14014; 1 molar eq.) was treated with (diethylamino) sulfur trifluoride (DAST) (2.5 molar eq.). The reaction was stirred at ambient for 72 hours then heated to 50° C. for 6 hours. The mixture was poured over ice and extracted with methylene chloride. The organic layer was washed with saturated sodium bicarbonate, dried over $Na_2SO_4$, filtered, and concentrated. The residue was purified via HPLC eluting with 2% ethyl acetate/hexanes.

Example D25

Synthesis of N-[N-(3,5-difluorophenylacetyl)-L-alaninyl]-D,L-phenylglycine

N-[N-(3,5-difluorophenylacetyl)-L-alaninyl]-L-phenylglycine methyl ester (from Example 111 below) was hydrolyzed according to Procedure AF. The acid was recrystallized from isooctane/EtOAc providing a mixture of diastereomers at the phenylglycine center. Elemental analysis; $C_{19}H_{18}F_2N_4O_4$ requires C, 60.63 H, 4.82 N, 7.44. Found; C, 60.65 H, 5.02 N, 7.37. Mass spectroscopy ($MH^+$377).

Example D26

Synthesis of 3-(4-Iodophenyl)propylamine

N-(3-bromopropyl)phthalimide (1 eq., Aldrich) and 4-iodophenol (1 eq., Aldrich) and potassium carbonate (2 eq.) was stirred in acetonitrile. The mixture was heated at reflux. After 64 hour, the reaction mixture was concentrated to a thick mixture which was slurried in water. A white solid was collected, washed with water and vacuum dried.

The white solid was stirred in ethanol. Anhydrous hydrazine (2 eq.) was added and mixture was heated at reflux for 18 hours. The reaction mixture was concentrated to yield a solid which was treated with 1N NaOH and extracted with $CHCl_3$. The organic portion was dried, concentrated then diluted with ether. The mixture was treated with dry HCl. The title compound was collected as a white solid and vacuum dried.

Example D27

Synthesis of 2-Amino-1-phthalimidopentane Hydrochloride

2-Amino-1-pentanol was stirred in a mixture of chloroform and saturated aqueous sodium bicarbonate. Di-tert-butyl dicarbonate (1.05 eq.) was added in one portion and the mixture was stirred until starting material was consumed. The organic portion was separated, dried (sodium sulfate) and concentrated. The crude material was purified by silica gel chromatrography using 1:1 ethyl acetate/hexanes.

The product was dissolved in THF. Triethylamine (1.1 eq.) was added and the mixture was cooled in an ice bath. Methanesulfonyl chloride (1.1 eq.) was added dropwise and the mixture was stirred until starting material was consumed. The mixture was concentrated under reduced pressure then was partitioned between ethyl acetate and water. The organic portion was separated, dried (sodium sulfate) and concentrated to yield a white solid which was chromatographed on silica gel using 30% ethyl acetate in hexanes and finally crystallized from 1-chlorobutane/hexanes.

The crystalline product was stirred in dry DMF and potassium phtalimide (1.1 eq.) was added. The mixture was stirred for 18 hours then was concentrated under reduced pressure. The residue was partitioned between ethyl acetate and water. The organic portion was dried and concentrated to yield a white solid. The solid was taken up in chloroform and filtered through a plug of silica. Eluent containing product was concentrated to yield the crude product as a white solid.

The white solid was taken up in dry dioxane and resulting solution was saturated with gaseous HCl. After stirring for 30 minutes, the mixture was concentrated to yield a white solid which was triturated in ether. The title compound was collected, washed with ether and dried in a vacuum oven.

Example D28

Synthesis of D,L-3,5-Difluorophenylglycine

KOH (11.76 grams), LiCl (2.95 grams), saturated aqueous ammonia (20 mL), and benzyltriethylammonium chloride (0.805 grams) were stirred and chilled in $CH_2Cl_2$ (17 mL). Gaseous ammonia was bubbled into this mixture with chilling (0° C.) to saturation. To the resulting mixture was added 3,5-difluorobenzaldehyde (5.0 grams) (Lancaster) and chloroform (4.46 mL), dissolved in $CH_2Cl_2$ (17.5 mL) with concurrent saturation with ammonia gas. The resulting mixture was stirred cold for 4 hours and at 22.5° C. for 96 hours. Water (60 mL) and $CH_2Cl_2$ (20 mL) were added; the layers separated, and the aqueous layer was extracted 3 times more with $CH_2Cl_2$. The aqueous layer was reduced in vacuo by 50%. The pH was adjusted to 6.5 with cold conc. HCl whereupon white crystals of D,L-3,5 difluorophenylglycine formed (3.4343 grams).

Example D29

Synthesis of L-3,5-Difluorophenylglycine Methyl Ester Tartate Salt 3.43 Grams of D,L-3,5 difluorophenylglycine (from Example D28 above) was slurried in 50 mL methanol and 2.5 mL conc. $H_2SO_4$. The reaction mixture was heated under gentle reflux for 18 hours. The mixture was chilled in and ice bath and the pH of the solution was adjusted to 7.0 with saturated aqueous ammonia. The volatile organic solvents were removed in vacuo and the aqueous portion was extracted three times with $CH_2Cl_2$; the combined organic layers dried, filtered, and reduced in vacuo to provide 2.680 grams of crude ester. This ester, benzaldehyde (1.4085 grams), and (−) tartaric acid (1.9921 grams), were dissolved in 20.5 mL of hot ethanol and stirred slowly for 72 hours as the title compound crystallized. The product was filtered and dried to provide 3.4805 grams of the (−) tartarate salt.

Example D30

Synthesis of N-(3,5-Difluorophenylacetyl)-L-3,5-difluorophenylglycine

L-3,5-Difluorophenylglycine (0.4291 g) (prepared from L-3,5-difluorophenylglycine (−)-tartarate salt (from Example D29 above) by neutralization) and 3,5-difluoroacetic acid 0.367 gram were dissolved in THF. EEDQ coupling using General Procedure AN afforded 0.7441 grams of the title compound as the methyl ester. The ester was dissolved in 1,4-dioxane (10 mL), chilled and LiOH.H$_2$O (89.0 mg) in water (10 mL) was added slowly and the mixture was stirred for 2 hours at 22.5° C. EtOAc (30 mL) and 1N HCl were added and the aqueous layer extracted two times. The combined organic layers were dried (MgSO$_4$) and reduced in vacuo to provide the title compound (700.8 mg).

Each of the compounds set forth in the following examples was prepared by one of the following general procedures, unless otherwise indicated.

GENERAL PROCEDURE A

EDC Coupling Procedure I

To a 1:1 mixture of the corresponding carboxylic acid and amino ester/amide in CH$_2$Cl$_2$ or DMF at 0° C. was added 1.5 equivalents triethylamine, followed by 2.0 equivalents hydroxybenzotriazole monohydrate, then 1.25 equivalents of 1-(3-dimethylaminopropyl)-3-ethylcarbodiimide hydrochloride (EDC). The reaction mixture was stirred overnight at room temperature and then transferred to a separatory funnel. The mixture was washed with water, saturated aqueous NaHCO$_3$, 1 N aqueous hydrochloric acid, and saturated aqueous sodium chloride, and then dried over MgSO$_4$. The solution was stripped free of solvent on a rotary evaporator to yield the crude product.

GENERAL PROCEDURE B

EDC Coupling Procedure II

The carboxylic acid was dissolved in methylene chloride in a round-bottomed flask. The amino acid (1 eq.), N-methylmorpholine (5 eq.) and hydroxybenzotriazole monohydrate (1.2 eq.) were added in sequence. A cooling bath was applied to the round-bottomed flask until the solution reached 0°. At that time, 1.2 eq. of 1-(3-dimethylaminopropyl)-3-ethylcarbodiimide hydrochloride was added. The solution was then allowed to stir overnight and come to room temperature under N$_2$ pressure. The reaction mixture was then washed with saturated aqueous Na$_2$CO$_3$, 0.1 M citric acid, and brine before drying with Na$_2$SO$_4$ and removing the solvents to yield the crude product. Pure products were typically obtained by flash chromatography in an appropriate solvent.

GENERAL PROCEDURE C

FDC Coupling Procedure III

A round-bottomed flask was charged with the appropriate carboxylic acid (1.0 eq), hydroxybenzotriazole hydrate (1.1 eq) and the appropriate amine (1.0 eq) in THF under a nitrogen atmosphere. An appropriate amount (1.1 eq. for the free amine and 2.2 eq. for amine hydrochloride salt) of a suitable base, such as Hunig's base was added to the stirred mixture, followed by 1-(3-dimethylaminopropyl)-3-ethylcarbodiimide hydrochloride (EDC) (1.1 eq). After stirring for about 4 h to 17 h at room temperature, the solvent was removed at reduced pressure and the residue taken up in EtOAc (or a similar solvent)/H$_2$O. The extracts were washed with saturated NaHCO$_3$, 1 N aqueous hydrochloric acid, brine and dried over Na$_2$SO$_4$. In some cases, the isolated product required further purification using standard procedures, such as chromatography and/or recrystallisation.

GENERAL PROCEDURE D

EDC Coupling Procedure IV

A round bottom flask containing a magnetic stir bar under an atmosphere of nitrogen at 0° C. was charged with THF, an amine or amine hydrochloride (1.0 eq.), carboxylic acid (1.1 eq.), 1-hydroxybenzotriazole hydrate (1.15–1.2 eq), N,N-diisopropylethylarnine (2.3 eq.), followed by 1-(3-dimethylaminopropyl)-3-ethylcarbodiimide hydrochloride (EDC) (1.15–1.2 eq.). The cooling bath was removed and the mixture allowed to warm to room temperature with stirring for 10–20 hours. The mixture was diluted with EtOAc and washed with 0.5 N aqueous. HCl (2x), dilute aqueous NaHCO$_3$ (1x), brine (1x) and dried over either Na$_2$SO$_4$ or MgSO$_4$. The drying agent was removed by filtration and the filtrate concentrated in vacuo. The residue was either used without further purification or purified by standard procedures, such as flash chromatography on silica gel and/or recrystallization.

GENERAL PROCEDURE E

EDC Coupling Procedure V

A round bottom flask containing a magnetic stir bar under an atmosphere of nitrogen at 0° C. or room temperature was charged with THF, carboxylic acid (1.0 eq), an amine or amine hydrochloride (1.0–1.1 eq.), 1-hydroxybenzotriazole hydrate (1.1–1.2 eq.), N,N-diisopropylethylamine (2.2–2.9 eq.), followed by 1-(3-dimethylaminopropyl)-3-ethylcarbodiimide hydrochloride (EDC) (1.1–1.2 eq.). The cooling bath was removed and the mixture allowed to warm to room temperature with stirring for 10–20 hours. The mixture was diluted with EtOAc and washed with 0.5 N aqueous HCl (2x), dilute aqueous NaHCO$_3$ (1x), brine (1x) and dried over either Na$_2$SO$_4$ or MgSO$_4$. The drying agent was removed by filtration and the filtrate concentrated in vacuo. The residue was either used without further purification or purified using standard procedures, such as flash chromatography on silica gel and/or recrystallization.

GENERAL PROCEDURE F

EDC Coupling Procedure VI

A round bottom flask containing a magnetic stir bar under an atmosphere of nitrogen at 0° C. was charged with THF, carboxylic acid (1.0 eq.), an amine or amine hydrochloride (1.1 eq.), N,N-diisopropylethylamine (2.2–2.3 eq.), followed by 1-(3-dimethylaminopropyl)-3-ethylcarbodiimide hydrochloride (EDC) (1.1–1.2 eq.). The cooling bath was removed and the mixture allowed to warm to room temperature with stirring for 10–20 hours. The mixture was diluted with EtOAc and washed with 0.2 N aqueous HCl (2x), dilute aqueous NaHCO$_3$ (1x), brine (1x) and dried over either Na$_2$SO$_4$ or MgSO$_4$. The drying agent was removed by filtration and the filtrate concentrated in vacuo. The residue was either used without further purification or purified using standard procedures, such as flash chromatography on silica gel and/or recrystallization.

GENERAL PROCEDURE G

Methyl Ester Preparation

To 1-methyl-3-nitro-1-nitrosoguanidine (1.2 eq.) in diethyl ether cooled to 0° C. was added 40% KOH until bubbling ceased. This mixture was then decanted into a plastic tube containing KOH pellets as a drying agent. The solution was then added to the appropriate carboxylic acid and the mixture was stirred until the reaction was complete (as determined, for example, by tlc). The reaction was then quenched with acetic acid and extracted into EtOAc. Removal of the solvent afforded the desired methyl ester.

GENERAL PROCEDURE H

Carboxylic Acid Ester Preparation

To the appropriate amino acid or carboxylic acid in the appropriate alcohol was bubbled anhydrous HCL gas until the solution was saturated. The reaction was stirred overnight at 25° C. and the solvent was then removed under reduced pressure. The residue was then dissolved in EtOAc and this solution was washed with sodium bicarbonate solution. The organic layer were then dried over sodium sulfate, filtered and solvent removed to afford the desired ester.

GENERAL PROCEDURE I tert-Butyl Ester Preparation I

To a solution of an N-CBZ-protected amino acid in $CH_2Cl_2$ was added 1.5 equivalents of N,N'-diisopropyl-O-t-butylisourea (prepared by standard literature methods such as those found in Synthesis (1979), p. 561), and the reaction was heated to reflux for 17 h. An additional 1.5 equivalents of isourea were then added, and reflux was continued for another 7 h. The reaction was then cooled to room temperature and filtered through a bed of Celite 545, then stripped to dryness to leave a clear oil. The residue was dissolved in hexanes and filtered to remove solids, and the filtrate was washed with saturated aqueous $NaHCO_3$, water, saturated aqueous NaCl, and dried over $MgSO_4$. The solution was concentrated under reduced pressure to leave the product.

GENERAL PROCEDURE J tert-Butyl Ester Preparation II

The reaction was conducted in a sealed tube using the appropriate carboxylic acid, a catalytic amount of $H_2SO_4$ (0.03 eq.) and an excess of condensed iso-butylene in dioxane or $CH_2Cl_2$ at −20° C. The reaction times varied from about 48 hours to about 120 hours. When the reaction was complete, the solvent was removed under reduced pressure and the residue dissolved in diethyl ether. This solution was washed with sodium bicarbonate solution and the organic layer dried over sodium sulfate, filtered and solvent removed. The resulting product was purified using standard procedures, such as HPLC or titration using, for example, diethyl ether/hexanes.

GENERAL PROCEDURE K

Amide Preparation I

To a solution of 3 equivalents of the desired amine in 1,2-dichloroethane was added 5.2 equivalents triethylaluminum subsurface. After stirring for 30 minutes at room temperature, a solution of the desired ester dissolved in 1,2-dichloroethane was added. The reaction was refluxed until tlc showed complete conversion, typically 3h. The reaction was then cooled to 0° C. and quenched with 10% aqueous hydrochloric acid (Note: the acid should be added slowly as some foaming occurs during its addition). The mixture was transferred to a separatory funnel and the layers were separated. The aqueous phase was washed with ethyl acetate, and the organic phases were washed with saturated aqueous NaCl, dried over $MgSO_4$, and concentrated under reduced pressure to leave the crude product.

Alternatively, if the product is acid soluble, after the reaction is quenched, the reaction volume was reduced to about one-third of its initial volume under reduced pressure. To the resulting solution was added 20% aqueous potassium sodium tartrate (Rochelle's salt) and ethyl acetate. The pH of the solution was then adjusted to ~13, and the aluminum salts dissolved in the aqueous solution. The organic phase was separated, and the aqueous phase was extracted with ethyl acetate. The combined organic solution was washed with saturated aqueous NaCl, dried over $MgSO_4$, and concentrated under reduced pressure to leave the crude product.

GENERAL PROCEDURE L

Amide Preparation II

The carboxamide was prepared from its corresponding ester using the procedure described in Hogberg, T., et.al., J. Org. Chem., 1987, 52, 2033–2036.

GENERAL PROCEDURE M

Amide Preparation III

To the appropriate carboxylic acid (1.0 eq.) in THF was added N-methylmorpholine (1.1 eq.) and the solution was cooled to −20° C. to 0° C. iso-butyl chloroformate (1.1 to 2.1 eq.) was then added and the reaction mixture was stirred at −20° C. to 0° C. for 30 min. A mixture of the appropriate amino acid, water and 1.5 eq. of potassium carbonate was then added, and the resulting mixture was allowed to warm to room temperature and stir for 2 hrs. The reaction mixture was then poured into water and washed with EtOAc. The pH of the water layer was then adjusted to 2.0 with 5 N HCl and the water layer was extracted with EtOAc. The combined organic layers were dried over sodium sulfate, filtered and the solvent removed under reduced pressure. The resulting crude amide was used without further purification or purified using standard procedures such as chromatography or titration using, for example, diethyl ether/hexanes or EtOAc/hexanes.

GENERAL PROCEDURE N

Hydrolysis of Carboxylic Acid Esters

To the ester in a 1:1 mixture of $CH_3OH/H_2O$ was added 2–5 equivalents of $K_2CO_3$. The mixture was heated to 50° C. for 0.5–1.5 h until tlc showed complete reaction. The reaction was cooled to room temperature and the methanol was removed on a rotary evaporator. The pH of the remaining aqueous solution was adjusted to about 2, and ethyl acetate was added to extract the product. The organic phase was then washed with saturated aqueous NaCl and dried over $MgSO_4$. The solution was stripped free of solvent on a rotary evaporator to yield the product.

GENERAL PROCEDURE O

Removal of N-Carbobenzyloxy (CBZ) Protecting Groups

The N-CBZ-protected compound was dissolved in ethanol in a hydrogenation flask and a catalytic amount of 10% Pd/C was added. The mixture was hydrogenated at 20 psi $H_2$ on a Parr shaker for 30 min. The reaction was then filtered through a pad of Celite 545 and stripped free of solvent on a rotary evaporator to yield the product.

GENERAL PROCEDURE P

Removal of the N-tert-Boc Protecting Group

The N-tert-Boc-amine was dissolved in a suitable dry solvent (such as 1,4-dioxane or ethyl acetate) and the solution was cooled in an ice bath. Gaseous HCl was introduced into the solution until the mixture was saturated with HCl. The mixture was then stirred until the reaction was complete. The resulting mixture was concentrated under reduced pressure to yield the amine hydrochloride. The amine hydrochloride was used without purification or was triturated using, for example, diethyl ether and the resulting solid was collected by filtration.

GENERAL PROCEDURE Q

Halide Exchange (Finkelstein) Reaction

The corresponding alkyl bromide or alkyl chloride was dissolved in 20 mL of methyl ethyl ketone and 1 eq. of NaI was added. The reaction was heated to 60° C. and stirred overnight. The cooled reaction mixture was extracted with dichloromethane (2×30 mL) and the combined extracts were roto-evaporated at reduced pressure to give the crude product. Pure products were typically obtained by flash chromatography in an appropriate solvent.

GENERAL PROCEDURE R

Oxime Reduction I

To the oxime ester in the alcohol corresponding to the ester was added formic acid (500 eq.) and water (500 eq.). The reaction mixture cooled to 5° C. and zinc dust (3.8 eq.) was added in portions over 20 min. The reaction was then allowed to warm to room temperature and stirring was continued for 3 hours. The reaction was then filtered over HYFLO and the solvent removed under reduced pressure. The residue was dissolved in EtOAc and this solution washed with saturated sodium bicarbonate solution. The organic layer was then dried over sodium sulfate, filtered and solvent removed to afford the product.

GENERAL PROCEDURE S

Reduction of Esters to Alcohols

To a 0° C. solution of the starting ester in anhydrous THF was added 1.0 equivalents of LiBH$_4$ in THF. The reaction was stirred at room temperature overnight and then quenched with water. The THF was removed on a rotary evaporator and ethyl acetate was added. The phases were separated and the organic phase was washed with saturated aqueous sodium chloride solution, dried over magnesium sulfate, and concentrated under reduced pressure to afford the alcohol product.

GENERAL PROCEDURE T

CDI Coupling Procedure

A solution of the appropriate acid (3.3 mmol) and 1,1'-carbodiimidazole (CDI) in 20 mL THF was stirred for 2 h. The amino acid ester hydrochloride (3.6 mmol) was added, followed by 1.5 mL (10.8 mmol) of triethylamine. The reaction mixture was stirred overnight and then dissolved in 100 mL of diethyl ether, washed with 10% HCl three times, brine once, 20% potassium carbonate once and brine once. The solution was dried over magnesium sulfate, filtered, and evaporated at reduced pressure to yield the product.

GENERAL PROCEDURE U

EDC Coupling Procedure VII

A mixture of the appropriate carboxylic acid (1 eq.), 1-hydroxybenzotriazole (1.6 eq.), the appropriate amine (1 eq.), N-methylmorpholine (3 eq.) and dichloromethane (or DMF for insoluble substrates), cooled in an ice-water bath, was stirred until a clear solution was obtained. EDC (1.3 eq.) was added to the reaction mixture and the cooling bath was allowed to warm to ambient temperature over 1–2 h. The reaction was then stirred overnight. The reaction mixture was then evaporated at reduced pressure to dryness under vacuum and 20% aqueous potassium carbonate was added to the residue. The mixture was shaken vigorously and allowed to stand for hours or overnight, if necessary, until the oily product to solidify. The solidified product was then filtered off, washed thoroughly with 20% potassium carbonate, water, 10% HCl, and water to give the product. No racemization was observed using this procedure.

GENERAL PROCEDURE V

O-Acylation of Alcohols

To a solution of the alcohol (e.g., N-[(S)-1a-hydroxyhex-2-yl]-N'-(3,5-difluorophenylacetyl)-L-alaninamide from Example 228 below) in pyridine was added 4 equivalents of acetic anhydride and the reaction was stirred at room temperature for 2.5 h. The reaction was quenched onto ice and then ethyl acetate was added and the phases were separated. The organic phase was washed with 10% HCl, water, saturated aqueous NaCl, and dried over MgSO$_4$. The solution was stripped free of solvent on a rotary evaporator to yield the product.

GENERAL PROCEDURE W

O-Esterification of Alcohols

To a suspension of 0.95 equivalents of NaH in THF was added an alcohol (e.g., N-[(S)-1-hydroxyhex-2-yl]-N'-(3,5-difluorophenylacetyl)-L-alaninamide from Example 228 below) dissolved in THF. This solution was cooled to 0° C., then 1.1 equivalents of an acyl chloride (e.g. trimethylacetyl chloride) was added. The reaction was stirred at room temperature overnight, then was quenched with water and ethyl acetate. The organic phase was washed with water, saturated aqueous NaCl, and dried over MgSO$_4$. The solution was stripped free of solvent on a rotary evaporator to yield the crude product.

GENERAL PROCEDURE X

BOP Coupling Procedure

A solution of the carboxylic acid (1.0 eq.) and N-methyl morpholine (1.5 eq.) in dichloromethane was cooled to −20° C. under nitrogen. BOP (1.05 eq.) was added in one portion and the reaction mixture was maintained at −20° C. for 15 minutes. The appropriate alcohol (1.2 eq.) was added and the reaction mixture was allowed to warm to room temperature and stirring was continued for 12 hours. The reaction mixture was then poured into water and extracted with ethyl acetate (3×) and the combined organic layers were washed with saturated aqueous citric acid (2×), saturated aqueous sodium bicarbonate (2×), brine (1×), and then rotoevaporated at reduced pressure to provide the crude product.

GENERAL PROCEDURE Y

BOC Removal Using TFA

The Boc-protected compound was added to a 1:1 mixture of dichloromethane and trifluoroacetic acid (TFA) and the reaction mixture was stirred until tlc indicated complete conversion, typically 2 hours. The solution was then stripped to dryness. The residue was suspended in dichloromethane and again stripped to dryness to remove excess TFA. The residue was placed under high vacuum for several hours to afford the desired TFA salt.

GENERAL PROCEDURE Z

Amide Preparation IV

The trichlorophenyl ester (1 eq.) was stirred in DMF or THF and the oxime or amine (1.2 eq.) was added. The mixture was stirred at ambient temperature for 1–4 hours. In cases where the hydrochloride salt form of an amine was used, a suitable base such as diisopropylethylamine (1.2 eq.) was also added. The resulting mixture was concentrated under reduced pressure to yield an oil or residue which was used without further purification or was purified by standard procedures, such as silica gel chromatography and/or recrystallization.

GENERAL PROCEDURE AA

Sodium Borohydride Reduction

The ketone was dissolved in MeOH and treated with 1.0 equivalent of sodium borohydride. The reaction was stirred until tlc showed the starting material was consumed, typically 1 hour. The reaction mixture was then evaporated at reduced pressure and chromatographed to afford the alcohol product.

GENERAL PROCEDURE AB

Preparation Amino Acid Derivatives Using Chiral Amines (S)-(−)-α-Methylbenzyl amine was added dropwise to a solution of arylaldehyde (1 molar eq.) in THF followed by the addition of 1.0 molar eqivalent of zinc chloride. The reaction mixture was allowed to stir at room temperature for 5 h. The cloudy mixture was then cooled to −30° C. and treated with alkylisocyanide (1.05 molar eq.). After 20 minutes, N-(3,5-difluorophenylacetyl)-L-alanine (Example B2) was added and stirring was continued at −30° C. for 120 h. The reaction mixture was then poured into a seperatory funnel and diluted with $CH_2Cl_2$, washed with sodium bicarbonate. The organic layer was then washed with 0.5 N HCl, followed by brine. The organic layer was then dried over $Na_2SO_4$, filtered and concentrated to give N-alkyl-N'-[N-(3,5-difluorophenylacetyl)-L-alaninyl]-N'-(S)-α-methylbenzyl-2-amino-2-(aryl)acetamide, as a mixture of isomers. At this stage, the isomers were typically separated by HPLC chromatography using, for example, a gradient of 30 to 35% EtOAc/hexanes. The α-methylbenzyl auxiliary group was then removed from the S,S isomer by adding 10 molar equivalents of triethylsilane and 20 molar equivalents of trifluoroacetic acid to the S,S isomer. The reaction was then heated to 37° C. for 3 h and then poured into ethyl acetate and washed with sodium bicarbonate. The organic layer was dried over $Na_2SO_4$, filtered and concentrated. The residue was purified by recrystallisation from ethyl acetate or ethyl acetate/hexanes.

GENERAL PROCEDURE AC

Oxime Reduction II

To a solution of the oxime ester in the alcohol corresponding to the ester was added a catalytic amount of acetic acid and 0.1 mole equivalent of 10% Pd/C. The reaction vessel (Parr shaker) was charged with hydrogen to 40 PSI and this mixture was shaken for 3 h. The reaction mixture was then filtered over HyFlo and concentrated. The residue was dissolved in ethyl acetate and washed with a saturated solution of sodium bicarbonate. The organic layer was then dried over $Na_2SO_4$, filtered and concentrated to give the desired amine.

GENERAL PROCEDURE AD

Mitsunobu Reaction

To a solution of N-[N-(3,5-difluorophenylacetyl)-L-alaninyl]-L-tyrosine methyl ester in 20 mL of THF was added 1.3 equivalents each of triphenylphosphine and diethyl azodicarboxylate (DEAD), and 1.0 equivalents of an alcohol. The mixture was stirred a room temperature overnight and the solvent was then removed. The residue was purified by standard procedures, such as chromatography and/or recrystallization.

GENERAL PROCEDURE AE

O-Alkylation of Tyrosine Derivatives

To a solution of N-[N-(3,5-difluorophenylacetyl)-L-alaninyl]-L-tyrosine methyl ester in 20 mL of acetone was added 1.3 equivalents of an alkyl bromide and 3.0 equivalents of potassium carbonate as a fine powder and a catalytic amount of sodium iodide. The reaction mixture was stirred at room temperature overnight and then partitioned between DCM and water. The organic layer was dried over anhydrous sodium sulfate, stripped of solvents and purified using standard procedures, such as chromatography and/or recrystallization.

GENERAL PROCEDURE AF

Hydrolysis of Carboxylic Acid Esters

A solution of the carboxylic acid ester (1.0 eq.) and lithium hydroxide (1.1 eq.) in 1:2 water/dioxane was stirred at 23° C. for 1 hour. The reaction mixture was then acidified to pH 3 with 1 N HCl and extracted with ethyl acetate. Concentration of the ethyl acetate extracts provided the product. In some cases, the product was further purified using standard procedures, such as chromatography and/or recrystallization.

GENERAL PROCEDURE AG

Methyl Ester Formation from Amino Acids

The amino acid (amino acid or amino acid hydrochloride) is suspended in methanol and chilled to 0° C. HCl gas is bubbled through this solution for 5 minutes. The reaction is allowed to warm to room temperature then stirred for 4 hours. The solvents are then removed to afford the desired amino acid methyl ester hydrochloride. This product is usually used without further purification.

GENERAL PROCEDURE AH

EEDQ Coupling Procedure

A round bottom flask containing a magnetic stir bar under as atmosphere of nitrogen at room temperature was charged with THF, the carboxylic acid (1 eq.), the amine hydrochloride (1.1 eq.) and EEDQ (1.1 eq.) and the reaction mixture was allowed to stir for 15 minutes. 4-Methylmorpholine (1.1 eq.) was added to the reaction and stirring was continued at room temperature for 15–20 hours. The reaction mixture was then concentrated in vacuo and the resulting residue was partitioned between ethyl acetate and water. The organic phase was separated and washed with saturated aq. $NH_4Cl$ (2×), saturated aq. $NaHCO_3$ (2×), followed by brine (1×). Organic phase dried over $Na_2SO_4$. The drying agent was removed by filtration and the filtrate concentrated in vacuo. The residue was either used without further purification or purified using standard procedures, such as flash chromatography on silica gel and/or recrystallization.

GENERAL PROCEDURE AI

N-tert-BOC Protection of Amino Acids

A round bottom flask containing a magnetic stir bar under an atmosphere of nitrogen at room temperature was charged with dioxane, water, 1.0 N aq. sodium hydroxide, and the amino acid (1 eq). Stirring was initiated and the flask was cooled in an ice bath. Di-t-butyldicarbonate (1.1 eq) was added to the reaction mixture, followed by removal of the ice bath and slow warming to room temperature over 1 hour. The reaction was partially concentrated on the rotary evaporator followed by the addition of ethyl acetate. The flask was re-cooled in an ice bath. and the mixture was acidified to a pH of 2–3 through the addition of potassium bisulfate. The reaction was transferred into a seperatory funnel and the organic layer was separated. The aqueous layer was extracted with ethyl acetate and the combined organic layers were dried over $Na_2SO_4$. The drying agent was removed by filtration and the filtrate concentrated in vacuo. The solid was used without further purification.

GENERAL PROCEDURE AJ

Removal of N-Carbobenzyloxy (CBZ) Protecting Groups

A round bottom flask containing a magnetic stir bar under an atmosphere of nitrogen at room temperature was charged with methanol, tetrahydrofuran, 20% $Pd(OH)_2/C$ (1 mass eq.), and the CBZ-protected dipeptide. Stirring was initiated and the flask was purged (3×) with hydrogen. The reaction mixture was allowed to stir at room temperature overnight under an atmosphere of hydrogen. The reaction was filtered and the filtrate was concentrated in vacuo. The resulting solid was used as is or purified via silica gel chromotography.

GENERAL PROCEDURE AK

Addition of N-Carbobenzyloxy (CBZ) Protecting Groups

A round bottom flask containing a magnetic stir bar under an atmosphere of nitrogen at room temperature was charged with water, sodium carbonate (2.2 eq.), and amino acid (1.0 eq.). The slurry was stirred at room temperature for 1 hour. Benzylchloroformate was added to the reaction and stirring was continued overnight. The reaction mixture was extracted with $CH_2Cl_2$ (3×) and the combined organic extracts were acidified to a pH of 2–3. The resulting solid was isolated via vacuum filtration.

GENERAL PROCEDURE AL

Preparation of Amino Acid Derivatives Using Chiral Amines II

A solution of aryl aldehyde (1 molar eq.) in THF was treated with S-(−)-α-methylbenzylamine (1 molar eq.), followed by $MgSO_4$. The reaction mixture was stirred for 1 hour then treated with tert-butylisocyanide (1.5–2.0 molar eq.) and N-(3,5-difluorophenylacetyl)-L-alanine (1.5–2.0 molar eq.). The reaction was allowed to stir for 60 hours. The reaction was diluted with methylene chloride and washed with 0.01 N HCl and saturated aqueous $NaHCO_3$. Each aqueous wash was back-extracted with methylene chloride. The combined organics were washed with brine, dried over $Na_2SO_4$, filtered and concentrated to give N-tert-butyl-N'-[N-(3,5-difluorophenylacetyl)-L-alaninyl]-N'-R-α-methylbenzyl-2-amino-2-DL-(aryl)acetamide. At this stage, the isomers were separated if possible by HPLC chromatography using, for example, a gradient of 20 to 25% ethyl acetate/hexanes. The α-methylbenzyl protecting group was then removed from the peptide by adding 10 molar equivalents of triethylsilane and 20 molar equivalents of trifluoroacetic acid to the compound. The reaction was heated to 37° C. for 3 hours and then poured into ethyl acetate and washed with sodium bicarbonate. The organic layer was dried over $Na_2SO_4$, filtered, and concentrated. The residue was purified by trituration with ether or ether/hexanes. Various other aldehydes, isocyanides, and carboxylic acid can be used in this procedure to provide for a variety of compounds useful in this invention.

GENERAL PROCEDURE AM

Preparation of Amino Acid Derivatives Using Chiral Amines III

A solution of an aromatic aldehyde (3 molar eq.) and S-(−)-α-methylbenzylamine (1 molar eq.) in methanol was treated with titanium(IV) isopropoxide (1.5 molar eq.). After stirring the mixture at ambient temperature for 6 hours, tert-butylisocyanide (1.1 molar eq.) was added followed by N-(3,5-difluorophenylacetyl)-L-alanine (1.2 molar eq.) (Example B2 above) 40 minutes later. The reaction mixture was stirred for 72 hours. The methanol was removed via rotary evaporation. The residue was dissolved in methylene chloride and washed with 0.01 N HCl . The emulsion was filtered through celite washing with methylene chloride. The layers were separated; the organic phase was washed with saturated $NaHCO_3$ and brine. The organic layer was dried over $Na_2SO_4$, filtered, and concentrated to give N-tert butyl-N'-[N-(3,5-difluorophenylacetyl)-L-alaninyl]-N'-R-α-methylbenzyl-2-amino-2-DL-(aryl)acetamide. At this stage the isomers were separated if possible by HPLC chromatography using, for example, a gradient of 20 to 25% ethyl acetate/hexanes. The α-methylbenzyl protecting group was then removed from the peptide by adding 10 molar equivalents of triethylsilane and 20 molar equivalents of trifluoroacetic acid to the compound. The reaction was heated to 37° C. for 3 hours and then poured into ethyl acetate and washed with sodium bicarbonate. The organic layer was dried over $Na_2SO_4$, filtered, and concentrated. The residue was purified by trituration with ether or ether/hexanes.

GENERAL PROCEDURE AN

EEDQ Coupling Procedure II

To a 1:1 mixture of the corresponding carboxylic acid and amino ester/amide in THF at 0° C. was added 1.1 equivalents of EEDQ. The reaction mixture was stirred for 18 hours at 22.5° C. The solvent was removed under reduced pressure or under a stream of nitrogen and the residue dissolved in EtOAc. The organic solution was washed 1 time with saturated $NaHCO_3$ solution, 1 time with N HCl, and dried over $MgSO_4$. The organic solution was reduced in vacuo to yield the product.

GENERAL PROCEDURE AO

Preparation of Primary Amides

A sealable pressure tube containing a magnetic stir bar under an atmosphere of nitrogen at room temperature was charged with a methyl ester (1 eq.), sodium cyanide (0.1 eq.) and a 7M solution of ammonia in methanol. The tube was sealed and heated to 45° C. with stirring for 18 hours. The reaction was allowed to cool to room temperature and the resulting precipitate was isolated by vacuum filtration. The solid was either washed with methanol or recrystallyzed from ethyl acetate/methanol.

Example 1

Synthesis of Methyl N-[N-(3,5-Difluorophenylacetyl)-L-alaninyl]-(S)-2-aminohexanoate Following General Procedure A (without the 1N HCl wash) and using N-(3,5-difluorophenylacetyl)-L-alanine (from Example B2) and norleucine methyl ester hydrochloride (Sigma), the title compound was prepared as a solid (mp=142–143° C.). The reaction was monitored by tlc (Rf=0.71 in 10% $CH_3OH/CH_2Cl_2$, 0.22 in 50% EtOAc/hexanes) and the product was purified by silica plug chromatography using $CH_2Cl_2$ as the eluent.

NMR data was as follows:

$^1$H-nmr ($CDCl_3$): δ=6.90 (d, J=7.69 Hz, 1H), 6.80 (m, 3H), 6.70 (m, 1H), 4.62 (quint, J=7.2 Hz, 1H), 4.48 (m, 1H), 3.72 (s, 3H), 3.51 (s, 2H), 1.78 (m, 1H), 1.60 (m, 1H), 1.36 (d, J=7.02 Hz, 3H), 1.25 (m, 4H), 0.85 (m, 3H). $^{13}$C-nmr ($CDCl_3$): δ=173.23, 172.69, 169.97, 165.30, 165.12, 162.00, 139.01, 138.88, 138.76, 112.93, 112.83, 112.70, 112.60, 103.63, 103.30, 102.97, 52.94, 49.38, 43.28, 32.32, 27.95, 22.75, 19.23, 14.35. $C_{18}H_{24}F_2N_2O_4$ (MW=370.40); mass spectroscopy (MH$^+$) 371.

Example 2

Synthesis of N-[N-(3,5-Difluorophenylacetyl)-L-alaninyl]-L-histidine Methyl Ester Following General Procedure A and using N-(3,5-difluorophenylacetyl)-L-alanine (from Example B2) and L-histidine methyl ester dihydrochloride (Sigma), the title compound was prepared as a solid (mp=195–197° C.). The reaction was monitored by tlc (Rf=0.29 in 10% $CH_3OH/CH_2Cl_2$).

NMR data was as follows:

$^1$H-nmr ($CD_3OD$): δ=7.60 (s, 1H), 7.00–6.81 (m, 4H), 4.70 (t, 1H), 4.39 (q, 1H), 3.72 (s, 3H), 3.60 (s, 2H), 3.22–3.00 (m, 2H), 1.38 (d, 3H). $^{13}$C-nmr ($CD_3OD$): δ=175.46, 172.56, 172.94, 166.64, 166.47, 163.38, 163.20, 141.73, 141.60, 141.47, 136.85, 113.92, 113.82, 113.70, 113.59, 103.89, 103.55, 103.21, 54.55, 53.31, 51.00, 43.21, 43.19, 30.36, 18.44. $C_{18}H_{20}F_2N_4O_4$ (MW=394.38); mass spectroscopy (MH$^+$) 395.

Example 3

Synthesis of N-Benzyl-N'-[N-(3,5-difluorophenylacetyl)-L-alaninyl]-(S)-2-aminohexanamide Following General Procedure K and using methyl N-[N-(3,5-difluorophenylacetyl)-L-alaninyl]-(S)-2-aminohexanoate (from Example 1 above) and benzylamine (Aldrich), the title compound was prepared as a solid (mp=>200° C.). The reaction was monitored by tlc (Rf=0.29 in 5% $CH_3OH/CH_2Cl_2$) and the product was purified by preparative plate chromatography.

NMR data was as follows:

$^1$H-nmr ($CDCl_3$): δ=7.05 (m, 5H), 6.65 (m, 3H), 4.10 (m, 4H), 3.35 (d, 2H), 1.35 (m, 9H), 0.65 (m, 3H). $^{13}$C-nmr ($CDCl_3$): δ=175.48, 174.75, 173.16, 166.64, 166.46, 163.37, 141.55, 141.42, 140.38, 130.04, 129.95, 129.05, 128.95, 128.73, 113.94, 113.83, 113.71, 113.60, 103.90, 103.88, 103.56, 103.22, 55.43, 51.26, 44.53, 43.21, 33.38, 29.56, 23.91, 18.28, 14.78. $C_{24}H_{29}F_2N_3O_3$ (MW=445.51); mass spectroscopy (MH$^+$) 446.

Example 4

Synthesis of N-2-(N,N-Dimethylamino)ethyl-N'-[N-(3,5-difluorophenylacetyl)-L-alaninyl]-(S)-2-aminohexanamide Following General Procedure K and using methyl N-[N-(3,5-difluorophenylacetyl)-L-alaninyl]-(S)-2-aminohexanoate (from Example 1 above) and N,N-dimethylethylenediamine (Aldrich), the title compound was prepared as a solid (mp=182–187° C.). The reaction was monitored by tlc (Rf=0.51 in 15% $CH_3OH/CH_2Cl_2$) and the product was purified by preparative plate chromatography using 15% $CH_3OH/CH_2Cl_2$ as the eluent.

NMR data was as follows:

$^1$H-nmr ($CDCl_3$): δ=7.21 (d, 1H), 6.80 (m, 5H), 4.64 (m, 1H), 4.48 (q, 1H) 3.57 (s, 2H), 3.30 (q, 2H), 2.41 (t, 2H), 2.22 (s, 6H), 1.70 (m, 2H), 1.32 (m, 7H), 0.87 (m, 3H). $^{13}$C-nmr ($CDCl_3$): δ=172.2, 172.0, 170.0, 165.4, 165.3, 163.9, 162.1, 162.0, 139.1, 138.8, 113.1, 112.8, 103.6, 103.3, 103.0, 58.1, 54.0, 49.7, 45.7, 43.3, 38.1, 33.2, 28.2, 23.0, 19.2, 14.4. $C_{21}H_{32}F_2N_4O_3$ (MW=426.51); mass spectroscopy (MH$^+$) 427.

Example 5

Synthesis of N-(2-Methoxyethyl)-N'-[N-(3,5-difluorophenylacetyl)-L-alaninyl]-(S)-2-aminohexanamide Following General Procedure K and using methyl N-[N-(3,5-difluorophenylacetyl)-L-alaninyl]-(S)-2-aminohexanoate (from Example 1 above) and 2-methoxyethylamine (Aldrich), the title compound was prepared as a solid (mp=>200° C.). The reaction was monitored by tlc (Rf=0.42 in 10% $CH_3OH/CH_2Cl_2$) and the product was purified by flash chromatography using 12% $CH_3OH/CH_2Cl_2$ as the eluent.

NMR data was as follows:

$^{13}$H-nmr ($CDCl_3$): δ=7.85 (bd, J=8.79 Hz, 0.5H), 7.64 (bd, J=7.81 Hz, 0.5H), 7.35 (m, 1H), 7.16 (bd, J=7.27 Hz, 0.5H), 7.06 (bs, 0.5H), 6.83 (m, 2H), 6.68 (m 1H), 4.70 (m, 2H), 3.56 (d, J=9.89 Hz, 2H), 3.40 (m, 7H), 1.57 (m, 10H), 0.84 (m 3H). $^{13}$C-nmr ($CDCl_3$): δ=172.62, 172.58, 172.14, 172.04, 170.02, 169.91, 165.33, 165.15, 162.08, 112.99, 112.92, 112.82, 112.77, 112.66, 112.59, 103.54, 103.34, 103.31, 103.29, 71.46, 71.44, 59.27, 59.24, 53.76, 49.64, 49.43, 43.29, 39.79, 33.26, 33.22, 28.10, 28.03, 22.97, 22.91, 19.71, 19.61, 19.56, 19.51, 14.46, 14.43. $C_{20}H_{29}F_2N_3O_4$ (MW=413.47); mass spectroscopy (MH$^+$) 414.

Example 6

Synthesis of N-2-(N,N-Dimethylamino)ethyl-N'-[N-(3,5-difluorophenylacetyl)-L-alaninyl]-L-phenylalaninamide Following General Procedure K and using N-[N-(3,5-difluorophenylacetyl)-L-alaninyl]-L-phenylalanine methyl ester (from Example 94 below) and N,N-dimethylethylenediamine (Aldrich), the title compound was prepared as a solid (mp=174–182° C.). The reaction was monitored by tlc (Rf=0.31 in 10% CH$_3$OH/CH$_2$Cl$_2$) and the product was purified by preparative plate chromatography using 10% CH$_3$OH/CH$_2$Cl$_2$ as the eluent.

NMR data was as follows:

$^1$H-nmr (CD$_3$OD): δ=7.22 (m, 5H), 6.85 (m, 3H), 4.51 (m, 1H), 4.18 (m, 1H), 3.57 (m, 2H), 3.50–2.45 (m, 6H), 2.39 (s, 6H), 1.26 (d, 2.4H), 1.10 (d, 0.6H) $^{13}$C-nmr (CD$_3$OD): δ=176.03, 175.50, 174.20, 173.99, 173.50, 173.22, 166.63, 166.46, 163.36, 163.19, 141.65, 141.52, 141.39, 139.38, 139.00, 130.90, 130.74, 130.05, 130.01, 128.37, 128.30, 114.03, 113.93, 113.80, 113.70, 103.96, 103.62, 103.57, 103.28, 59.18, 59.14, 56.78, 56.51, 51.93, 51.74, 45.53, 45.47, 43.21, 43.18, 42.92, 38.84, 38.65, 37.94, 37.85, 18.09, 17.73. C$_{24}$H$_{30}$F$_2$N$_4$O$_3$ (MW=460.53); mass spectroscopy (MH$^+$) 461.

Example 7

Synthesis of N-(4-Pyridyl)methyl-N'-[N-(3,5-difluorophenylacetyl)-L-alaninyl]-L-phenylalaninamide Following General Procedure K and using N-[N-(3,5-difluorophenylacetyl)-L-alaninyl]-L-phenylalanine methyl ester (from Example 94 below) and 4-(aminomethyl)pyridine (Aldrich), the title compound was prepared as a solid (mp=>200° C.). The reaction was monitored by tlc (Rf=0.46 in 10% CH$_3$OH/CH$_2$Cl$_2$) and the product was purified by recrystallization from ethyl acetate.

NMR data was as follows:

$^1$H-nmr (CD$_3$OD): δ=8.37 (d, 2H), 7.25 (m, 5H), 7.11 (d, 2H), 6.85 (m, 3H) 4.56 (t, 1H), 4.29 (m, 3H), 3.64 (s, 2H), 3.08 (m, 2H), 1.30 (d, 3H). $^{13}$C-nmr (CD$_3$OD): δ=175.46, 174.04, 173.26, 166.60, 166.43, 163.34, 163.16, 150.97, 150.44, 141.59, 141.45, 138.84, 130.95, 130.13, 128.44, 124.28, 113.98, 113.87, 113.75, 113.64, 103.91, 103.57, 103.23, 62.08, 57.01, 43.33, 43.12, 38.93, 21.41, 18.16, 15.02. C$_{26}$H$_{26}$F$_2$N$_4$O$_3$ (MW=480.52); mass spectroscopy (MH$^+$) 481.

Example 8

Synthesis of N-(3-Pyridyl)methyl-N'-[N-(3,5-difluorophenylacetyl)-L-alaninyl]-L-phenylalaninamide Following General Procedure K and using N-[N-(3,5-difluorophenylacetyl)-L-alaninyl]-L-phenylalanine methyl ester (from Example 94 below) and 4-(aminomethyl) pyridine (Aldrich), the title compound was prepared as a solid (mp=199–210° C.). The reaction was monitored by tlc (Rf=0.46 in 10% CH$_3$OH/CH$_2$Cl$_2$, minor isomer Rf=0.50) and the product was purified by preparative plate chromatography using 10% CH$_3$OH/CH$_2$Cl$_2$ as the eluent.

NMR data was as follows:

$^1$H-nmr (CD$_3$OD): δ=8.42 (m, 2H), 7.61 (m, 1H), 7.29 (m, 6H), 6.90 (m, 3H), 4.61 (m, 1H), 4.33 (m, 3H), 3.58 (s, 1.5H), 3.54 (s, 0.5H), 3.10 (m, 2H), 1.33 (d, 2.25H), 1.15 (d, 0.75H). $^{13}$C-nmr (CD$_3$OD): δ=176.00, 175.34, 174.03, 173.81, 173.23, 166.61, 166.44, 163.35, 163.17, 149.93, 149.20, 141.48, 139.20, 138.72, 138.10, 138.03, 136.88, 136.79, 130.89, 130.70, 130.06, 130.02, 128.40, 128.33, 125.71, 113.97, 113.87, 113.74, 113.64, 103.92, 103.58, 103.53, 103.23, 56.88, 56.66, 55.74, 53.21, 43.22, 43.15, 42.89, 42.06, 41.98, 39.04, 38.88, 38.77, 18.18, 17.79. C$_{26}$H$_{26}$F$_2$N$_4$O$_3$ (MW=480.52); mass spectroscopy (MH$^+$) 481.

Example 9

Synthesis of N-(4-Pyridyl)methyl-N'-[N-(3,5-difluorophenylacetyl)-L-alaninyl]-(S)-2-aminohexanamide Following General Procedure K and using methyl N-[N-(3,5-difluorophenylacetyl)-L-alaninyl]-(S)-2-aminohexanoate (from Example 1 above) and 4-(aminomethyl)pyridine (Aldrich), the title compound was prepared as a solid (mp=181–205° C.). The reaction was monitored by tlc (Rf=0.51 in 10% CH$_3$OH/CH$_2$Cl$_2$) and the product was purified by preparative plate chromatography using 10% CH$_3$OH/CH$_2$Cl$_2$ as the eluent.

NMR data was as follows:

1H-nmr(CD$_3$OD): δ=8.48 (m, 0.8H), 8.42 (m, 1.2H), 7.37 (d, J=6.10, 0.8H), 7.28 (d, J=6.11, 1.2H), 6.85 (m, 3H), 4.39 (m, 4H), 3.61 (s, 0.8H), 3.53 (d, J=2.99, 1.2H), 2.05–1.25 (m, 9H), 0.90 (m, 3H). $^{13}$C-nmr (CD$_3$OD): δ=176.61, 175.71, 175.33, 175.29, 173.32, 173.24, 166.49, 166.32, 163.22, 163.05, 151.30, 151.24, 150.55, 150.41, 141.54, 141.41, 124.35, 124.20, 113.95, 113.85, 113.72, 113.62, 103.86, 103.57, 103.52, 103.18, 55.72, 55.64, 51.98, 43.38, 43.19, 42.82, 33.07, 32.57, 29.87, 29.67, 23.90, 23.82, 18.24, 17.86, 14.80. C$_{23}$H$_{28}$F$_2$N$_4$O$_3$ (MW=446.50); mass spectroscopy (MH$^+$) 447.

Example 10

Synthesis of tert-butyl N-[N-(3,5-Difluorophenylacetyl)-L-alaninyl]-(S)-2-aminohexanoate Step A—t-Butyl Ester Formation To a solution of Z-norleucine-OH in CH$_2$Cl$_2$ was added 1.5 equivalents of N,N'-diisopropyl-O-t-butylisourea (prepared by the method of Synthesis (1979) p.561 for review) and the reaction was heated to reflux for 17 hours. An additional 1.5 equivalents of isourea was then added, and reflux was continued for another 7 hours. The reaction was then cooled to room temperature and filtered through a bed of Celite 545, then stripped to dryness to leave a clear oil. The residue was dissolved in hexanes and filtered to remove solids, and the filtrate was washed with saturated aqueous NaHCO$_3$, water, saturated aqueous NaCl, and dried over MgSO$_4$. The solution was concentrated under reduced pressure to leave the product.

Step B—CBZ Removal

The CBZ-protected amino ester was dissolved in ethanol in a hydrogenation flask and a catalytic amount of 10% Pd/C was added. The mixture was hydrogenated at 20 psi H$_2$ on a Parr shaker for 30 min. The reaction was then filtered through a pad of Celite 545 and stripped free of solvent on a rotary evaporator to yield the product, norleucine tert-butyl ester hydrochloride.

Step C

Following General Procedure D and using N-(3,5-difluorophenylacetyl)-L-alanine (from Example B2 above) and the norleucine tert-butyl ester hydrochloride, the title compound was prepared as a semi-solid. The reaction was monitored by tlc (Rf=0.41 in 50% EtOAc/hexanes) and the product was purified by flash chromatography using 50% EtOAc/hexanes as the eluent, followed by preparative plate chromatography using 50% EtOAc/hexanes as the eluent.

NMR data was as follows:

$^1$H-nmr (CDCl$_3$): δ=7.63 (d, J=7.7 Hz, 1H), 7.34 (d, J=7.7 Hz, 1H), 6.8 (m, 2H), 6.7 (m, 1H), 4.8 (m, 1H), 4.36 (q, J=5.6 Hz, 1H), 3.52 (s, 2H), 1.8–1.1 (m, 15H), 0.8 (m, 3H). $^{13}$C-nmr (CDCl$_3$): δ=173.0, 171.8, 170.2, 165.1, 165.0, 161.9, 161.7, 139.6, 139.4, 139.3, 112.8, 112.7, 112.6, 112.5, 103.2, 102.9, 102.6, 82.3, 53.6, 49.3, 43.0, 32.2, 28.4, 27.8, 22.7, 19.4, 14.7, 14.2. C$_{21}$H$_{30}$F$_2$N$_2$O$_4$ (MW=412.48); mass spectroscopy (MH$^+$) 413.

Example 11

Synthesis of N-[N-(Pent-4-enoyl)-L-alaninyl]-L-phenylalanine Methyl Ester

Following General Procedure A and using N-(L-alaninyl)-L-phenylalanine methyl ester (prepared by coupling N-BOC-L-alanine (Sigma) and L-phenylalanine methyl ester (Sigma) using General Procedure A, followed by removal of the BOC-group using General Procedure Y) and pent-4-enoic acid (Aldrich), the title compound was prepared as a solid (mp=125.5–126.5° C.). The reaction was monitored by tlc (Rf=0.32 in 50% EtOAc/hexanes; 0.51 in 10% CH$_3$OH/CH$_2$Cl$_2$) and the product was purified by flash chromatography using 10% CH$_3$OH/CH$_2$Cl$_2$ as the eluent.

NMR data was as follows:

$^1$H-nmr (CDCl$_3$): δ=7.27 (bd, J=7.82 Hz, 1H), 7.25–7.05 (m, 5H), 6.72 (bd, J=7.57 Hz, 1H), 5.75 (m, 1H), 4.96 (m, 2H), 4.59 (quint, J=7.2 Hz, 1H), 3.65 (s, 3H), 3.05 (m, 4H), 2.40–2.18 (m, 4H), 1.28 (d, J=7.02 Hz, 3H). $^{13}$C-nmr (CDCl$_3$): δ=173.06, 172.77, 172.36, 137.47, 136.53, 129.76, 129.07, 116.09, 54.10, 52.87, 49.06, 38.31, 25.93, 30.03, 19.17. C$_{18}$H$_{24}$N$_2$O$_4$ (MW=332.40); mass spectroscopy (MNa$^+$) 355.0.

Example 12

Synthesis of N-[N-(Dec-4-enoyl)-L-alaninyl]-L-phenylalanine Methyl Ester

Following General Procedure A and using N-(L-alaninyl)-L-phenylalanine methyl ester (prepared by coupling N-BOC-L-alanine (Sigma) and L-phenylalanine methyl ester (Sigma) using General Procedure A, followed by removal of the BOC-group using General Procedure Y) and dec-4-enoic acid (prepare from ethyl dec-4-enoate (ICM) using General Procedure N), the title compound was prepared as a solid (mp=115.5–117.5° C.). The reaction was monitored by tlc (Rf=0.52 in 50% EtOAc/hexanes; 0.60 in 10% CH$_3$OH/CH$_2$Cl$_2$) and the product was purified by flash chromatography using 10% CH$_3$OH/CH$_2$Cl$_2$ as the eluent.

NMR data was as follows:

$^1$H-nmr (CDCl$_3$): δ=7.54 (bd, J=7.69 Hz, 1H), 7.22–7.04 (m, 5H), 6.91 (bd, J=7.69 Hz, 1H), 5.37 (m, 2H), 4.73 (q, J=6.9 Hz, 1H), 4.63 (quint, J=7.2 Hz, 1H), 3.61 (s, 3H), 3.02 (m, 2H), 2.40–2.10 (m, 4H), 1.89 (m, 2H), 1.35–1.13 (m, 9H), 0.82 (m, 3H). $^{13}$C-nmr (CDCl$_3$): δ=173.26, 173.05, 172.38, 136.65, 132.30, 129.74, 128.99, 128.68, 127.48, 54.19, 52.74, 48.97, 38.28, 36.70, 33.04, 31.93, 29.68, 29.09, 23.06, 19.23, 14.61. C$_{23}$H$_{34}$N$_2$O$_4$ (MW=402.54); mass spectroscopy (MNa$^+$) 425.0.

Example 13

Synthesis of N-[N-(3,5-Difluorophenylacetyl)-L-alaninyl]-L-4-[3-(N,N-dimethylamino)propoxy]phenylalanine Methyl Ester Following General Procedure A and using N-(3,5-difluorophenylacetyl)-L-alanine (from Example B2) and L-4-[3-(N,N-dimethylamino)propoxy]-phenylalanine methyl ester (prepared from N-BOC-L-tyrosine methyl ester (B achem) and 3-dimethylamino-1-propanol (Aldrich) using a Mitsunobu procedure essentially as described in General Procedure AD, followed by removal of the BOC-group using General Procedure Y), the title compound was prepared as a solid (mp=153–155° C.). The reaction was monitored by tlc (Rf=0.36 in 10% MeOH/DCM/1%TEA) and the product was purified by acid\base washes.

NMR data was as follows:

$^1$H-nmr (CDCl$_3$): δ=6.973–6.947 (d, 2H); 6.794–6.766 (d, 2H); 6.743–6.714 (d, 2H); 6.735–6.676 (t, 1H); 4.761–4.735 (q, 1H); 4.511–4.463 (q, 1H); 3.967–3.924 (t, 2H); 3.703 (s, 3H); 3.473 (s, 2H); 3.019–2.977 (t, 2H); 2.443–2.394 (t, 2H); 2.233 (s, 6H); 1.944–1.897 (t, 2H); 1.319–1.296 (d, 3H). $^{13}$C-nmr (CDCl$_3$): δ172.292; 172.256; 169.808; 158.747; 130.731; 127.887; 115.149; 112.900; 112.672; 66.690; 56.945; 54.039; 52.971; 49.400; 46.105; 43.302; 37.421; 28.129; 19.029. C$_{26}$H$_{33}$F$_2$N$_3$O$_5$ (MW=505); mass spectroscopy (MH$^+$) 506.

Example 14

Synthesis of N-[N-(3,5-Difluorophenylacetyl)-L-alaninyl]-L-4-[(tert-butyloxycarbonyl)methoxy]phenylalanine Methyl Ester Following General Procedure AE and using tert-butyl bromoacetate (Aldrich) and N-[N-(3,5-difluorophenylacetyl)-L-alaninyl]-L-tyrosine methyl ester (from Example 15 below), the title compound was prepared as a solid (mp=116–119° C.). The reaction was monitored by tlc (Rf=0.54 in 50% EtOAc/hexanes) and the product was purified by silica gel column chromatography.

NMR data was as follows:

$^1$H-nmr (CDCl$_3$): δ7.648–7.615 (d, 1H); 7.513–7.407 (d, 1H); 6.943–6.914 (d, 2H); 6.756–6.669 (d+t, 4H); 6.621–6.562 (t, 1H); 4.662–4.590 (q+quintex, 2H); 4.382 (s, 2H); 3.571 (s, 3H); 3.406 (s, 2H); 3.006–2.648 (m, 2H); 1.417 (s, 9H); 1.243–1.221 (d, 3H). $^{13}$C-nmr (CDCl$_3$): δ=173.14; 173.001; 172.294; 170.273; 168.614; 168.546; 165.107; 161.816; 157.428; 139.493; 130.749; 129.385; 115.077; 112.803; 103.250; 828.270; 66.039; 54.361; 52.730; 49.172; 42.832; 37.288; 28.509; 19.018. C$_{27}$H$_{32}$F$_2$N$_2$O$_7$ (MW=534); mass spectroscopy (MH$^+$) 535.

Example 15

Synthesis of N-[N-(3,5-Difluorophenylacetyl)-L-alaninyl]-L-tyrosine Methyl Ester Following General Procedure A and using N-(3,5-difluorophenylacetyl)-L-alanine (from Example B2 above) and L-tyrosine methyl ester (Bachem), the title compound was prepared as a solid (mp=85–88° C.). The reaction was monitored by tlc (Rf=0.27 in 50% EtOAc/hexanes) and the product was purified by silica gel column chromatography.

NMR data was as follows:

$^1$H-nmr (CDCl$_3$): δ=8.036 (b, 1H); 7.369–7.344 (d, 1H); 7.205–7.151 (d, 1H); 6.869–6.841 (d, 2H); 6.763–6.738 (d, 2H); 6.657–6.615 (m, 3H); 4.741–4.697 (q, 1H); 4.566–4.491 (q, 1H); 3.671 (s, 3H); 3.415 (s, 2H); 3.061–2.771 (dm, 2H); 1.271–1.250 (d, 3H). $^{13}$C-nmr (CDCl$_3$): δ=173.049; 172.666; 172.444; 170.768; 165.211; 161.917; 156.098, 130.862; 127.542; 116.093, 112.990; 112.659; 103.236; 61.112; 54.306; 49.441; 42.947; 18.923. C$_{21}$H$_{22}$F$_2$N$_2$O$_5$ (MW=420); mass spectroscopy (MH$^+$) 421.

Example 16

Synthesis of N-[N-(3,5-Difluorophenylacetyl)-L-alaninyl]-L-4-(carboxymethoxy)phenylalanine Methyl Ester

Following General Procedure N and using N-[N-(3,5-difluorophenylacetyl)-L-alaninyl]-L-4-[(tert-butyloxycarbonyl)methoxy]phenylalanine methyl ester (from Example 14 above), the title compound was prepared. The reaction was monitored by tlc (Rf=0.49 in 10% MeOH/DCM+1% AcOH) and the product was purified by silica gel column chromatography.

NMR data was as follows:

$^1$H-nmr (CDCl$_3$): δ7.817 (s, 1H); 7.648–7622 (d, 1H); 7.544–7.520 (d, 1H); 6.956–6.914 (d, 2H); 6.762–6.703 (d+d, 4H); 6.650–6.590 (t, 1H); 4.678–4.636 (q, 1H); 4.567–4.503 (quinex+s, 3H); 3.622 (s, 3H); 3.431 (s, 2H); 2.987–2.811 (m, 2H); 1.241–1.219 (d, 3H). $^{13}$C-nmr (CDCl$_3$): δ173.618; 173.534; 172.215; 171.209; 171.108; 165.148; 164.973; 161.855; 161.683; 157.309; 139.052; 130.887; 129.376; 115.104; 112.895; 112.667; 103.083; 65.324; 54.155; 52.933; 50.538; 49.384; 42.683; 37.168; 18.678. C$_{23}$H$_{24}$F$_2$N$_2$O$_7$ (MW=478); mass spectroscopy (MH$^+$) 479.

Example 17

Synthesis of N-[N-(3,5-Difluorophenylacetyl)-L-alaninyl-L-4-(2-morpholinoethoxy)phenylalanine Methyl Ester

Following General Procedure AD and using N-[N-(3,5-difluorophenylacetyl)-L-alaninyl]-L-tyrosine methyl ester (from Example 15 above) and 4-(2-hydroxyethyl)morpholine (Aldrich), the title compound was prepared as a solid (mp=138–141° C.). The reaction was monitored by tlc (Rf=0.56 in 10%MeOH/DCM+1%TEA) and the product was purified by silica gel column chromatography, followed by trituation using diethyl ether.

NMR data was as follows:

$^1$H-nmr (CDCl$_3$): δ6.974–6.945 (d, 2H); 6.795–6.726 (d+t, 2H); 6.697–6.682 (t, 1H); 4.755–4.689 (q, 1H); 4.535–4.468 (quintex, 1H); 4.050–4.012 (t, 2H); 3.723–3.606 (t+s, 7H); 3.463 (s, 2H); 3.039–2.892 (m, 2H); 2.779–2.741 (t, 2H); 2.562–2.531 (t, 4H); 1.297–1.274 (d, 3H). $^{13}$C-nmr (CDCl$_3$): δ=1721.477; 172.428; 172.303; 169.925; 158.397; 130.778; 128.504; 115.179; 112.988; 112.769; 112.659; 67.457; 66.249; 58.187; 54.631; 54.119; 52.956; 49.358; 43.202; 37.496; 19.028. C$_{27}$H$_{33}$F$_2$N$_3$O$_6$ (MW=533); mass spectroscopy (MH$^+$) 534.

Example 18

Synthesis of Methyl N-[N-(3,5-Difluorophenylacetyl)-L-alaninyl]-(S)-2-amino-6-(N,N-dimethylamino)hexanoate

Following General Procedure A and using N-(3,5-difluorophenylacetyl)-L-alanine (from Example B2 above) and Nε,Nε-dimethyl-L-lysine methyl ester hydrochloride (Bachem), the title compound was prepared as a solid (mp=123–126° C.). The reaction was monitored by tlc (Rf=0.22 in 10% MeOH/DCM+1% TEA) and the product was purified by silica gel column chromatography.

NMR data was as follows:

$^1$H-nmr (CDCl$_3$): δ=7.019–6.993 (d, 1H); 6.828–6.801 (dd, 2H); 6.753–6.723 (m, 1H); 6.617–6.592 (d, 1H); 4.557–4.447 (q+q, 2H); 3.730 (s, 3H); 3.522 (s, 2H); 2.593–2.572 (m, 2H); 2.196 (s, 6H); 1.837–1.642 (m, 2H); 1.486–1.344 (m+d, 7H). $^{13}$C-nmr (CDCl$_3$): δ=173.070; 172.544, 169.809; 112.986; 112.655; 103.384: 59.393; 52.991; 49.368; 45.947; 43.427; 43.403; 43.375; 31.870; 27.376; 23.378; 19.155. C$_{20}$H$_{29}$F$_2$N$_3$O$_4$ (MW=413); mass spectroscopy (MH$^+$) 414.

Example 19

Synthesis of Methyl N-[N-(3,5-Difluorophenylacetyl)-L-alaninyl]-(S)-$^2$-amino-3-(2-pyridyl)propionate

Following General Procedure A and using N-(3,5-difluorophenylacetyl)-L-alanine (from Example B2) and methyl (S)-2-amino-3-(2-pyridyl)propionate hydrochloride (Synthetech), the title compound was prepared as a solid (mp=121–124° C.). The reaction was monitored by tlc (Rf=0.39 in 10%MeOH/DCM) and the product was purified by silica gel column chromatography.

NMR data was as follows:

$^1$H-nmr (CDCl$_3$): δ=8.474–8.458 (d, 1H); 7.767–7.631 (m, 1H); 7.625–7.574 (t, 1H); 7.178–7.102 (t+d, 2H); 6.818–6.811 (d, 2H); 6.734–6.667 (t, 1H); 6.593–6.542 (m, 1H); 4.933–4.873 (m, 1H); 4.566–4.496 (m, 1H); 3.646 (s, 3H); 3.499 (s, 2H); 3.375–3.196 (m, 2H); 1.393–1.370 (d, 3H). $^{13}$C-nmr (CDCl$_3$): δ=172.453; 172.020; 169.527; 157.454; 149.608; 137.449; 124.366; 124.328; 122.694; 113.032; 112.992; 112.661; 103.333; 53.032; 52.997; 52.349; 52.252; 49.427; 49.405; 43.464; 43.437; 38.486; 19.548; 19.232. C$_{20}$H$_{21}$F$_2$N$_3$O$_4$ (MW=405); mass spectroscopy (MH$^+$) 406.

Example 20

Synthesis of Methyl N-[N-(3,5-Difluorophenylacetyl)-L-alaninyl]-(S)-2-amino-3-(3-pyridyl)propionate

Following General Procedure A and using N-(3,5-difluorophenylacetyl)-L-alanine (from Example B2) and methyl (S)-2-amino-3-(3-pyridyl)propionate hydrochloride (Synthetech), the title compound was prepared as a solid (mp=101–103° C.). The reaction was monitored by tlc (Rf=0.48 in 10% MeOH/DCM) and the product was purified by silica gel column chromatography.

NMR data was as follows:

$^1$H-nmr (CDCl$_3$): δ=8.492–8.396 (m, 1H); 8.359–8.322 (m, 1H); 7.505–7.452 (m, 1H); 7.248–7.170 (m, 1H); 6.976–6.908 (m, 1H); 6.855–6.668 (m, 3H); 6.352–6.288 (m, 1H); 4.866–4.798 (m, 1H); 4.784–4.429 (m, 1H); 3.750 (s, 3H); 3.513 (s, 2H); 3.220–2.964 (m, 2H); 1.310–1.287 (d, 3H). $^{13}$C-nmr (CDCl$_3$): δ=172.867; 171.831; 170.307; 161.942; 150.892; 150.753; 148.907; 148.750; 137.523; 137.388; 132.460; 124.106; 124.034; 112.981; 112.754; 103.228; 53.623; 53.461; 53.146; 49.368; 49.259; 43.137; 43.115; 43.086; 35.485; 18.664. C$_{20}$H$_{21}$F$_2$N$_3$O$_4$ (MW=405); mass spectroscopy (MH$^+$) 406.

Example 21

Synthesis of N-[N-(3,5-Difluorophenylacetyl)-L-alaninyl]-L-proline Methyl Ester

Following General Procedure A and using N-(3,5-difluorophenylacetyl)-L-alanine (from Example B2 above) and L-proline methyl ester hydrochloride (Bachem), the title compound was prepared as a viscous solid. The reaction was monitored by tlc (Rf=0.57 in 10% MeOH/DCM) and the product was purified by acid/base washes.

NMR data was as follows:

$^1$H-nmr (CDCl$_3$): δ=7.524–7.498 (d, 1H); 6.813–6.793 (d, 2H); 6.681–6.613 (m, 1H); 4.788–4.717 (m, 1H); 4.484–4.442 (m, 1H); 3.705–3.590 (m+s, 4H); 3.465 (s, 2H); 2.217–1.902 (m, 5H); 1.332–1.309 (d, 3H). $^{13}$C-nmr (CDCl$_3$): δ=172.753; 172.152; 169.843; 165.185; 161.894; 112.953; 112.850; 112.727; 112.624; 103.331; 102.996; 102.662; 59.352; 52.735; 47.495; 47.267; 43.069; 29.472; 25.403; 18.243. C$_{17}$H$_{20}$F$_2$N$_2$O$_4$ (MW=354); mass spectroscopy (Mn$^+$) 355.

Example 22

Synthesis of Methyl 1-[N-(3,5-Difluorophenylacetyl)-L-alaninyl]piperidine-2-carboxylate Following General Procedure B and using N-(phenylacetyl)-L-alanine (from Example B1 above) and methyl pipecolinate hydrochloride (Aldrich), the title compound was prepared as an oil. The reaction was monitored by tlc (Rf=0.30 in 50% EtOAc/hexanes) and the product was purified by silica gel chromatography.

NMR data was as follows:

$^1$H-nmr (CDCl$_3$): δ=7.2 (m, 5H), 6.95 (dd, J=7.2, 15.2, 7.2 Hz, 1H), 5.21 (dd, J=5.0, 11.0, 5.0 Hz, 1H), 4.89 (q, J=7.1, 7.1 Hz, 1H), 3.7 (m, 1H), 3.59 (s, 3H), 3.47 (s, 2H), 3.1 (m, 1H), 2.16 (d, J=11.5 Hz, 1H), 1.4 (m, 4H), 1.22 (dd, J=1.3, 4.4, 1.2 Hz, 3H). $^{13}$C-nmr (CDCl$_3$): δ172.6, 171.8, 170.7, 135.5, 129.8, 129.3, 127.6, 52.9, 52.8, 46.0, 43.9, 27.1, 26.8, 25.6, 21.4, 19.9, 18.5. C$_{18}$H$_{24}$N$_2$O$_4$ (MW=332); mass spectroscopy (MH$^+$) 333.

Example 23

Synthesis of Methyl N-[N-(3,5-Difluorophenylacetyl)-L-alaninyl]-(S)-2-amino-3-(4-pyridyl)propionate Step A—Preparation of 3-(3-pyridyl)alanine methyl ester dihydrochloride Sodium metal (1.40 g, 61 mmol) was dissolved in EtOH (100 mL) and diethyl acetamidomalonate (6.62 g, 30.5 mmol) and 3-picolylchloride hydrochloride (5.00 g, 30.5 mmol) were added. The mixture was heated to reflux for 6 hours, and then cooled and filtered to remove NaCl (washed with EtOH). The solvent was removed in vacuo and the mixture was taken up into saturated aqueous NaHCO$_3$ (100 mL) and extracted with EtOAc (3×100 mL). The solvent was removed and the residue purified by silica gel flash chromatography (95:5 CH$_2$Cl$_2$/MeOH) to give diethyl 2-(3-pyridylmethyl)-2-acetamidomalonate (2.84 g, 30%).

Diethyl 2-(3-pyridylmethyl)-2-acetamidomalonate was dissolved in 6N HCl (30 mL) and heated to reflux for 19 hours whereupon it was cooled to room temperature and the HCl solution was removed by evaporation in vacuo. The intermediate amino acid dihydrochloride salt was taken up into MeOH (30 mL) saturated with HCl gas and stirred for 3.5 hours. The MeOH/HCl was removed by evaporation in vacuo to give 3-(3-pyridyl)alanine methyl ester dihydrochloride (2.235 g, 100%).

Step B—Preparation of Methyl N-[N-(3,5-Difluorophenylacetyl)-L-alaninyl]-(S)-2-amino-3-(4-pyridyl)propionate Following General Procedure A and using N-(3,5-difluorophenylacetyl)-L-alanine (from Example B2 above) and methyl (S)-2-amino-3-(4-pyridyl)propionate hydrochloride (prepared by the method set forth above using 4-picolylchloride hydrochloride), the title compound was prepared as a solid. The reaction was monitored by tlc (Rf=0.49 in 10% MeOH/DCM) and the product was purified by silica gel column chromatography.

NMR data was as follows:

$^1$H-nmr (CDCl$_3$): δ=8.423–8.335 (dd, 2H); 7.832–7.754 (q, 1H); 7.342–7.246 (dd, 1H); 7.032–6.972 (dd, 2H); 6.764–6.667 (t, 2H); 6.659–6.599 (m, 1H); 4.837–4.768 (m, 1H); 4.590–4.515 (m, 1H); 3.675 (s, 3H); 3.426 (s, 2H); 3.112–2.804 (m, 2H); 1.256–1.106 (dd, 3H). $^{13}$C-nmr (CDCl$_3$): δ=173.037; 171.739; 170.258; 170.225; 165.201; 165.012; 161.904; 161.721; 150.183; 150.063; 146.115; 146.012; 139.100; 125.180; 125.122; 112.951; 112.915; 112.846; 103.492; 103.153; 53.088, 49.318; 42.977, 37.593; 37.547; 19.297; 18.882. C$_{20}$H$_{21}$F$_2$N$_3$O$_4$ (MW=405); mass spectroscopy (MH$^+$) 406.

Example 24

Synthesis of Methyl N-[N-(3,5-Difluorophenylacetyl)-L-alaninyl]-2-amino-3-methoxypropionate Following General Procedure A and using N-(3,5-difluorophenylacetyl)-L-alanine (from Example B2 above) and methyl 2-amino-3-methoxypropionate hydrochloride (Bachem), the title compound was prepared as a solid (mp=165–168° C.). The reaction was monitored by tlc (Rf=0.48 in 10% MeOH/DCM) and the product was purified by acid/base washes.

NMR data was as follows:

$^1$H-nmr (CDCl$_3$): δ=6.971–6.944 (d, 1H); 6.813–6.801 (m, 2H); 6.741–6.678 (m, 1H); 6.585–6.526 (m, 1H); 4.692–4.561 (quintex+q, 2H); 3.836–3.802 (m, 1H); 3.738 (s, 3H); 3.592–3.516 (m+ds, 3H); 3.312 (s, 3H); 1.408–1.355 (dd, 3H), $^{13}$C-nmr (CDCl$_3$): δ=172.705; 172.680; 170.908; 113.019; 112.978; 112.687; 112.646; 103.347; 72.434; 72.405; 59.885; 59.837; 53.263; 53.240; 49.413; 49.329; 19.389; 18.9196. C$_{16}$H$_{20}$F$_2$N$_2$O$_5$ (MW=358); mass spectroscopy (MH$^+$) 359.

Example 25

Synthesis of Methyl N-[N-(3,5-Difluorophenylacetyl)-L-alaninyl]-2-amino-3-morpholinopropionate Step A methyl (2-N-CBZ-amino)-3-morpholino-propioniate To a solution of N-CBZ-dehydro-alanine methyl ester (Sigma) in acetonitrile was added 2.0 equivalent of morpholine and 0.25 equivalents of anhydrous ferric chloride. The mixture was stirred for 16 hours and monitored by TLC. The solvent was stripped off and the residue extracted with ethyl acetate and washed with 1N HCl. The aqueous layer was basified with 1N potassium carbonate to pH=9 and extracted with ethyl acetate again, dried over sodium sulfate and rotovapped to dryness to give methyl (2-N-CBZ-amino)-3-morpholino-propionate as a clear tan oil. See Perez et al., Tetrahedron 51(3) 8355–62 (1995)

Step B Methyl N-[N-(3,5-Difluorolphenylacetyl)-L-alaninyl]-2-amino-3-morpholinopropionate Following General Procedure A and using N-(3,5-difluorophenylacetyl)-L-alanine (from Example B2 above) and methyl 2-amino-3-morpholinopropionate hydrochloride (prepared by General Procedure O above from methyl (2-N-CBZ-amino)-3-morpholino-propionate), the title compound was prepared as a viscous solid. The reaction was monitored by tlc (Rf=0.44 in 10% MeOH/DCM) and the product was purified by acid/base washes.

NMR data was as follows:
$^1$H-nmr (CDCl$_3$): δ=7.408–7.384 (d, 1H); 7.247–7.173 (mn, 1H); 6.774–6.614 (m+t, 3H); 4.605–4.468 (to, H); 3.667 (s, 3H); 3.642 (s, 2H); 3.576–3.561 (t, 4H); 3.479–3.461 (s+s, 2H); 2.639–2.618 (d, 2H); 2.39552.366 (, 4H); 1.344–1.307 (t, 3H). $^{13}$C-nmr (CDCl$_3$): δ=173.120; 172.245; 172.192; 170.275; 170.159; 165.189; 165.020; 161.897; 161.727; 139.167; 112.937; 112.863; 112.759; 112.610; 112.533; 103.103; 102.774; 67.379; 67.301; 59.346; 59.110; 54.030; 52.936; 51.116; 49.283; 43.053; 18.980; 18.921. C$_{19}$H$_{26}$F$_2$N$_3$O$_5$ (MW=413); mass spectroscopy (MH$^+$) 414.

Example 26

Synthesis of N-(2-Methoxyethyl)-N'-[N-(3,5-difluorophenylacetyl)-L-alaninyl]-L4-(2-morpholinoethoxy)phenylalaninamide Following General Procedure K and using 2-methoxyethylamine (Aldrich) and N-[N-(3,5-difluorophenylacetyl)-L-alaninyl]-L-4-(2-morpholinoethoxy)-phenylalanine methyl ester (from Example 17 above), the title compound was prepared as a solid (mp=165–168° C.). The reaction was monitored by tlc (Rf=0.67 in 10% MeOH/DCM+1% TEA) and the product was purified by acid/base washes.

NMR data was as follows:
$^1$H-nmr (CDCl$_3$): δ=8.258–8.232 (d, 1H); 8.014–7.989 (d, 1H); 7.532–7.370 (t, 1H); 7.035–7.008 (d, 2H); 6.842–6.630 (m, 5H); 4.980–4.905 (m, 1H); 4.794–4.772 (m, 1H); 4.026–3.992 (t, 2H); 3.713–3.642 (t, 4H); 3.594–3.453 (dd, 2H); 3.404–3.267 (t, 2H); 3.179 (s, 3H); 2.930–2.914 (t, 2H); 2.763–2.731 (t, 2H); 2.538–2.502 (m, 4H); 1.335–1.314 (d, 3H). $^{13}$C-nmr (CDCl$_3$): δ=172.956; 172.918; 171.756; 170.142; 161.677; 158.131; 130.973; 129.270; 114.968; 114.875; 112.908; 112.696; 112.571; 71.423; 71.367; 67.440; 66.164; 59.072; 58.232; 58.188; 54.636; 42.827; 42.800; 39.757; 39.642; 20.449; 20.135. C$_{29}$H$_{38}$F$_2$N$_4$O$_6$ (MW=576); mass spectroscopy (MH$^+$) 577.

Example 27

Synthesis of N-(2-Methoxyethyl)-N'-[N-(3,5-difluorophenylacetyl)-L-alaninyl]-2-amino-3-methoxypropionamide Following General Procedure K and using 2-methoxyethylamine (Aldrich) and methyl N-[N-(3,5-difluorophenylacetyl)-L-alaninyl]-2-amino-3-methoxypropionate (from Example 24 above), the title compound was prepared as a solid (mp=181–184° C.). The reaction was monitored by tlc (Rf=0.43 in 10% MeOH/DCM) and the product was purified by acidibase washes.

NMR data was as follows:
$^1$H-nmr (CDCl$_3$): δ=6.728–6.706 (d, 2H); 6.648–6.586 (t, 1H); 4.244–4213 (m 1H); 4.092–4.068 (m, 1H); 3.553–3.503 (m, 2H); 3.393–3.347 (m, 2H); 3.210–3.073 (m+s, 7H); 3.053 (s, 3H); 1.183–1.138 (d, 3H). $^{13}$C-nmr (CDCl$_3$): δ=176.31; 173.28; 172.59; 141.65; 114.02; 113.79; 113.69; 109.467; 103.528; 80.369; 73.210; 72.265; 72.011; 59.839; 59.801; 59.374; 55.584; 51.773; 51.731; 51.445; 42.915; 40.846; 17.751. C$_{18}$H$_{25}$F$_2$N$_3$O$_5$ (MW=401); mass spectroscopy (MH$^+$) 402.

Example 28

Synthesis of N-[N-(3,5-Difluorophenylacetyl)-L-alaninyl]glycine Methyl Ester Following General Procedure A and using N-(3,5-difluorophenylacetyl)-L-alanine (from Example B2 above) and glycine methyl ester hydrochloride (Bachem), the title compound was prepared as a solid (mp=158–160° C.). The reaction was monitored by tlc (Rf=0.61 in 10%MeOH/DCM) and the product was purified by silica gel chromatography.

NMR data was as follows:
$^1$H-nmr (CDCl$_3$): δ=6.882–6.866 (m, 1H); 6.827–6.794 (m, 2H); 6.748–6.689 (t, 1H); 6.520–6.494 (d, 1H); 4.611–4.563 (quintex, 1H); 4.00–3.99 (d, 2H); 3.746 (s, 3H); 3.528 (s, 2H); 1.389–1.366 (d, 3H). $^{13}$C-nmr (CDCl$_3$): δ=172.926; 172.524; 170.524; 113.056; 112.951; 112.723; 103.769; 103.437; 103.214; 103.105; 85.309; 53.009; 49.333; 43.292; 41.692; 18.810. C$_{14}$H$_{16}$F$_2$N$_2$O$_4$ (MW=314); mass spectroscopy (MH$^+$) 315.

Example 29

Synthesis of N-(2-Methoxyethyl)-N'-[N-(3,5-difluorophenylacetyl)-L-alaninyl]-2-amino-3-(4-pyridyl)propionamide Following General Procedure K and using 2-methoxyethylamine and methyl N-[N-(3,5-difluorophenylacetyl)-L-alaninyl]-(S)-2-amino-3-(4-pyridyl)propionate (from Example 23 above), the title compound was prepared as a solid (mp=202–206° C.). The reaction was monitored by tlc (Rf=0.72 in 10%MeOH/DCM) and the product was purified by acid/base washes.

NMR data was as follows:
$^1$H-nmr (CDCl$_3$): δ=8.214–8.198 (d, 2H); 7.117–7.100 (d, 2H); 6.707–6.687 (m, 2H); 6.638–6.576 (t, 1H); 4.498–4.448 (m, 1H); 3.985–3.939 (q, 1H); 3.386 (s, 2H); 3.190–3.084 (m, 4H); 3.060 (s, 3H); 2.918–2.629 (m, 2H); 1.077–0.905 (d, 3H). $^{13}$C-nmr (CDCl$_3$): δ=175.831; 173.229; 150.440; 150.249; 126.887; 113.995; 113.662; 103.662; 103.529; 72.081; 59.370; 55.201; 51.674; 42.949; 40.889; 38.350; 17.933. C$_{22}$H$_{26}$F$_2$N$_4$O$_4$ (MW=448); mass spectroscopy (MH$^+$) 449.

Example 30

Synthesis of N-(2-Methoxyethyl)-N'-[N-(3,5-difluorophenylacetyl)-L-alaninyl]-2-amino-3-(2-pyridyl)propionamide Following General Procedure K and using 2-methoxyethylamine and methyl N-[N-(3,5-difluorophenylacetyl)-L-alaninyl]-(S)-2-anion-3-(2-pyridyl)propionate (from Example 19 above), the title compound was prepared as a solid (mp=183–187° C.). The reaction was monitored by tlc (Rf=0.39 in 10% MeOH/DCM) and the product was purified by recrystallization from MeOH/DCM.

NMR data was as follows:
$^1$H-nmr (CDCl$_3$): δ=8.457–8.442 (d, 1H); 8.029–8.005 (d, 1H); 7.642–7.585 (t, 1H); 7.395–7.379 (m, 1H); 7.267–7.141 (d+t, 2H); 6.828–6.802 (m, 2H); 6.754–6.679 (t, 1H); 6.604–6.581 (m, 1H); 4.871–4.809 (q, 1H); 4.532–4.485 (quintex, 1H); 3.537 (s, 2H); 3.342–3.118 (m, 6H); 3.248 (s, 3H); 1.394–1.371 (d, 3H). $^{13}$C-nmr (CDCl$_3$): δ=172.360; 171.140; 158.43; 149.113; 137.59; 124.98; 122.54; 113.02; 112.69; 103.40; 71.376; 59.203; 53.143; 49.984; 43.355; 43.328; 39.685; 39.626; 19.295. C$_{22}$H$_{26}$F$_2$N$_4$O$_4$ (MW=448); mass spectroscopy (MH$^+$) 449.

Example 31

Synthesis of Methyl N-[N-(3,5-Difluorophenylacetyl)-L-alaninyl]-(S)-2-amino-3-(thiazol-4-yl)propionate Following General Procedure A and using N-(3,5-difluorophenylacetyl)-L-alanine (from Example B2 above)

and methyl (S)-2-amino-3-(thiazol-4-yl)propionate hydrochloride (General Procedure H with methanol and HCl on methyl (S)-2-amino-3-(thiazol-4-yl)propyl acid (Synthetech)), the title compound was prepared as a solid (mp=136–139° C.). The reaction was monitored by tlc (Rf=0.4 in 10% MeOH/DCM) and the product was purified by recrystallization from DCM.

NMR data was as follows:

$^1$H-nmr (CDCl$_3$): δ=8.737–8.731 (d, 1H); 7.410–7.385 (d, 1H); 7.065–7.059 (d, 1H); 6.828–6.802 (m, 2H); 6.747–6.687 (m, 1H); 6.542–6.518 (d, 1H); 4.904–4.844 (q, 1H); 4.553–4.505 (quintex, 1H); 3.678 (s, 3H); 3.515 (s, 2H); 3.402–3.232 (dq, 2H); 1.384–1.361 (d, 3H). $^{13}$C-nmr (CDCl$_3$): δ=172.497; 171.726; 169.619; 153.831; 152.613; 116.431; 113.019; 112.688; 112.014; 103.396; 53.113; 52.625; 49.476; 43.460; 43.435; 32.850; 19.422. $C_{18}H_{19}F_2N_3O_4S$ (MW=411); mass spectroscopy (MH$^+$) 412.

Example 32

Synthesis of Methyl 2-[N-(3,5-Difluorophenylacetyl)-L-alaninyl]-1,2,3,4-tetrahydroisoquinoline-3-carboxylate Following General Procedure A and using N-(3,5-difluorophenylacetyl)-L-alanine (from Example B2 above) and methyl 1,2,3,4-tetrahydroisoquinoline-3-carboxylate (Aldrich), the title compound was prepared as a solid (mp=37–40° C.). The reaction was monitored by tlc (Rf=0.64 in 10% MeOH/DCM).

NMR data was as follows:

$^1$H-nmr (CDCl$_3$): δ=7.500–7.475 (d, 1H); 7.161–7.057 (m, 4H); 6.815–6.795 (dm, 2H); 6.656–6.596 (t, 1H); 5.336–5.088 (m, 2H); 4.924–4.841 (m, 1H); 4.718–4.453 (m, 1H); 3.530 (s, 3H); 3.500 (s, 2H); 3.329–3.058 (m, 2H); 1.423–1.400, 1.327–1.304 (d, 3H). $^{13}$C-nmr (CDCl$_3$): δ=173.428; 173.329; 171.690; 171.559; 169.558; 165.020; 161.899; 161.728; 139.368; 132.549; 128.912; 127.723; 126.648; 112.929; 103.360; 60.915; 53.318; 53.001; 46.377; 43.121; 31.027; 21.537; 19.545; 18.771; 14.716. $C_{22}H_{22}F_2N_2O_4$ (MW=416); mass spectroscopy (MH$^+$) 417.

Example 33

Synthesis of N-(3-Methoxybenzyl)-N'-[N-(3,5-difluorophenylacetyl)-L-alaninyl]-L-phenylalaninamide Following General Procedure B and using N-[N-(3,5-difluorophenylacetyl)-L-alaninyl]-L-phenylalanine (prepared by coupling N-(3,5-difluorophenylacetyl)-L-alanine (from Example B2 above) with L-phenylalanine methyl ester hydrochloride (Sigma) using General Procedure E, followed by hydrolysis using General Procedure C) and 3-methoxybenzylamine (TCI), the title compound was prepared as a solid (mp=117–130° C.). The reaction was monitored by tlc (Rf=0.8 in 3% MeOH/methylene chloride) and the product was purified by recrystallization from MeOH.

NMR data was as follows:

$^1$H-nmr (DMSO-d$_6$): δ=8.4 (t, 1H), 8.32 (d, 1H), 8.1 (d, 1H), 6.95–7.2 (m, 9H), 6.7 (m, 3H), 4.5 (m, 1H), 4.2 (m, 3H), 3.7 (s, 3H), 3.5 (s, 2H), 3.3 (d, 2H), 3.0 (m, 2H), 2.5 (s, 3H), 1.2 (m, 4H). $^{13}$C-nmr (DMSO-d$_6$): δ=172.40, 171.08, 169.28, 159.62, 141.09, 138.06, 129.62, 129.51, 128.41, 126.63, 119.56, 112.97, 112.79, 112.59, 112.46, 55.31, 48.77, 40.69, 40.42, 40.28, 40.14, 40.03, 39.86, 39.70, 39.58, 39.46, 39.44, 39.31, 39.20, 39.03, 18.45. $C_{28}H_{29}N_3O_4F_2$ (MW=509); mass spectroscopy (MH$^+$) 509.

Example 34

Synthesis of Methyl N-[N-(3,5-Difluorophenylacetyl)-L-alaninyl]-(S)-2-amino-3-(1-naphthyl)propionate Following General Procedure B and using N-(3,5-difluorophenylacetyl)-L-alanine (from Example B2 above) and methyl (S)-2-amino-3-(1-naphthyl)propionate hydrochloride (Bachem), the title compound was prepared as a solid (mp=103–130° C.). The reaction was monitored by tlc (Rf=0.8 in 5% MeOH/methylene chloride) and the product was purified by flash column chromatography using 6% MeOH/methylene chloride as the eluent.

NMR data was as follows:

$^1$H-nmr (CDCl$_3$): δ=8.10 (d, 1H), 7.85 (d, 1H), 7.71 (d, 1H), 7.50 (m, 3H), 7.35 (t, 1H), 7.20 (d, 1H), 6.70 (m, 4H), 6.30 (d, 1H), 4.90 (m, 1H), 4.45 (m, 1H), 3.3–3.7 (m, 8H), 1.7 (bs, 1H), 1.3 (d, 3H). $^{13}$C-nmr (CDCl$_3$): δ=172.43, 172.29, 169.77, 134.41, 132.61, 132.58, 129.51, 128.63, 128.33, 128.28, 128.06, 126.97, 126.80, 126.42, 126.29, 125.94, 125.86, 124.06, 123.90, 112.96, 112.63, 103.44, 78.03, 77.61, 77.19, 61.01, 54.02, 53.83, 52.99, 51.40, 49.33, 43.29, 35.64, 18.82, 14.77. $C_{24}H_{24}N_2O_4F_2$ (MW=442); mass spectroscopy (MH$^+$) 442.

Example 35

Synthesis of Methyl N-[N-(3,5-Difluorophenylacetyl)-L-alaninyl]-(S)-2-amino-3-(2-naphthyl)propionate Following General Procedure B and using N-(3,5-difluorophenylacetyl)-L-alanine (from Example B2 above) and methyl (S)-2-amino-3-(2-naphthyl)propionate hydrochloride (Bachem), the title compound was prepared as a solid (mp=166° C.). The reaction was monitored by tlc (Rf=0.55 in 5% MeOH/methylene chloride) and the product was purified by preparative tlc using 5% MeOH/methylene chloride as the eluent.

NMR data was as follows:

$^1$H-nmr (CDCl$_3$): δ=1.3 (d, 3H), 3.2 (m, 2H), 3.3 (s, 2H), 3.7 (s, 3H), 4.55 (m, 1H), 4.9 (quart, 1H), 6.7 (m, 4H), 7.05 (d, 1H), 7.20 (d, 1H), 7.45 (m, 2H), 7.55 (s, 1H), 7.80 (m, 3H). $^{13}$C-nmr (CDCl$_3$): δ=172.43, 172.26, 169.86, 133.93, 133.76, 133.02, 128.86, 128.64, 128.23, 128.20, 127.69, 126.85, 126.45, 112.95, 112.62, 103.37, 78.05, 77.62, 77.20, 53.93, 53.05, 49.37, 43.12, 38.46, 18.81. $C_{24}H_{24}N_2O_4F_2$ (MW=442); mass spectroscopy (MH$^+$) 442.

Example 36

Synthesis of Methyl N-[N-(3,5-Difluorophenylacetyl)-L-alaninyl]-(S)-2-amino-3-(2-thienyl)propionate Following General Procedure B and using N-(3,5-difluorophenylacetyl)-L-alanine (from Example B2 above) and methyl (S)-2-amino-3-(2-thienyl)-propionate (Bachem), the title compound was prepared as a solid (mp=145–147° C.). The reaction was monitored by tlc (Rf=0.9 in 100% EtOAc) and the product was purified by preparative tlc using EtOAc as the eluent.

NMR data was as follows:

¹H-nmr (CDCl₃): δ=7.15 (d, 1H), 6.9 (t, 1H), 6.7–6.8 (m, 5H), 6.3 (d, 1H), 4.8 (m, 1H), 4.5 (m, 1H), 3.8 (s, 3H), 3.5 (s, 2H), 3.35 (d, 2H), 1.35 (d, 3H). ¹³C-nmr (CDCl₃): δ=172.22, 171.56, 169.79, 137.47, 127.71, 125.55, 113.04, 112.71, 103.48, 78.03, 77.60, 77.18, 53.78, 53.25, 49.51, 43.41, 32.37, 18.97. $C_{19}H_{20}N_2O_4F_2S$ (MW=410); mass spectroscopy (MH⁺) 410.

Example 37

Synthesis of N-[N-(3,5-Difluorophenylacetyl)-L-alaninyl]-L-phenylalanine Benzyl Ester Following General Procedure B and using N-(3,5-difluorophenylacetyl)-L-alanine (from Example B2 above) and L-phenylalanine benzyl ester hydrochloride (Bachem), the title compound was prepared as a solid (mp=170–171 °C.). The reaction was monitored by tlc (Rf=0.7 in 5% MeOH/methylene chloride) and the product was purified by recrystallization from MeOH.

NMR data was as follows:

¹H-nmr (MeOH): δ=7.3 (m, 10H), 6.9 (m, 3H), 5.2 (s, 2H), 4.75 (t, J=7 Hz, 1H), 4.4 (quart, J=6 Hz, 1H), 3.6 (s, 2H), 3.1 (m, J=6 Hz, 2H), 1.35 (d, J=7 Hz, 3H). ¹³C-nmr (MeOH): δ=175.29, 173.09, 172.78, 141.54, 138.35, 137.53, 130.88, 130.08, 130.05, 129.92, 128.42, 113.93, 113.83, 113.60, 103.90, 103.55, 103.21, 68.59, 55.87. $C_{27}H_{26}N_2O_4F_2$ (MW=480); mass spectroscopy (MH⁺) 480.

Example 38

Synthesis of N-[N-(3,5-Difluorophenylacetyl)-L-alaninyl]-L-phenylalanine 3-Bromopropyl Ester Following General Procedure B and using N-[N-(3,5-difluorophenylacetyl)-L-alaninyl]-L-phenylalanine (prepared by coupling N-(3,5-difluorophenylacetyl)-L-alanine (from Example B2 above) and L-phenylalanine (Aldrich) using General Procedure B) and 3-bromo-1-propanol (Aldrich), the title compound was prepared as a solid (mp=138–142° C.). The reaction was monitored by tlc (Rf=0.75 in 60% EtOAc/hexanes) and the product was purified by flash column chromatography using 60% EtOAc/hexanes as the eluent.

NMR data was as follows:

¹H-nmr (CDCl₃): δ=7.3–6.6 (m, 10H), 4.8 (m, 1H), 4.55 (m, 1H), 4.2 (t, J=6 Hz, 2H), 3.51 (s, 2H), 3.3 (m, 2H), 3.05 (m, J=6 and 8 Hz, 2H), 2.1 (m, 2H), 1.3–1.2 (m, J=7 Hz, 3H). ¹³C-nmr (CDCl₃): δ=172.49, 171.78, 171.71, 170.01, 169.96, 165.31, 162.02, 161.84, 138.91, 138.78, 138.66, 136.26, 136.19, 129.76, 129.72, 129.22, 129.18, 127.80, 113.04, 113.02, 112.93, 112.91, 112.82, 112.79, 112.71, 112.69, 103.72, 103.69, 103.36, 103.05, 103.03, 63.75, 63.70, 54.11, 53.91, 49.38, 49.32, 43.26, 38.56, 38.51, 31.92, 29.76, 29.71, 19.14, 19.06. $C_{23}H_{25}N_2O_4F_2Br$ (MW=511.1); mass spectroscopy (MH⁺) 512.

Example 39

Synthesis of N-[N-(3,5-Difluorophenylacetyl)-L-alaninyl]-L-phenylalanine 3-Iodopropyl Ester Following General Procedure B and using N-[N-(3,5-difluorophenylacetyl)-L-alaninyl]-L-phenylalanine (prepared by coupling IV-(3,5-difluorophenylacetyl)-L-alanine (from Example B2 above) and L-phenylalanine (Aldrich) using General Procedure B) and 3-iodo-1-propanol (Aldrich), the title compound was prepared as a solid. The reaction was monitored by tlc (Rf=0.45 in 5% MeOH/methylene chloride) and the product was purified by preparative tlc using 5% MeOH/methylene chloride.

NMR data was as follows:

¹H-nmr (CDCl₃): δ=7.4–7.0 (m, 5H), 6.9–6.6 (m, 4H), 6.3 (m, 1H), 4.8 (m, 1H), 4.5 (m, 1H), 4.2 (t, 2H), 3.5 (s, 2H), 3.1 (m, 4H), 2.1 (m, 2H), 1.7 (s, 1H), 1.35–1.25 (m, 3H). ¹³C-nmr (CDCl₃): δ=172.24, 171.72, 169.95, 136.12, 136.09, 129.77, 129.75, 129.28, 129.24, 127.87, 113.06, 113.02, 112.73, 112.70, 103.80, 103.49, 103.47, 65.73, 65.70, 54.00, 53.84, 49.42, 49.33, 43.38, 38.54, 38.50, 32.57, 18.97, 18.91.

Example 40

Synthesis of N-[N-(3,5-Difluorophenylacetyl)-L-alaninyl]-L-leucine tert-Butyl Ester Following General Procedure B and using N-(3,5-difluorophenylacetyl)-L-alanine (from Example B2 above) and L-leucine tert-butyl ester hydrochloride (Bachem), the title compound was prepared as a solid (mp=128° C.). The reaction was monitored by tlc (Rf=0.85 in 5% MeOH/methylene chloride) and the product was purified by flash column chromatography using 5% MeOH/methylene chloride as the eluent.

NMR data was as follows:

¹H-nmr (CDCl₃): δ=6.9–6.5 (m, 5H), 4.6 (m, 1H), 4.4 (m, 1H), 3.5 (s, 2H), 1.7–1.4 (m, 15H), 0.9 (t, 6H). ¹³C-nmr (CDCl₃): δ=172.41, 172.20, 169.87, 165.30, 162.00, 161.83, 139.01, 138.89, 112.92, 112.82, 112.69, 112.59, 103.62, 103.29, 102.95, 82.50, 78.03, 77.61, 77.18, 52.12, 49.39, 43.34, 41.86, 28.52, 25.42, 23.26, 22.46, 19.18. $C_{27}H_{30}N_2O_4F_2$ (MW=412.48); mass spectroscopy (MH⁺) 413.

Example 41

Synthesis of N'-[N-(3,5-Difluorophenylacetyl)-L-alaninyl]-2-amino-2-(2-pyridyl)acetamide Following General Procedure L and using ethyl N-[N-(3,5-difluorophenylacetyl)-L-alaninyl]-2-amino-2-(2-pyridyl)acetate (from Example 65 below), the title compound was prepared as a solid. The reaction was monitored by tlc (Rf=0.1 in 9:1 CHCl₃/MeOH) and the product was purified by recrystallizaion from EtOH.

NMR data was as follows:

¹H-nmr (DMSO-d₆): δ=8.54 (m, 1H), 8.43 (d, 1H), 7.77 (m, 1H), 7.59 (bs, 1H), 7.46 (m, 1H), 7.33 (m, 1H), 7.22 (m, 1H), 7.09 (m, 1H), 6.98 (m, 2H), 5.41 (m, 1H), 4.46 (m, 1H), 4.46 (m, 1H), 3.52 (s, 2H), 1.26 (m, 3H). $C_{18}H_{17}N_3O_3F_2$ (MW=376.3); mass spectroscopy (MH⁺) 377.

Example 42

Synthesis of N'-[N-(3,5-Difluorophenylacetyl)-L-alaninyl]-2-amino-2-(3-pyridyl)acetamide Following General Procedure L and using ethyl N-[N-(3,5-difluorophenylacetyl)-L-alaninyl]-2-amino-2-(3-pyridyl)acetate (from Example 53 below), the title compound was prepared as a solid. The reaction was monitored by tlc (Rf=0.1 in 9:1 CHCl₃/MeOH) and the product was purified by recrystallization from EtOH.

NMR data was as follows:

¹H-nmr (DMSO-d₆): δ=8.64 (m, 1H), 8.55 (d, 1H); 8.52 (d, 1H), 8.41 (d, 1H), 7.79 (m, 1H), 7.37 (m, 1H), 7.32 (m, 1H), 7.09 (m, 1H), 6.98 (m, 2H), 5.42 (m, 1H), 4.42 (m, 1H), 3.53 (s, 2H), 1.26 (m, 3H). $C_{18}H_{17}N_4O_3F_2$ (MW=376.3); mass spectroscopy (MH$^+$) 377.

Example 43

Synthesis of N-[N-(3,5-Difluorophenylacetyl)-L-alaninyl]-N$_\epsilon$-(tert-butoxycarbonyl)-L-lysine Methyl Ester Following General Procedure A and using N-(3,5-difluorophenylacetyl)-L-alanine (from Example B2 above) and N-ε(tert-butoxycarbonyl)-L-lysine methyl ester (Bachem), the title compound was prepared as an oil. The reaction was monitored by tlc (Rf=0.40 in 50% EtOAc/hexanes) and the product was purified by flash chromatography using 50% EtOAc/hexanes as the eluent.

NMR data was as follows:

$^1$H-nmr (CDCl$_3$): δ=6.80 (d, 2H), 6.66 (t, 1H), 4.82 (bs, 1H), 3.73 (s, 3H), 3.52 (s, 2H), 3.04 (bs, 2H), 1.60–1.15 (m, 2H), 1.38 (s, 9H), 1.32 (d, 2H), 1.20–1.30 (m, 2H). $^{13}$C-nmr(CDCl$_3$): δ=173.00, 172.80, 165.28, 165.11, 161.98, 161.78, 156.79, 138.95, 129.06, 128.72, 103.59, 103.26, 102.92, 79.81, 52.99, 52.76, 49.44, 43.25, 31.92, 29.98, 28.99, 22.95, 18.94. $C_{23}H_{33}F_2N_3O_6$ (MW=485–53); mass spectroscopy (MH$^+$) N/A.

Example 44

Synthesis of Methyl N-[N-(3,5-Difluorophenylacetyl)-L-alaninyl]-(S)-2-amino-4-phenylbutanoate Following General Procedure A and using N-(3,5-difluorophenylacetyl)-L-alanine (from Example B2 above) and methyl (S)-2-amino-4-phenylbutanoate (prepared from (+)-α-amino-4-phenylbutyric acid (Bachem) using General Procedure AG), the title compound was prepared as a solid (mp=147–149.5° C.). The reaction was monitored by tlc (Rf=0.32 in 50% EtOAc/hexanes) and the product was purified by flash chromatography using EtOAc/hexanes as the eluent.

NMR data was as follows:

$^1$H-nmr (CDCl$_3$): δ=7.63 (bd, 2H), 7.04 (m, 5H), 6.56–6.82 (m, 3H), 4.80 (p, 1H), 4.48 (q, 1H), 3.65 (s, 3H), 3.49 (s, 2H), 2.50–2.65 (m, 2H), 1.80–2.16 (m, 2H), 1.29 (d, 3H). $^{13}$C-nmr (CDCl$_3$): δ=173.48, 172.89, 170.43, 165.17, 161.71, 140.91, 139.34, 129.07, 129.01, 128.89, 126.81, 126.76, 112.90, 112.67, 103.37, 103.03, 102.69, 52.86, 52.71, 49.36, 42.99, 33.79, 32.21, 19.34. $C_{22}H_{24}F_2N_2O_4$ (MW=418.44); mass spectroscopy (MH$^+$) 419.

Example 45

Synthesis of N-[N-(3,5-Difluorophenylacetyl)-L-alaninyl]glycine 2-Phenylethyl Ester Following General Procedure X and using N-[N-(3,5-difluorophenylacetyl)-L-alaninyl]glycine (prepared from N-[N-(3,5-difluorophenylacetyl)-L-alaninyl]glycine benzyl ester (from Example 73 below) using General Procedure O) and 2-phenylethanol (Aldrich), the title compound was prepared as a solid (mp=154.0–155.2° C.). The reaction was monitored by tlc (Rf=0.15 in 15% EtOAc/hexanes) and the product was purified by flash chromatography using 15% EtOAc/hexanes as the eluent.

NMR data was as follows:

$^1$H-nmr (CDCl$_3$): δ=7.35–7.20 (m, 5H), 6.76 (bs, 1H), 6.72–6.67 (m, 3H), 6.54 (bd, 1H), 4.58 (p, 1H), 4.34 (t, 2H), 3.96 (d, 2H), 3.52 (s, 2H), 2.93 (t, 2H), 1.26 (d, 3H). $^{13}$C-nmr (CDCl$_3$): δ=172.9, 170.1, 169.9, 137.8, 129.4, 129.1, 127.3, 112.94, 103.4, 103.0, 65.5, 49.3, 43.2, 41.8, 35.4, 18.8. $C_{21}H_{22}N_2O_4F_2$ (MW=404.42); mass spectroscopy (MH$^+$) 405.

Example 46

Synthesis of N-[N-(3,5-Difluorophenylacetyl)-L-alaninyl]glycine 3-Phenylpropyl Ester Following General Procedure X and using N-[N-(3,5-difluorophenylacetyl)-L-alaninyl]glycine (prepared from N-[N-(3,5-difluorophenylacetyl)-L-alaninyl]glycine benzyl ester (from Example 73 below) using General Procedure O) and and 3-phenyl-1-propanol (Aldrich), the title compound was prepared as a solid (mp=137° C.). The reaction was monitored by tlc (Rf=0.15 in 50% EtOAc/hexanes) and the product was purified by flash chromatography using 50% EtOAc/hexanes as the eluent.

NMR data was as follows:

$^1$H-nmr (CDCl$_3$): δ=7.55–7.32 (m, 5H), 6.73 (d, 2H), 6.65 (m, 1H), 4.74 (p, 1H), 4.14 (t, 2H), 3.93 (m, 2H), 3.49 (s, 2H), 2.66 (t, 2H), 1.94 (p, 2H), 1.41 (d, 3H). $^{13}$C-nmr (CDCl$_3$): δ=173.8, 170.5, 170.1, 165.2, 165.0, 161.9, 161.7, 141.5, 139.2, 129.1, 128.9, 126.7, 112.9, 112.8, 103.4, 103.1, 102.8, 65.4, 49.3, 42.9, 41.8, 32.6, 30.6, 19.3. $C_{22}H_{24}N_2O_4F_2$ (MW=418.44); mass spectroscopy (MH$^+$) 419.

Example 47

Synthesis of N'-[N-(3,5-Difluorophenylacetyl)-L-alaninyl]-2-amino-2-(4-pyridyl)acetamide Following General Procedure L and using ethyl N-[N-(3,5-difluorophenylacetyl)-L-alaninyl]-2-amino-2-(4-pyridyl) acetate (from Example 66), the title compound was prepared as a solid. The reaction was monitored by tlc (Rf=0.1 in CHCl$_3$/MeOH 9:1) and the product was purified by silica gel chromatography using 9:1 CHCl$_3$/MeOH as the eluent.

NMR data was as follows:

$^1$H-nmr (DMSO-d$_6$): δ=8.53 (m, 2H), 8.88 (bs, 1H), 7.41 (m, 2H), 7.12 (m, 1H), 7.02 (m, 2H), 5.46 (m, 1H), 4.46 (m, 1H), 3.55 and 3.52 (s, 2H), 1.21 (m, 3H). $C_{18}H_{18}N_4O_3F_2$ (MW=376.3); mass spectroscopy (MH$^+$) 377.

Example 48

Synthesis of N-[N-(Phenylacetyl)-L-alaninyl]-L-threonine Methyl Ester

Following General Procedure U and using N-(phenylacetyl)-L-alanine (from Example B1 above) and L-threonine methyl ester hydrochloride (Bachem), the title compound was prepared as a solid.

NMR data was as follows:

$^1$H-nmr (CDCl$_3$): δ=7.45 (d, J=8.9 Hz, 1H), 7.11–7.27 (m, 6H), 4.55 (quintet, J=7.2 Hz, 1H), 4.43 (dd, J=2.6, 8.8 Hz, 1H), 4.20 (m, 1H), 3.62 (s, 3H), 3.46 (s, 2H), 1.29 (d, J=7.0 Hz, 3H), 1.04 (d, J=6.4 Hz, 3H). $^{13}$C-nmr (CDCl$_3$): δ=172.8, 171.1, 170.9, 134.5, 128.9, 128.4, 126.8, 67.5, 57.7, 52.1, 48.7, 42.8, 19.6, 18.3. $C_{16}H_{22}N_2O_5$ (MW=322.36); mass spectroscopy (MH$^+$) 323.

Example 49

Synthesis of N'-[N-(Phenylacetyl)-L-alaninyl]-L-leucinamide

Following General Procedure T and using N-(phenylacetyl)-L-alanine (from Example B1 above) and L-leucinamide hydrochloride (Aldrich), the title compound was prepared as a solid (mp=207–209° C.). The product was purified by extraction with EtOAc and washing with aqueous potassium carbonate and aqueous hydrochloric acid.

NMR data was as follows:

$^1$H-nmr (CD$_3$OD): δ7.00–7.12 (m, 5H), 4.10–4.20 (m, 2H), 3.34 (s, 2H), 1.30–1.50 (m, 2H), 1.12–1.23 (m, 4H), 0.65–0.76 (m, 6H). $^{13}$C-nmr (CD$_3$OD): δ=177.5, 174.9, 174.1, 136.8, 130.1, 129.6, 127.9, 52.8, 50.7, 43.4, 41.9, 25.8, 23.5, 21.8, 17.7.

Example 50

Synthesis of N'-[N-(Phenylacetyl)-L-alaninyl]-L-alaninamide

Following General Procedure U and using N-(phenylacetyl)-L-alanine (from Example B1 above) and L-alaninamide hydrochloride (Bachem), the title compound was prepared as a solid (mp=>260° C.). The product was purified by washing with aqueous sodium hydroxide and aqueous hydrochloric acid.

NMR data was as follows:

$^1$H-nmr (DMSO-d$_6$): δ=8.27 (d, J=7.1 Hz, 1H), 7.88 (d, J=7.6 Hz, 1H), 7.26 (m, 6H), 6.99 (s, 1H), 4.25 (quintet, J=7.1 Hz, 1H), 4.16 (quintet, J=7.1 Hz, 1H), 3.46 (s, 2H), 1.19 (t, J=6.3 Hz, 6H). $^{13}$C-nmr (DMSO-d$_6$): δ=174.1, 171.8, 170.0, 136.3, 129.0, 128.1, 126.3, 48.3, 47.9, 42.0, 18.3, 18.1.

Example 51

Synthesis of N'[N-(Phenylacetyl)-L-alaninyl]-L-phenylalaninamide

Following General Procedure T and using N-(phenylacetyl)-L-alanine (from Example B1 above) and L-phenylalaninamide (Bachem), the title compound was prepared as a solid (mp=224–225° C.).

NMR data was as follows: $^1$H-nmr (DMSO-d$_6$): δ=8.24 (d, J=7.2 Hz, 1H), 7.89 (d, J=8.2 Hz, 1H), 7.36 (s, 1H), 7.13–7.34 (m, 10H), 7.11 (s, 1H), 4.40 (m, 1H), 4.21 (quintet, J=7.1 Hz, 1H), 3.44 (d, 2H), 3.01 (dd, J=4.9, 13.7 Hz, 1H), 2.82 (dd, J=9.0, 13.7 Hz, 1H), 1.13 (d, J=6.9 Hz, 3H). $^{13}$C-nmr (DMSO-d$_6$): δ=172.7, 172.0, 170.0, 137.8, 136.3, 129.2, 129.0, 128.2, 128.0, 126.3, 126.2, 53.6, 48.5, 41.9, 37.3, 18.0.

Example 52

Synthesis of N'-[N-(Phenylacetyl)-L-alaninyl)-L-valinamide

Following General Procedure T and using N-(phenylacetyl)-L-alanine (from Example B1 above) and L-valinamide hydrochloride (Bachem), the title compound was prepared as a solid (mp=>261 ° C.).

NMR data was as follows:

$^1$H-nmr (DMSO-d$_6$): δ=8.31 (d, J=7.5 Hz, 1H), 7.62 (d, J=9.0 Hz, 1H), 7.38 (s, 1H), 7.15–7.30 (m, 5H), 7.05 (s, 1H), 4.34 (quintet, J=7.2 Hz, 1H), 4.08 (dd J=6.4, 15.3 Hz, 1H), 3.45 (s, 2H), 1.91 (m, 1H), 1.19 (d, J=7.0 Hz, 3H), 0.79 (d, J=6.7 Hz, 3H), 0.76 (d, J=6.8 Hz, 3H). $^{13}$C-nmr (DMSO-d6): δ=172.8, 172.1, 170.0, 136.3, 129.0, 128.2, 126.3, 57.2, 48.2, 42.0, 30.5, 19.2, 17.9, 17.8.

Example 53

Synthesis of Ethyl N-[N-(3,5-Difluorophenylacetyl)-L-alaninyl]-2-amino-2-(3-pyridyl)acetate Following General Procedure C and using N-(3,5-difluorophenylacetyl)-L-alanine (from Example B2 above) and ethyl 2-amino-2-(3-pyridyl)acetate (prepared as described in P. Kolar et al., *J. Heterocyclic Chem.*, 28, 1715 (1991) and references cited therein), the title compound was prepared as a solid (mp=146–157° C.). The reaction was monitored by tlc (Rf=0.1 in CHCl$_3$/MeOH 98:2) and the product was purified by silica gel chromatography using 959:5 CHCl$_3$/MeOH as the eluent, followed by recrystallization from chlorobutane.

NMR data was as follows:

$^1$H-nmr (CDCl$_3$): δ=8.60 (m, 1H), 8.56 and 8.52 (m, 1H), 7.91 (m, 1H), 7.63 (m, 1H), 7.22 (m, 1H), 6.90 (m, 1H), 6.74 (m, 2H), 5.55 (m, 1H), 4.69 (m, 1H) 4.17 (m, 2H), 3.50 and 3.41 (s, 2H), 1.33 and 1.29 (d, 3H), 1.21 (m, 3H), 1.18 (m, 3H). C$_{20}$H$_{21}$N$_3$O$_4$F$_2$ (MW=405.4); mass spectroscopy (MH$^+$) 405.

Example 54

Synthesis of N-Methyl-N'-[N-(phenylacetyl)-L-alaninyl]-L-leucinamide

Following General Procedure U and using N-(phenylacetyl)-L-alanine (from Example B1 above) and N-methyl-L-leucinamide (prepared from N-methyl-N'-BOC-L-leucinamide (from Example D5 above) using General Procedure Y), the title compound was prepared as a solid (mp=233–235 ° C.). The product was purified by recrystallization from MeOH.

NMR data was as follows:

$^1$H-nmr (CDCl$_3$/CD$_3$OD): δ=7.25–7.40 (m, 5H), 4.36 (quartet, J=7.2 Hz, 1H), 4.27 (dd, J=5.1, 14.6 Hz, 1H), 3.56 (s, 2H), 2.72 (s, 3H), 1.40–1.61 (m, 2H), 1.32 (d, J=7.1 Hz, 3H), 0.89 (d, J=6.2 Hz, 3H), 0.86 (d, J=6.2 Hz, 3H).

Example 55

Synthesis of N,N-Dimethyl-N'-[N-(phenylacetyl)-L-alaninyl]-L-phenylalaninamide

Following General Procedure U and using N-(phenylacetyl)-L-alanine (from Example B1 above) and N,N-dimethyl-L-phenylalaninamide (prepared by coupling N-BOC-L-phenylalanine (Bachem) with dimethylamine hydrochloride (Aldrich) using General Procedure B, followed by removal of the BOC-group using General Procedure Y), the title compound was prepared as a solid (mp=152–155° C.). The product was purified by extraction with EtOAc, washing with aqueous sodium carbonate and aqueous hydrochloric acid, and trituration with Et$_2$O.

NMR data was as follows:

$^1$H-nmr (CDCl$_3$): δ=7.49 (d, J=8.2 Hz, 1H), 7.20–7.26 (m, 8H), 7.14 (m, 2H), 6.45 (d, J=7.5 Hz, 1H), 5.08 (quartet, J=8.0 Hz, 1H), 4.60 (quintet, J=7.3 Hz, 1H), 3.56 (s, 2H), 2.95 (m, 2H), 2.86 (s, 3H), 2.61 (s, 3H), 1.26 (d, J=6.9 Hz, 3H). $^{13}$C-nmr (CDCl$_3$): δ=171.6, 170.8, 170.4, 136.0, 134.7, 129.3, 129.2, 128.9, 128.8, 128.3, 127.1, 50.2, 48.7, 43.4, 39.5, 36.8, 35.6, 18.8.

Example 56

Synthesis of N,N-Dimethyl-N'-[N-(phenylacetyl)-L-alaninyl]-L-leucinamide

Following General Procedure U and using N-(phenylacetyl)-L-alanine (from Example B 1 above) and N,N-dimethyl-L-leucinamide (prepared by coupling N-BOC-L-leucine (Bachem) with dimethylamine hydrochloride (Aldrich) using General Procedure B, followed by removal of the BOC-group using General Procedure Y), the title compound was prepared as a solid (mp=130–132° C.). The product was purified by extraction by EtOAc, washing with aqueous sodium carbonate and aqueous hydrochloric acid, and trituration with Et$_2$O.

NMR data was as follows:

$^1$H-nmr (CDCl$_3$): δ=7.23–7.36 (m, 5H), 7.04 (d, J=8.7 Hz, 1H), 6.30 (d, J=7.6 Hz, 1H), 4.92 (m, 1H), 4.56 (quintet, J=7.2 Hz, 1H), 3.56 (s, 2H), 3.07 (s, 3H), 2.94 (s, 3H), 1.33–1.64 (m, 3H), 1.27 (d, J=6.9 Hz, 3H), 0.94 (d, J=6.4 Hz, 3H), 0.88 (d, J=6.5 Hz, 3H). $^{13}$C-nmr (CDCl$_3$): δ=172.0, 171.7, 170.4, 134.6, 129.2, 128.8, 127.2, 48.7, 47.3, 43.5, 42.1, 36.9, 35.8, 24.6, 23.3, 21.8, 18.6.

Example 57

Synthesis of N,N-Dimethyl-N'-[N-(phenylacetyl)-L-alaninyl]-L-valinamide

Following General Procedure U and using N-(phenylacetyl)-L-alanine (from Example B 1 above) and NN-dimethyl-L-valinamide (prepared by coupling N-BOC-L-valine (Bachem) with dimethylamine hydrochloride (Aldrich) using General Procedure B, followed by removal of the BOC-group using General Procedure Y), the title compound was prepared as a solid (mp=147–149° C.). The product was purified by extraction by EtOAc, washing with aqueous sodium carbonate and aqueous hydrochloric acid, and trituration with Et$_2$O.

NMR data was as follows:

$^1$H-nmr (CDCl$_3$): δ=7.24–7.38 (m, 5H), 6.64 (d, 1H), 6.05 (d, 1H), 4.74 (dd, J=5.9, 8.9 Hz, 1H), 4.50 (quintet, J=7.1 Hz, 1H), 3.59 (s, 2H), 3.08 (s, 3H), 2.96 (s, 3H), 1.97 (m, 1H), 1.28 (d, J=7.0 Hz, 3H), 0.91 (d, J=6.8 Hz, 3H), 0.84 (d, J=6.8 Hz, 3H). $^{13}$C-nmr (CDCl$_3$): δ=172.3, 171.4, 170.4, 134.6, 129.0, 128.5, 126.8, 53.5, 48.5, 43.2, 37.3, 35.6, 31.2, 19.2, 18.6, 17.5. C$_{18}$H$_{27}$N$_3$O$_3$ (MW=333.43); mass spectroscopy (MH$^+$) 334.

Example 58

Synthesis of N-Methyl-N'-[N-(phenylacetyl)-L-alaninyl]-L-phenylalaninamide

Following General Procedure U and using N-(phenylacetyl)-L-alanine (from Example B1 above) and N-methyl-L-phenylalaninamide (prepared by coupling N-BOC-L-phenylalanine (Bachem) with methylamine hydrochloride (Aldrich) using General Procedure B, followed by removal of the BOC-group using General Procedure Y), the title compound was prepared as a solid. The product was purified by washing with aqueous sodium carbonate and aqueous hydrochloric acid.

NMR data was as follows:

$^1$H-nmr (DMSO-d$_6$): δ=8.23 (d, J=7.0 Hz, 1H), 7.95 (d, J=8.2 Hz, 1H), 7.79 (d, J=4.4 Hz, 1H), 7.10–7.32 (m, 10H), 4.37 (quintet, J=5.4 Hz, 1H), 4.19 (quintet, J=7.1 Hz, 1H), 3.44 (s, 2H), 2.96. (dd, J=5.5, 13.7 Hz, 1H), 2.78 (dd, J=9.2, 13.7 Hz, 1H), 2.52 (d, J=4.4 Hz, 3H), 1.11 (d, J=7.0 Hz, 3H). $^{13}$C-nmr (DMSO-d$_6$): δ=172.9, 171.0, 170.1, 137.8, 136.3, 129.11, 129.07, 128.2, 128.1, 126.31, 126.26, 53.9, 48.5, 41.9, 37.5, 25.5, 18.0.

Example 59

Synthesis of N-Methyl-N'-[N-(phenylacetyl)-L-alaninyl]-L-valinamide

Following General Procedure U and using N-(phenylacetyl)-L-alanine (from Example B1 above) and N-methyl-L-valinamide (prepared by coupling N-BOC-L-valine (Bachem) with methylamine hydrochloride (Aldrich) using General Procedure B, followed by removal of the BOC-group using General Procedure Y), the title compound was prepared as a solid. The product was purified by washing with aqueous sodium carbonate and aqueous hydrochloric acid.

NMR data was as follows:

$^1$H-nmr (DMSO-d$_6$): δ=8.30 (d, J=7.6 Hz, 1H), 7.88 (d, J=4.7 Hz, 1H), 7.69 (d, J=9.1 Hz, 1H), 7.17–7.32 (m, 5H), 4.34 (quintet, J=7.2 Hz, 1H), 4.04 (dd, J=7.0, 8.9 Hz, 1H), 3.45 (s, 2H), 2.56 (d, J=4.6 Hz, 3H), 1.87 (m, 1H), 1.18 (d, J=7.0 Hz, 3H), 0.76 (d, J=6.6 Hz, 3H), 0.75 (d, J=6.7 Hz, 3H). $^{13}$C-nmr (DMSO-d$_6$): δ=172.0, 171.1, 170.0, 136.3, 129.0, 128.1, 126.3, 57.6, 48.2, 42.0, 30.6, 25.4, 19.2, 18.1, 17.9.

Example 60

Synthesis of N-Methyl-N'-[N-(3,5-difluorophenylacetyl)-L-alaninyl]-(S)-2-aminohexanamide Following General Procedure U and using N-(3,5-difluorophenylacetyl)-L-alanine (from Example B2 above) and N-methyl-L-norleucinamide (prepared by coupling N-BOC-L-norleucine (Bachem) with methylamine hydrochloride (Aldrich) using General Procedure B, followed by removal of the BOC-group using General Procedure Y), the title compound was prepared as a solid. The product was purified by washing with aqueous sodium carbonate and aqueous hydrochloric acid.

NMR data was as follows:

$^1$H-nmr (DMSO-d$_6$): δ=8.37 (d, 7.1, 1H), 7.88 (d, 8.1, 1H), 7.78 (d, 4.4, 1H), 7.08 (t, 9.5, 1H), 6.98 (d, 6.90, 2H), 4.27 (quintet, 7.0, 1H), 4.13 (quartet, 5.5, 1H), 3.51 (s, 2H), 2.54 (d, 4.4, 3H), 1.58 (m, 1H), 1.46 (m, 1H), 1.19 (m, 7H), 0.81 (t, 6.5, 3H). $^{13}$C-nmr (DMSO-d$_6$): δ=172.0, 171.9, 169.0, 162.2(dd, J=13.6, 244.0 Hz), 140.7, 112.2 (dd, J=8.3, 17.0 Hz), 101.9 (t, J=25.5 Hz), 52.4, 48.4, 41.3, 31.8, 27.4, 25.5, 21.8, 17.9, 13.8. C$_{18}$H$_{25}$N$_3$O$_3$F$_2$ (MW=369.42); mass spectroscopy (MH$^+$) 384.

Example 61

Synthesis of N,N-Dimethyl-N'-[N-(3,5-difluorophenylacetyl)-L-alaninyl]-(S)-2-aminohexanamide Following General Procedure U and using N-(3,5-difluorophenylacetyl)-L-alanine (from Example B2 above) and N,N-dimethyl-L-norleucinamide (prepared by coupling N-BOC-L-norleucine (Bachem) with dimethylamine hydrochloride (Aldrich) using General Procedure B, followed by removal of the BOC-group using General Procedure Y), the title compound was prepared as a solid (mp=138–140° C.). The product was pied by extraction with EtOAc and washing with aqueous sodium carbonate and aqueous hydrochloric acid.

NMR data was as follows:

$^1$H-nmr (CDCl$_3$): δ=7.11 (d, 8.1, 1H), 6.81 (m, 2H), 6.71 (m, 1H), 6.60 (d, 7.6, 1H), 4.89 (q, J=5.0, 1H), 4.57 (quint, J=7.1, 4H), 3.53 (s, 2H), 3.08 (s, 3H), 2.97 (s, 3H), 1.70 (m, 1H), 1.55 (m, 1H), 1.20–1.38 (m, 7H), 0.85 (t, 6.9, 3 Hz). $^{13}$C-nmr (CDCl$_3$): δ=171.6, 171.5, 168.9, 163.0 (dd, J=12.9, 247.3 Hz), 138.4, 112.2 (dd, J=7.8, 17.0 Hz), 102.7 (t, J=25.0 Hz), 49.1, 48.9, 42.9, 37.1, 35.8, 32.6, 27.1, 22.4, 19.1, 13.8. $C_{19}H_{27}N_3O_3F_2$ (MW=383.44); mass spectroscopy (MH+) 384.

Example 62

Synthesis of N'-[N-(3,5-Difluorophenylacetyl)-L-alaninyl]-(S)-2-aminohexanamide Following General Procedure U and using N-(3,5-difluorophenylacetyl)-L-alanine (from Example B2 above) and L-norleucinamide (prepared from N-BOC-L-norleucinamide (from Example D6 above) using General Procedure Y), the title compound was prepared as a solid (mp=>215° C.). The product was purified by precipitation from water.

NMR data was as follows:

$^1$H-nmr (DMSO-d$_6$): δ=8.37 (d, 7.4, 1H), 7.83 (d, 8.0, 1H), 7.29 (s, 1H), 6.95–7.14 (m, 4H), 4.29 (quintet, J=7.2, 1H), 4.14 (quartet, J=5.0, 1H), 3.52 (s, 2H), 2H), 1.61 (m, 1H), 1.46 (m, 1H), 1. 2 1 (m, 7H), 0.82 (m, 3H). $^{13}$C-nmr (DMSO-d$_6$): δ=173.6, 171.9, 168.9, 162.0 (dd), 140.7, 112.2 (dd, J=7.5, 16.6 Hz), 101.9 (t), 52.2, 48.3, 41.3, 31.8, 27.4, 21.8, 18.0, 13.8. $C_{17}H_{23}N_3O_3F_2$ (MW=355.39); mass spectroscopy (MH+) 356.

Example 63

Synthesis of Methyl N-[N-(3,5-Difluorophenylacetyl)-L-alaninyl]-2-amino-2-(3-methoxyphenyl)acetate Following General Procedure C and using N-(3,5-difluorophenylacetyl)-L-alanine (from Example B2 above) and methyl 2-amino-2-(3-methoxyphenyl)acetate hydrochloride (prepared by the Bucherer Modification of the Strecker procedure as described in J. P. Greenstein et al., "The Chemistry of Amino Acids", Vol. 1, p. 698, Wiley, New York (1961)), the title compound was prepared as a solid (mp=163–170° C.). The reaction was monitored by tlc (Rf=0.45 in 9:1 CHCl$_3$/MeOH) and the product was purified by silica gel chromatography using 97:3 CHCl$_3$/MeOH as the eluent.

NMR data was as follows:

$^1$H-nmr (CDCl$_3$): δ=7.27 (m, 1H), 7.18 and 7.06 (m, 1H), 6.87–6.67 (m, 6H) 6.25 (m, 1H), 5.46 (m, 1H), 4.58 (m, 1H), 3.82 (s, 3H), 3.71 and 3.69 (s, 3H), 3.53 and 3.48 (s, 3H), 1.39 and 1.30 (d, 3H). $C_{21}H_{22}N_2O_5F_2$ (MW=420.42); mass spectroscopy (MH+) 421.

Example 64

Synthesis of Methyl N-[N-(3,5-Difluorophenylacetyl)-L-alaninyl]-2-amino-2-(4-methoxyphenyl)acetate Following General Procedure C and using N-(3,5-difluorophenylacetyl)-L-alanine (from Example B2 above) and methyl 2-amino-2-(4-methoxyphenyl)acetate hydrochloride (prepared by the Bucherer Modification of the Strecker procedure as described in J. P. Greenstein et al., "The Chemistry of Amino Acids", Vol. 1, p. 698, Wiley, New York (1961)), the title compound was prepared as a solid (mp=170–174° C.). The reaction was monitored by tlc (Rf=0.1 in 98:2 CHCl$_3$/MeOH) and the product was purified by silica gel chromatography using 98:2 CHCS$_3$/MeOH as the eluent.

NMR data was as follows:

$^1$H-nmr (CDCl$_3$): δ=7.26 (mn, 2H), 7.01–6.68 (m, 5H), 6.14 (m, 1H), 5.41 (m, 1H), 4.56 (m, 1H), 3.80 (s, 3H), 3.74 and 3.71 (s, 3H), 3.54 and 3.47 (s, 3H), 1.39 and 1.29 (d, 3H). $C_{21}H_{22}N_2O_5F_2$ (MW=420.42); mass spectroscopy (MH+) 421.

Example 65

Synthesis of Ethyl N-[N-(3,5-Difluorophenylacetyl)-L-alaninyl]-2-amino-2-(2-pyridyl)acetate Following General Procedure C and using N-(3,5-difluorophenylacetyl)-L-alanine (from Example B2 above) and ethyl 2-amino-2-(2-pyridyl)acetate hydrochloride (prepared as described in P. Kolar et al., *J. Heterocyclic Chem.*, 28, 1715 (1991) and references cited therein), the title compound was prepared as a solid (mp=123–125° C.). The reaction was monitored by tlc (Rf=0.1 in 98:2 CHCl$_3$/MeOH) and the product was purified by silica gel chromatography using 95:5 CHCl$_3$/MeOH as the eluent, followed by recrystallization from chlorobutane.

NMR data was as follows:

$^1$H-nmr (CDCl$_3$): δ=8.53 (m, 1H), 7.70 (m, 2H); 7.48 (m, 1H), 7.27 (m, 1H), 6.86 (m, 2H), 6.74 (m, 1H), 6.52 (m, 1H), 5.58 (m, 1H), 4.67 (m, 1H), 4.18 (m, 2H), 3.54 and 3.50 (s, 2H), 1.48 and 1.39 (d, 3H), 1.21 (m, 3H). $C_{20}H_{21}N_3O_4F_2$ (MW=405.4); mass spectroscopy (MH+) 405.

Example 66

Synthesis of Ethyl N-[N-(3,5-Difluorophenylacetyl)-L-alaninyl]-2-amino-2-(4-pyridyl)acetate Following General Procedure C and using N-(3,5-difluorophenylacetyl)-L-alanine (from Example B2 above) and ethyl 2-amino-2-(4-pyridyl)acetate hydrochloride (prepared as described in P. Kolar et al., *J. Heterocyclic Chem.*, 28, 1715 (1991) and references cited therein), the title compound was prepared as a solid (mp=175–181° C.). The reaction was monitored by tlc (Rf=0.1 in 98:2 CHCl$_3$/MeOH) and the product was purified by silica gel chromatography using 95:5 CHCl$_3$/MeOH as the eluent, followed by recrystallization from chlorobutane.

NMR data was as follows:

$^1$H-nmr (CDCl$_3$): δ=8.59 (m, 2H), 7.39 (m, 1H), 7.26 (mn, 2H), 6.80 (m, 3H), 6.21 (m, 1H), 5.51 (m, 1H), 4.62 (m, 1H), 4.21 (m, 2H), 3.57 and 3.51 (s, 2H), 1.38 (m, 3H), 1.23 (m, 3H). $C_{20}H_{21}N_3O_4F_2$ (MW=405.4); mass spectroscopy (MH+) 405.

Example 67

Synthesis of N-[N-(Cyclohexylacetyl)-L-alaninyl]-L-phenylalanine Methyl Ester Following General Procedure U and using cyclohexylacetic acid (Aldrich) and N-(L-alaninyl)-L-phenylalanine methyl ester (prepared by coupling N-BOC-L-alanine (Bachem) with L-phenylalanine methyl ester hydrochloride (Bachem) using General Procedure U, followed by removal of the BOC-group using General Procedure Y), the title compound was prepared as a solid (mp=156–158° C.). The reaction was monitored by tlc (Rf=0.25 in 1:1 EtOAc/hexanes).

NMR data was as follows:

$^1$H-nmr (CDCl$_3$): δ=0.95 (m, 2H), 1.10–1.38 (m, 3H), 1.33 (d, J=7.0 Hz, 3H), 1.60–1.86 (m, 6H), 2.02 (d, J=7.5 Hz, 2H), 3.10 (m, 2H), 3.71 (s, 3H), 4.49 (m, 1H), 4.81 (m, 1H), 6.10 (d, J=7.3 Hz, 1H), 6.65 (d, J=7.7 Hz, 1H), 7.11 (m, 2H), 7.26 (m, 3H). $^{13}$C-nmr (CDCl$_3$): δ=18.4, 26.0, 26.1, 33.0, 33.1, 35.3, 37.8, 44.5, 48.5, 52.4, 53.3, 127.1, 128.6, 129.2, 135.6, 171.6, 172.0, 172.2. C$_{21}$H$_{30}$N$_2$O$_4$ (MW=374.48); mass spectroscopy (MH$^+$) 375.

Example 68

Synthesis of N-[N-(Cyclopentylacetyl)-L-alaninyl]-L-phenylalanine Methyl Ester

Following General Procedure U and using cyclopentylacetic acid (Aldrich) and N-(L-alaninyl)-L-phenylalanine methyl ester (prepared by coupling N-BOC-L-alanine (Bachem) with L-phenylalanine methyl ester hydrochloride (Bachem) using General Procedure U, followed by removal of the BOC-group using General Procedure Y), the title compound was prepared as a solid (mp=137–139° C.). The reaction was monitored by tlc (Rf=0.23 in 1:1 EtOAc/hexanes).

NMR data was as follows:

$^1$H-nmr (CDCl$_3$): δ=1.13 (m, 2H), 1.33 (d, J=7.0 Hz, 3H), 1.58 (m, 4H), 1.80 (m, 2H), 2.17 (m, 3H), 3.10 (m, 2H), 3.71 (s, 3H), 4.50 (m, 1H), 4.83 (m, 1H), 6.12 (d, J=7.4 Hz, 1H), 6.69 (d, J=7.7 Hz, 1H), 7.2 (m, 2H), 7.25 (m, 3H). $^{13}$C-nmr (CDCl$_3$): δ=18.3, 24.9, 32.4, 32.5, 37.0, 37.7, 42.7, 48.4, 52.3, 53.3, 127.1, 128.5, 129.2, 135.7, 171.6, 172.0, 172.6. C$_{20}$H$_{28}$N$_2$O$_4$ (MW=360.46); mass spectroscopy (MH$^+$) 361.

Example 69

Synthesis of N-[N-(Cyclohex-1-enylacetyl)-L-alaninyl]-L-phenylalanine Methyl Ester Following General Procedure U and using cyclohex-1-enylacetic acid (Alfa) and N-(L-alaninyl)-L-phenylalanine methyl ester (prepared by coupling N-BOC-L-alanine (Bachem) with L-phenylalanine methyl ester hydrochloride (Bachem) using General Procedure U, followed by removal of the BOC-group using General Procedure Y), the title compound was prepared as a solid (mp=139–142° C.). The reaction was monitored by tlc (Rf=0.27 in 1:1 EtOAc/hexanes).

NMR data was as follows: $^1$H-nmr (CDCl$_3$): δ=1.31 (d, J=7.0 Hz, 3H), 1.58 (m, 4H), 1.89 (m, 2H), 2.04 (br s, 2H), 2.83 (s, 2H), 3.00–3.20 (m, 2H), 3.71 (s, 3H), 4.47 (m, 1H), 4.81 (m, 1H), 5.60 (s, 1H), 6.26 (d, J=7.3 Hz, 1H), 6.67 (d, J=7.7 Hz, 1H), 7.11 (m, 2H), 7.26 (m, 3H). $^{13}$C-nmr (CDCl$_3$): δ=18.1, 21.9, 22.7, 25.3, 28.3, 37.7, 46.0, 48.4, 52.3, 53.3, 127.1, 127.2, 128.5, 129.1, 132.2, 135.7, 171.0, 171.6, 171.8. C$_{21}$H$_{28}$N$_2$O$_4$ (MW=372.47); mass spectroscopy (MH$^+$) 373.

Example 70

Synthesis of Methyl N-[N-(3,5-Difluorophenylacetyl)-L-alaninyl]-1-aminocyclopropane-1-carboxylate Following General Procedure C and using N-(3,5-difluorophenylacetyl)-L-alanine (from Example B2 above) and methyl 1-aminocyclopropane-1-carboxylate hydrochloride (Sigma), the title compound was prepared as a solid. The reaction was monitored by tlc (Rf=0.3 in 95:5 CHCl$_3$/MeOH) and the product was purified by silica gel chromatography using 97:3 CHCl$_3$/MeOH as the eluent.

NMR data was as follows:

$^1$H-nmr (CDCl$_3$): δ=6.96 (bs, 1H), 6.82 (m, 2H), 6.69 (m, 1H), 6.48 (d, 1H), 4.50 (m, 1H), 3.67 (s, 3H), 3.54 (s, 2H), 1.58 (m, 2H), 1.40 (d, 2H), 1.12 (m, 2H). Optical Rotation: [α]$_{23}$=−18° (c 1, MeOH).

Example 71

Synthesis of N-2-(N,N-Dimethylamino)ethyl-N-methyl-N'-[N-(3,5-difluorophenylacetyl)-L-alaninyl]-L-alaninamide Following General Procedure C and using N-[N-(3,5-difluorophenylacetyl)-L-alaninyl]-L-alanine (from Example D7 above) and N,N,N'-trimethylethylene-diamine (Aldrich), the title compound was prepared as a solid.

NMR data was as follows:

$^1$H-nmr (DMSO-d$_6$): δ=8.37 (m, 2H), 8.19 (d, 1H), 8.08 (d, 2H), 7.10 (m, 1H), 6.99 (m, 2H), 4.67 (m, 1H), 4.30 (m, 1H), 3.52 (s, 2H), 3.01 and 2.86 (s, 3H), 2.47 (t, 1H), 2.31 (t, 1H), 2.15 (s, 6H), 1.19 (m, 6H). Optical Rotation: [α]$_{23}$=−85° (c 1, MeOH). C$_{19}$H$_{28}$N$_4$O$_3$F$_2$ (MW=398.45); mass spectroscopy (MH$^+$) 398.

Example 72

Synthesis of N-[N-(Cyclopropylacetyl)-L-alaninyl]-L-phenylalanine Methyl Ester

Following General Procedure U and using cyclopropylacetic acid (Lancaster) and N-(L-alaninyl)-L-phenylalanine methyl ester (prepared by coupling N-BOC-L-alanine (Bachem) with L-phenylalanine methyl ester hydrochloride (Bachem) using General Procedure U, followed by removal of the BOC-group using General Procedure Y), the title compound was prepared as a solid (mp=128–131° C.). The reaction was monitored by tlc (Rf=0.14 in 1:1 EtOAc/hexanes).

NMR data was as follows:

$^1$H-nmr (CDCl$_3$): δ=0.17 (m, 2H), 0.59 (m, 2H), 0.92 (m, 1H), 1.35 (d, J=7.0 Hz, 3H), 2.11 (m, 2H), 3.05 (dd, J=6.7, 13.9 Hz, 1H), 3.16 (dd, J=5,5, 13.9 Hz, 1H), 3.73 (s, 3H), 4.52 (m, 1H), 4.82 (m, 1H), 6.47 (d, J=7.1 Hz, 1H), 6.70 (d, J=7.5 Hz, 1H), 7.12 (m, 2H), 7.28 (m, 3H). $^{13}$C-nmr (CDCl$_3$): δ=4.6, 6.9, 18.2, 37.7, 41.2, 48.4, 52.4, 53.2, 127.1, 128.5, 129.2, 135.7, 171.7, 171.9, 172.3. C$_{18}$H$_{24}$N$_2$O$_4$ (MW=332.40); mass spectroscopy (MH$^+$) 333.

Example 73

Synthesis of N-[N-(3,5-Difluorophenylacetyl)-L-alaninyl]glycine Benzyl Ester

Following General Procedure A and using N-(3,5-difluorophenylacetyl)-L-alanine (from Example B2 above) and glycine benzyl ester (prepared from N-BOC-glycine (Bachem) and benzyl alcohol (Aldrich) using General Procedure X, followed by removal of the BOC-group using General Procedure Y), the title compound was prepared as a solid (mp=167.5° C.). The reaction was monitored by tlc (Rf=0.35 in 2% MeOH/CH$_2$Cl$_2$) and the product was purified by flash chromotography using 2% MeOH/CH$_2$Cl$_2$ as the eluent.

NMR data was as follows:

$^1$H-nmr (CDCl$_3$): δ=7.12 (m, 5H), 6.71 (m, 3H), 6.60 (m, 2H), 4.95 (s, 2H 4.18 (q, 1H), 3.76 (dd, 2H), 3.35 (s, 2H), 1.13 (d, 3H). $^{13}$C-nmr (CDCl$_3$): δ=176.0, 172.9, 171.5, 166.46, 163.30, 141.54, 137.70, 130.11, 129.88, 113.98, 113.87, 113.75, 113.64, 103.89, 103.55, 103.21, 68.44, 50.93, 43.25, 42.61, 18.65. C$_{20}$H$_{20}$N$_2$O$_4$F$_2$ (MW=390.39); mass spectroscopy (MH$^+$) 391.

Example 74

Synthesis of N-[N-(Isovaleryl)-L-phenylglycinyl]-L-alanine Ethyl Ester

Following General Procedure C and using N-(isovaleryl)-L-phenylglycine (prepared from isovaleric acid (Aldrich) and L-phenylglycine methyl ester hydrochloride (Aldrich) using General Procedure C, followed by hydrolysis using General Procedure AF) and L-alanine ethyl ester hydrochloride (Sigma), the title compound was prepared as a solid (mp=198–201 °C.). The reaction was monitored by tlc (Rf=0.3 in 1:1 EtOAc/hexanes) and the product was purified by silica gel chromatography using 5% MeOH/CHCl$_3$ as the eluent, followed by rerystallization from EtOAc.

NMR data was as follows:

$^1$H-nmr (DMSO-d$_6$)(1:5 mixture of diastereomers): δ=1.25 and 1.30 (two d, 3H), 5.57 (d, 1H), 5.60 (d, 1H). C$_{18}$H$_{26}$N$_2$O$_4$ (MW=334.42); mass spectroscopy (MH$^+$) 335.

Example 75

Synthesis of N-[N-(3-Nitrophenylacetyl)-L-alaninyl]-L-phenylalanine Methyl Ester

Following General Procedure Z and using N-(3-nitrophenylacetyl)-L-alanine 2,4,5-trichlorophenyl ester (from Example D8 above) and L-phenylalanine methyl ester hydrochloride (Sigma), the title compound was prepared as a solid (mp=154–158° C.). The reaction was monitored by tlc (Rf=0.3 in 1:1 EtOAc/hexanes) and the product was purified by silica gel chromatography using 50–100% EtOAc/hexanes as the eluent.

NMR data was as follows:

$^1$H-nmr (DMSO-d$_6$)(1:3 mixture of diastereomers): δ=1.00 and 1.18 (two d, 3H), 2.96 (m, 2H). C$_{21}$H$_{23}$N$_3$O$_6$ (MW=413.43); mass spectroscopy (MH$^+$) 413.

Example 76

Synthesis of N-[N-(3-Nitrophenylacetyl)-L-alaninyl]-L-alanine Ethyl Ester

Following General Procedure Z and using N-(3-nitrophenylacetyl)-L-alanine 2,4,5-trichlorophenyl ester (from Example D8 above) and L-alanine ethyl ester hydrochloride (Sigma), the title compound was prepared as a solid (mp=193–195° C.). The reaction was monitored by tlc (Rf=0.4 in EtOAc) and the product was purified by silica gel chromatography using EtOAc as the eluent.

NMR data was as follows:

$^1$H-nmr (DMSO-d$_6$): δ=1.20 (mn, 9H), 3.65 (s, 2H); 4.05 (mn, 2H). Optical Rotation: [α]$_{20}$=−27.3° @ 589 nm, (c=1.02, DMSO). C$_{16}$H$_{21}$N$_3$O$_6$ (MW=351.36); mass spectroscopy (MH$^+$) 352.

Example 77

Synthesis of N-[N-(3-Nitrophenylacetyl)-L-alaninyl] glycine Ethyl Ester

Following General Procedure C and using N-(3-nitrophenylacetyl)-L-alanine (prepared from 3-nitrophenylacetic acid (Aldrich) and L-alanine ethyl ester hydrochloride (Sigma) using General Procedure C, followed by hydrolysis using General Procedure AF) and glycine ethyl ester hydrochloride (Sigma), the title compound was prepared as a solid (mp=164–165 °C.). The product was purified by silica gel chromatography using EtOAc as the eluent, followed by recrystallization from EtOAc.

NMR data was as follows:

$^1$H-nmr (DMSO-d$_6$): δ=1.20 (m, 6H), 4.08 (q, 2H); 4.32 (m, 1H). Optical Rotation: [α]$_{20}$=−25° @ 589 mn, (c=1.00, DMSO). C$_{15}$H$_{19}$N$_3$O$_6$ (MW=337.33); mass spectroscopy (MH$^+$) 338.

Example 78

Synthesis of N-Hydroxy-N'[N-(3-nitrophenylacetyl)-L-alaninyl]-D,L-threoninamide

Following General Procedure Z and using N-(3-nitrophenylacetyl)-L-alanine 2,4,5-trichlorophenyl ester (from Example D8 above) and D,L-threonine hydroxamate (Sigma), the title compound was prepared as a solid (mp=180–183° C.). The reaction was monitored by tlc (Rf=0.25 in 15% MeOH/CHCl$_3$) and the product was purified by silica gel chromatography using 15% MeOH/CHCl$_3$ as the eluent, followed by recrystallization from EtOAc.

NMR data was as follows:

$^1$H-nmr (DMSO-d$_6$)(1:1 mixture of diastereomers): δ=1.22 (m, 3H); 0.98 (m, 3H). C$_{15}$H$_{20}$N$_4$O$_7$ (MW=368.35); mass spectroscopy (MH$^+$) 368.

Example 79

Synthesis of N-[N-(Isovaleryl)-L-phenylglycinyl]-L-alanine iso-butyl Ester

Following General Procedure C and using N-(isovaleryl)-L-phenylglycine (prepared from isovaleric acid (Aldrich) and L-phenylglycine methyl ester hydrochloride (Aldrich) using General Procedure C, followed by hydrolysis using General Procedure AF) and L-alanine iso-butyl ester hydrochloride (prepared from N-BOC-L-alanine (Sigma) and 2-methyl-1-propanol (Aldrich) using General Procedure C (with catalystic DMAP), followed by removal of the BOC-group using General Procedure P), the title compound was prepared as a solid (mp=181–186° C.). The reaction was monitored by tlc (Rf=0.4 in 1:1 EtOAc/hexanes) and the product was purified by silica gel chromatography using 1:1 EtOAc/hexanes as the eluent.

NMR data was as follows:

$^1$H-nmr (DMSO-d$_6$): δ=1.31 (d, 3H); 5.59 (d, 1H). Optical Rotation: [α]$_{20}$=+19.0° @ 589 nm, (c=1.03, DMSO). C$_{20}$H$_{29}$N$_2$O$_4$ (MW=362.47); mass spectroscopy (MH$^+$) 363.

Example 80

Synthesis of Methyl N-[N-(3-nitrophenylacetyl)-L-alaninyl]-2-amino-3-(3-hydroxyphenyl)propionate

Following General Procedure C and using N-(3-nitrophenylacetyl)-L-alanine (prepared from 3-nitrophenylacetic acid (Aldrich) and L-alanine ethyl ester hydrochloride (Sigma) using General Procedure C, followed by hydrolysis using General Procedure AF) and methyl 2-amino-3-(3-hydroxyphenyl)propionate (prepared from 2-amino-3-(3-hydroxyphenyl)propionate (Biosynth AG, Switzerland) and methanol using General Procedure H), the title compound was prepared as a solid (mp=155–159° C.). The reaction was monitored by tlc (Rf=0.4 in EtOAc) and the product was purified by silica gel chromatography using EtOAc as the eluent.

NMR data was as follows:

$^1$H-nmr (DMSO-d$_6$)(1:1 mixture of diastereomers): δ=1.02 and 1.20 (two d, 3H); 3.62(2 s, 3H). C$_{21}$H$_{23}$N$_2$O$_7$ (MW=429.43); mass spectroscopy (MH$^+$) 429.

Example 81

Synthesis of N-[N-(3-Nitrophenylacetyl)-L-alaninyl]-L-tyrosine Ethyl Ester

Following General Procedure C and using N-(3-nitrophenylacetyl)-L-alanine (prepared from 3-nitrophenylacetic acid (Aldrich) and L-alanine ethyl ester hydrochloride (Sigma) using General Procedure C, followed by hydrolysis using General Procedure AF) and L-tyrosine ethyl ester (Sigma), the title compound was prepared as a solid (mp=117–119° C.). The reaction was monitored by tlc (Rf=0.5 in EtOAc) and the product was purified by silica gel chromatography using EtOAc as the eluent.

NMR data was as follows:

$^1$H-nmr (DMSO-d$_6$): δ=1.07 (t, 3H); 1.20 (d, 3H); 9.23 (s, 1H). Optical Rotation: [α]$_{20}$=−13.1° @ 589 nm, (c=1.08, DMSO). C$_{22}$H$_{25}$N$_3$O$_7$ (MW=443.46); mass spectroscopy (MH$^+$) 443/444.

Example 82

Synthesis of N-[N-(Isovaleryl)-L-isoleucinyl]-L-alanine iso-butyl Ester

Following General Procedure C and using N-(isovaleryl)-L-isoleucine (prepared from isovaleric acid (Aldrich) and L-isoleucine methyl ester hydrochloride (Aldrich) using General Procedure C, followed by hydrolysis using General Procedure AF) and L-alanine iso-butyl ester hydrochloride (prepared from N-BOC-L-alanine (Sigma) and 2-methyl-1-propanol (Aldrich) using General Procedure C (with catalystic DMAP), followed by removal of the BOC-group using General Procedure P), the title compound was prepared as a solid (mp=142–146° C.). The reaction was monitored by tlc (Rf=0.4 in 1:1 EtOAc/hexanes) and the product was purified by silica gel chromatography using 1:1 EtOAc/hexanes as the eluent.

NMR data was as follows:

$^1$H-nmr (DMSO-d$_6$)(1:4 mixture of diastereomers): δ=1.26 (d, 3H), 7.70, 7.80 (doublets, 1H); 8.30, 8.40 (doublets, 1H). C$_{18}$H$_{34}$N$_2$O$_4$ (MW=342.48); mass spectroscopy (MH$^+$) 343.

Example 83

Step A—Synthesis of N-[N-[N-(tert-Butoxycarbonyl)-L-valinyl]-D,L-phenylglycinyl]-L-alanine iso-butyl Ester Following General Procedure A and using N-[N-BOC-L-valinyl]-D,L-phenylglycine (prepared by coupling N-BOC-L-valine (Bachem) and L-phenylglycine methyl ester hydrochloride (Sigma) using General Procedure C, followed by hydrolysis of the methyl ester using General Procedure AF) and L-alanine iso-butyl ester hydrochloride (prepared from N-BOC-L-alanine (Sigma) and 2-methyl-1-propanol (Aldrich) using General Procedure C (with catalytic DMAP), followed by removal of the BOC-group using General Procedure P), the title compound was prepared. The reaction was monitored by tlc (Rf=0.3 in 5% MeOH/CH$_2$Cl$_2$) and the product was purified by silica gel chromatography using 5% MeOH/CH$_2$Cl$_2$ as the eluent.

NMR data was as follows:

$^1$H-nmr (DMSO-d$_6$)(1:1 mixture of diastereomers): δ=1.25 (d, 3H); 5.58 (d, 1H). C$_{25}$H$_{39}$N$_3$O$_6$ (MW=477.61); mass spectroscopy (MH$^+$) 478.

Step B—Synthesis of N-[N-(L-Valinyl)-L-phenylglycinyl]-L-alanine iso-butyl Ester Hydrochloride Following General Procedure P and using the product from Example 83—Step A above, the title compound was prepared as a solid (mp=225–232° C.). The product was purified by trituration in Et$_2$O.

NMR data was as follows:

$^1$H-nmr (DMSO-d$_6$)(1:2 mixture of diastereomers): δ=1.26, 1.32 (doublets, 3H); 5.60, 5.65 (doulets, 1H). C$_{20}$H$_{32}$N$_3$O$_4$Cl (MW=413.94); mass spectroscopy (MH$^+$) 378 (free base).

Step C—Synthesis of N-[N-[N-(Isovaleryl)-L-valinyl]-L-phenylglycinyl]-L-alanine iso-butyl Ester Following General Procedure C and using isovaleric acid (Aldrich) and the product from Example 83—Step B above, the title compound was prepared as a solid (mp=217–221 ° C.). The reaction was monitored by tlc (Rf=0.25 in 5% MeOH/CHCl$_3$) and the product was purified by silica gel chromatography using 5% MeOH/CHCl$_3$) as the eluent.

NMR data was as follows:

$^1$H-nmr (DMSO-d$_6$)(1:3 mixture of diastereomers): δ=5.52, 5.58 (doublets, 1H). C$_{25}$H$_{39}$N$_3$O$_5$ (MW=461.60); mass spectroscopy (MH$^+$) 462.

Example 84

Synthesis of N-[N-(Isovaleryl)-L-phenylalaninyl]-L-alanine iso-butyl Ester

Following General Procedure C and using isovaleric acid (Aldrich) and N-(L-phenylalaninyl)-L-alanine iso-butyl ester hydrochloride (prepared from N-BOC-L-phenylalanine (Sigma) and L-alanine iso-butyl ester hydrochloride (prepared as described in Example 83A above) using General Procedure C, followed by removal of the BOC-group using General Procedure P), the title compound was prepared as a solid (mp=135–138° C.). The reaction was monitored by tlc (Rf=0.3 in 3% MeOH/CHCl$_3$) and the product was purified by silica gel chromatography using 3% MeOH/CHCl$_3$ as the eluent.

NMR data was as follows:

$^1$H-nmr (DMSO-d$_6$): δ=0.75 (d, 3H), 0.84 (d, 3H); 0.90 (d, 6H); 1.33 (d, 3H). Optical Rotation: [α]$_{20}$=+4.710° @ 589 nm, (c=1.02, DMSO). C$_{21}$H$_{32}$N$_2$O$_4$ (MW=376.50); mass spectroscopy (MH$^+$) 376.

Example 85

Synthesis of N-[N-(3,5-Difluorophenylacetyl)-L-alaninyl]-L-alanine Ethyl Ester Following General Procedure C and using 3,5-difluorophenylacetic acid (Oakwood) and L-alanine ethyl ester hydrochloride (Sigma), the title compound was prepared as a solid (mp=197–199° C.). The reaction was monitored by tlc (Rf=0.6 in EtOAc) and the product was purified from bi-products by silica gel chromatography using EtOAc as the eluent, followed by recrystallization from EtOAc.

NMR data was as follows:

$^1$H-nmr (DMSO-d$_6$): δ=1.22 (m, 9H); 3.52 (s, 2H). Optical Rotation: [α]$_{20}$=−76.1° @ 589 nm, (c=1.01, DMSO). C$_{16}$H$_{20}$N$_2$O$_4$F$_2$ (MW=342.34); mass spectroscopy (MH$^+$) 343.

Example 86

Synthesis of Ethyl 1-[N-(3-Nitrophenylacetyl)-L-alaninyl] indoline-(S)-2-carboxylate Following General Procedure C and using N-($^3$-nitrophenylacetyl)-L-alanine (prepared from 3-nitrophenylacetic acid (Aldrich) and L-alanine ethyl ester hydrochloride (Sigma) using General Procedure C, followed by hydrolysis using General Procedure AF) and ethyl (S)-indoline-2-carboxylate (prepared from (S)-indoline-2-carboxylic acid (Aldrich) and ethanol using General Procedure H), the title compound was prepared as a solid. The reaction was monitored by tlc (Rf=0.4 in 2:1 EtOAc/hexanes) and the product was purified by silica gel chromatography using 2:1 EtOAc/hexanes as the eluent.

NMR data was as follows:

$^1$H-nmr (DMSO-d$_6$)(1:2 mixture of diastereomers): δ=1.05, 1.17 (triplets, 3H); 1.29, 1.39 (doublets, 3H). $C_{22}H_{23}N_3O_6$ (MW=425.44); mass spectroscopy (MH$^+$) 425.

Example 87

Synthesis of N'-[N-(3,5-Difluorophenylacetyl)-L-alaninyl]-L-alaninamide

Following General Procedure C and using N-(3,5-difluorophenylacetyl)-L-alanine (from Example B2 above) and L-alaninamide hydrochloride (Sigma), the title compound was prepared as a solid (mp=285–288° C.). The reaction was monitored by tlc (Rf=0.35 in 10% MeOH/CHCl$_3$) and the product was purified by silica gel chromatography using 10% MeOH/CHCl$_3$ as the eluent, followed by recrystallization from EtOH.

NMR data was as follows:

$^1$H-nmr (DMSO-d$_6$): δ=1.21 (m, 6H); 7.95 (d, 1H); 8.37 (d, 1H). Optical Rotation: [α]$_{20}$=−26.84° @ 589 nm, (c=1.01, DMSO). $C_{14}H_{17}N_3O_3F_2$ (MW=313.31); mass spectroscopy (MH$^+$) 314.

Example 88

Synthesis of N-Methoxy-N-methyl-N'-[N-(isovaleryl)-L-phenylglycinyl]-L-alaninamide Following General Procedure C and using N-[N-(isovaleryl)-L-phenylglycinyl]-L-alanine (prepared from N-[N-(isovaleryl)-L-phenylglycinyl]-L-alanine ethyl ester (from Example 74 above) using General Procedure AF) and N,O-dimethylhydroxylamine (Aldrich), the title compound was prepared as a solid. The reaction was monitored by tlc (Rf=0.6 in EtOAc) and the product was purified by silica gel chromatography using EtOAc as the eluent.

NMR data was as follows: $^1$H-nmr (DMSO-d$_6$)(1:1 mixture of diastereomers): δ=3.67, 3.73 (singlets, 3H), 5.62 (m, 1H). $C_{18}H_{27}N_3O_4$ (MW=349.43); mass spectroscopy (MH$^+$) 350.

Example 89

Synthesis of N-iso-butyl-N'-[N-(3,5-difluorophenylacetyl)-L-alaninyl]-L-alaninamide Following General Procedure C and using N'-[N-(3,5-difluorophenylacetyl)-L-alaninyl]-L-alanine (prepared from N-[N-(3,5-difluorophenylacetyl)-L-alaninyl]-L-alanine ethyl ester (from Example 85 above) using General Procedure AF) and iso-butylamine (Aldrich), the title compound was prepared as a solid (mp=258–260° C.). The reaction was monitored by tlc (Rf=0.4 in 10% MeOH/CHCl$_3$) and the product was purified by silica gel chromatography using 10% MeOH/CHCl$_3$ as the eluent.

NMR data was as follows:

$^1$H-nmr (DMSO-d$_6$): δ=0.80 (d, 6H); 1.20 (m, 6H). Optical Rotation: [α]$_{20}$=−30.4° @ 589 nm, (c=1.01, DMSO). $C_{18}H_{25}N_3O_3F_2$ (MW=369.41); mass spectroscopy (MH$^+$) 369.

Example 90

Synthesis of N,N-Di-n-propyl-N'-[N-(3,5-difluorophenylacetyl)-L-alaninyl]-L-alaninamide Following General Procedure C and using N-[N-(3,5-difluorophenylacetyl)-L-alaninyl]-L-alanine (prepared from N-[N-(3,5-difluorophenylacetyl)-L-alaninyl]-L-alanine ethyl ester (from Example 85 above) and di-n-propylamine (Aldrich), the title compound was prepared as a solid (mp=137–146° C.). The reaction was monitored by tlc (Rf=0.5 in 10% MeOH/CHCl$_3$) and the product was purified by silica gel chromatography using 5% MeOH/CHCl$_3$ as the eluent.

NMR data was as follows:

$^1$H-nmr (DMSO-d$_6$)(1:2 mixture of diastereomers): δ=3.50 (s, 2H), 4.30 (m, 1H), 4.63 (m, 1H). $C_{20}H_{29}N_3O_3F_2$ (MW=397.46); mass spectroscopy (MH$^+$) 397.

Example 91

Synthesis of N'-[N-(3,5-Difluorophenylacetyl)-L-alaninyl]-L-valinamide

Following General Procedure C and using N-(3,5-difluorophenylacetyl)-L-alanine (from Example B2 above) and L-valinamide hydrochloride (Sigma), the title compound was prepared as a solid. The reaction was monitored by tlc (Rf=0.3 in 10% MeOH/CHCl$_3$) and the product was purified by silica gel chromatography using 10% MeOH/CHCl$_3$ as the eluent.

NMR data was as follows:

$^1$H-nmr (DMSO-d$_6$)(1:4 mixture of diastereomers): δ=1.22 (m, 3H); 1.97 (m, 1H). $C_{16}H_{21}N_3O_3F_2$ (MW=341.36) mass spectroscopy (MH$^+$) 342.

Example 92

Synthesis of N-(4-Nitrophenyl)-N'-[N-(3,5-difluorophenylacetyl)-L-alaninyl]-L-alaninamide Following General Procedure C and using N-(3,5-difluorophenylacetyl)-L-alanine (from Example B2 above) and N-(4-nitrophenyl)-L-alaninamide hydrochloride (Fluka), the title compound was prepared as a solid (mp=242–244° C.). The reaction was monitored by tlc (Rf=0.4 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.24 (d, 3II); 1.33 (d, 3H). Optical Rotation: [α]$_{20}$=−5.18° @ 589 nm, (c=1.00, DMSO). $C_{20}H_{20}N_4O_5F_2$ (MW=434.40); mass spectroscopy (MH$^+$) 434.

Example 93

Synthesis of N'-[N-[N-(Isovaleryl)-L-phenylglycinyl]-L-alaninyl]-L-phenylalaninamide Following General Procedure C and using N-(isovaleryl)-L-phenylglycine (prepared from isovaleric acid (Aldrich) and L-phenylglycine methyl ester hydrochloride (Aldrich) using General Procedure C, followed by hydrolysis using General Procedure AF) and N'-(L-alaninyl)-L-phenylalaninamide hydrochloride (prepared from N-BOC-L-alanine (Sigma) and L-phenylalaninamide (Sigma) using General Procedure C, followed by removal of the BOC-group using General Procedure P), the title compound was prepared as a solid (mp=272–276° C.). The reaction was monitored by tlc (Rf=0.25 in 10% MeOH/CHCl$_3$) and the product was purified by silica gel chromatography using 10% MeOH/CHCl$_3$ as the eluent.

NMR data was as follows:

$^1$H-nmr (DMSO-d$_6$)(1:1 mixture of diastereomers): δ=1.07, 1.17 (doublets, 3H); 5.40, 5.52 (doublets, 1H). C$_{25}$H$_{32}$N$_4$O$_4$ (MW=452.55); mass spectroscopy (MH$^+$) 453.

Example 94

Synthesis of N-[N-(3,5-Difluorophenylacetyl)-L-alaninyl]-L-phenylalanine Methyl Ester Following General Procedure C and using 3,5-difluorophenylacetic acid (Oakwood) and N-(L-alaninyl)-L-phenylalanine methyl ester hydrochloride (prepared from N-BOC-L-alanine (Sigma) and L-phenylalanine methyl ester hydrochloride (Sigma) using General Procedure C, followed by removal of the BOC-group using General Procedure P), the title compound was prepared as a solid (mp=173–175° C.). The reaction was monitored by tlc (Rf=0.6 in 10% MeOH/CHCl$_3$) and the product was purified by silica gel chromatography using 4% MeOH/CHCl$_3$ as the eluent, followed by recrystallization from 1-chlorobutane/acetonitrile.

$^1$NMR data was as follows:

$^1$H-nmr (DMSO-d$_6$): δ=1.17 (d, 3H); 3.48 (s, 2H).

Optical Rotation: [α]$_{20}$=−32.47° @ 589 nm, (c=1.01, MeOH). C$_{21}$H$_{22}$N$_2$O$_4$F$_2$ (MW=404.41); mass spectroscopy (MH$^+$) 404.

Example 95

Synthesis of N'-[N-(3,5-Difluorophenylacetyl)-L-alaninyl]-L-phenylalaninamide

Following General Procedure C and using 3,5-difluorophenylacetic acid (Oakwood) and N'-(L-alaninyl)-L-phenylalaninamide hydrochloride (prepared from N-BOC-L-alanine (Sigma) and L-phenylalaninamide (Sigma) using General Procedure C, followed by removal of the BOC-group using General Procedure P), the title compound was prepared as a solid (mp=252–253 ° C.). The reaction was monitored by tlc (Rf=0.5 in 15% MeOH/CHCl$_3$) and the product was purified by silica gel chromatography using 15% MeOH/CHCl$_3$ as the eluent, followed by recrystallization from EtOH.

NMR data was as follows:

$^1$H-nmr (DMSO-d$_6$): δ=1.15 (d, 3H); 3.51 (s, 2H). Optical Rotation: [α]$_{20}$=−24.4° @ 589 nm, (c=1.01, DMSO). C$_{20}$H$_{21}$N$_3$O$_3$F$_2$ (MW=389.41); mass spectroscopy (MH$^+$) 389.

Example 96

Synthesis of N-iso-butyl-N'-[N-(isovaleryl)-L-phenylglycinyl]-L-alaninamide

Following General Procedure C and using N-[N-(isovaleryl)-L-phenylglycinyl]-L-alanine (prepared from N-[N-(isovaleryl)-L-phenylglycinyl]-L-alanine ethyl ester (from Example 74 above) using General Procedure AF) and iso-butylamine (Aldrich), the title compound was prepared as a solid (mp=227–232° C.). The reaction was monitored by tlc (Rf=0.3 in 5% MeOH/CHCl$_3$) and the product was purified by silica gel chromatography using 5% MeOH/CHCl$_3$ as the eluent, followed by recrystallization from acetonitrile.

NMR data was as follows:

$^1$H-nmr (DMSO-d$_6$)(1:4 mixture of diastereomers): δ=1.58 (m, 1H); 1.95 (m, 1H); 5.55 (d, 1H). C$_{20}$H$_{31}$N$_3$O$_3$ (MW=361.48); mass spectroscopy (ME+) 361.

Example 97

Synthesis of N-(2-Methoxyethyl)-N'-[N-(3,5-difluorophenylacetyl)-L-alaninyl]-L-phenylalaninamide Following General Procedure C and using N-[N-(3,5-difluorophenylacetyl)-L-alaninyl]-L-phenylalanine (prepared from N-[N-(3,5-difluorophenylacetyl)-L-alaninyl]-L-phenylalanine methyl ester (from Example 94) using General Procedure AF) and 2-methoxyethylamine (Aldrich), the title compound was prepared as a solid (mp=206–208 ° C.). The reaction was monitored by tlc (Rf=0.3 in 10% MeOH/CHCl$_3$) and the product was purified by silica gel chromatography using 10% MeOH/CHCl$_3$ as the eluent, followed by recrystallization from 1-chlorobutane/acetonitrile.

NMR data was as follows:

$^1$H-nmr (DMSO-d$_6$): δ=1.14 (d, 3H); 4.22 (m, 1H); 4.45 (m, 1H). Optical Rotation: [α]$_{20}$=−25° @ 589 nm, (c=1.00, DMSO). C$_{23}$H$_{27}$N$_3$O$_4$F$_2$ (MW=447.49); mass spectroscopy (MH$^+$) 447.

Example 98

Synthesis of N-(4-Nitrobenzyl)-N'-[N-(3,5-difluorophenylacetyl)-L-alaninyl]-L-alaninamide Following General Procedure C and using N-[N-(3,5-difluorophenylacetyl)-L-alaninyl]-L-alanine (prepared from N-[N-(3,5-difluorophenylacetyl)-L-alaninyl]-L-alanine ethyl ester (from Example 85 above) using General Procedure AF) and 4-nitrobenzylamine (Aldrich), the title compound was prepared as a solid (mp=257–259° C.). The reaction was monitored by tlc (Rf=0.4 in 10% MeOH/CHCl$_3$) and the product was purified by silica gel chromatography using 10% MeOH/CHCl$_3$ as the eluent, followed by recrystallization from EtOH/acetonitrile.

NMR data was as follows:

$^1$H-nmr (DMSO-d$_6$): δ=3.53 (s, 2H); 4.39 (d, 2H). Optical Rotation: [α]$_{20}$=−29.30° @ 589 nm, (c=1.00, DMSO). C$_{21}$H$_{22}$N$_4$O$_5$F$_2$ (MW=448.43); mass spectroscopy (MH$^+$) 448.

Example 99

Synthesis of N-(4-Nitrophenyl)-N'-[N-[N-(isovaleryl)-L-phenylglycinyl]-L-alaninyl]-L-alaninamide Following General Procedure C and using N-[N-(isovaleryl)-L-phenylglycinyl]-L-alanine (prepared from N-[N-(isovaleryl)-L-phenylglycinyl]-L-alanine ethyl ester (from Example 74 above) using General Procedure AF) and N-(4-nitrophenyl)-L-alaninamide hydrochloride (Fluka), the title compound was prepared as a solid (mp=255–257° C.). The reaction was monitored by tlc (Rf=0.5 in 10% MeOH/CHCl$_3$) and the product was purified by silica gel chromatography using 10% MeOH/CHCl$_3$ as the eluent, followed by recrystallization from 1-chlorobutane/acetonitrile.

NMR data was as follows:

$^1$H-nmr (DMSO-d$_6$)(1:2 mixture of diastereomers): δ=5.45, 5.55 (doublets, 1H); 10.20, 10.54 (singlets, 1H). C$_{25}$H$_{31}$N$_4$O$_6$ (MW=497.56); mass spectroscopy (MH$^+$) 497.

Example 100

Synthesis of N-(4-Nitrophenyl)-N'-N-(3,5-difluorophenylacetyl)-L-alaninyl]-L-phenylalaninamide Following General Procedure C and using N-(3,5-difluorophenylacetyl)-L-alanine (from Example B2 above) and N-(4-nitrophenyl)-L-phenylalaninamide hydrochloride (Lancaster), the title compound was prepared as a solid (mp=253–254° C.). The reaction was monitored by tlc (Rf=0.5 in 10% MeOH/CHCl$_3$) and the product was purified by silica gel chromatography using 8% MeOH/CHCl$_3$ as the eluent.

NMR data was as follows:

$^1$H-nmr (DMSO-d$_6$): δ=1.17 (d, 3H); 10.52 (s, 1H). Optical Rotation: [α]$_{20}$=+40.6° @ 589 nm, (c=1.00, DMSO). C$_{26}$H$_{24}$N$_4$O$_5$F$_2$ (MW=510.50); mass spectroscopy (MH$^+$) 510.

Example 101

Synthesis of N-Benzyl-N-methyl-N'-[N-(3,5-difluorophenylacetyl)-L-alaninyl]-L-alaninamide Following General Procedure C and using N-[N-(3,5-difluorophenylacetyl)-L-alaninyl]-L-alanine (prepared from N-[N-(3,5-difluorophenylacetyl)-L-alaninyl]-L-alanine ethyl ester (from Example 85 above) using General Procedure AF) and N-benzyl-N-methylamine (Aldrich), the title compound was prepared as a solid (mp=167–169° C.). The reaction was monitored by tlc (Rf=0.4 in 5% MeOH/CHCl$_3$) and the product was purified by silica gel chromatography using 5% MeOH/CHCl$_3$ as the eluent, followed by recrystallization from acetonitrile.

NMR data was as follows:

$^1$H-nmr (DMSO-d$_6$)(1:3 mixture of diastereomers): δ=3.52 (singlets, 2H); 2.95 (s, 2H). Optical Rotation: [α]$_{20}$=−55.8° @ 589 nm, (c=1.01, DMSO). C$_{22}$H$_{25}$N$_3$O$_3$F$_2$ (MW=417.45); mass spectroscopy (MH$^+$) 417.

Example 102

Synthesis of N-(3,5-Difluorobenzyl)-N'-[N-(3,5-difluorophenylacetyl)-L-alaninyl]-L-alaninamide Following General Procedure C and using N-(3,5-difluorophenylacetyl)-L-alanine (from Example B2 above) and N-(3,5-difluorobenzyl)-L-alaninamide hydrochloride (prepared from N-BOC-L-alanine (Sigma) and 3,5-difluorobenzylamine (Lancaster) using General Procedure C, followed by removal of the BOC-group using General Procedure P), the title compound was prepared as a solid (mp=267–269° C.). The reaction was monitored by tlc (Rf=0.25 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.21 (d, 3H), 1.24 (d, 3H). Optical Rotation: [α]$_{20}$=+26.9° @ 589 nm, (c=1.01, DMSO). C$_{21}$H$_{21}$N$_3$O$_3$F$_4$ (MW=439.41); mass spectroscopy (MH$^+$) 439.

Example 103

Synthesis of N-(3-Nitrobenzyl)-N'-N-(3,5-difluorophenylacetyl)-L-alaninyl]-L-alaninamide Following General Procedure C and using N-(3,5-difluorophenylacetyl)-L-alanine (from Example B2 above) and N-(3-nitrobenzyl)-L-alaninamide hydrochloride (prepared from N-BOC-L-alanine (Sigma) and 3-nitrobenzylamine hydrochloride (Aldrich) using General Procedure C, followed by removal of the BOC-group using General Procedure P), the title compound was prepared as a solid (mp=245–247° C.). The reaction was monitored by tlc (Rf=0.4 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.21 (d, 3H); 1.25 (d, 3H). Optical Rotation: [α]$_{20}$=−32.8° @ 589 nm, (c=1.00, DMSO). C$_{21}$H$_{22}$N$_4$O$_5$F$_2$ (MW=448.43); mass spectroscopy (MH$^+$) 449.

Example 104

Synthesis of N-Benzyl-N'-[N-(3,5-difluorophenylacetyl)-L-alaninyl]-L-alaninamide Following General Procedure C and using N-(3,5-difluorophenylacetyl)-L-alanine (from Example B2 above) and N-benzyl-L-alaninamide hydrochloride (prepared from N-BOC-L-alanine (Sigma) and benzylamine (Aldrich) using General Procedure C, followed by removal of the BOC-group using General Procedure P), the title compound was prepared as a solid (mp=260–262° C.). The reaction was monitored by tlc (Rf=0.3 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.20 (d, 3H); 1.24 (d, 3H). Optical Rotation: [α]$_{20}$=−29.30° @ 589 nm, (c=1.03, DMSO). C$_{21}$H$_{23}$N$_3$O$_3$F$_2$ (MW=403.43); mass spectroscopy (MH$^+$) 403.

Example 105

Synthesis of N-(4-Nitrobenzyl)-N'-[N-(3,5-difluorophenylacetyl)-L-alaninyl]-L-phenylalaninamide Following General Procedure C and using N-[N-(3,5-difluorophenylacetyl)-L-alaninyl]-L-phenylalanine (prepared from N-[N-(3,5-difluorophenylacetyl)-L-alaninyl]-L-phenylalanine methyl ester (from Example 94) using General Procedure AF) and 4-nitrobenzylamine hydrochloride (Aldrich), the title compound was prepared as a solid (mp=248–250° C.). The reaction was monitored by tlc (Rf=0.4 in 12% MeOH/CHCl$_3$) and the product was purified by silica gel chromatography using 12% MeOH/CHCl$_3$ as the eluent, followed by recrystallization from acetonitrile.

NMR data was as follows:

$^1$H-nmr (DMSO-d$_6$): δ=1.15 (d, 3H); 7.35 (d, 2H); 8.12 (d, 2H). Optical Rotation: [α]$_{20}$=−27.6° @ 589 nm (c=1.01, DMSO). C$_{27}$H$_{26}$N$_4$O$_5$F$_2$ (MW=524.52); mass spectroscopy (MH$^+$) 524.

Example 106

Synthesis of N-[N-(3,5-Difluorophenylacetyl)-L-alaninyl]-L-tryptophan Methyl Ester Following General Procedure C and using N-(3,5-difluorophenylacetyl)-L-alanine (from Example B2 above) and L-tryptophan methyl ester hydrochloride (Sigma), the title compound was prepared as a solid (mp=191–193° C.). The reaction was monitored by tlc (Rf=0.4 in 10% MeOH/CHCl$_3$) and the product was purified by silica gel chromatography using 5% MeOH/CHCl$_3$ as the eluent, followed by recrystallization from 1-chlorobutane/acetonitrile.

NMR data was as follows:

$^1$H-nmr (DMSO-d$_6$): δ=1.20 (d, 3H); 3.55 (s, 3H). Optical Rotation: [α]$_{20}$=−8.82° @ 589 nm (c=1.02, DMSO). C$_{23}$H$_{23}$N$_3$O$_4$F$_2$ (MW=443.45); mass spectroscopy (MH$^+$) 443.

Example 107

Synthesis of N-(4-Methoxybenzyl)-N'-[N-(3,5-difluorophenylacetyl)-L-alaninyl]-L-alaninamide Following General Procedure C and using N-(3,5-difluorophenylacetyl)-L-alanine (from Example B2 above) and N-(4-methoxybenzyl)-L-alaninamide hydrochloride (prepared from N-BOC-L-alanine (Sigma) and 4-methoxybenzylamine hydrochloride (Aldrich) using General Procedure C, followed by removal of the BOC-group using General Procedure P), the title compound was prepared as a solid (mp=234–236 ° C.). The reaction was monitored by tlc (Rf=0.3 in 10% MeOH/CHCl$_3$) and the product was purified by silica gel chromatography using 10% MeOH/CHCl$_3$ as the eluent, followed by recrystallization from EtOH/acetonitrile.

NMR data was as follows:

$^1$H-nmr (DMSO-d$_6$): δ=1.20 (d, 6H); 3.51 (s, 2H); 3.72 (s, 3H). Optical Rotation: [α]$_{20}$=+27.9° @ 589 nm (c=1.00, DMSO). C$_{22}$H$_{25}$N$_3$O$_4$F$_2$ (MW=433.46); mass spectroscopy (MH$^+$) 433.

Example 108

Synthesis of N-[N-(Phenylacetyl)-L-phenylglycinyl]-L-alanine Ethyl Ester

Following General Procedure C and using phenylacetic acid (Aldrich) and N-(L-phenylglycinyl)-L-alanine ethyl ester hydrochloride (prepared from N-BOC-L-phenylglycine (Advanced Chemtech) and L-alanine ethyl ester hydrochloride (Aldrich) using General Procedure C, followed by removal of the BOC-group using General Procedure P), the title compound was prepared as a. solid (mp=208–210° C.). The reaction was monitored by tlc (Rf=0.4 in 5% MeOH/CHCl$_3$) and the product was purified by silica gel chromatography using 5% MeOH/CHCl$_3$ as the eluent, followed by recrystallization from 1-chlorobutane/acetonitrile.

NMR data was as follows:

$^1$H-nmr (DMSO-d$_6$): δ=3.55 (s, 2H); 5.55 (d, 1H). Optical Rotation: [α]$_{20}$=+44.8° @ 589 nm (c=1.02, DMSO). C$_{21}$H$_{24}$N$_2$O$_4$ (MW=368.43); mass spectroscopy (MH$^+$) 369.

Example 109

Synthesis of N-[N-[N-(3,5-Difluorophenylacetyl)-L-alaninyl]-L-phenylalaninyl]-L-phenylglycine Methyl Ester Following General Procedure C and using N-[N-(3,5-difluorophenylacetyl)-L-alaninyl]-L-phenylalanine (prepared from N-[N-(3,5-difluorophenylacetyl)-L-alaninyl]-L-phenylalanine methyl ester (from Example 94) using General Procedure AF) and L-phenylglycine methyl ester hydrochloride (Aldrich), the title compound was prepared as a solid (mp=203–207° C.). The reaction was monitored by tlc (Rf=0.3 in 10% MeOH/CHCl$_3$) and the product was purified by silica gel chromatography using 10% MeOH/CHCl$_3$ as the eluent, followed by trituration using 1-chlorobutane.

NMR data was as follows:

$^1$H-nmr (DMSO-d$_6$):=1.13 (d, 3H); 3.62 (s, 3H). Optical Rotation: [α]$_{20}$=+42.1° @ 589 nm (c 1.03, DMSO). C$_{29}$H$_{29}$N$_3$O$_5$F$_2$ (MW=537.56); mass spectroscopy (MH$^+$) 537.

Example 110

Synthesis of N-[N-(Cyclohexylacetyl)L-phenylglycinyl]-L-alanine Ethyl Ester

Following General Procedure C and using cyclohexylacetic acid (Aldrich) and N-(L-phenylglycinyl)-L-alanine ethyl ester hydrochloride (prepared from N-BOC-L-phenylglycine (Advanced Chemtech) and L-alanine ethyl ester hydrochloride (Aldrich) using General Procedure C, followed by removal of the BOC-group using General Procedure P), the title compound was prepared as a solid (mp=196–198 ° C.). The reaction was monitored by tlc (Rf=0.3 in 5% MeOH/CHCl$_3$) and the product was purified by silica gel chromatography using 5% MeOH/CHCl$_3$ as the eluent, followed by trituration using 1-chlorobutane.

NMR data was as follows:

$^1$H-nmr (DMSO-d$_6$): δ=2.08 (d, 2H); 5.56 (d, 1H). Optical Rotation: [α]$_{20}$=+26.3° @ 589 nm (c=1.01, DMSO). C$_{21}$H$_{30}$N$_2$O$_4$ (MW=374.48); mass spectroscopy (MH$^+$) 375.

Example 111

Synthesis of N-[N-(3,5-Difluorophenylacetyl)-L-alaninyl]-L-phenylglycine Methyl Ester Following General Procedure C and using N-(3,5-difluorophenylacetyl)-L-alanine (from Example B2 above) and L-phenylglycine methyl ester hydrochloride (Aldrich), the title compound was prepared as a solid (mp=198–200° C.). The reaction was monitored by tlc (Rf=0.4 in 4% MeOH/CHCl$_3$) and the product was purified by silica gel chromatography using 4% MeOH/CHCl$_3$ as the eluent, followed by recrystallization from 1-chlorobutane/acetonitrile.

NMR data was as follows:

$^1$H-nmr (DMSO-d$_6$): δ=1.26 (d, 3H); 3.64 (s, 3H). Optical Rotation: (DMSO) [α]$_{20}$=+69.9° @ 589 nm (c=1.01, DMSO). C$_{20}$H$_{20}$N$_2$O$_4$F$_2$ (MW=390.39); mass spectroscopy (MH$^+$) 391.

Example 112

Synthesis of N-[N-[N-(3,5-Difluorophenylacetyl)-L-alaninyl]-L-alaninyl]-L-phenylglycine Methyl Ester Following General Procedure C and using N-(3,5-difluorophenylacetyl)-L-alanine (from Example B2 above) and N-(L-alaninyl)-L-phenylglycine methyl ester hydrochloride (prepared from N-BOC-L-alanine (Sigma) and L-phenylglycine methyl ester hydrochloride (Aldrich) using General Procedure C, followed by removal of the BOC-group using General Procedure P), the title compound was prepared as a solid (mp=243–245 ° C.). The reaction was monitored by tlc (Rf=0.5 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.19 (d, 31H); 1.24 (d, 3H). Optical Rotation: [α]$_{20}$=+38.2° @ 589 nm (c=1.02, DMSO). C$_{23}$H$_{25}$N$_3$O$_5$F$_2$ (MW=461.46); mass spectroscopy (MH$^+$) 461.

Example 113

Synthesis of N-(2-Phenylethyl)-N'-[N-(3,5-difluorophenylacetyl)-L-alaninyl]-L-alaninamide Following General Procedure C and using N-(3,5-difluorophenylacetyl)-L-alanine (from Example B2 above) and N-(2-phenylethyl)-L-alaninamide hydrochloride (prepared from N-BOC-L-alanine (Sigma) and phenethylamine (Aldrich) using General Procedure C, followed by removal of the BOC-group using General Procedure P), the title compound was prepared as a solid (mp=241–243° C.). The reaction was monitored by tlc (Rf=0.3 in 8% MeOH/CHCl$_3$) and the product was purified by silica gel chromatography using 8% MeOH/CHCl$_3$ as the eluent, followed by recrystallization from acetonitrile.

NMR data was as follows:

$^1$H-nmr (DMSO-d$_6$): δ=1.14 (d, 3H); 1.21 (d, 3H). Optical Rotation: [α]$_{20}$=−33.7° @ 589 nm (c=1.00, DMSO). C$_{22}$H$_{25}$N$_3$O$_3$F$_2$ (MW=417.45); mass spectroscopy (MH$^+$) 417.

Example 114

Synthesis of N'-[N-(3,5-Difluorophenylacetyl)-L-alaninyl]-L-tryptophanamide

Following General Procedure C and using 3,5-difluorophenylacetic acid (Oakwood) and N'-(L-alaninyl)-L-tryptophanamide hydrochloride (prepared from N-BOC-L-alanine (Sigma) and L-tryptophanamide hydrochloride (Sigma) using General Procedure C, followed by removal of the BOC-group using General Procedure P), the title compound was prepared as a solid (mp=199–202° C.). The reaction was monitored by tlc (Rf=0.3 in 15% MeOH/CHCl$_3$) and the product was purified by silica gel chromatography using 15% MeOH/CHCl$_3$ as the eluent, followed by recrystallization from acetonitrile.

NMR data was as follows:

$^1$H-nmr (DMSO-d$_6$): δ=1.17 (d, 3H); 4.26 (m, 1H); 4.44 (m, 1H). Optical Rotation: [α]$_{20}$=−31.0° @ 589 nm (c=1.05, DMSO). C$_{22}$H$_{22}$N$_4$O$_3$F$_2$ (MW=428.44); mass spectroscopy (MH$^+$) 428.

Example 115

Synthesis of Methyl N-[N-(3,5-Difluorophenylacetyl)-L-alaninyl]-(S)-$^2$-amino-3-cyclohexylpropionate Following General Procedure C and using N-(3,5-difluorophenylacetyl)-L-alanine (from Example B2 above) and methyl (S)-$^2$-amino-3-cyclohexylpropionate (Novabiochem), the title compound was prepared as a solid (mp=116–119° C.). The reaction was monitored by tlc (Rf=0.4 in 4% MeOH/CHCl$_3$) and the product was purified by silica gel chromatography using 4% MeOH/CHCl$_3$ as the eluent, followed by recrystallization from 1-chlorobutane/hexanes.

NMR data was as follows:

$^1$H-nmr (DMSO-d$_6$): δ=1.22 (d, 3H); 3.62 (s, 3H). Optical Rotation: [α]$_{20}$=−21.2° @ 589 nm (c=1.01, DMSO). C$_{21}$H$_{27}$N$_2$O$_4$F$_2$ (MW=410.46); mass spectroscopy (MH$^+$) 411.

Example 116

Synthesis of N-(2-Methoxyethyl)-N'-[N-(3,5-difluorophenylacetyl)-L-alaninyl]-(S)-2-amino-3-(4-nitrophenyl)propionamide Following General Procedure C and using N-(3,5-difluorophenylacetyl)-L-alanine (from Example B2 above) and N-(2-methoxyethyl)-(S)-2-amino-3-(4-nitrophenyl)propionamide hydrochloride (prepared from N-BOC-L-4-nitrophenylalanine (Advanced Chemtech) and 2-methoxyethylamine (Aldrich) using General Procedure C, followed by removal of the BOC-group using General Procedure P), the title compound was prepared as a solid (mp=263–265 ° C.). The reaction was monitored by tlc (Rf=0.5 in 10% MeOH/CHCl$_3$) and the product was purified by silica gel chromatography using 10% MeOH/CHCl$_3$ as the eluent, followed by recrystallization from EtOH/acetonitrile.

NMR data was as follows:

$^1$H-nmr (DMSO-d$_6$): δ=1.15 (d, 3H); 4.23 (m, 1H); 4.54 (m, 1H). Optical Rotation: [α]$_2$=−19.9° @ 589 nm (c=1.00, DMSO). C$_{23}$H$_{26}$N$_4$O$_6$F$_2$ (MW=492.48); mass spectroscopy (MH$^+$) 493.

Example 117

Synthesis of N-[N-(3-Nitrophenylacetyl)-L-alaninyl]-L-serine Ethyl Ester

Following General Procedure C and using N-(3-nitrophenylacetyl)-L-alanine (prepared from 3-nitrophenylacetic acid (Aldrich) and L-alanine ethyl ester hydrochloride (Sigma) using General Procedure C, followed by hydrolysis using General Procedure AF) and L-serine ethyl ester hydrochloride (Sigma), the title compound was prepared as a solid (mp=179–181 ° C.). The reaction was monitored by tlc (Rf=0.2 in 5% MeOH/CHCl$_3$) and the product was purified by silica gel chromatography using 5% MeOH/CHCl$_3$ as the eluent.

NMR data was as follows:

$^1$H-nmr (DMSO-d$_6$): δ=1.20 (m, 6H); 4.30 (m, 1H); 4.41 (m, 1H); 5.04 (t, 1H). Optical Rotation: [α]$_{20}$=−19.7° @ 589 nm (c=1.01, DMSO). C$_{16}$H$_{21}$N$_3$O$_7$ (MW=367.36); mass spectroscopy (MH$^+$) 368.

Example 118

Synthesis of N-[(R)-α-Methylbenzyl]-N'-[N-(3,5-difluorophenylacetyl)-L-alaninyl]-L-alaninamide Following General Procedure C and using N-(3,5-difluorophenylacetyl)-L-alanine (from Example B2 above) and N-(R)-α-methylbenzyl-L-alaninamide hydrochloride (prepared from N-BOC-L-alanine (Sigma) and (R)-α-methylbenzylamine (Aldrich) using General Procedure C, followed by removal of the BOC-group using General Procedure P), the title compound was prepared as a solid (mp=240–242° C.). The reaction was monitored by tlc (Rf=0.4 in 10% MeOH/CHCl$_3$) and the product was purified by silica gel chromatography using 9% MeOH/CHCl$_3$ as the eluent, followed by recrystallization from acetonitrile.

NMR data was as follows:

$^1$H-nmr (DMSO-d$_6$): δ=1.19 (t, 6H); 1.31 (d, 3H). Optical Rotation: [α]$_{20}$=+1.0° @ 589 nm (c=1.00, DMSO). C$_{22}$H$_{25}$N$_3$O$_3$F$_2$ (MW=417.45); mass spectroscopy (MH$^+$) 417.

Example 119

Synthesis of N-[(S)-α-Methylbenzyl]-N'-[N-(3,5-difluorophenylacetyl)-L-alaninyl]-L-alaninamide Following General Procedure C and using N-(3,5-difluorophenylacetyl)-L-alanine (from Example B2 above)

and N-(S)-α-methylbenzyl-L-alaninamide hydrochloride (prepared from N-BOC-L-alanine (Sigma) and (R)-α-methylbenzylamine (Aldrich) using General Procedure C, followed by removal of the BOC-group using General Procedure P), the title compound was prepared as a solid (mp=293–295° C.). The reaction was monitored by tlc (Rf=0.4 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.20 (m, 6H); 1.30 (d, 3H). Optical Rotation: [α]$_{20}$=−65.9° @ 589 nm (c=1.05, DMSO). C$_{22}$H$_{25}$N$_3$O$_3$F$_2$ (MW=417.45); mass spectroscopy (MH$^+$) 417.

Example 120

Synthesis of N-(4-Fluorobenzyl)-N'-(N-(3,5-difluorophenylacetyl)-L-alaninyl]-L-alaninamide Following General Procedure C and using N-(3,5-difluorophenylacetyl)-L-alanine (from Example B2 above) and N-(4-fluorobenzyl)-L-alaninamide hydrochloride (prepared from N-BOC-L-alanine (Sigma) and 4-fluorobenzylamine (Aldrich) using General Procedure C, followed by removal of the BOC-group using General Procedure P), the title compound was prepared as a solid (mp=257–259° C.). The reaction was monitored by tlc (Rf=0.4 in 10% MeOH/CHCl$_3$) and the product was purified by silica gel chromatography using 9% MeOH/CHCl$_3$ as the eluent, followed by trituration using 1-chlorobutane.

NMR data was as follows:

$^1$H-nmr (DMSO-d$_6$): δ=1.20 (m, 6H); 3.52 (s, 2H). Optical Rotation: [α]$_{20}$=−28.7° @ 589 nm (c=1.00, DMSO). C$_{21}$H$_{22}$N$_3$O$_3$F$_3$ (MW=421.42); mass spectroscopy (MH$^+$) 421.

Example 121

Synthesis of N-(4-Pyridylmethyl)-N'-[N-(3,5-difluorophenylacetyl)-L-alaninyl]-L-alaninamide Following General Procedure C and using N-(3,5-difluorophenylacetyl)-L-alanine (from Example B2 above) and N-(4-pyridylmethyl)-L-alaninamide dihydrochloride (prepared from N-BOC-L-alanine (Sigma) and 4-(aminomethyl)pyridine (Aldrich) using General Procedure C, followed by removal of the BOC-group using General Procedure P), the title compound was prepared as a solid (mp=244–247° C.). The reaction was monitored by tlc (Rf=0.3 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.21 (d, 3H); 1.26 (d, 3H). Optical Rotation: [α]$_{20}$−30.3° @ 589 nm (c=1.00, DMSO). C$_{20}$H$_{22}$N$_4$O$_3$F$_2$ (MW 404.42); mass spectroscopy (MH$^+$) 405.

Example 122

Synthesis of N-4-Trifluoromethylbenzyl)-N'-[N-(3,5-difluorophenylacetyl)-L-alaninyl]-L-alaninamide Following General Procedure C and using N-(3,5-difluorophenylacetyl)-L-alanine (from Example B2 above) and N-(4-trifluoromethylbenzyl)-L-alaninamide hydrochloride (prepared from N-BOC-L-alanine (Sigma) and 4-(trifluoromethyl)benzylamine (Aldrich) using General Procedure C, followed by removal of the BOC-group using General Procedure P), the title compound was prepared as a solid (mp=244–247° C.). The reaction was monitored by tlc Rf=0.4 in 10% MeOH/CHCl$_3$) and the product was purified by silica gel chromatography using 8% MeOH/CHCl$_3$ as the eluent, followed by triturated using 1-chlorobutane.

NMR data was as follows:

$^1$H-nmr (DMSO-d$_6$): δ=3.52 (s, 2H); 4.35 (d, 2H). Optical Rotation: [α]$_{20}$=−27.4° @ 589 nm (c=1.05, DMSO). C$_{22}$H$_{22}$N$_3$O$_3$F$_5$ (MW=471.43); mass spectroscopy (MH$^+$) 471.

Example 123

Synthesis of Ethyl N-[N-(3,5-Difluorophenylacetyl)-L-alaninyl]-2-amino-2-phenylpropionate Following General Procedure C and using 3,5-difluorophenylacetic acid (Oakwood) and ethyl N-(L-alaninyl)-2-amino-2-phenylpropionate hydrochloride (prepared from N-BOC-L-alanine (Sigma) and D,L-α-methylphenylglycine ethyl ester (from Example D9 above) using General Procedure C, followed by removal of the BOC-group using General Procedure P), the title compound was prepared as a solid (mp=128–130° C.). The reaction was monitored by tlc (Rf=0.2 in 3% MeOH/CHCl$_3$) and the product was purified by silica gel chromatography using 3% MeOH/CHCl$_3$ as the eluent.

NMR data was as follows:

$^1$H-nmr (DMSO-d$_6$)(1:1 mixture of diastereomers): δ=1.72, 1.77 (singlets, 3H); 3.52 (s, 2H). C$_{22}$H$_{24}$N$_2$O$_4$F$_2$ (MW=418.44); mass spectroscopy (MH$^+$) 418.

Example 124

Synthesis of N-[N-(3,5-Difluorophenylacetyl)-L-alaninyl]-L-phenylalanine tert-Butyl Ester Following General Procedure C and using 3,5-difluorophenylacetic acid (Oakwood) and N-(L-alaninyl)-L-phenylalanine tert-butyl ester hydrochloride (prepared from N-BOC-L-alanine (Sigma) and L-phenylalanine tert-butyl ester hydrochloride (Advanced Chemtech) using General Procedure C, followed by removal of the BOC-group using General Procedure P), the title compound was prepared as a gel. The reaction was monitored by tlc (Rf=0.5 in 4% MeOH/CHCl$_3$) and the product was purified by silica gel chromatography using 4% MeOH/CHCl$_3$ as the eluent.

NMR data was as follows:

$^1$H-nmr (DMSO-d$_6$): δ=1.19 (d, 3H); 1.30 (s, 9H). C$_{24}$H$_{28}$N$_2$O$_4$F$_2$ (MW=446.50); mass spectroscopy (MH$^+$) 446.

Example 125

Synthesis of Methyl N-[N-(3,5-Difluorophenylacetyl)-L-alaninyl]-2-amino-2-methylpropionate Following General Procedure C and using N-(3,5-difluorophenylacetyl)-L-alanine (from Example B2 above) and methyl 2-aminoisobutyrate (prepared from 2-aminoisobutyric acid (Aldrich) using General Procedure H), the title compound was prepared as a solid. The reaction was monitored by tlc (Rf=0.25 in CHCl$_3$/MeOH 95:5).

NMR data was as follows:

$^1$H-nmr (DMSO-d$_6$): δ=8.32 (m, 3H), 7.13 (m, 1H), 7.00 (m, 2H), 4.31 (m, 1H), 3.53 (m, 5H), 7.08 (m, 1H), 1.36 (s, 3H), 1.34 (s, 3H), 1.19 (d, 3H). Optical Rotation: [α]$_{23}$=−25° (c 1, MeOH). C$_{16}$H$_{20}$N$_2$O$_4$F$_2$ (MW=342.34); mass spectroscopy (MH$^+$) 343.

Example 126

Synthesis of Ethyl N-[N-(3,5-Difluorophenylacetyl)-L-alaninyl]-2-amino-2-cyclohexylacetate Following General Procedure C and using N-(3,5-difluorophenylacetyl)-L-alanine (from Example B2 above) and ethyl 2-amino-2-cyclohexylacetate hydrochloride (prepared from cyclohexylglycine (Advanced Chemtech) using General Procedure H), the title compound was prepared as a solid (mp=146–150° C.). The reaction was monitored by tlc (Rf=0.3 in 3% MeOH/CHCl$_3$) and the product was purified by silica gel chromatography using 3% MeOH/CHCl$_3$ as the eluent.

NMR data was as follows:

$^1$H-nmr (DMSO-d$_6$)(1:1 mixture of diastereomers): δ=1.60 (m, 6H); 3.50 (s, 2H). C$_{21}$H$_{28}$N$_2$O$_4$F$_2$ (MW=410.46); mass spectroscopy (MH$^+$) 410.

Example 127

Synthesis of N-(2-Methoxyethyl)-N'-[N-(3,5-difluorophenylacetyl)-L-alaninyl]-L-phenylglycinamide Following General Procedure C and using N-(3,5-difluorophenylacetyl)-L-alanine (from Example B2 above) and N-(2-methoxyethyl)-L-phenylglycinamide hydrochloride (prepared from N-BOC-L-phenylglycine (Advanced Chemtech) and 2-methoxyethylamine (Aldrich) using General Procedure C, followed by removal of the BOC-group using General Procedure P), the title compound was prepared as a solid (mp=252–254° C.). The reaction was monitored by tlc (Rf=0.3 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.22 (d, 3H); 5.43 (d, 1H). Optical Rotation: [α]$_{20}$=+6.17° @ 589 nm (c=1.04, DMSO). C$_{22}$H$_{25}$N$_3$O$_4$F$_2$ (MW=433.46); mass spectroscopy (MH$^+$) 434.

Example 128

Synthesis of N-[N-(Isovaleryl)-2-amino-2-cyclohexylacetyl]-L-alanine Ethyl Ester Following General Procedure C and using N-(isovaleryl)-2-amino-2-cyclohexylacetic acid (prepared from isovaleric acid (Aldrich) and D,L-α-cyclohexylglycine ethyl ester hydrochloride (prepared from cyclohexylglycine (Advanced Chemtech) and ethanol using General Procedure H) using General Procedure C, followed by removal of the BOC-group using General Procedure P) and L-alanine ethyl ester hydrochloride (Sigma), the title compound was prepared as a solid (mp=220–224° C.). The reaction was monitored by tlc (Rf=0.2 in 5% MeOH/CHCl$_3$) and the product was purified by silica gel chromatography using 5% MeOH/CHCl$_3$ as the eluent, followed by recrystallization from 1-chlorobutane/acetonitrile.

NMR data was as follows:

$^1$H-nmr (DMSO-d$_6$): δ=0.85 (d, 6H); 4.04 (m, 2H). C$_{18}$H$_{32}$N$_2$O$_4$ (MW=340.46); mass spectroscopy (MH$^+$) 341.

Example 129

Synthesis of N-2-(N,N-Dimethylamino)ethyl-N'-[N-(3,5-difluorophenylacetyl)-L-alaninyl]-L-phenylglycinamide Following General Procedure C and using N-(3,5-difluorophenylacetyl)-L-alanine (from Example B2 above) and N-2-(N,N-dimethylamino)ethyl-L-phenylglycinamide dihydrochloride (prepared from N-BOC-L-phenylglycine (Advanced Chemtech) and N,N-dimethylethylenediamine (Aldrich) using General Procedure C, followed by removal of the BOC-group using General Procedure P), the title compound was prepared as a solid (mp=234–236° C.). The reaction was monitored by tlc (Rf=0.3 in 15% MeOH/CHCl$_3$) and the product was purified by silica gel chromatography using 10% MeOH/CHCl$_3$, followed by slurrying in acetonitrile.

NMR data was as follows:

$^1$H-nmr (DMSO-d$_6$): δ=1.22 (d, 3H); 5.41 (d, 1H). Optical Rotation: [α]$_{20}$=+5.7° @ 589 nm (c=1.01, DMSO). C$_{23}$H$_{28}$N$_4$O$_3$F$_2$ (MW=446.50); mass spectroscopy (MH$^+$) 446.

Example 130

Synthesis of N-(2-Pyridylmethyl)-N'-[N-(3,5-difluorophenylacetyl)-L-alaninyl]-L-phenylglycinamide Following General Procedure C and using N-(3,5-difluorophenylacetyl)-L-alanine (from Example B2 above) and N-(2-pyridylmethyl)-L-phenylglycinamide dihydrochloride (prepared from N-BOC-L-phenylglycine (Advanced Chemtech) and 2-(aminomethyl)pyridine (Aldrich) using General Procedure C, followed by removal of the BOC-group using General Procedure P), the title compound was prepared as a solid (mp=272–275° C.). The reaction was monitored by tlc (Rf=0.4 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.24 (d, 3H); 5.50 (d, 1H). Optical Rotation: [α]$_{20}$=+12.4° @ 589 nm (c=1.02, DMSO). C$_{25}$H$_{24}$N$_4$O$_3$F$_2$ (MW=466.49); mass spectroscopy (MH$^+$) 467.

Example 131

Synthesis of N-[N-(3-Pyridylacetyl)-L-alaninyl]-L-phenylalanine Methyl Ester

Following General Procedure C and using 3-pyridylacetic acid hydrochloride (Aldrich) and N-(L-alaninyl)-L-phenylalanine methyl ester hydrochloride (prepared from N-BOC-L-alanine (Sigma) and L-phenylalanine methyl ester hydrochloride (Sigma) using General Procedure C, followed by removal of the BOC-group using General Procedure P), the title compound was prepared as a solid (mp=150–152° C.). The reaction was monitored by tlc (Rf=0.3 in 10% MeOH/CHCl$_3$) and the product was purified by silica gel chromatography using 10% MeOH/CHCl$_3$ as the eluent, followed by recrystallization from acetonitrile.

NMR data was as follows:

$^1$H-nmr (DMSO-d$_6$): δ=1.16 (d, 3H); 347 (s, 2H). Optical Rotation: [α]$_{20}$=−19.0° @ 589 nm (c=1.03, DMSO). C$_{20}$H$_{23}$N$_3$O$_4$ (MW=369.42); mass spectroscopy (MH$^+$) 369.

Example 132

Synthesis of N-[N-(2-Pyridylacetyl)-L-alaninyl]-L-phenylalanine Methyl Ester

Following General Procedure C and using 2-pyridylacetic acid hydrochloride (Aldrich) and N-(L-alaninyl)-L-phenylalanine methyl ester hydrochloride (prepared from N-BOC-L-alanine (Sigma) and L-phenylalanine methyl ester hydrochloride (Sigma) using General Procedure C, followed by removal of the BOC-group using General Procedure P), the title compound was prepared as a solid (mp=137–139° C.). The reaction was monitored by tlc (Rf=0.4 in 8% MeOH/CHCl$_3$) and the product was purified by silica gel chromatography using 8% MeOH/CHCl$_3$ as the eluent, followed by recrystallization from 1-chlorobutane/acetonitrile.

NMR data was as follows:

$^1$H-nmr (DMSO-d$_6$): δ=1.17 (d, 3H); 3.65 (s, 2H). Optical Rotation: [α]$_{20}$=−17.48° @ 589 nm (c=1.09, DMSO). C$_{20}$H$_{23}$N$_3$O$_4$ (MW=369.42); mass spectroscopy (MH$^+$) 369.

Example 133

Synthesis of N-[N-(4-Pyridylacetyl)-L-alaninyl]-L-phenylalanine Methyl Ester

Following General Procedure C and using 4-pyridylacetic acid hydrochloride (Aldrich) and N-(L-alaninyl)-L-phenylalanine methyl ester hydrochloride (prepared from N-BOC-L-alanine (Sigma) and L-phenylalanine methyl ester hydrochloride (Sigma) using General Procedure C, followed by removal of the BOC-group using General Procedure P), the title compound was prepared as a solid (mp=152–154° C.). The reaction was monitored by tlc (Rf=0.4 in 10% MeOH/CHCl$_3$) and the product was purified by silica gel chromatography using 10% MeOH/CHCl$_3$ as the eluent, followed by recrystallization from 1-chlorobutane/acetonitrile.

NMR data was as follows:

$^1$H-nmr (DMSO-d$_6$): δ=1.17 (d, 3H); 3.47 (s, 2H). Optical Rotation: [α]$_{20}$=−17° @ 589 nm (c=1.00, DMSO). C$_{20}$H$_{23}$N$_3$O$_4$ (MW=369.42); mass spectroscopy (MH$^+$) 369.

Example 134

Synthesis of Ethyl N-[N-(3,5-Difluorophenylacetyl)-L-alaninyl]-2-amino-2-(4-fluorophenyl)acetate Following General Procedure C and using N-(3,5-difluorophenylacetyl)-L-alanine (from Example B2 above) and ethyl 2-amino-2-(4-fluorophenyl)acetate hydrochloride (prepared from 4-fluorophenylglycine (Fluka) and ethanol using General Procedure H), the title compound was prepared as a solid (mp=169–183° C.). The reaction was monitored by tlc (Rf=0.3 in 4% MeOH/CHCl$_3$) and the product was purified by silica gel chromatography using 4% MeOH/CHCl$_3$ as the eluent, followed by recrystallization from 1-chlorobutane/acetonitrile.

NMR data was as follows:

$^1$H-nmr (DMSO-d$_6$)(1:1 mixture of diastereomers): δ=3.49, 3.53 (singlets, 2H); 5.40 (m, 1H). C$_{21}$H$_{21}$2O$_4$F$_3$ (MW=422.4); mass spectroscopy (MH$^+$) 422.

Example 135

Synthesis of Ethyl N-[N-(3,5-Difluorophenylacetyl)-L-alaninyl]-2-amino-2-(2-fluorophenyl)acetate Following General Procedure C and using N-(3,5-difluorophenylacetyl)-L-alanine (from Example B2 above) and ethyl 2-amino-2-(2-fluorophenyl)acetate hydrochloride (prepared from 2-fluorophenylglycine (Fluka) and ethanol using General Procedure H), the title compound was prepared as a solid (mp=153–170° C.). The reaction was monitored by tlc (Rf=0.3 in 5% MeOH/CHCl$_3$) and the product was purified by silica gel chromatography using 5% MeOH/CHCl$_3$ as the eluent, followed by recrystallization from 1-chlorobutane/acetonitrile.

NMR data was as follows:

$^1$H-nmr (DMSO-d$_6$)(1:1 mixture of diastereomers): δ=3.50, 3.54 (singlets, 2H), 5.66 (m, 1H). C$_{21}$H$_{21}$N$_2$O$_4$F$_3$ (MW=422.40); mass spectroscopy (MH$^+$) 422.

Example 136

Synthesis of N-[N-(3,5-Difluorophenylacetyl)-L-phenylglycinyl]-L-alanine Ethyl Ester Following General Procedure C and using 3,5-difluorophenylacetic acid (Oakwood) and N-(L-phenylglycinyl)-L-alanine ethyl ester hydrochloride (prepared from N-BOC-L-phenylglycine (Advanced Chemtech) and L-alanine ethyl ester hydrochloride (Aldrich) using General Procedure C, followed by removal of the BOC-group using General Procedure P), the title compound was prepared as a solid. The reaction was monitored by tlc (Rf=0.3 in 3% MeOH/CHCl$_3$) and the product was purified by silica gel chromatography using 3% MeOH/CHCl$_3$ as the eluent, followed by recrystallization from 1-chlorobutane/acetonitrile.

NMR data was as follows:

$^1$H-nmr (DMSO-d$_6$): δ=3.50 (s, 2H), 5.53 (d, 1H). C$_{21}$H$_{22}$N$_2$O$_4$F$_2$ (MW=404.42); mass spectroscopy (MH$^+$) 405.

Example 137

Synthesis of Ethyl N-[N-(3,5-Difluorophenylacetyl)-L-alaninyl]-2-amino-3-phthalimidopropionate Following General Procedure C and using N-(3,5-difluorophenylacetyl)-L-alanine (from Example B2 above) and ethyl 2-amino-3-phthalimidopropionate hydrochloride (from Example D10 above), the title compound was prepared as a solid (mp=197–201° C.). The reaction was monitored by tlc (Rf=0.5 in 10% MeOH/CHCl$_3$) and the product was purified by silica gel chromatography using 5% MeOH/CHCl$_3$ as the eluent.

NMR data was as follows:

$^1$H-nmr (DMSO-d$_6$)(1:1 mixture of diastereomers): δ=7.88 (m, 4H), 8.29 (t, 1H), 8.48, 8.55 (doublets, 1H). C$_{24}$H$_{23}$N$_3$O$_6$F$_2$ (MW=487.46); mass spectroscopy (MH$^+$) 487.

Example 138

Synthesis of N-[N-(3,5-Difluorophenylacetyl)-L-alaninyl]-L-phenylglycine Neopentyl Ester Following General Procedure C and using N-(3,5-difluorophenylacetyl)-L-alanine (from Example B2 above)

and L-phenylglycine neopentyl ester hydrochloride (prepared from N-BOC-L-phenylglycine (Advanced Chemtech) and 2,2-dimethyl-1-propanol (Aldrich) using General Procedure C (with catalytic DMAP), followed by removal of the BOC-group using General Procedure P), the title compound was prepared as a solid (mp=133–136° C.). The reaction was monitored by tlc (Rf=0.7 in 10% MeOH/CHCl$_3$) and the product was purified by silica gel chromatography using 4% MeOH/CHCl$_3$ as the eluent, followed by recrystallization from 1-chlorobutane/hexanes.

NMR data was as follows: $^1$H-nmr (DMSO-d$_6$): δ=3.50 (s, 2H), 5.42 (d, 1H). Optical Rotation: [α]$_{20}$=+45.9° @ 589 nm (c=1.02, DMSO). C$_{24}$H$_{28}$N$_2$O$_4$F$_2$ (MW=446.50); mass spectroscopy (MH$^+$) 446.

Example 139

Synthesis of N-tert-Butyl-N'-[N-(3,5-difluorophenylacetyl)-L-alaninyl]-L-phenylglycinamide Following General Procedure AB and using N-(3,5-difluorophenylacetyl)-L-alanine (from Example B2 above), S-(+)-α-methylbenzylamine (Aldrich), benzaldehyde (Aldrich) and tert-butylisocyanide (Aldrich), the title compound was prepared as a solid (mp=233–235° C.). The reaction was monitored by tlc (Rf=0.4 in 10% MeOH/CHCl$_3$) and the product was purified by silica gel chromatography using 8% MeOH/CHCl$_3$ as the eluent, followed by recrystallization from 1-chlorobutane/acetonitrile.

NMR data was as follows:
$^1$H-nmr (DMSO-d$_6$)(1:1 mixture of diastereomers): δ=3.52 (s, 2H), 5.40 (m, 1H). C$_{23}$H$_{27}$N$_3$O$_3$F$_2$ (MW=431.49); mass spectroscopy (MH$^+$) 432.

Example 140

Synthesis of N-[N-(3,5-Difluorophenylacetyl)-L-alaninyl]-L-phenylglycine tert-Butyl Ester Following General Procedure C and using N-(3,5-difluorophenylacetyl)-L-alanine (from Example B2 above) and L-phenylglycine tert-butyl ester hydrochloride (Advanced Chemtech), the title compound was prepared as a solid (mp=145–147° C.). The reaction was monitored by tlc (Rf=0.5 in 5% MeOH/CHCl$_3$) and the product was purified by silica gel chromatography using 2.5% MeOH/CHCl$_3$ as the eluent, followed by recrystallization from 1-chlorobutane/hexanes.

NMR data was as follows:
$^1$H-nmr (DMSO-d$_6$): δ=1.26 (d, 3H); 5.20 (d, 1H). Optical Rotation: [α]$_{20}$=+14.8° @ 589 nm (c=1.01, MeOH). C$_{23}$H$_{26}$N$_2$O$_4$F$_2$ (MW=432.47); mass spectroscopy (MH$^+$) 433.

Example 141

Synthesis of N'-[N-(3,5-Difluorophenylacetyl)-L-alaninyl]-L-phenylglycinamide Following General Procedure C and using N-(3,5-difluorophenylacetyl)-L-alanine (from Example B2 above) and L-phenylglycinamide hydrochloride (prepared from N-BOC-L-phenylglycine (Advanced Chemtech) and ammonia using General Procedure C, followed by removal of the BOC-group using General Procedure P), the title compound was prepared as a solid (mp=288–290° C.). The reaction was monitored by tlc (Rf=0.4 in 15% MeOH/CHCl$_3$) and the product was purified by silica gel chromatography using 15% MeOH/CHCl$_3$ as the eluent, followed by recrystallization from EtOH.

NMR data was as follows:
$^1$H-nmr (DMSO-d$_6$): δ=1.22 (d, 3H), 5.36 (d, 1H). Optical Rotation: [α]$_{20}$=+27.5° @ 589 nm (c=1.03, DMSO). C$_{19}$H$_{19}$N$_3$O$_3$F$_2$ (MW=375.38); mass spectroscopy (MH$^+$) 376.

Example 142

Synthesis of 4-[N-[N-(3-Nitrophenylacetyl)-L-alaninyl]-L-valinyl]morpholine Following General Procedure C and using N-(3-nitrophenylacetyl)-L-alanine (from Example D11 above) and 4-(L-valinyl)morpholine (prepared from N-BOC-L-valine (Aldrich) and morpholine (Aldrich) using General Procedure M, followed by removal of the BOC-group using General Procedure P), the title compound was prepared as a solid. The reaction was monitored by tlc (Rf=0.5 in 9:1 CHCl$_3$/MeOH) and the product was purified by silica gel chromatography using 98:2 CHCl$_3$/MeOH as the eluent.

NMR data was as follows:
$^1$H-nmr (CDCl$_3$): δ=8.12 (d, 2H), 8.08 (dd, 1H), 7.59 (d, 1H, J=7 Hz), 7.42 (t, 1H), 7.32 (d, J=8 Hz, 1H), 7.03(d, J=8 Hz, 1H), 4.78 (m, 1H), 4.68 (m, 1H), 3.61 (m, 10H), 1.90 (m, 1H), 1.96 (d, 3H), 1.31 (d, 3H), 0.88 (d, 3H), 0.80 (d, 3H). Optical Rotation: [α]$_{23}$=−5° (c 5, MeOH).

Example 143

Synthesis of N-[N-(3-Nitrophenylacetyl)-L-alaninyl]-L-valine Ethyl Ester

Following General Procedure C and using N-(3-nitrophenylacetyl)-L-alanine (from Example D11 above) and L-valine ethyl ester hydrochloride (Aldrich), the title compound was prepared as a solid. The reaction was monitored by tlc (Rf=0.2 in 97:3 CHCl$_3$/MeOH) and the product was purified by silica gel chromatography using 97:3 CHCl$_3$/MeOH as the eluent.

NMR data was as follows: $^1$H-nmr (CDCl$_3$): δ=8.13 (m, 2H), 7.62 (d, J=7 Hz, 1H), 7.47 (t, 1H), 6.52 (m, 2H), 4.57 (m, 1H), 4.46 (m, 1H), 4.19 (m, 2H), 3.65 (s, 2H), 2.13 (m, 1H), 1.38 (d, 3H), 1.22 (t, 3H), 0.82 (d, 3H). Optical Rotation: [α]$_{23}$=−24.3° @ 589 nm (c 1, DMSO). C$_{18}$H$_{25}$N$_3$O$_6$ (MW=379.42); mass spectroscopy (MH$^+$) 380.

Example 144

Synthesis of N-[N-(3-Nitrophenylacetyl)-L-alaninyl]-L-threonine Methyl Ester Following General Procedure C and using N-(3-nitrophenylacetyl)-L-alanine (from Example D11 above) and L-threonine methyl ester hydrochloride (Aldrich), the title compound was prepared as a solid. The reaction was monitored by tlc (Rf=0.1 in 95:5 CHCl$_3$/MeOH) and the product was purified by silica gel chromatography using 95:5 CHCl$_3$/MeOH as the eluent.

NMR data was as follows:
$^1$H-nmr (CDCl$_3$): δ=8.08 (d, 1H), 7.96 (d, 1H), 7.59 (d, 1H), 7.45 (d, 1H), 7.34 (t, 1H), 7.20 (d, 1H), 4.43 (m, 1H), 4.39 (dd, 1H), 4.13 (m, 1H), 3.59 (s, 3H), 3.51 (s, 2H), 1.20 (d, 3H), 1.03 (d, 3H). Optical Rotation: [α]$_{23}$=−20.8° (c 5, MeOH). C$_{16}$H$_{20}$N$_2$O$_7$ (MW=367.3); mass spectroscopy (MH$^+$) 368.

Example 145

Synthesis of 4-[N-[N-(3-Nitrophenylacetyl)-L-alaninyl]-(S)-2-amino-3-tert-butoxybutyryl]morpholine Following General Procedure C and using N-(3-nitrophenylacetyl)-L-alanine (from Example D11 above) and 4-[(S)-2-amino-3-tert-butoxybutyryl]-morpholine (prepared from N-BOC-O-tert-butyl-L-threonine (Sigma) and morpholine (Aldrich) using General Procedure M, followed by removal of the BOC-group using General Procedure P), the title compound was prepared as a solid. The reaction was monitored by tlc (Rf=0.1 in 95:5 $CHCl_3$/MeOH) and the product was purified by silica gel chromatography using 96:4 $CHCl_3$/MeOH as the eluent.

NMR data was as follows:

$^1$H-nmr ($CDCl_3$): δ=8.12 (m, 2H), 7.66 (d, 1H), 7.47 (t, 1H), 6.88 (d, 1H), 6.32 (d, 1H), 4.78 (m, 1H), 4.50 (m, 1H), 3.90–3.40 (m, 11H), 1.40 (d, 3H), 1.18 (s, 9H), 1.0 (d, 3H). $C_{23}H_{33}N_3O_7$ (MW=478.5); mass spectroscopy (MH$^+$) 479.

Example 146

Synthesis of 4-[N-[N-(3-Nitrophenylacetyl)-L-alaninyl]-L-isoleucynyl]morpholine

Following General Procedure C and using N-(3-nitrophenylacetyl)-L-alanine (from Example D11 above) and 4-(L-isoleucinyl)morpholine (prepared from N-BOC-L-isoleucine (Aldrich) and morpholine (Aldrich) using General Procedure M, followed by removal of the BOC-group using General Procedure P), the title compound was prepared as a solid (mp=156–160° C.). The reaction was monitored by tlc (Rf=0.45 in 9:1 $CHCl_3$/MeOH) and the product was purified by silica gel chromatography using 98:2 $CHCl_3$/MeOH as the eluent.

NMR data was as follows:

$^1$H-nmr ($CDCl_3$): δ=8.16 (d, 1H), 8.09 (d, 1H), 7.63 (d, 1H), 7.45 (t, 1H), 7.30 (d, 1H), 6.89 (d, 1H), 4.78 (m, 1H), 4.62 (m, 1H), 3.6 (m, 10H), 1.65 (m, 1H), 1.4 (m, 1H), 1.29 (d, 3H), 1.03 (d, 3H), 0.90–0.76 (m, 6H). Optical Rotation: $[α]_{23}$=−55° @ 589 nm (c 1, MeOH).

Example 147

Synthesis of N-[N-(3-Nitrophenylacetyl)-L-alaninyl]-L-isoleucine Methyl Ester

Following General Procedure C and using N-(3-nitrophenylacetyl)-L-alanine (from Example D11 above) and L-isoleucine methyl ester hydrochloride (Aldrich), the title compound was prepared as a solid. The reaction was monitored by tlc (Rf=0.15 in 97:3 $CHCl_3$/MeOH) and the product was purified by silica gel chromatography using 97:3 $CHCl_3$/MeOH as the eluent.

NMR data was as follows:

$^1$H-nmr ($CDCl_3$): δ=8.12 (m, 2H), 7.66 (d, 1H), 7.49 (t, 1H), 6.50 (m, 2H), 4.52 (m, 2H), 3.72 (s, 3H), 3.61 (s, 2H), 1.87 (m, 1H), 1.32 (m, 4H), 1.07 (m, 1H), 0.81 (d, 6H). Optical Rotation: $[α]_{23}$=−7.3° (c 5, MeOH). $C_{18}H_{25}N_2O_6$ (MW=379); mass spectroscopy (MH$^+$) 379.

Example 148

Synthesis of N-[N-(3-Nitrophenylacetyl)-L-alaninyl]-L-isoleucine

Following General Procedure AF and using N-[N-(3-nitrophenylacetyl)-L-alaninyl]-L-isoleucine methyl ester (from Example 147 above), the title compound was prepared as a solid.

NMR data was as follows:

$^1$H-nmr (DMSO-$d_6$): δ=8.41 (d, 1H), 8.15 (s, 1H), 8.07 (d, 1H), 7.91 (d, 1H), 7.68 (d, 1H), 7.53 (t, 1H), 4.36 (m, 1H), 4.12 (m, 1H), 3.62 (s, 2H), 1.71 (m, 1H), 1.31 (m, 1H), 1.18 (d, 3H), 1.07 (m, 1H), 0.79 (m, 6H). Optical Rotation: $[α]_{23}$=−42° (c 5, MeOH). $C_{17}H_{23}N_2O_6$ (MW=365.3); mass spectroscopy (MH$^+$) 366.

Example 149

Synthesis of N-[N-[N-(3-Nitrophenylacetyl)-L-alaninyl]-L-threoninyl]-L-valine Ethyl Ester Following General Procedure C and using N-[N-(3-nitrophenylacetyl)-L-alaninyl]-L-threonine (prepared from N-[N-(3-nitrophenylacetyl)-L-alaninyl]-L-threonine methyl ester (from Example 144 above) using General Procedure AF) and L-valine ethyl ester hydrochloride (Aldrich), the title compound was prepared as a solid. The reaction was monitored by tlc (Rf=0.1 in 96:4 $CHCl_3$/MeOH) and the product was purified by silica gel chromatography using 96:4 $CHCl_3$/MeOH as the eluent.

NMR data was as follows:

$^1$H-nmr ($CDCl_3$): δ=8.12 (m, 1H), 7.60 (d, 1H), 7.48 (t, 1H), 7.05 (d, 1H), 6.98 (d, 1H), 6.48 (d, 1H), 4.60 (m, 1H), 4.47 (m, 3H), 4.22 (m, 2H) 3.65 (s, 2H), 2.19 (m, 1H), 1.38 (d, 3H), 1.28 (t, 3H), 1.09 (d, 3H), 0.87 (m, 6H). Optical Rotation: $[α]_{23}$=−85° (c 5, MeOH).

Example 150

Synthesis of Methyl N-[N-(3-nitrophenylacetyl)-L-alaninyl]-(S)-2-aminopentanoate Following General Procedure C and using N-(3-nitrophenylacetyl)-L-alanine (from Example D11 above) and methyl (S)-2-aminopentanoate hydrochloride (prepared from (S)-2-aminopentanoic acid (Novabiochem) using General Procedure H), the title compound was prepared as a solid. The reaction was monitored by tlc (Rf=0.4 in 9:1 $CHCl_3$/MeOH).

NMR data was as follows:

$^1$H-nmr (DMSO-$d_6$): δ=8.39 (m, 1H), 8.28 (m, 1H), 8.19 (m, 1H), 8.11 (m, 1H), 7.73 (d, 1H), 7.61 (d, 1H), 4.36 (m, 1H), 4.22 (m, 1H), 3.64 (m, 5H), 1.62 (m, 2H), 1.26 (m, 2H), 1.22 (d, 3H), 0.86 (m, 3H). Optical Rotation: $[α]_{23}$=−29° (c 1, MeOH). $C_{17}H_{23}N_3O_6$ (MW=365); mass spectroscopy (MH$^+$) 366.

Example 151

Synthesis of N-[N-(3-Nitrophenylacetyl)-L-alaninyl]-L-leucine Methyl Ester

Following General Procedure C and using N-(3-nitrophenylacetyl)-L-alanine (from Example D11 above) and L-leucine methyl ester hydrochloride (Aldrich), the title compound was prepared as a solid. The reaction was monitored by tlc (Rf=0.75 in 9:1 $CHCl_3$/MeOH) and the product was purified by silica gel chromatography using 97:3 $CHCl_3$/MeOH as the eluent.

NMR data was as follows:

$^1$H-nmr ($CDCl_3$): δ=8.12 (m, 2H), 8.04 (m, 1H), 7.58 (m, 1H), 7.48–7.30 (m, 2H), 7.11 (d, 1H), 4.63 (m, 1H), 4.48 (m, 1H), 3.68 (s, 2H), 3.64 (s, 3H), 1.63 (m, 1H), 1.31 (m, 2H), 0.85 (d, 3H), 0.82 (m, 3H). Optical Rotation: $[α]_{23}$=−32° (c 1, MeOH). $C_{18}H_{25}N_3O_6$ (MW=379); mass spectroscopy (MH$^+$) 380.

Example 152

Synthesis of N-[N-(3,5-Difluorophenylacetyl)-L-alaninyl]-L-leucine Methyl Ester

Following General Procedure C and using N-(3,5-difluorophenylacetyl)-L-alanine (from Example B2 above) and L-leucine methyl ester hydrochloride (Aldrich), the title compound was prepared as a solid. The reaction was monitored by tlc (Rf=0.5 in 9:1 $CHCl_3$/MeOH).

NMR data was as follows:

$^1$H-nmr ($CDCl_3$): δ=6.78 (m, 2H), 6.69 (m, 1H), 4.52 (m, 2H), 3.73 (m, 1H), 3.52 (d, 2H), 1.63 (m, 2H), 1.36 (m, 3H), 0.88 (m, 3H). Optical Rotation: $[α]_{23}$=−34° (c 1, MeOH). $C_{18}H_{24}N_2O_4F_2$ (MW=370); mass spectroscopy ($MH^+$) 370.

Example 153

Synthesis of N-2-Methoxyethyl-N'-[N-(3,5-difluorophenylacetyl)-L-alaninyl]-L-alaninamide Following General Procedure C and using N-[N-(3,5-difluorophenylacetyl)-L-alaninyl]-L-alanine (from Example D7 above) and 2-methoxyethylamine (Aldrich), the title compound was prepared as a solid. The reaction was monitored by tlc (Rf=0.35 in 9:1 $CHCl_3$/MeOH).

NMR data was as follows:

$^1$H-nmr (DMSO-$d_6$): δ=8.32 (m, 1H), 7.98 (d, 1H), 7.82 (m, 1H), 7.07 (m, 1H), 6.97 (m, 2H), 4.25 (m, 2H), 3.52 (s, 2H), 3.32 (m, 3H), 3.20 (m, 4H), 1.19 (m, 6H). Optical Rotation: $[α]_{23}$=−50° (c 1, MeOH). $C_{17}H_{23}N_3O_4F_2$ (MW=371); mass spectroscopy ($MH^+$) 372.

Example 154

Synthesis of N-2-(N,N-Dimethylamino)ethyl-N'-[N-(3,5-difluorophenylacetyl)-L-alaninyl]-L-alaninamide Following General Procedure C and using N-[N-(3,5-difluorophenylacetyl)-L-alaninyl]-L-alanine (from Example D7 above) and N,N-dimethyl-ethylenediamine (Aldrich), the title compound was prepared as a solid. The reaction was monitored by tlc (Rf=0.05 in 9:1 $CHCl_3$/MeOH).

NMR data was as follows:

$^1$H-nmr (DMSO-$d_6$): δ=8.38 (m, 1H), 8.02 (m, 1H), 7.66 (m, 1H), 7.09 (m, 1H), 6.97 (m, 2H), 4.22 (m, 2H), 3.53 (s, 2H), 3.08 (m, 2H), 2.22 (m, 2H), 2.11 (m, 6H), 1.21 (d, 6H). Optical Rotation: $[α]_{23}$=−55° (c 1, MeOH). $C_{18}H_{26}N_4O_3F_2$ (MW=384); mass spectroscopy ($MH^+$) 384.

Example 155

Synthesis of N-Cyclohexyl-N'-[N-(3,5-difluorophenylacetyl)-L-alaninyl]-L-alaninamide Following General Procedure C and using N-[N-(3,5-difluorophenylacetyl)-L-alaninyl]-L-alanine (from Example D7 above) and cyclohexylamine (Aldrich), the title compound was prepared as a solid (mp=239–244° C.). The reaction was monitored by tlc (Rf=0.25 in 9:1 $CHCl_3$/MeOH).

NMR data was as follows:

$^1$H-nmr (DMSO-$d_6$): δ=8.39 (m, 1H), 7.94 (m, 1H), 7.56 (m, 1H), 7.08 (m, 1H), 6.97 (m, 2H), 4.20 (m, 2H), 3.32 (s, 2H), 3.27 (m, 1H), 1.64 (m, 4H), 1.54 (m, 2H), 1.20 (m, 10H). Optical Rotation: $[α]_{23}$=−58° (c 1, MeOH). $C_{20}H_{27}N_3O_3F_2$ (MW=395); mass spectroscopy ($MH^+$) 395.

Example 156

Synthesis of N-Neopentyl-N'-[N-(3,5-difluorophenylacetyl)-L-alaninyl]-L-alaninamide Following General Procedure C and using N-[N-(3,5-difluorophenylacetyl)-L-alaninyl]-L-alanine (from Example D7 above) and neopentylamine (Aldrich), the title compound was prepared as a solid. The reaction was monitored by tlc (Rf=0.25 in 9:1 $CHCl_3$/MeOH).

NMR data was as follows:

$^1$H-nmr (DMSO-$d_6$): δ=8.37 (d, 1H), 8.01 (m, 1H), 7.67 (m, 1H), 7.11 (m, 1H), 6.98 (m, 2H), 4.28 (m, 2H), 3.51 (s, 2H), 2.88 (m, 2H), 1.23 (d, 3H), 0.80 (m, 9H). Optical Rotation: $[α]_{23}$=−54° (c 1, MeOH). $C_{19}H_{27}N_3O_3F_2$ (MW=383); mass spectroscopy ($MH^+$) 383.

Example 157

Synthesis of N-Tetrahydrofurfuryl-N'-[N-(3,5-difluorophenylacetyl)-L-alaninyl]-L-alaninamide Following General Procedure C and using N-[N-(3,5-difluorophenylacetyl)-L-alaninyl]-L-alanine (from Example D7 above) and tetrahydrofurfurylamine (Aldrich), the title compound was prepared as a solid. The reaction was monitored by tlc (Rf=0.20 in 9:1 $CHCl_3$/MeOH).

NMR data was as follows:

$^1$H-nmr(DMSO-$d_6$): δ=8.36 (d, 1H), 8.01 (m, 1H), 7.81 (m, 1H), 7.11 (m, 1H), 6.99 (m, 2H), 4.25 (m, 2H), 3.77 (m, 2H), 3.58 (m, 1H), 3.51 (s, 2H), 3.21 (m, 1H), 1.78 (m, 4H), 1.46 (m, 1H), 1.19 (m, 6H). Optical Rotation: $[α]_{23}$=−70° (c 1, MeOH). $C_{19}H_{25}N_3O_4F_2$ (MW=397); mass spectroscopy ($MH^+$) 398.

Example 158

Synthesis of N-2-Pyridylmethyl-N'-[N-(3,5-difluorophenylacetyl)-L-alaninyl]-L-alaninamide Following General Procedure C and using N-[N-(3,5-difluorophenylacetyl)-L-alaninyl]-L-alanine (from Example D7 above) and 2-(aminomethyl)pyridine (Aldrich), the title compound was prepared as a solid. The reaction was monitored by tlc (Rf=0.1 in 9:1 $CHCl_3$/MeOH).

NMR data was as follows:

$^1$H-nmr (DMSO-$d_6$): δ=8.49 (m, 1H), 8.41 (m, 2H), 8.14 (d, 1H), 7.74 (m, 1H), 7.28 (m, 2H), 7.09 (m, 1H), 6.98 (m, 2H), 4.33 (m, 4H), 3.52 (s, 2H), 1.24 (m, 6H). Optical Rotation: $[α]_{23}$=−68° (c 5, MeOH). $C_{20}H_{22}N_4O_3F_2$ (MW=404); mass spectroscopy ($MH^+$) 405.

Example 159

Synthesis of 3-[N-[N-(3,5-Difluorophenylacetyl)-L-alaninyl]-L-alaninyl]thiazolidine Following General Procedure C and using N-[N-(3,5-difluorophenylacetyl)-L-alaninyl]-L-alanine (from Example D7 above) and thiazolidine (Aldrich), the title compound was prepared as a solid. The reaction was monitored by tlc (Rf=0.25 in 9:1 $CHCl_3$/MeOH).

NMR data was as follows:

$^1$H-nmr (DMSO-$d_6$): δ=8.34 (m, 2H), 8.22 (m, 1H), 7.09 (m, 1H), 6.98 (m, 2H), 4.68–4.23 (m, 4H), 3.81–3.6 (m, 2H), 3.52 (s, 2H), 3.01 (m, 2H), 1.19 (m, 6H). Optical Rotation: $[α]_{23}$=−67° (c 1, MeOH). $C_{17}H_{21}N_3O_3F_2$ (MW=385); mass spectroscopy ($MH^+$) 385.

Example 160

Synthesis of Methyl N-[N-(3,5-difluorophenylacetyl)-L-alaninyl]-(S)-2-aminobutanoate

Following General Procedure C and using N-(3,5-difluorophenylacetyl)-L-alanine (from Example B2 above) and methyl (S)-2-aminobutanoate hydrochloride (prepared from (S)-(+)-2-aminobutyric acid (Aldrich) using General Procedure H), the title compound was prepared as a solid (mp=103–106° C.).

NMR data was as follows:

$^1$H-nmr (CDCl$_3$): δ=6.83 (m, 2H), 6.72 (m, 1H), 6.49 (d, 1H), 4.55 (m, 1H), 4.48 (m, 1H), 3.72 (s, 3H), 3.49 (s, 2H), 1.85 (m, 1H), 1.69 (m, 1H), 1.39 (d, 3H), 0.86 (t, 3H). Optical Rotation: $[α]_{23}$=−70° (c 1, MeOH). $C_{16}H_{20}N_2O_4F_2$ (MW=342.35); mass spectroscopy (MH$^+$) 342.

Example 161

Synthesis of Methyl N-[N-(3,5-difluorophenylacetyl)-L-alaninyl]-(S)-2-aminopentanoate

Following General Procedure C and using N-(3,5-difluorophenylacetyl)-L-alanine (from Example B2 above) and methyl (S)-2-aminopentanoate hydrochloride (prepared from (S)-2-aminopentanoic acid (Novabiochem) using General Procedure H), the title compound was prepared as a solid (mp=154–155° C.).

NMR data was as follows:

$^1$H-nmr (CDCl$_3$): δ=6.80 (m, 2H), 6.69 (m, 1H), 6.45 (d, 1H), 6.28 (d, 1H), 4.52 (m, 2H), 3.71 (s, 3H), 3.51 (s, 2H), 1.77 (m, 1H), 1.58 (m, 1H), 1.35 (d, 3H), 1.27 (m, 2H), 0.87 (t, 3H). Optical Rotation: $[α]_{23}$=−69° (c 1, MeOH).

Example 162

Synthesis of Methyl N-[N-(3-nitrophenylacetyl)-L-alaninyl]-(S)-2-aminobutanoate

Following General Procedure C and using N-(3-nitrophenylacetyl)-L-alanine (from Example D11 above) and methyl (S)-2-aminobutanoate hydrochloride prepared from (S)-(+)-2-aminobutyric acid (Aldrich) using General Procedure H), the title compound was prepared as a solid (mp=154–157° C.).

NMR data was as follows:

$^1$H-nmr (CDCl$_3$): δ=8.13 (m, 1H), 8.04 (m, 1H), 7.57 (m, 1H), 7.38 (m, 1H), 4.72 (m, 1H), 4.39 (m, 1H), 3.69 (s, 3H), 3.41 (s, 2H), 1.73 (m, 1H), 1.61 (m, 1H), 1.34 (d, 3H), 0.79 (t, 3H). Optical Rotation: $[α]_{23}$=−75° (c 1, MeOH).

Example 163

Synthesis of N-(R)-sec-Butyl-N'-[N-(3,5-difluorophenylacetyl)-L-alaninyl]-L-alaninamide

Following General Procedure C and using N-[N-(3,5-difluorophenylacetyl)-L-alaninyl]-L-alanine (from Example D7 above) and (R)-(−)-sec-butylamine (Aldrich), the title compound was prepared as a solid. The reaction was monitored by tlc (Rf=0.15 in 95:5 CHCl$_3$/MeOH) and the product was purified by silica gel chromatography using 95:5 CHCl$_3$ MeOH as the eluent.

NMR data was as follows:

$^1$H-nmr (DMSO-d$_6$): δ=8.39 (m, 1H), 7.95 (m, 1H), 7.49 (m, 1H), 7.09 (m, 1H), 7.01 (m, 2H), 4.20 (m, 4H), 3.61 (m, 1H), 3.52 (s, 2H), 1.34 (m, 2H), 1.21 (m, 6H), 0.97 (d, 3H), 0.79 (m, 3H). Optical Rotation: $[α]_{23}$=−50° (c 1, MeOH). $C_{18}H_{25}N_3O_3F_2$ (MW=369.41); mass spectroscopy (MH$^+$) 370.

Example 164

Synthesis of 1-[N-[N-(3,5-Difluorophenylacetyl)-L-alaninyl]-L-alaninyl]pyrrolidine

Following General Procedure C and using N-[N-(3,5-difluorophenylacetyl)-L-alaninyl]-L-alanine (from Example D7 above) and pyrrolidine (Aldrich), the title compound was prepared as a solid. The reaction was monitored by tlc (Rf=0.15 in 95:5 CHCl$_3$/MeOH) and the product was purified by silica gel chromatography using CHCl$_3$/MeOH as the eluent.

NMR data was as follows:

$^1$H-nmr (DMSO-d$_6$): δ=8.31 (m, 1H), 8.08 (m, 1H), 7.09 (m, 1H), 6.99 (m, 2H), 4.48 (m, 1H), 4.29 (m, 1H), 3.51 (s, 2H), 3.44–3.22 (m, 4H), 1.80 (m, 4H), 1.27 (m, 6H). $C_{18}H_{23}N_3O_3F_2$ (MW=367.40); mass spectroscopy (MH$^+$) 367.

Example 165

Synthesis of N-(S)-sec-Butyl-N'-[N-(3,5-difluorophenylacetyl)-L-alaninyl]-L-alaninamide

Following General Procedure C and using N-[N-(3,5-difluorophenylacetyl)-L-alaninyl]-L-alanine (from Example D7 above) and (S)-(+)-sec-butylamine (Aldrich), the title compound was prepared as a solid. The reaction was monitored by tlc (Rf=0.25 in 9:1 CHCl$_3$/MeOH) and the product was purified by silica gel chromatography using CHCl$_3$/MeOH as the eluent.

NMR data was as follows:

$^1$H-nmr (DMSO-d$_6$): δ=8.38 (m, 1H), 7.92 (m, 1H), 7.30 (m, 1H), 7.18 (m, 1H), 6.99 (m, 2H), 4.20 (m, 4H), 3.62 (m, 1H), 3.52 (s, 2H), 1.34 (m, 2H), 1.20 (m, 6H), 1.01 (m, 3H), 0.81 (t, 3H). Optical Rotation: $[α]_{23}$=−52° (c 1, MeOH). $C_{19}H_{25}N_3O_3F_2$ (MW=369.41); mass spectroscopy (NM$^+$) 370.

Example 166

Synthesis of N-[N-(3,5-Difluorophenylacetyl)-L-alaninyl]-L-valine Methyl Ester

Following General Procedure C and using N-(3,5-difluorophenylacetyl)-L-alanine (from Example B2 above) and L-valine methyl ester hydrochloride (Aldrich), the title compound was prepared as a solid.

NMR data was as follows:

$^1$H-nmr (CDCl$_3$): δ=6.81 (m, 2H), 6.73 (m, 1H), 6.48 (d, 1H), 6.22 (d, 1H), 4.48 (m, 2H), 3.70 (s, 3H), 3.51 (s, 2H), 2.16 (m, 1H), 1.37 (m, 1H), 0.87 (t, 3H). Optical Rotation: $[α]_{23}$=−65° (c 1, MeOH). $C_{17}H_{22}N_2O_4F_2$ (MW=356.37); mass spectroscopy (MH$^+$) 360.

Example 167

Synthesis of N-2-Fluoroethyl-N'-[N-(3,5-difluorophenylacetyl)-L-alaninyl]-L-alaninamide

Following General Procedure C and using N-[N-(3,5-difluorophenylacetyl)-L-alaninyl]-L-alanine (from Example D7 above) and 2-fluoroethylamine hydrochloride (Aldrich), the title compound was prepared as a solid (mp=230–235° C.).

NMR data was as follows:

$^1$H-nmr (DMSO-d$_6$): δ=8.38 (d, 1H), 8.04 (m, 2H), 7.07 (m, 1H), 6.99 (m, 2H), 4.39 (m, 2H), 4.24 (m, 1H), 3.53 (s, 2H), 3.35 (m, 2H), 1.20 (m, 6H). Optical Rotation: [α]$_{23}$=−33° (c 1, MeOH). C$_{16}$H$_{20}$N$_3$O$_3$F$_3$ (MW=359.37); mass spectroscopy (MH$^+$) 359.

Example 168

Synthesis of N-[(S)-6-Methyl-3-oxohept-2-yl]-N'-(3,5-difluorophenylacetyl)-L-alaninamide Following General Procedure M and using N-(3,5-difluorophenylacetyl)-L-alanine (from Example B2 above) and (S)-6-methyl-3-oxohept-2-ylamine hydrochloride (prepared by treating N-BOC-L-alanine N-methoxy-N-methyl amide (Weinreb et al., Tetrahedron Lett., 22, 3815 (1981)) with isopropyl magnesium bromide (Aldrich), followed by removal of the BOC group using General Procedure P), the title compound was prepared as a solid. The product was purified by silica gel chromatography using CHCl$_3$/MeOH as the eluent.

NMR data was as follows:

$^1$H-nmr (CDCl$_3$): δ=6.84 (m, 2H), 6.69 (m, 1H), 6.31 (m, 1H), 4.50 (m, 2H), 3.51 (s, 2H), 2.48 (m, 2H), 1.47 (m, 2H), 1.32 (m, 7H), 0.90 (d, 6H). Optical Rotation: [α]$_{23}$=−42° (c 1, MeOH). C$_{19}$H$_{26}$N$_2$O$_3$F$_2$ (MW=368); mass spectroscopy (MH$^+$) 368.

Example 169

Synthesis of N-4-Nitrobenzyl-N'-[N-(3,5-difluorophenylacetyl)-L-alaninyl]-(S)-2-aminobutyramide Following General Procedure C and using N-[N-(3,5-difluorophenylacetyl)-L-alaninyl]-(S)-2-aminobutyric acid (prepared from methyl N-[N-(3,5-difluorophenylacetyl)-L-alaninyl]-(S)-2-aminobutanoate (from Example 160 above) using General Procedure AF) and 4-nitrobenzylamine (Aldrich), the title compound was prepared as a solid. The reaction was monitored by tlc (Rf=0.3 in 95:5 CHCl$_3$/MeOH) and the product was purified by silica gel chromatography using 97:3 CHCl$_3$/MeOH as the eluent.

NMR data was as follows:

$^1$H-nmr (DMSO-d$_6$): δ=8.57 (t, 1H), 8.40 (d, 1H), 8.21 (d, 2H), 8.02 (d, 1H), 7.50 (d, 2H), 7.08 (m, 1H), 6.98 (m, 2H), 4.42 (d, 2H), 4.37 (m, 1H), 4.17 (m, 1H), 3.53 (s, 2H), 1.64 (m, 2H), 1.21 (m, 3H), 0.83 (t, 3H). Optical Rotation: [α]$_{23}$=−42° (c 1, MeOH). C$_{22}$H$_{24}$N$_4$O$_5$F$_2$ (MW=462.45); mass spectroscopy (MH$^+$) 462.

Example 170

Synthesis of N-4-Nitrobenzyl-N'-[N-(3,5-difluorophenylacetyl)-L-alaninyl]-(S)-2-aminopentanamide Following General Procedure C and using N-[N-(3,5-difluorophenylacetyl)-L-alaninyl]-(S)-2-aminopentanoic acid (prepared from methyl N-[N-(3,5-difluorophenylacetyl)-L-alaninyl]-(S)-2-aminopentanoate (from Example 161 above) using General Procedure AF) and 4-nitrobenzylamine (Aldrich), the title compound was prepared as a solid. The reaction was monitored by tlc (Rf=0.3 in 95:5 CHCl$_3$/MeOH) and the product was purified by recrystallization from acetonitrile.

NMR data was as follows:

$^1$H-nmr (DMSO-d$_6$): δ=8.57 (m, 1H), 8.41 (d, 1H), 8.22 (d, 2H), 8.06 (d, 1H), 7.51 (d, 2H), 7.12 (m, 1H), 7.00 (m, 2H), 4.43 (d, 2H), 4.30 (m, 2H), 3.56 (s, 2H), 1.65 (m, 2H), 1.29 (m, 5H), 0.91 (t, 3H). Optical Rotation: [α]$_{23}$=+97° (c 1, MeOH). C$_{23}$H$_{26}$N$_4$O$_5$F$_2$ (MW=4.76.4); mass spectroscopy (MH$^+$) 476.

Example 171

Synthesis of Methyl N-[N-(3,5-Difluorophenylacetyl)-L-alaninyl]-2-amino-2-(3-fluorophenyl)acetate Following General Procedure C and using N-(3,5-difluorophenylacetyl)-L-alanine (from Example B2 above) and methyl 2-amino-2-(3-fluorophenyl)acetate hydrochloride (from Example D12 above), the title compound was prepared as a solid. The reaction was monitored by tlc (Rf=0.2 in 95:5 CHCl$_3$/MeOH) and the product was purified by silica gel chromatography using 95:5 CHCl$_3$/MeOH as the eluent.

NMR data was as follows:

$^1$H-nmr (CDCl$_3$): δ=7.36 (m, 1H), 7.18 (m, 1H), 7.13 (m, 1H), 7.06 (m, 1H), 6.87 (m, 2H), 6.74 (m, 1H), 6.09 (m, 1H), 5.49 (d, 1H), 4.59 (m, 1H), 3.74 (s, 3H), 3.57 (s, 2H), 1.35 (d, 3H), 0.97 (d, 3H). C$_{20}$H$_{19}$N$_2$O$_4$F$_3$ (MW=408.38); mass spectroscopy (MH$^+$) 408.

Example 172

Synthesis of N'-[N-(3,5-Difluorophenylacetyl)-L-alaninyl]-(S)-2-amino-2-(2-thienyl)acetamide Following General Procedure L and using methyl N-[N-(3,5-difluorophenylacetyl)-L-alaninyl]-(S)-2-amino-2-(2-thienyl)acetate (from Example 178 below), the title compound was prepared as a solid (mp=decomposition at 190° C.). The product was purified by preparative LC 2000 chromatography using 8:2 EtOAc/hexanes as the eluent.

NMR data was as follows:

$^1$H-nmr (CDCl$_3$/DMSO-d$_6$): δ=8.9–6.14 (Ar+NH's 10H), 5.43–5.39 (m, 1H), 4.16–4.10 (m, J=7 Hz, 1H), 3.19 (s, 2H), 1.15 (d, J=7.05 Hz, 3H). C$_{17}$H$_{17}$F$_2$N$_3$O$_3$S (MW=381.4); mass spectroscopy (MH$^+$) 381.

Example 173

Synthesis of Methyl N-[N-(3,5-Difluorophenylacetyl)-L-alaninyl]-2-amino-2-(5-chlorobenzothiophen-2-yl)acetate Following General Procedure C and using N-(3,5-difluorophenylacetyl)-L-alanine (from Example B2 above) and methyl 2-amino-2-(5-chlorobenzothiophen-2-yl)acetate (prepared from 5-chlorobenzothiophene-2-acetic acid [CAS No. 23799-65-7] using General Procedure G, followed by amination using a procedure essentially the same as that described in Example D4 above), the title compound was prepared as a solid (mp=189–190° C.). The product was purified by titration using Et2O/hexanes.

NMR data was as follows:

$^1$H-nmr (CDCl$_3$): δ=7.7–7.63 (m, 2H), 7.33–7.17 (m, 2H), 6.89–6.63 (m, 3H), 6.16–6.03 (m, 1H), 5.85 (dd, 1H), 4.7–4.53 (m, 1H), 3.83 (s, 1.5H), 3.8 (s, 1.5H), 3.59 (s, 1H), 3.5 (s, 1H), 1.4 (dt, 3H). C$_{22}$H$_{19}$ClF$_2$N$_2$O$_4$S (MW=481); mass spectroscopy (MH$^+$) 480.

Example 174

Synthesis of Ethyl N-[N-(3,5-Difluorophenylacetyl)-L-alaninyl]-2-amino-2-(benzothiophen-2-yl)acetate Following General Procedure C and using N-(3,5-difluorophenylacetyl)-L-alanine (from Example B2 above)

and ethyl 2-amino-2-(benzothiophen-2-yl)acetate [CAS No. 98800-64-7], the title compound was prepared as a solid (mp=189–190° C.). The product was purified by preparative LC 2000 chromatography using 2:8 EtOAc/hexanes as the eluent.

NMR data was as follows: $^1$H-nmr (CDCl$_3$): δ=7.8–7.75 (m, 2H), 7.34–7.27 (m, 2H), 7.25–7.09 (m, 3H), 6.81–6.76 (m, 1H), 6.76–6.63 (m, 1H), 6.23 (dd, J=7 Hz, 1H), 5.84 (d, J=7.07 Hz, 1H), 4.61–4.59 (m, 1H), 4.33–4.2 (m, 2H), 3.54 (s, 1H), 3.50 (s, 1H), 1.70 (d, J=11.9 Hz, 1.5H), 1.38 (d, J=1.19 Hz, 1.5H), 1.36–1.23 (dt, 3H). $C_{23}H_{22}N_2O_4SF_2$ (MW=460.49); mass spectroscopy (MH$^+$) 460.

Example 175

Synthesis of Methyl N-[N-(3,5-Difluorophenylacetyl)-L-alaninyl]-2-amino-2-(benzothiophen-3-yl)acetate Following General Procedure C and using N-(3,5-difluorophenylacetyl)-L-alanine (from Example B2 above) and methyl 2-amino-2-(benzothiophen-3-yl)acetate (prepared from 2-amino-2-(benzothiophen-3-yl)acetic acid [CAS 95834-94-9] using General Procedure H), the title compound was prepared as a solid (mp=185–186° C.).

NMR data was as follows: $^1$H-nmr (CDCl$_3$): δ=7.86 (m, 2H), 7.4–7.3 (m, 3H), 7.4–7.2 (m, 2H), 6.9–6.6 (m, 3H), 6.3–6.13 (m, 1H), 5.95–5.85 (m, 1H), 4.55–4.5 (m, 1H), 3.75 (s, 1.5H), 3.65 (s, 1.5H), 3.55 (s, 1H), 3.35 (s, 1H), 1.4 (d, 1.5H), 1.3 (d, 1.5H). $C_{22}H_{20}N_2O_4F_2S$ (MW=446); mass spectroscopy (MH$^+$) 446.

Example 176

Synthesis of Methyl N-[N-(3,5-Difluorophenylacetyl)-L-alaninyl]-2-amino-2-(2-thienyl)acetate Following General Procedure C and using N-(3,5-difluorophenylacetyl)-L-alanine (from Example B2 above) and methyl 2-amino-2-(2-thienyl)acetate (prepared from L-α-2-thienylglycine (Sigma) using General Procedure G), the title compound was prepared as a solid (mp=161–162° C.). The product was purified by preparative LC 2000 chromatography using 1:4 EtOAc/hexanes.

NMR data was as follows:
$^1$H-nmr (CDCl$_3$): δ=7.3–6.65 (Ar, 7H), 6.25 (bt, 1H), 5.8 (dd, 1H), 4.68–4.5 (m, 1H), 3.85 (s, 1H), 3.75 (s, 1H), 3.52 (s, 1H), 3.5 (s, 1H), 1.35 (overlaying d, 3H). $C_{18}H_{18}N_2O_4F_2S$ (MW=396); mass spectroscopy (MH$^+$) 396.1.

Example 177

Synthesis of Ethyl N-[N-(3,5-Difluorophenylacetyl)-L-alaninyl]-2-amino-2-(benzothiophen-5-yl)acetate Following General Procedure C and using N-(3,5-difluorophenylacetyl)-L-alanine (from Example B2 above) and ethyl 2-amino-2-(benzothiophen-5-yl)acetate (prepared as described in S. Kukolja et al., *J Med. Chem.*, 1985, 28, 1896–1903), the title compound was prepared as a solid (mp=126.5–127.5° C.). The product was purified by preparative LC 2000 chromatography using 1:1 hexanes/EtOAc as the eluent.

NMR data was as follows:
$^1$H-nmr (CDCl$_3$): δ=8.1 (s, 1H), 8.05 (s, 1H), 7.6–7.5 (m, 2H), 7.4–7.25 (m, 3H), 7.15 (bd, J=12 Hz, 5H), 7.05 (bd, J=12 Hz, 5H), 6.89–6.675 (m, 2H), 6.225 (bd, J=12 Hz, 5H), 6.075 (bd, J=12 Hz, 5H), 4.55 (q, J=7.5 Hz, 1H), 4.2 (dq, 2H), 3.575 (s, 1H), 3.242 (s, 1H), 1.4 (d, J=7.05 Hz, 1.5H), 1.15 (d, J=7.05 Hz, 1.5H). $C_{23}H_{22}N_2O_4F_2S$ (MW=460); mass spectroscopy (MH$^+$) 460.1.

Example 178

Synthesis of Methyl N-[N-(3,5-Difluorophenylacetyl)-L-alaninyl]-(S)-2-amino-2-(2-thienyl)acetate Following General Procedure G and using N-[N-(3,5-difluorophenylacetyl)-L-alaninyl]-(S)-2-amino-2-(2-thienyl)acetic acid (from Example 180 below), the title compound was prepared as a solid (mp=180–181° C.). The product was purified by preparative LC 2000 chromatography using 6:4 EtOAc/hexanes as the eluent.

NMR data was as follows:
$^1$H-nmr (CDCl$_3$): δ=7.3–6.6 (Ar+NH, 7H), 6.37 (bd, J=7 Hz, 1H), 5.77 (d, J=7 Hz, 1H), 4.6–4.56 (m, J=7 Hz, 1H), 3.7 (s, 3H), 3.4 (s, 2H), 1.38 (d, J=7 Hz, 3H). $C_{18}H_{18}N_2O_4SF_2$ (MW=396); mass spectroscopy (MH$^+$) 396.1.

Example 179

Synthesis of tert-Butyl N-[N-(3,5-Difluorophenylacetyl)-L-alaninyl]-(S)-2-amino-2-(2-thienyl)acetate Following General Procedure J and using N-[N-(3,5-difluorophenylacetyl)-L-alaninyl]-(S)-2-amino-2-(2-thienyl)acetic acid (from Example 180 below), the title compound was prepared as a solid (mp=117–118° C.). The product was purified by tituraration using ether/hexanes.

NMR data was as follows:
$^1$H-nmr (CDCl$_3$): δ=7.24 (d, J=6.5 Hz, 1H), 7.05–6.63 (m, 6H), 6.19 (bd, J=7.2 Hz, 1H), 5.66 (d, J=7.5 Hz, 1H), 4.6–4.5 (m, 1H), 3.5 (s, 2H), 1.44 (s, 9H), 1.38 (d, J=7.1 Hz, 3H). $C_{21}H_{24}N_2O_4SF_2$ (MW=438.5); mass spectroscopy (MH$^+$) 438.

Example 180

Synthesis of N-[N-(3,5-Difluorophenylacetyl)-L-alaninyl]-(S)-2-amino-2-(2-thienyl)acetic Acid Following General Procedure M and using N-(3,5-difluorophenylacetyl)-L-alanine (from Example B2 above) and L-α-2-thienylglycine (Sigma), the title compound was prepared as a solid. The product was purified by tituration using EtOAc/hexanes.

NMR data was as follows:
$^1$H-nmr (DMSO-d$_6$): δ=8.73 (d, J=7 Hz, 1H), 8.38 (d, J=7 Hz, 1H), 7.56–7.4 (m, 1H), 7.2–6.9 (m, 4H), 5.54 (d, J=8 Hz, 1H), 4.5–4.3 (m, 1H), 3.33 (s, 2H), 1.23 (d, J=7 Hz, 3H). $C_{17}H_{16}N_2O_4SF_2$ (MW=382); mass spectroscopy (MH$^+$) 382.

Example 181

Synthesis of Methyl N-[N-(3,5-Difluorophenylacetyl)-L-alaninyl]-2-amino-2-(1H-tetrazol-5-yl)acetate Following General Procedure C and using N-(3,5-difluorophenylacetyl)-L-alanine (from Example B2 above) and methyl 2-amino-2-(1H-tetrazol-5-yl)acetate (prepared from ethyl 1H-tetrazole-5-acetate [CAS 173367-99-2] using procedures essentially the same as those described in S. Kukolja, *J. Med. Chem.*, 1985, 28, 1886–1896), the title compound was prepared as a solid. The reaction was product was purified by tituration using EtOAc/hexanes.

NMR data was as follows:

$^1$H-nmr (DMSO-d$_6$): δ=9.13 (d, J=7.6 Hz, 1H), 8.39 (t, J=7 Hz, 1H), 7.1–6.95 (m, 3H), 5.9 (dd, 1H), 4.4–4.3 (m, 1H), 4.14 (q, J=7 Hz, 2H), 3.5 (s, 3H), 1.27–1.11 (m, 6H). $C_{16}H_{18}N_6O_4F_2$ (MW=396.3); mass spectroscopy (MH$^+$) 396.3.

Example 182

Synthesis of Methyl N-[N-(3,5-Difluorophenylacetyl)-L-alaninyl]-(S)-2-amino-2-(6-methoxy-2-naphthyl)acetate Following General Procedure C and using N-(3,5-difluorophenylacetyl)-L-alanine (from Example B2 above) and methyl (S)-2-amino-2-(6-methoxy-2-naphthyl)acetate (from Example D3 above), the title compound was prepared as a solid (mp=177–178° C.). The product was purified by tituration using hexanes/EtOAc.

NMR data was as follows:

$^1$H-nmr (DMSO-d$_6$): δ=8.84 (d, J=9 Hz, 1H), 8.4 (d, J=9 Hz, 1H), 7.90–7.76 (m, 2H), 7.247–6.90 (m, 5H), 5.5 (J=7 Hz, 1H), 4.243 (d, J=3.5 Hz, 1H), 3.86 (s, 3H), 3.6 (s, 3H), 3.29 (s, 2H), 1.26 (d, J=7.5 Hz, 3H). $C_{25}H_{24}N_2O_5F_2$ (MW=470.48); mass spectroscopy (MH$^+$) 470.

Example 183

Synthesis of Methyl N-[N-(3,5-Difluorophenylacetyl)-L-alaninyl]-2-amino-2-(3-trifluoromethylphenyl)acetate Following General Procedure C and using N-(3,5-difluorophenylacetyl)-L-alanine (from Example B2 above) and methyl 2-amino-2-(3-trifluoromethylphenyl)acetate (prepared from 2-(hydroxyimino)-2-(3-trifluoromethylphenyl)acetic acid [CAS 179811-81-5] using General Procedures G and R above), the title compound was prepared as a solid (mp=133–134° C.). The product was purified by tituration from EtOAc/hexanes.

NMR data was as follows:

$^1$H-nmr (CDCl$_3$): δ=7.57–7.37 (m, 4H), 6.8–6.6 (m, 3H), 6.05 (BA, 1H), 5.5 (A, J=7.5 Hz, 1H), 3.7 (s, 1.5H), 3.675 (s, 1.5H), 3.5 (s, 1H), 3.45 (s, 1H), 1.33 (d, J=7.5 Hz, 1.5H), 1.275 (d, J=7.5 Hz, 1.5H). $C_{21}H_{19}N_2O_4F_5$ (MW=458.39); mass spectroscopy (MH$^+$) 459.

Example 184

Synthesis of Methyl N-[N-(3,5-Difluorophenylacetyl)-L-alaninyl]-2-amino-2-(4,5,6,7-tetrahydrobenzothiophen-2-yl)acetate Following General Procedure C and using N-(3,5-difluorophenylacetyl)-L-alanine (from Example B2 above) and methyl 2-amino-2-(4,5,6,7-tetrahydrobenzothiophen-2-yl)acetate (prepared from N-Boc-2-amino-2-(4,5,6,7-tetrahydrobenzothiophen-2-yl)acetic acid [CAS 95361-97-0] using General Procedures G above and the Boc removal procedure described in Example D3 above), the title compound was prepared as a solid. The product was purified by tituration using Et$_2$O/hexanes.

NMR data was as follows:

$^1$H-nmr (CDCl$_3$): δ=7.05 (d, J=5 Hz, 1H), 7.02 (d, J=5 Hz, 1H), 6.82–6.66 (m, 3H), 6.31 (bd, J=8 Hz, 1H), 5.66 (dd, J=7.2 Hz, 1H), 4.63–4.55 (m, 1H), 3.76 (s, 1.5H), 3.75 (s, 1.5H), 3.52 (s, 1H), 3.50 (s, 1H), 2.67–2.65 (m, 2H), 2.54–2.52 (m, 2H), 1.77–1.7 (m, 4H), 1.36 (dd, J=7 Hz, 3H). $C_{22}H_{24}N_2O_4F_2S$ (MW=450); mass spectroscopy (MH$^+$) 450.

Example 185

Synthesis of Methyl N-[N-(3,5-Difluorophenylacetyl)-L-alaninyl]-2-amino-2-(thieno[2,3-b]thiophen-2-yl)acetate Following General Procedure C and using N-(3,5-difluorophenylacetyl)-L-alanine (from Example B2 above) and methyl 2-amino-2-(thieno[2,3-b]thiophen-2-yl)acetate (from Example D4 above), the title compound was prepared as a solid. The product was purified by tituration from Et$_2$O/hexanes.

NMR data was as follows:

$^1$H-nmr (CDCl$_3$): δ=7.35 (d, J=7.5 Hz, 1H), 7.2–7.0 (m, 3H), 6.9–6.69 (m, 3H), 6.13–6.0 (m, 1H), 5.8 (dd, 1H), 4.63–4.5 (m, 1H), 3.8 (s, 3H), 3.58 (s, 1H), 3.469 (1H), 1.4 (dd, 3H). $C_{20}H_{18}N_2O_4F_2S_2$ (MW=452); mass spectroscopy (MH$^+$) 452.

Example 186

Synthesis of Methyl N-[N-(3,5-Difluorophenylacetyl)-L-alaninyl]-2-amino-2-(2-methylthiazol-4-yl)acetate Following General Procedure C and using N-(3,5-difluorophenylacetyl)-L-alanine (from Example B2 above) and methyl 2-amino-2-(2-methylthiazol-4-yl)acetate (prepared from N-Boc-2-amino-2-(2-methylthiazol-4-yl) acetic acid [CAS 105381-90-6] using General Procedure H above), the title compound was prepared as a solid. The product was purified by tituration using Et$_2$O/hexanes.

NMR data was as follows:

$^1$H-nmr (CDCl$_3$): δ=7.2–6.66 (pr+NH, 5H), 5.69–5.6 (m, 1H), 4.8–4.69 (m, 1H), 3.76 (s, 3H), 3.56 (s, 1H), 3.5 (s, 1H), 2.69 (s, 3H), 1.4 (d, J=14 Hz, 1.5H), 1.35 (s, J=14 Hz, 1.5H). $C_{18}H_{19}N_3O_4F_2S$ (MW=411); mass spectroscopy (MH$^+$) 411.

Example 187

Synthesis of Methyl (3S,4S)-N-[N-(3,5-Difluorophenylacetyl)-L-alaninyl]-4-amino-3-hydroxy-5-phenylpentanoate Following General Procedure C and using N-(3,5-difluorophenylacetyl)-L-alanine (from Example B2 above) and methyl (3S,4S)-4-amino-3-hydroxy-5-phenylpentanoate (Novabiochem), the title compound was prepared as a solid. The reaction was monitored by tlc (Rf=0.2 in 95:5 CHCl$_3$/MeOH) and the product was purified by flash column chromatography using 95:5 CHCl$_3$/MeOH as the eluent.

NMR data was as follows:

$^1$H-nmr (CDCl$_3$): δ=8.29 (d, 1H), 7.65 (d, 1H), 7.40–7.20 (m, 5H), 7.10 (m, 1H), 6.99 (m, 2H), 5.27 (d, 1H), 4.47 (bs, 2H), 4.09 (m, 2H), 3.57 and 3.51 (m, 3H), 2.72 (m, 2H), 2.31 (m, 2H), 1.19 (m, 2H). Optical Rotation: [α]$_{23}$=−66° (c 1, MeOH). $C_{23}H_{26}N_2O_5F_2$ (MW=448); mass spectroscopy (MH$^+$) 449.

Example 188

Synthesis of Methyl N-[N-(3,5-Difluorophenylacetyl)-L-alaninyl]-(S)-2-aminohex-4-enoate Step A—Synthesis of (S)-3-(Hex-4-enoyl)-4-(phenylmethyl)-2-oxazolidinone To a mechanically stirred solution of 9.50 g (83.2 mmol, 1.10 equiv.) of 4-hexenoic acid (commericially available from Lancaster, Catalog #252-427-6) and 13.9 mL (10.1 g, 99.7 mmol, 1.33 equiv.) of triethylamine in 150 mL of dry THF, cooled to −78° C. under dry N$_2$, was added 10.71 mL (10.49 g, 87.0 mmol, 1.15 equiv.) of pivaloyl chloride (Aldrich). The mixture was warmed to 0° C. for 60 min, and then recooled to −78° C. A solution of 13.4 g (75.6 mmol, 1.00 equiv) of (S)-(−)-(phenylmethyl)-2-oxazolidone (Aldrich) and 22 mg of triphenylmethane (indicator) in 150 mL of dry THF, stirred at −30° C. to −45° C. under N$_2$, was treated dropwise with n-butyllithium (~2.5 M in hexanes) (Aldrich) until an orange color persisted (~30 mL required). The resulting solution was cooled to −78° C. and then added, via rapid cannulation, to the above stirred mixture containing the mixed anhydride. The residual lithiated oxazolidone was rinsed in with two 10-mL portions of dry THF and the resulting mixture was stirred at −78° C. for 1.5 h, and then at 0° C. for 1 h. The mixture was partitioned between CH$_2$Cl$_2$ and pH 7 phosphate buffer. The CH$_2$Cl$_2$ phase was washed with saturated aqueous NaHCO$_3$ followed by half-saturated aqueous NaCl, dried (MgSO$_4$), and evaporated in vacuo. The residual cream-colored solid (22.4 g) was chromatographed (Waters Prep 2000, 5.0 cm×25 cm 10µ Kromasil KR60-10SIL-5025 column) in two batches eluting with 85:15 hexanes/EtOAc. The chromatographed product was recrystallized from hexane to yield 14.34 g (first crop, 69%) of the title compound as fine white needles. $^1$H NMR (300 MHz, CDCl$_3$) δ 7.37–7.20 (m, 5H, —C$_6$H$_5$), 5.60–5.43 (m, 2H, CH=CHCH$_3$), 4.71–4.63 (m, 1H, NCH(Ph)CH$_2$O), 4.23–4.14 (m, 2H, NCH(Ph)CH$_2$O), 3.295(dd, J=13.3, 3.3 Hz, 1H, CHHC$_6$H$_5$), 3.11–2.90 (m, 2H, CH$_2$C=O), 2.758 (dd, J=13.3, 9.6 Hz, 1H, CHHC$_6$H$_5$), 2.42–2.34 (m, 2H, CH=CHCH$_2$), 1.67–1.65 (m, 2H, CH=CHCH$_3$).

Step B—Synthesis of (4S)-3-[(S)-2-Azidohex-4-enoyl]-4-(phenylmethyl)-2-oxazolidinone A solution of 5.47 g (20.0 mmol, 1.00 equiv) of the product from Step A above in 60 mL of dry THF, stirred at −78° C. under dry N$_2$, was added via rapid cannulation to a stirred, cooled (−78° C.) solution of 43.6 mL (22.0 mmol, 1.10 equiv) of potassium hexamethyldisilazide (0.505 M in toluene) (Aldrich) and 60 mL of dry TIF. The residual imide solution was rinsed in with two 5-mL portions of dry THF. The resulting solution was stirred at −78° C. for 30 min. To the above solution of the K-enolate, stirred at −78° C. under dry N$_2$, was added a cooled (−78° C.) solution of 7.43 g (24.0 mmol, 1.2 equiv) of trisylazide (prepared as described in R. E. Harmon et al., *J. Org. Chem.*, 1973, 38, 11–16) in 60 mL of dry THF via rapid cannulation. (Note the reaction exothermed to −68° C. during the addition). After 1–2 min, 4.24 mL (4.45 g, 74.1 mmol, 3.7 equiv) of glacial acetic acid was added in one portion. The resulting mixture was stirred at −78° C. for 15 min, and was then allowed to warm to 25° C. on stirring overnight. The mixture was partitioned between CH$_2$Cl$_2$ and pH 7 phosphate buffer. The aqueous phase was extracted with CH$_2$Cl$_2$ (3×) and the organic extracts were combined, washed with dilute aqueous NaHCO$_3$, dried (MgSO$_4$), and evaporated in vacuo. The residual oil (9.55 g) was chromatographed (Waters Prep 2000, 5.0 cm×25 cm 10µ Kromasil KR60-10SIL-5025 column) eluting with a 3 L linear gradient from 30:70 to 80:20 CH$_2$Cl$_2$/hexanes. After rechromatographing the mixed fractions (2×), a total of 5.27 g (84% yield) of the title compound (faster eluting, major diastereomer) was isolated as a colorless, viscous oil. $^1$H NMR (300 MHz; CDCl$_3$) δ 7.38–7.20 (m, 5H, —C$_6$H$_5$), 5.73–5.62 (m, 1H, CH=CHCH$_3$), 5.52–5.41 (m, 1H, CHH=CHCH$_3$), 5.011 (dd, J=8.3, 5.5 Hz, 1H, CH(N$_3$) C=O), 4.71–4.63 (m, 1H, NCH(Ph)CH$_2$O), 4.236 (d, J=5.1 Hz, 2H, NCH(Ph)CH$_2$O), 3.338 (dd, J=13.4, 3.3 Hz, 1H, CHHC$_6$H$_5$), 2.827 (dd, J=13.4, 9.5 Hz, 1H, CHHC$_6$H$_5$), 2.64–2.46 (m, 2H, CH$_2$CH=CHCH$_3$), 1.694 (dd, J=6.4, 1.1 Hz, 3H, CH=CHH$_3$).

Step C—Synthesis of (S)-2-Azidohex-4-enoic Acid

A solution of 5.00 g (15.91 mmol) of the product from Step B above in 240 mL of THF and 80 mL of deionized water, stirred at 0° C. under N$_2$, was treated with 762 mg (31.8 mmol, 2.00 equiv) of LiOH (anhydrous powder). After stirring at 0° C. for 30 min, 100 mL of 0.5 N aqueous NaHCO$_3$ was added and the THF was removed by rotary evaporation in vacuo. The residue was diluted to 400–500 mL with H$_2$O and extracted with 5 portions of CH$_2$Cl$_2$. The aqueous phase was acidified to pH 1–2 by the cautious addition of 5 N HCl, and then was extracted with 4 portions of EtOAc. The EtOAc extracts were combined, dried (Na$_2$SO$_4$), and evaporated in vacuo to yield 2.45 g (99%) of the title compound as a light amber oil. $^1$H NMR (300 MHz, CDCl$_3$) δ 11.38 (br s, 1H, CO$_2$H), 5.73–5.62 (m, 1H, CH$_3$CH=CH), 5.48–5.38 (m, 1H, CH=CHCH$_2$), 3.928 (dd, J=7.8, 5.4 Hz, 1H, CH(N$_3$)CO$_2$H), 2.66–2.47 (m, 2H, CH=CHCH$_2$), 1.703 (dd, J=6.4, 1.1 Hz, 3H, CH$_3$).

Step D—Methyl N-[N-tert-Butoxycarbonyl-L-alaninyl]-(S)-2-aminohex-4-enoate A solution of 504.7 mg (3.25 mmol) of the product from Step C above in diethyl ether, cooled to 0° C, was treated dropwise with ethereal diazomethane (prepared as described in L. F. Fieser et al., "Reagents for Organic Synthesis", Vol. 1, p. 191, Wiley & Sons (1967)) until a yellow color persisted. The excess diazomethane was removed by entraining with N$_2$, and the ether was evaporated under a stream of N$_2$. The residual oil was dissolved in 10 mL of anhydrous methanol. The solution was cooled to 0° C. under dry N$_2$ and 1.24 g (6.54 mmol, 2.0 equiv) of anhydrous SnCl$_2$ was added. The mixture was stirred at ≦25° C. for 4 h, and the solvent was evaporated in vacuo to afford a solid tin-amine complex.

A solution of 1.23 g (6.50 mmol, 2.00 equiv.) of N-Boc-L-alanine (Sigma) and 0.715 mL (0.658 g, 6.50 mmol, 2.0 equiv.) of 4-methylmorpholine (redistilled, 99.5%) (Aldrich) in 15 mL of anhydrous THF, cooled to −15 to −20° C. under dry N$_2$, was treated dropwise with 0.861 mL (0.907 g, 6.50 mmol, 2.00 equiv.) of iso-butyl chloroformate (Aldrich). After stirring at −15 to −20° C. for 20 min, the resulting mixture containing the mixed anhydride was added via cannulation to the solid tin-amine complex (vide supra). The residual mixed anhydride was rinsed in with 7 mL of THF and 1.1 g (13.1 mmol, 4.0 equiv.) of NaHCO$_3$ powder and 5 mL of H$_2$O was added. The mixture was stirred at 0° C. for 5 h. An additional 1.1 g (13.1 mmol, 4.0 equiv.) of NaHCO$_3$ powder and 5 mL of H$_2$O was added and the mixture was stirred at 20° C. for 1.5 h. The mixture was filtered to remove the gelatinous precipitate, and the filter cake was washed with several portions of EtOAc. The filtrate was washed with saturated aqueous NaHCO$_3$ (the aqueous phase was back-extracted with 3 portion of EtOAc), followed by pH 4–5 phosphate buffer (the aqueous phase was back-extracted with 3 portions of EtOAc). The organic phase was dried (Na$_2$SO$_4$) and evaporated in vacuo. The residual straw colored oil (1.21 g) was chromatographed (Waters Prep 2000, 5.0 cm×25 cm 10µ Kromasil KR60-10SIL-5025 column) eluting with a 3 L linear gradient from 80:20 to 40:60 hexane/EtOAc to yield 0.9088 g (89%) of the title compound as a white solid. Tlc R$_f$ 0.25 [silica, hexane/EtOAc 6:4)]; $^1$H NMR (300 MHz, CDCl$_3$) δ 6.61 (d, J=7.6

Hz, 1H, NH), 5.60–5.48 (m, 1H, CH=C<u>H</u>CH₃), 5.33–5.23 (m, 1H, C<u>H</u>=CHCH₃), 5.08 (d, J=7.3 Hz, 1H, NH), 4.591 (dt, J$_d$=7.8 Hz, J$_t$=5.7 Hz, 1H, HNC<u>H</u>(CH₂CH=CHCH₃)), 4.19 (br m, 1H, HNC<u>H</u>(CH₃), 3.74 (s, 3H, OCH₃), 2.56–2.39 (sym m, 2H, C<u>H</u>₂CH=CHCH₃), 1,658 (dd, J=6.4, 1.2 Hz, 3H, CH₂CH=CHC<u>H</u>₃), 1.454 (s, 9H, OC(CH₃)₃), 1.358 (d, J=7.1 Hz, 3H, HNC<u>H</u>(CH₃)).

Step E—Synthesis of Methyl N-[N-(3,5-Difluorophenylacetyl)-L-alaninyl]-(S)-2-aminohex-4-enoate A solution of 0.811 g (2.58 mmol) of the product from Step D above in 5 mL of CH₂Cl₂ was cooled to 0° C. under dry N₂ and 5 mL of trifluoroacetic acid was introduced by syringe at ≦4° C. The solution was stirred at 0° C. for 40 min. Toluene (15 mL) was added and the mixture was evaporated in vacuo on the rotary evaporator. The addition of toluene and solvent evaporation was repeated. The residue was dissolved in 20 mL of CH₂Cl₂ and the solution was cooled to 0° C. under dry N₂. To this was added 1.35 mL (1.00 g, 7.74 mmol, 3.0 equiv) of ethyldiisopropylamine (Aldrich), followed by the dropwise addition at ≦6° C. of 0.728 mL (0.938 g, 5.16 mmol, 2.0 equiv) of 3,5-difluorophenylacetyl chloride (prepared from 3,5-difluorophenylacetic acid (Aldrich) using General Procedure H'). The resulting solution was stirred at 0° C. for 2 h. Excess saturated aqueous NaHCO₃ was added and the two phase mixture was stirred in an ice bath for 30 min. The mixture was diluted with CH₂Cl₂ and washed successively with aqueous NaHCO₃/Na₂CO₃ (pH 10), 1 N aqueous NaHSO₄, and saturated aqueous NaCl. The CH₂Cl₂ solution was dried (Na₂SO₄) and evaporated in vacuo to afford 1.17 g of a yellow solid. This was recrystallized from EtOAc to yield 602 mg (63%) of the title compound as a fluffy white solid. This material was found by 300 mHz $^1$H NMR analysis to consist of a 92:8 mixture of E and Z isomers, respectively.

NMR data was as follows:

$^1$H-nmr (300 MHz, CDCl₃): δ=6.85–6.69 (m, 3H), 6.335 (br d, J=7.8 Hz, 1H), 6.289 (br d, J=7.0 Hz, 1H), 5.58–5.47 (m, 1H), 5.28–5.18 (m, 1H), 4.58–4.45 (m, 2H) 3.745 (s, 3H), 3.528 (s, 2H), 2.457 (apparent t, J=6.4 Hz, 2H), 1.650 (dd, J=6.5, 1.3 Hz, 3H), 1.58 (dm, J=6.5 Hz, 0.08H), 1.375 (d, J=7.0 Hz, 3H). IR (CHCl₃) 3421, 1742, 1667, 1626, 1597, 1503, and 1120 cm, Anal. Calcd for C₁₈H₂₂F₂N₂O₄: C, 58.69; H, 6.02; N, 7.60. Found: C, 58.83, H, 5.89; N, 7.67. C₁₈H₂₂F₂N₂O₅ (MW=368); mass spectroscopy (MH⁺) 368.

Example 189

Synthesis of N-[N-(Cyclopropylacetyl)-L-alaninyl]-L-phenylglycine tert-Butyl Ester Following General Procedure U and using cyclopropylacetic acid (Lancaster) and N-(L-alaninyl)-L-phenylglycine tert-butyl ester (General Procedure U of Z-alanine (Bachem) to phenylglycine-t-butyl (Novabio) and then General Procedure O), the title compound was prepared as a solid (mp=105–107° C.). The reaction was monitored by tlc (Rf=0.33 in 1:1 EtOAc/hexane, 0.13 in 5% MeOH/DCM).

NMR data was as follows:

$^1$H-nmr (CDCl₃): δ=0.15 (m, 2H), 0.56 (m, 2H), 0.91 (m, 1H), 1.38 (m, 12H), 2.09 (d, J=7.1 Hz, 2H), 4.62 (m, 1H), 5.39 (d, J=7.2 Hz, 1H), 6.52 (d, J=7.2 Hz, 1H), 7.31 (m, 6H). $^{13}$C-nmr (CDCl₃): δ=4.53, 4.55, 6.9, 18.4, 27.8, 41.2, 48.4, 57.1, 82.6, 127.0, 128.2, 128.7, 136.8, 169.4, 171.4, 172.3. C₂₀H₂₈N₂O₄ (MW=360.46); mass spectroscopy (MH⁺) 361.

Example 190

Synthesis of N-tert-Butyl-N'-[N-(3,5-Difluorophenylacetyl)-L-alaninyl]-(S)-2-amino-2-(4-phenylphenyl)acetamide Following General Procedure AB and using tert-butylisocyanide (Aldrich) and 4-biphenylcarboxaldehyde (Aldrich), the title compound was prepared as a solid (mp=266–267° C.). The product was purified by recrystallization from EtOAc and/or EtOAc/hexanes.

NMR data was as follows:

$^1$H-nmr (DMSO-d₆): δ=8.42 (d, 1H, J=7 Hz), 8.31 (d, 1H, J=7 Hz), 7.91 (s, 1H), 7.6–7.56 (m, 4H), 7.42–7.59 (m, 5H), 7.2–7.69 (m, 3H), 5.42 (d, 1H, J=8 Hz), 4.42 (pentet, 1H, J=8 Hz), 3.5 (s, 1H), 1.2 (doublet on top of a singlet, 12H). C₂₉H₃₁N₃O₃F₂ (MW=508); mass spectroscopy (MH⁺) 508.4.

Example 191

Synthesis of N-[N-(3,5-Difluorophenylacetyl)-(S)-2-aminobutanoyl]-L-phenylglycine tert-Butyl Ester Following General Procedure D and using 3,5-difluorophenylacetic acid (Aldrich) and N-[(S)-2-aminobutanoyl]-L-phenylglycine tert-butyl ester (from Example D13 above), the title compound was prepared as a solid (mp=138.7–140.0° C.). The reaction was monitored by tlc (Rf=0.24 in 2/1 hexanes:EtOAc) and the product was purified by flash chromromatography and HPLC.

NMR data was as follows:

$^1$H-nmr (DMSO-d₆, 250 MHz): δ=8.66 (d, J=6.75 Hz, 1H), 8.30 (d, J=8.26 Hz, 1H), 7.37 (bs, 5H), 7.11–6.96 (m, 3H), 5.23 (d, J=7.00 Hz, 1H), 4.36 (td, J=7.88, 5.50 Hz, 1H), 3.53 (AB$_q$, J$_{AB}$=14.05 Hz, Δv$_{AB}$=7.75 Hz, 2H), 1.85–1.48 (m, 2H), 1.34 (s, 9H), 0.88 (t, J=7.38 Hz, 3H). Optical Rotation: [α]₂₀=21.8° (c 1.0, MeOH). C₂₄H₂₈N₂O₄F₂ (MW 446.50); mass spectroscopy (MH⁺, minus CO₂-tBu) 345.2.

Example 192

Synthesis of N-[N-(3,5-Difluorophenylacetyl)-L-valinyl]-L-phenylglycine tert-Butyl Ester Following General Procedure D and using 3,5-difluorophenylacetic acid (Aldrich) and N-(L-valinyl)-L-phenylglycine tert-butyl ester (from Example D14 above), the title compound was prepared as a solid (mp=170.5–171.8° C.). The reaction was monitored by tlc (Rf=0.39 in 2:1 hexanes/EtOAc) and the product was purified by flash chromromatography and HPLC.

NMR data was as follows:

$^1$H-nmr (DMSO-d₆, 250 MHz): δ=8.71 (d, J=6.75 Hz, 1H), 8.22 (d, J=9.26 Hz, 1H), 7.37 (bs, 5H), 7.11–6.96 (m, 3H), 5.23 (d, J=6.50 Hz, 1H), 4.36 (dd, J=8.88, 6.38 Hz, 1H), 3.55 (AB$_q$, J$_{AB}$=13.88 Hz, Δv$_{AB}$=21.56 Hz, 2H), 2.10–1.95 (m, 1H), 1.34 (s, 9H), 0.88 (d, J=6.75 Hz, 3H), 0.86 (d, J=6.50 Hz, 3H). Optical Rotation: [α]₂₀=20.8° (c 1.0, MeOH). C₂₅H₃₀N₂O₄F₂ (MW=460.53); mass spectroscopy (MH⁺, minus CO₂-tBu) 359.2.

Example 193

Synthesis of N-[N-(3,5-Difluorophenylacetyl)-L-methioninyl]-L-phenylglycine Methyl Ester Following General Procedure E and using 3,5-difluorophenylacetic acid (Aldrich) and N-(L-methioninyl)-L-phenylglycine methyl ester hydrochloride (prepared from N-BOC-L-methionine (Sigma) and L-phenylglycine methyl ester hydrochloride (Aldrich) using General Procedure E, followed by removal of the BOC-group using General Procedure P), the title compound was prepared as a solid (mp=189.3° C.). The reaction was monitored by tlc (Rf=0.53 in 5:95 MeOH/CH₂Cl₂) and the product was purified by recrystallization from ethyl acetate/hexanes.

NMR data was as follows:

$^1$H-nmr (DMSO-d$_6$): δ=8.85 (d, J=6.7 Hz, 1H), 8.41 (d, J=8.1 Hz, 1H), 7.38 (m, 5H), 7.09 (m, 1H), 6.98 (m, 2H), 5.38 (d, J=6.6 Hz, 1H), 4.47 (m, J=8.2 Hz, 1H), 3.62 (s, 3H), 3.51 (d, 2H), 2.46 (t, 2H), 2.04 (s, 3H), 1.89 (m, 2H). $^{13}$C-nmr (DMSO-d$_6$): δ=172.036, 171.729, 169.883, 164.658, 164.479, 161.406, 161.227, 141.689, 141.557, 141.427, 136.524, 129.512, 129.213, 128.717, 126.274, 113.187, 113.085, 112.961, 112.862, 103.023, 102.684, 102.340, 93.065, 57.205, 53.063, 42.231, 33.075, 30.221, 15.465. $C_{22}H_{24}N_2O_4F_2S$ (MW=450.51); mass spectroscopy (MH$^+$) 450.

Example 194

Synthesis of N-[N-(3,5-Difluorophenylacetyl)-L-valinyl]-L-phenylglycine Methyl Ester Following General Procedure E and using 3,5-difluorophenylacetic acid (Aldrich) and N-(L-valinyl)-L-phenylglycine methyl ester hydrochloride (prepared from N-BOC-L-valine (Sigma) and L-phenylglycine methyl ester hydrochloride (Aldrich) using General Procedure E, followed by removal of the BOC-group using General Procedure P), the title compound was prepared as a solid (mp=226.5° C.). The reaction was monitored by tlc (Rf=0.49 in 5:95 MeOH/CH$_2$Cl$_2$) and the product was purified by flash chromatography using MeOH/CH$_2$Cl$_2$ as the eluent.

NMR data was as follows:

$^1$H-nmr (DMSO-d$_6$): δ=8.84 (d, J=6.2 Hz, 1H), 8.23 (d, J=8.8 Hz, 1H), 7.38 (m, 5H), 7.07 (m, 1H), 6.98 (m, 2H), 5.37 (d, J=6.5 Hz, 1H), 4.34 (m, J=8.9 Hz, 1H), 3.55 (m, 5H), 2.01 (m, 1H), 0.87 (m, 6H). $^{13}$C-nmr (DMSO-d$_6$): δ=171.988, 171.690, 169.861, 164.633, 164.456, 161.382, 161.204, 141.987, 141.859, 141.727, 136.553, 129.470, 129.192, 128.791, 113.128, 113.026, 112.902, 112.803, 102.961, 102.619, 102.281, 57.914, 57.262, 52.935, 42.274, 31.728, 19.845, 18.815. $C_{22}H_{24}N_2O_4F_2$ (MW=418.44); mass spectroscopy (MH$^+$) 418.1.

Example 195

Synthesis of N-[N-(3,5-Difluorophenylacetyl)-2-aminobutanoyl]-L-phenylglycine Methyl Ester Following General Procedure E and using 3,5-difluorophenylacetic acid (Aldrich) and N-(2-aminobutanoyl)-L-phenylglycine methyl ester hydrochloride (prepared from N-BOC-L-aminobutyric acid (Sigma) and L-phenylglycine methyl ester hydrochloride (Aldrich) using General Procedure E, followed by removal of the BOC-group using General Procedure P), the title compound was prepared as a solid (mp=215.3° C.). The reaction was monitored by tlc (Rf=0.46 in 5:95 MeOH/CH$_2$Cl$_2$) and the product was purified by recrystallization from ethyl acetate/hexanes.

NMR data was as follows:

$^1$H-nmr (DMSO-d$_6$): δ=8.83 (d, J=6.8 Hz, 1H), 8.32 (d, J=8.1 Hz, 1H), 7.38 (m, 5H), 7.08 (m, 1H), 6.98 (m, 2H), 5.38 (d, J=6.8 Hz, 1H), 4.35 (m, J=7.9 Hz, 1H), 3.61 (s, 3H), 3.52 (d, 2H), 1.64 (m, 2H), 0.88 (t, 3H). $^{13}$C-nmr (DMSO-d$_6$): δ=171.684, 170.934, 168.984, 164.193, 163.980, 160.295, 160.083, 141.059, 140.902, 140.743, 135.857, 128.689, 128.372, 127.892, 112.387, 112.257, 112.131, 111.999, 102.254, 101.845, 101.438, 56.351, 53.441, 52.212, 41.436, 25.675, 10.067. $C_{21}H_{22}N_2O_4F_2$ (MW=404.42); mass spectroscopy (MH$^+$) 405.1.

Example 196

Synthesis of N-[N-(3,5-Difluorophenylacetyl)-L-leucinyl]-L-phenylglycine Methyl Ester Following General Procedure E and using 3,5-difluorophenylacetic acid (Aldrich) and N-(L-leucinyl)-L-phenylglycine methyl ester hydrochloride (prepared from N-BOC-L-leucine (Aldrich) and L-phenylglycine methyl ester hydrochloride (Aldrich) using General Procedure E, followed by removal of the BOC-group using General Procedure P), the title compound was prepared as a solid (mp=178.4° C.). The reaction was monitored by tlc (Rf=0.51 in 5:95 MeOH/CH$_2$Cl$_2$) and the product was purified by flash chromotograph using MeOH/CH$_2$Cl$_2$ as the eluent.

NMR data was as follows:

$^1$H-nmr (DMSO-d$_6$): δ=8.85 (d, J=6.8 Hz, 1H), 8.33 (d, J=8.3 Hz, 1H), 7.37 (m, 5H), 7.08 (m, 1H), 6.95 (m, 2H), 5.37 (d, J=6.8 Hz, 1H), 4.46 (m, J=8.3 Hz, 1H), 3.60 (s, 3H), 3.49 (d, 2H), 1.55 (m, 3H), 0.89 (d, 3H), 0.82 (d, 3H). $^{13}$C-nmr (DMSO-d$_6$): δ=172.225, 170.899, 168.888, 164.197, 163.984, 160.298, 160.086, 141.029, 140.887, 140.723, 135.875, 128.657, 128.348, 127.944, 112.340, 112.207, 112.084, 111.951, 102.251, 101.842, 101.435, 56.343, 52.214, 50.697, 41.510, 40.982, 24.449, 23.056, 21.575. $C_{23}H_{26}N_2O_4F_2$ (MW=432.47); mass spectroscopy (MH$^+$) 432.1.

Example 197

Synthesis of N-[N-(3,5-Difluorophenylacetyl)-L-phenylalaninyl]-L-phenylglycine Methyl Ester Following General Procedure E and using 3,5-difluorophenylacetic acid (Aldrich) and N-(L-phenylalaninyl)-L-phenylglycine methyl ester hydrochloride (prepared from N-BOC-L-phenylalanine (Aldrich) and L-phenylglycine methyl ester hydrochloride (Aldrich) using General Procedure E, followed by removal of the BOC-group using General Procedure P), the title compound was prepared as a solid (mp=188.3° C.). The reaction was monitored by tlc (Rf=0.59 in 5:95 MeOH/CH$_2$Cl$_2$) and the product was purified by flash chromatography using MeOH/CH$_2$Cl$_2$ as the eluent.

NMR data was as follows:

$^1$H-nmr (DMSO-d$_6$): δ=8.99 (d, J=6.9 Hz, 1H), 8.44 (d, J=8.6 Hz, 1H), 7.4 (m, 5H), 7.21 (m, 5H), 7.03 (m, 1H), 6.77 (m, 2H), 5.42 (d, J=6.9 Hz, 1H), 4.70 (m, J=8.5 Hz, 1H), 3.63 (s, 3H), 3.40 (m, 2H), 3.08 (m, 1H), 2.76 (m, 1H). $^{13}$C-nmr (DMSO-d$_6$): δ=171.428, 170.896, 168.853, 164.127, 163.915, 160.222, 160.010, 140.756, 140.601, 140.438, 137.662, 135.918, 130.638, 129.247, 128.737, 128.415, 127.908, 126.281, 112.147, 112.025, 111.892, 102.189, 101.782, 101.373, 56.411, 53.461, 52.306, 41.513, 37.796. $C_{26}H_{24}N_2O_4F_2$ (MW=466.49); mass spectroscopy (MH$^+$) 466.

Example 198

Synthesis of N-[N-(3,5-Difluorophenylacetyl) glycinyl]-L-phenylglycine Methyl Ester Following General Procedure E and using 3,5-difluorophenylacetic acid (Aldrich) and N-(glycinyl)-L-phenylglycine methyl ester hydrochloride (prepared from N-BOC-glycine (Aldrich) and L-phenylglycine methyl ester hydrochloride (Aldrich) using General Procedure E, followed by removal of the BOC-group using General Procedure P), the title compound was prepared as a solid (mp=142.3° C.). The reaction was monitored by tlc (Rf=0.33 in 5:95 MeOH/CH$_2$Cl$_2$) and the product was purified by recrystallization from diethyl ether/hexanes.

NMR data was as follows:

$^1$H-nmr (DMSO-d$_6$): δ=8.82 (d, J=7.2 Hz, 1H), 8.39 (t, 1H), 7.37 (m, 5H), 7.05 (m, 3H), 5.44 (d, 7.1 Hz, 1H), 3.83

(d, 2H), 3.62 (s, 3H), 3.53 (s, 2H). $^{13}$C-nmr (DMSO-d$_6$): δ=170.956, 169.427, 168.788, 164.226, 164.013, 160.329, 160.115, 140.817, 140.663, 140.499, 136.222, 128.728, 128.338, 127.687, 112.494, 112.360, 112.238, 112.104, 102.310, 101.900, 101.492, 56.200, 52.321, 41.731, 41.464. C$_{19}$H$_{18}$N$_2$O$_4$F$_2$ (MW=376.36); mass spectroscopy (MH$^+$) 376.0.

Example 199

Synthesis of N-[N-(3,5-Difluorophenylacetyl)-L-phenylglycinyl]-L-phenylglycine Methyl Ester Following General Procedure E and using 3,5-difluorophenylacetic acid (Aldrich) and N-(L-phenylglycinyl)-L-phenylglycine methyl ester hydrochloride (prepared from N-BOC-L-phenylglycine (Novabiochem) and L-phenylglycine methyl ester hydrochloride (Aldrich) using General Procedure AH, followed by removal of the BOC-group using General Procedure P), the title compound was prepared as a solid (mp=222.8° C.). The reaction was monitored by tlc (Rf=0.61 in 5:95 MeOH/CH$_2$Cl$_2$) and the product was purified by recrystallization from ethyl acetate.

NMR data was as follows:

$^1$H-nmr (DMSO-d$_6$): δ=9.22 (d, J=6.8 Hz, 1H), 8.85 (d, J=8.2 Hz, 1H), 7.37 (m, 10H), 7.08 (m, 1H), 6.97 (d, 2H), 5.69 (d, J=8.2 Hz, 1H), 5.43 (d, J=6.8 Hz, 1H), 3.61 (d, 2H), 3.55 (s, 3H). $^{13}$C-nmr (DMSO-d$_6$): δ=170.606, 169.727, 168.777, 164.194, 163.982, 160.296, 160.082, 140.920, 140.757, 140.603, 138.391, 135.900, 128.732, 128.425, 128.233, 127.871, 127.556, 127.222, 112.467, 112.340, 112.209, 112.082, 102.292, 101.884, 101.475, 56.431, 55.621, 52.203, 41.205. C$_{25}$H$_{22}$N$_2$O$_4$F$_2$ (MW=452.46); mass spectroscopy (MH$^+$) 452.2.

Example 200

Synthesis of N-[N-(Phenylacetyl)-L-alaninyl]-L-alanine Methyl Ester

Following General Procedure A and using N-(phenylacetyl)-L-alanine (from Example B1 above) and L-alanine methyl ester hydrochloride (Aldrich), the title compound was prepared as a solid (mp=140.5–142° C.). The reaction was monitored by tlc (Rf=0.17 in 50% EtOAc/hexanes).

NMR data was as follows:

$^1$H-nmr (CDCl$_3$): δ=1.3–1.4 (m, 6H), 3.55 (s, 2H), 3.75 (s, 3H), 4.4–4.6 (m, 2H), 6.1–6.3 (brd, 1H), 6.6–6.7 (brd, 1H), 7.2–7.4 (m, 5H). $^{13}$C-nmr (CDCl$_3$): δ=18.4, 19.0, 44.1, 48.6, 49.3, 53.0, 127.9, 129.5, 129.8, 135.1, 171.5, 172.4, 173.6. C$_{15}$H$_{20}$N$_2$O$_4$ (MW 292.34); mass spectroscopy (MH$^+$) 293.

Example 201

Synthesis of N-[N-(Phenylacetyl)-L-alaninyl]-L-leucine Methyl Ester

Following General Procedure A and using N-(phenylacetyl)-L-alanine (from Example B1 above) and L-leucine methyl ester hydrochloride (Aldrich), the title compound was prepared as a solid (mp=102.5–105° C.). The reaction was monitored by tlc (Rf=0.25 in 50% EtOAc/hexanes).

NMR data was as follows:

$^1$H-nmr (CDCl$_3$): δ=0.8–0.95 (m, 6H), 1.3 (d, J=7 Hz, 3H), 1.4–1.6 (m, 3H), 3.58 (s, 2H), 3.75 (s, 3H), 4.4–4.6 (m, 2H), 6.2 (brd, 1H), 6.7 (brd, 1H), 7.2–7.4 (m, 5H). $^{13}$C-nmr (CDCl$_3$): δ=18.7, 22.3, 23.4, 25.3, 41.5, 44.1, 49.2, 51.4, 52.8, 127.9, 129.5, 129.8, 135.0, 171.5, 172.6, 173.7. C$_{18}$H$_{26}$N$_2$O$_4$ (MW=334.42); mass spectroscopy (MH$^+$) 335.

Example 202

Synthesis of N-[N-(Phenylacetyl)-L-alaninyl]-L-isoleucine Methyl Ester

Following General Procedure A and using N-(phenylacetyl)-L-alanine (from Example B1 above) and L-isoleucine methyl ester hydrochloride (Sigma), the title compound was prepared. The reaction was monitored by tlc (Rf=0.24 in 50% EtOAc/hexanes).

NMR data was as follows:

$^1$H-nmr (CDCl$_3$): δ=0.8–0.95 (m, 6H), 1.0–1.2 (m, 1H), 1.2–1.4 (m including 1.3 (d, J=7 Hz, 4H)), 1.8–1.9 (m, 1H), 3.58 (s, 2H), 3.75 (s, 3H), 4.4–4.6 (m, 2H), 6.2 (brd, 1H), 6.7 (brd, 1H), 7.2–7.4 (m, 5H). $^{13}$C-nmr (CDCl$_3$): δ=12.1, 16.0, 18.5, 25.6, 38.1, 44.1, 49.3, 52.7, 57.2, 127.9, 129.6, 129.8, 135.0, 171.5, 172.5, 172.6. C$_{18}$H$_{26}$N$_2$O$_4$ (MW=334.42); mass spectroscopy (MH$^+$) 335.

Example 203

Synthesis of N-[N-(Phenylacetyl)-L-alaninyl]-L-proline Methyl Ester

Following General Procedure A and using N-(phenylacetyl)-L-alanine (from Example B1 above) and L-proline methyl ester hydrochloride (Bachem), the title compound was prepared as an oil. The reaction was monitored by tlc (Rf=0.12 in 50% EtOAc/hexanes).

NMR data was as follows:

$^1$H-nmr (CDCl$_3$): δ=1.33 (d, J=7 Hz, 3H), 1.9–2.1 (m, 3H), 2.1–2.25 (m, 1H), 3.5–3.8 (m including 3.58 (s) and 3.75 (s), total 7H), 4–4.4 (m, 1H), 4.7–4.8 (m, 1H), 6.5 (brd, 1H), 7.2–7.4 (m, 5H). $^{13}$C-nmr (CDCl$_3$): δ=18.5, 25.5, 29.5, 44.1, 47.3, 47.4, 52.8, 59.3, 127.8, 129.42, 129.48, 129.9, 135.2, 170.9, 171.8, 172.8. C$_{17}$H$_{22}$N$_2$O$_4$ (MW=318.38); mass spectroscopy (MH$^+$) 319.

Example 204

Synthesis of N-[N-(Phenylacetyl)-L-alaninyl]-L-phenylalanine Methyl Ester

Following General Procedure A and using N-(phenylacetyl)-L-alanine (from Example B1 above) and L-phenylalanine methyl ester hydrochloride (Aldrich), the title compound was prepared as a solid (mp=148–149.5° C.). The reaction was monitored by tlc (Rf=0.24 in 50% EtOAc/hexanes) and the product was not purified.

NMR data was as follows:

$^1$H-nmr (CDCl$_3$): δ=1.25 (d, J=7 Hz, 3H), 3.02 (dd, J=7, 14 Hz, 1H), 3.12 (dd, J=5, 14 Hz, 1H), 3.53 (s, 2H), 3.72 (s, 3H), 4.4–4.5 (m, 1H), 4.75–4.85 (m, 1H), 5.9 (brd, 1H), 6.5 (brd, 1H), 7.0–7.5 (m, 10H). $^{13}$C-nmr (CDCl$_3$): δ=18.6, 38.3, 44.0, 49.2, 52.9, 53.9, 127.7, 128.0, 129.1, 129.6, 129.8, 129.9, 135.0, 136.3, 171.4, 172.2, 172.3. C$_{21}$H$_{24}$N$_2$O$_4$ (MW=368.44); mass spectroscopy (MH$^+$) 369.

Example 205

Synthesis of N-[N-(Phenylacetyl)-L-alaninyl]-N$_\epsilon$-(tert-butoxycarbonyl)-L-lysine Methyl Ester Following General Procedure A and using N-(phenylacetyl)-L-alanine (from Example B1 above) and $N_\epsilon$-(tert-butoxycarbonyl)-L-lysine methyl ester hydrochloride (Bachem), the title compound was prepared as a solid (mp=119–121° C.). The reaction was monitored by tlc (Rf=0.46 in 90:10:1 $CH_2Cl_2$/MeOH/$NH_4OH$).

NMR data was as follows:

$^1$H-nmr ($CDCl_3$): δ=1.2–1.9 (m, 18H)(includes 1.3 (d, J=7 Hz) and 1.4 (s)), 3.0–3.15 (m, 2H), 3.12 (dd, J=5, 14 Hz, 1H), 3.57 (s, 2H), 3.72 (s, 3H), 4.4–4.5 (m, 2H), 4.75–4.85 (m, 1H), 6.2 (brd, 1H), 6.75 (brd, 1H), 7.2–7.4 (m, 5H). $^{13}$C-nmr ($CDCl_3$): δ=18.6, 22.9, 29.0, 29.9, 32.0, 40.5, 44.0, 49.4, 52.7, 53.0, 79.8, 127.9, 129.5, 129.8, 135.1, 156.7, 171.6, 172.7, 173.0. $C_{23}H_{35}N_3O_6$ (MW=449.55); mass spectroscopy (MH$^+$)=450.

Example 206

Synthesis of N-[N-(Phenylacetyl)-L-alaninyl] glycine Methyl Ester

Following General Procedure A and using N-(phenylacetyl)-L-alanine (from Example B1 above) and glycine methyl ester hydrochloride (Aldrich), the title compound was prepared as a solid (mp=152–153.5° C.). The reaction was monitored by tlc (Rf=0.10 in 50% EtOAc/hexanes).

NMR data was as follows:

$^1$H-nmr ($CDCl_3$): δ=1.33 (d, J=7 Hz, 3H), 3.59 (s, 2H), 3.75 (s, 3H), 3.97 (d, J=6.5 Hz, 2H), 4.5–4.6 (m, 1H), 6.1 (brd, 1H), 6.8 (brs, 1H), 7.2–7.6 (m, 5H), $^{13}$C-nmr ($CDCl_3$): δ=18.7, 41.6, 43.9, 49.2, 52.9, 127.9, 129.5, 129.9, 135.0, 170.6, 171.7, 173.2. $C_{14}H_{18}N_2O_4$ (MW=278.31); mass spectroscopy (MH$^+$) 279.

Example 207

Synthesis of N-[N-(Phenylacetyl)-L-alaninyl]-L-valine Methyl Ester

Following General Procedure A and using N-(phenylacetyl)-L-alanine (fromo Example B1 above) and L-valine methyl ester hydrochloride (Aldrich), the title compound was prepared as a solid (mp=112–115° C.). The reaction was monitored by tlc (Rf=0.33 in 50% EtOAc/hexanes) and the product was not purified.

NMR data was as follows:

$^1$H-nmr ($CDCl_3$): δ=0.8–0.9 (overlapping d appearing as t, J=6 Hz, 6H), 2.0–2.2 (m, 1H), 3.57 (s, 2H), 3.72 (s, 3H), 4.4–4.5 (m, 1H), 4.5–4.65 (m, 1H), 6.2 (brd, 1H), 6.75 (brd, 1H), 7.2–7.4 (m, 5H). $^{13}$C-nmr ($CDCl_3$): δ=18.3, 18.5, 19.5, 31.5, 44.1, 49.3, 52.7, 57.9, 127.9, 129.5, 129.8, 135.0, 171.5, 172.7, 172.7. $C_{17}H_{24}N_2O_4$ (MW=320.39); mass spectroscopy (MH$^+$) 321.

Example 208

Synthesis of Methyl N-[N-(Phenylacetyl)-L-alaninyl]-2-(S)-aminobutanoate

Following General Procedure A and using N-(phenylacetyl)-L-alanine (from Example B1 above) and methyl L-2-aminobutanoate hydrochloride (prepared from L-2-aminobutanoic acid (Bachem) using General Procedure H (without extractions)), the title compound was prepared as a solid (mp=120° C.). The reaction was monitored by tlc (Rf=0.2 in 50% EtOAc/hexanes).

NMR data was as follows:

$^1$H-nmr ($CDCl_3$): δ=0.85 (t, J=6 Hz, 3H), 1.32 (d, J=7 Hz, 3H), 1.6–1.9 (m, 2H), 3.57 (s, 2H), 3.72 (s, 3H), 4.4–4.6 (m, 2H), 6.2 (brd, 1H), 6.75 (brd, 1H), 7.2–7.4 (m, 5H). $^{13}$C-nmr ($CDCl_3$): δ=10.2, 18.9, 25.8, 44.0, 49.3, 52.8, 54.0, 127.9, 129.5, 129.8, 135.1, 171.5, 172.7, 173.0. $C_{16}H_{22}N_2O_4$ (MW=306.36); mass spectroscopy (MH$^+$) 307.

Example 209

Synthesis of Methyl N-[N-(Phenylacetyl)-L-alaninyl]-2-(S)-aminopentanoate

Following General Procedure A and using N-(phenylacetyl)-L-alanine (from Example B1 above) and methyl 2-(S)-aminopentanoate hydrochloride (prepared from L-2-aminovaleric acid (Bachem) using General Procedure H (without extractions)), the title compound was prepared as a solid (mp=135–137° C.). The reaction was monitored by tlc (Rf=0.30 in 50% EtOAc/hexanes).

NMR data was as follows:

$^1$H-nmr ($CDCl_3$): δ=0.87 (t, J=6 Hz, 3H), 1.2–1.4 (m with d, J=7 Hz, 5H), 1.5–1.8 (m, 2H), 3.57 (s, 2H), 3.72 (s, 3H), 4.4–4.5 (m, 2H), 6.4 (brd, 1H), 7.0 (brd, 1H), 7.2–7.4 (m, 5H). $^{13}$C-nmr ($CDCl_3$): δ=14.2, 19.0, 19.2, 34.5, 44.0, 49.2, 52.7, 52.8, 127.8, 129.4, 129.8, 135.2, 171.5, 172.8, 173.3. $C_{17}H_{24}N_2O_4$ (MW=320.39); mass spectroscopy (MH$^+$) 321.

Example 210

Synthesis of N-[N-(3-Nitrophenylacetyl)-L-alaninyl]-L-valine

Following General Procedure AF and using N-[N-(3-nitrophenylacetyl)-L-alaninyl]-L-valine ethyl ester (from Example 143 above), the title compound was prepared as a solid. The reaction was monitored by tlc (Rf=0.05 in 9:1 $CHCl_3$/MeOH).

NMR data was as follows:

$^1$H-nmr (DMSO-$d_6$): δ=8.41 (d, 1H), 8.13 (s, 1H), 8.09 (d, 1H), 7.91 (d, 1H), 7.68 (d, 1H), 7.56 (t, 1H), 4.4 (m, 1H), 4.10 (m, 1H), 3.63 (s, 2H), 2.01 (m, 1H), 1.19 (m, 3H), 0.89 (d, 6H). Optical Rotation: [α]$_{23}$=−49° (c 1, MeOH). $C_{16}H_{21}N_3O_6$ (MW=351.3); mass spectroscopy (MH$^+$) 352.

Example 211

Synthesis of N-[N-(Phenylacetyl)-L-alaninyl]-L-N-methylalanine Methyl Ester

Following General Procedure A and using N-(phenylacetyl)-L-alanine (from Example B1 above) and L-N-methylalanine methyl ester hydrochloride (prepared from L-N-methylalanine hydrochloride (Bachem) using General Procedure H (without extractions)), the title compound was prepared as an oil. The reaction was monitored by tlc (Rf=0.13 in 50% EtOAc/hexanes) and the product was purified by column chromatography using 60% EtOAc/hexanes as the eluent.

NMR data was as follows:

$^1$H-nmr ($CDCl_3$): δ=1.2–1.6 (m including 1.32 (d, J=7 Hz, 6H), 2.97 (s (rotomers), 3H), 3.57 (s, 2H), 3.7–3.8 (s (rotomers), 3H), 4.4–5.2 (m, 2H), 6.6 (brd, 1H), 7.2–7.4 (m, 5H). $^{13}$C-nmr ($CDCl_3$): δ=14.7, 15.0, 18.8, 19.1, 31.6, 32.3, 44.3, 46.2, 46.3, 52.7, 52.88, 52.93, 53.6, 127.81, 127.85, 129.45, 129.48, 129.9, 135.2, 170.60, 170.67, 172.19, 172.4, 173.25. 173.31. $C_{16}H_{22}N_2O_4$ (MW=306.36); mass spectroscopy (MH$^+$) 307.

Example 212

Synthesis of N-[N-(Isovaleryl)-L-phenylglycinyl]-L-alanine Isobutyl Ester

Following General Procedure C and using N-(isovaleryl)-L-phenylglycine (prepared from isovaleric acid (Aldrich)

and L-phenylglycine methyl ester hydrochloride (Aldrich) using General Procedure C, followed by hydrolysis using General Procedure AF) and L-alanine isobutyl ester hydrochloride (prepared from N-BOC-L-alanine (Sigma) and 2-methyl-1-propanol (Aldrich) using General Procedure C (with catalystic DMAP), followed by removal of the BOC-group using General Procedure P), the title compound was prepared as a solid (mp=181–186° C.). The reaction was monitored by tlc (Rf=0.4 in 1:1 EtOAc/hexanes) and the product was purified by silica gel chromatography using 1:1 EtOAc/hexanes as the eluent.

NMR data was as follows:

$^1$H-nmr (CDCl$_3$): δ=1.31 (d, 3H), 5.59 (d, 1H). Optical Rotation: [α]$_{20}$=+19° @ 589 nm (c 1.03, DMSO). C$_{20}$H$_{30}$N$_2$O$_4$ (MW=362); mass spectroscopy (MH$^+$) 363.

Example 213

Synthesis of N-[N-(Isovaleryl)-L-isoleucinyl]-L-alanine Isobutyl Ester

Following General Procedure C and using N-(isovaleryl)-L-isoleucine (prepared from isovaleric acid (Aldrich) and L-isoleucine methyl ester hydrochloride (Aldrich) using General Procedure C, followed by hydrolysis using General Procedure AF) and L-alanine isobutyl ester hydrochloride (prepared from N-BOC-L-alanine (Sigma) and 2-methyl-1-propanol (Aldrich) using General Procedure C (with catalystic DMAP), followed by removal of the BOC-group using General Procedure P), the title compound was prepared as a solid (mp=142–146° C.). The reaction was monitored by tlc (Rf=0.4 in 1:1 EtOAc/hexanes) and the product was purified by silica gel chromatography using 1:1 EtOAc/hexanes as the eluent to provide a 1:4 mixture of diastereomers.

NMR data was as follows:

$^1$H-nmr (DMSO-d$_6$): δ=1.26 (d, 3H), 7.70 (d, 1H), 7.80 (d, 1H), 8.30 (d, 1H) 8.40 (d, 1H). C$_{18}$H$_{34}$N$_2$O$_4$ (MW=342.48); mass spectroscopy (MH$^+$) 343.

Example 214

Synthesis of N-Cyclohexyl-N'-[N-(3,5-difluorophenylacetyl)-L-alaninyl]-L-phenylglycinamide Following General Procedure C and using N-(3,5-difluorophenylacetyl)-L-alanine (from Example B2 above) and N-cyclohexyl-L-phenylglycinamide (prepared from N-BOC-L-phenylglycine (Advanced Chemtech) and cyclohexylamine (Aldrich) using General Procedure M, followed by removal of the BOC-group using General Procedure P), the title compound was prepared as a solid. The reaction was monitored by tlc (Rf=0.5 in 9:1 CHCl$_3$/MeOH) and the product was purified by trituration from ethanol.

NMR data was as follows:

$^1$H-nmr (CDCl$_3$): δ=8.55 (m, 2H), 8.08 (d, 1H), 7.30 (m, 5H), 7.08 (m, 1H), 6.97 (d, 2H), 5.37 (m, 1H), 3.47 (s, 2H), 1.8–1.6 (m, 6H), 1.23–0.98 (m, 7H). Optical Rotation: [α]$_{23}$=−32.7° (c 1, MeOH). C$_{25}$H$_{29}$F$_2$N$_3$O$_3$ (MW=457); mass spectroscopy (MH$^+$) 458.

Example 215

Synthesis of N-[N-(3,5-Difluorophenylacetyl)-L-alaninyl]-L-4-hydroxyproline Ethyl Ester Following General Procedure F and using N-(3,5-difluorophenylacetyl)-L-alanine (from Example B2 above) and L-4-hydroxyproline ethyl ester hydrochloride (Pfaltz & Bauer), the title compound was prepared as a foam. The reaction was monitored by tlc (Rf=0.32 in 95:5 CH$_2$Cl$_2$/MeOH) and the product was purified by flash column chromatography.

NMR data was as follows:

$^1$H-nmr (CDCl$_3$, 250 Mz): δ=7.31 (d, 1H, J=7.00 Hz), 6.83–6.64 (m, 3H), 4.67 (p, 1H, J=7.09 Hz), 4.58 (t, 1H, J=8.26 Hz), 4.47 (bs, 1H), 4.25–4.06 (m, 2H), 3.81 (bd, 1H, J=11.01 Hz), 3.62 (dd, 1H, J=10.76, 3.75 Hz), 3.46 (s, 2H), 2.30 (dd, 1H, J=13.51, 8.26 Hz), 1.96 (ddd, 1H, J=13.44, 8.82, 4.56 Hz), 1.33 (d, 3H, J=6.75 Hz), 1.24 (t, 3H, J=7.13 Hz). C$_{18}$H$_{23}$F$_2$N$_2$O$_5$ (MW=384.38); mass spectroscopy (MH$^+$) 385.1.

Example 216

Synthesis of N-[N-(3,5-Difluorophenylacetyl)-L-alaninyl]-L-lysine Methyl Ester

Following General Procedure Y and using N-[N-(3,5-difluorophenylacetyl)-L-alaninyl]-N$_\epsilon$-(tert-butoxycarbonyl)-L-lysine methyl ester (from Example 43 above), the title compound was prepared as an oil. The title compound was isolated as the trifluoroacetic acid salt (containing about 5% excess trifluoroacetic acid).

NMR data was as follows:

$^1$H-nmr (CDCl$_3$+2 drops of CD$_3$OD): δ=6.40–6.52 (m, 3H), 4.17 (t, 1H), 4.40 (q, 1H), 3.42 (s, 3H), 3.23 (s, 3H), 2.53 (bs, 2H), 1.60 (m, 1H), 1.32 (m, 3H), 1.02–1.13 (m, 2H), 1.10 (d, 2H). $^{13}$C-nmr (CDCl$_3$+2 drops of CD$_3$OD): δ=174.1, 166.4, 166.2, 163.1, 163.0, 141.3, 113.8, 113.7, 113.5, 103.5, 55.2, 56.3, 43.0, 40.9, 32.2, 28.1, 24.0, 18.2. C$_{21}$H$_{26}$F$_5$N$_3$O$_6$ (MW=511.4); mass spectroscopy (MH$^+$) 512.

Example 217

Synthesis of N'-[N-(3,5-Difluorophenylacetyl)-L-alaninyl]-L-glutamide

Following General Procedure B and using N-(3,5-difluorophenylacetyl)-L-alanine (from Example B2 above) and L-glutamide hydrochloride (Bachem), the title compound was prepared as a solid (mp=260–263° C.). The reaction was monitored by tlc (Rf=0.77 in 10% MeOH/DCM) and the product was purified by silica gel chromatography.

NMR data was as follows:

$^1$H-nmr (CDCl$_3$): δ=8.40 (d, J=7.1 Hz, 1H), 8.02 (d, J=6.9, 1H), 7.2 (m, 2H), 7.0 (m, 4H), 6.76 (s, 1H), 4.2 (m, 1H), 3.56 (s, 2H), 2.1 (m, 2H), 1.9 (m, 2H), 1.21 (d, J=7.0 Hz, 3H). $^{13}$C-nmr (CDCl$_3$): δ=173.5, 172.4, 169.5, 112.5, 110.4, 102.3, 52.5, 49.0, 41.6, 35.7, 31.8, 28.1, 18.4. C$_{16}$H$_{20}$F$_2$N$_4$O$_4$ (MW=370); mass spectroscopy (MH$^+$) 371.

Example 218

Synthesis of Methyl 1-[N-(3,5-Difluorophenylacetyl)-L-alaninyl]piperidine-2-carboxylate Following General Procedure A and using N-(3,5-difluorophenylacetyl)-L-alanine (from Example B2 above) and methyl pipecolinate hydrochloride (Aldrich), the title compound was prepared as a solid (mp=114–118° C.). The reaction was monitored by tlc (Rf=0.71 in 10% MeOH/DCM) and the product was purified by acid/base washes.

NMR data was as follows:

$^1$H-nmr (CDCl$_3$): δ=6.95 (dd, J=7.1, 7.1, 7.1 Hz; 1H), 6.81 (d, J=6.1 Hz, 2H), 6.7 (m, 1H), 5.28 (dd, J=5.0 Hz, 12.6, 5.4, 1H), 4.93 (q, J=7.0, 6.9, 7.0 Hz, 1H), 3.75 (s, 1H), 3.70 (s, 3H), 3.50 (s, 2H), 3.2 (m, 1H), 2.27 (d, J=3.5 Hz, 1H), 1.5 (m, 5H), 1.31 (d, J=5.2 Hz, 3H). $^{13}$C-nmr (CDCl$_3$): δ=172.8; 172.6; 171.7; 171.6; 169.2; 169.1; 112.9; 112.8; 112.7; 112.6; 103.2; 102.8; 53.0; 52.9; 52.9; 52.7; 46.2; 46.1; 43.9; 43.9; 27.1; 26.8; 25.6; 21.4; 19.9; 18.5. C$_{18}$H$_{22}$F$_2$N$_2$O$_4$ (MW=368); mass spectroscopy (MH$^+$) 369.

Example 219

Synthesis of N-[(S)-3-Hydroxy-6-methylhept-2-yl]-N'-(3,5-difluorophenylacetyl)-L-alaninamide Following General Procedure AA and using N-[(S)-6-methyl-3-oxohept-2-yl]-N'-(3,5-difluorophenylacetyl)-L-alaninamide (from Example 168 above), the title compound was prepared as a solid. The reaction was monitored by tlc (Rf=0.75 in 9:1 CHCl$_3$/MeOH) and the product was purified by silica gel chromatography using 99:1 CHCl$_3$/MeOH as the eluent.

NMR data was as follows:

$^1$H-nmr (CDCl$_3$): δ=6.81 (m, 1H), 6.72 (m, 2H), 6.39 (m, 2H), 4.45 (m, 1H), 3.97 (m, 1H), 3.60 (m, 1H), 3.52 (s, 2H), 1.54 (m, 1H), 1.4 (m, 5H), 1.09 (m, 3H), 0.9 (m, 6H). Optical Rotation: [α]$_{23}$=−39° (c 1, MeOH). C$_{19}$H$_{28}$F$_2$N$_2$O$_3$ (MW=448); mass spectroscopy (MH$^+$) 449.

Example 220

Synthesis of N-[(S)-2-Hydroxy-1-phenyleth-1-yl]-N'-(3,5-Difluorophenylacetyl)-L-alaninamide Following General Procedure C and using N-(3,5-difluorophenylacetyl)-L-alanine (from Example B2 above) and (S)-2-hydroxy-1-phenyleth-1-ylamine (e.g., (S)-phenylglycinol) (Aldrich), the title compound was prepared as a solid (mp=204–206° C.). The reaction was monitored by tlc (Rf=0.5 in 10% MeOH/CHCl$_3$) and the product was purified by silica gel chromatography using 5% MeOH/CHCl$_3$ as the eluent, followed by recrystallization from acetonitrile.

NMR data was as follows:

$^1$H-nmr (DMSO-d$_6$): δ=1.24 (d, 3H), 4.38 (m, 1H), 4.80 (m, 2H). Optical Rotation: [α]$_{20}$=+3.56° @ 589 nm (c 1.10, DMSO). C$_{19}$H$_{20}$F$_2$N$_2$O$_3$ (MW=362.38); mass spectroscopy (MH$^+$) 363.

Example 221

Synthesis of N-[N-(3,5-Difluorophenyl-α-fluoroacetyl)-L-alaniny]-L-phenylglycine tert-Butyl Ester Following General Procedure M and using 3,5-difluorophenyl-α-fluoroacetic acid (from Example D1 above) and N-(L-alaniny)-L-phenylglycine tert-butyl ester (prepared using N-BOC-L-alanine (Sigma) and L-phenylglycine tert-butyl ester hydrochloride (Bachem) using General Procedure C, followed by removal of the BOC group using General Procedure P), the title compound was prepared as a clear oil. The reaction was monitored by tlc (Rf=0.44 and 0.51 in 1:1 EtOAc/hexanes) and the product was purified by LC 2000 chromatography using 20% EtOAc/hexanes as the eluent.

NMR data was as follows:

$^1$H-nmr (CDCl$_3$)(1:1 mixture of diastereomers): δ=1.37 (s, 9H), 1.39 (s, 9H), 1.42 (d, J=7.0 Hz, 3H), 1.48 (d, J=7.0 Hz, 3H), 3.80 (d, J=7.0 Hz, 1H), 4.62 (pent, J=7.0 Hz, 2H), 5.36 (d, J=7.1 Hz, 1H), 5.42 (d, J=7.2 Hz, 1H), 5.60 (d, J=4.7 Hz, 1H), 5.73 (d, J=4.7 Hz, 1H), 6.80 (m, 2H), 6.97 (m, 4H), 7.20–7.33 (m, 12H). C$_{23}$H$_{25}$F$_3$N$_2$O$_4$ (MW=450.2); mass spectroscopy (MH$^+$) 451.

Example 222

Synthesis of N-[(S)-α-Hydroxy-α'-phenylisopropyl]-N'-(3,5-difluorophenylacetyl)-L-alaninamide Following General Procedure C and using N-(3,5-difluorophenylacetyl)-L-alanine (from Example B2 above) and (S)-α-hydroxy-α'-phenylisopropylamine (e.g., L-phenylalaninol) (Aldrich), the title compound was prepared as a solid. The reaction was monitored by tlc (Rf=0.5 in 9:1 CHCl$_3$/MeOH) and the product was purified by silica gel chromatography using 95:5 CHCl$_3$/MeOH as the eluent.

NMR data was as follows:

$^1$H-nmr (CDCl$_3$): δ=7.33–7.17 (m, 5H), 6.72 (m, 3H), 6.62 (d, 1H), 6.32 (d, 1H), 4.43 (m, 1H), 4.10 (m, 1H), 3.61 (m, 2H), 3.45 (s, 2H), 2.84 (m, 2H), 1.32 (d, 3H). Optical Rotation: [α]$_{23}$=−60° (c 1, MeOH). C$_{20}$H$_{22}$F$_2$N$_2$O$_3$ (MW=376); mass spectroscopy (MH$^+$) 377.

Example 223

Synthesis of N-[(1S,2R)-1-Hydroxy-1-phenylprop-2-yl]-N'-(3,5-difluorophenylacetyl)-L-alaninamide Following General Procedure C and using N-(3,5-difluorophenylacetyl)-L-alanine (from Example B2 above) and (1S,2R)-1-hydroxy-1-phenylprop-2-ylamine hydrochloride (e.g., (1S,2R)-norephedrine hydrochloride) (Aldrich), the title compound was prepared as a solid. The reaction was monitored by tlc (Rf=0.5 in 9:1 CHCl$_3$/MeOH) and the product was purified by silica gel chromatography using 98:2 CHCl$_3$/MeOH as the eluent.

NMR data was as follows:

$^1$H-nmr (CDCl$_3$): δ=7.31 (m, 5H), 6.84–6.64 (m, 4H), 4.86 (m, 1H), 4.51 (m, 1H), 4.23 (m, 1H), 3.52 (s, 2H), 1.38 (d, 3H), 0.97 (d, 3H). Optical Rotation: [α]$_{23}$=−44° (c 1, MeOH). C$_{20}$H$_{22}$F$_2$N$_2$O$_3$ (MW=376); mass spectroscopy (MH$^+$) 377.

Example 224

Synthesis of N-2-Methoxyethyl-N'-[N-(3,5-difluorophenylacetyl)-L-alaninyl]glycinamide Following General Procedure K and using N-[N-(3,5-difluorophenylacetyl)-L-alaninyl]glycine methyl ester (from Example 28 above) and 2-methoxyethylamine (Aldrich), the title compound was prepared as a solid (mp=148–151° C.). The reaction was monitored by tlc (Rf=0.53 in 10% MeOH/DCM+1% TEA) and the product was purified by silica gel chromatography.

NMR data was as follows:

$^1$H-nmr (CDCl$_3$): δ=8.2 (m, 1H), 7.1 (m, 1H), 6.6 (m, 8H0, 4.7 (m, 1H), 4.0 (m, 1H), 3.6 (m, 2H), 3.39 (s, 2H), 3.2 (m, 4H), 3.1 (s, 3H), 1.17 (d, J=7.2 Hz, 3H). $^{13}$C-nmr (CDCl$_3$): δ=176.3, 173.4, 172.2, 166.5, 163.4, 150.4, 141.6, 114.1, 114.0, 113.9, 113.8, 103.9, 103.5, 72.2, 72.1, 59.4, 51.9, 44.0, 43.0, 40.7, 17.9. C$_{16}$H$_{21}$F$_2$N$_3$O$_4$ (MW=357); mass spectroscopy (MH$^+$) 358.

Example 225

Synthesis of N-[N-(3,5-Difluorophenylacetyl)-2-(S)-aminocyclohexylacetyl]-L-phenylglycine Methyl Ester Following General Procedure E and using 3,5-difluorophenylacetic acid (Aldrich) and N-[2-(S)-aminocyclohexylacetyl]-L-phenylglycine methyl ester hydrochloride (prepared from N-BOC-L-cyclohexylglycine (Sigma) and L-phenylglycine methyl ester hydrochloride (Aldrich) using General Procedure E, followed by removal of the BOC-group using General Procedure P), the title compound was prepared as a solid (mp=234.4° C.). The reaction was monitored by tlc (Rf=0.65 in 5:95 MeOH/DCM) and the product was purified by recrystallization from ethyl acetate.

NMR data was as follows:

$^1$H-nmr (DMSO-d$_3$): δ=8.85 (d, J=6.5 Hz, 1H), 8.21 (d, J=8.9 Hz, 1H), 7.37 (s, 5H), 7.07 (m, 1H), 6.97 (d, 2H), 5.36 (d, J=6.4 Hz, 1H), 4.35 (t, J=7.7Hz, 1H), 3.53 (m, 5H), 1.65 (m, 6H), 1.06 (m, 5H). $^{13}$C-nmr (DMSO-d$_3$): δ=171.065, 170.865, 168.953, 164.179, 163.967, 160.282, 160.070, 141.210, 141.058, 135.766, 128.657, 128.374, 128.004, 112.371, 112.238, 112.115, 111.981, 102.217, 101.808, 101.399, 56.568, 56.471, 41.467, 40.354, 28.884, 28.025, 25.926, 25.669. $C_{25}H_{28}N_2O_4F_2$ (MW=458.51); mass spectroscopy (MH$^+$) 458.1.

Example 226

Synthesis of N-[(1R,2S)-1-Hydroxy-1-phenylprop-2-yl]-N'-(3,5-difluorophenylacetyl)-L-alaninamide Following General Procedure C and using N-(3,5-difluorophenylacetyl)-L-alanine (from Example B2 above) and (1R,2S)-1-hydroxy-1-phenylprop-2-ylamine hydrochloride (e.g., (1R,2S)-norephedrine hydrochloride) (Aldrich), the title compound was prepared as a foam. The reaction was monitored by tlc (Rf=0.5 in 9:1 CHCl$_3$/MeOH).

NMR data was as follows:

$^1$H-nmr (CDCl$_3$): δ=7.35 (m, 5H), 7.75 (m, 3H), 6.57 (d, 1H), 4.47 (d, 1H), 4.26 (m, 1H), 3.48 (s, 2H), 1.32 (d, 3H), 1.01 (d, 3H). Optical Rotation: [α]$_{23}$=−64° (c 1, MeOH). $C_{20}H_{22}F_2N_2O_3$ (MW=376); mass spectroscopy (MH$^+$) 377.

Example 227

Synthesis of N-[(1R,2S)-1-hydroxy-1,2-diphenyleth-2-yl]-N'-(3,5-difluorophenylacetyl)-L-alaninamide Following General Procedure C and using N-(3,5-difluorophenylacetyl)-L-alanine (from Example B2 above) and (1R,2S)-2-amino-1,2-diphenylethanol (Aldrich), the title compound was prepared as a solid (mp=217–219° C.). The reaction was monitored by tlc (Rf–0.4 in 10% MeOH/CHCl$_3$) and the product was purified by silica gel chromatography using 7% MeOH/CHCl$_3$ as the eluent, followed by recrystallization from acetonitrile.

NMR data was as follows:

$^1$H-nmr (DMSO-d$_6$): δ=0.76 (d, 3H), 5.43 (d, 1H). Optical Rotation: [α]$_{20}$=−6.9° @ 589 nm (c 1.10, DMSO). $C_{25}H_{24}F_2N_2O_3$ (MW=438.48); mass spectroscopy (MH$^+$) 439.

Example 228

Synthesis of N-[(S)-1-Hydroxyhex-2-yl]-N'-(3,5-difluorophenylacetyl)-L-alaninamide Following General Procedure S and using methyl N-[N-(3,5-difluorophenylacetyl)-L-alaninyl]-(S)-2-aminohexanoate (from Example 1 above), the title compound was prepared as a solid (mp=157–158.5° C.). The reaction was monitored by tlc (Rf=0.62 in 10% CH$_3$OH/CH$_2$Cl$_2$).

NMR data was as follows:

$^1$H-nmr (CD$_3$OD): δ=5.9 (m, 2H), 5.8 (m, 1H), 4.37 (q, 1H), 3.8 (m, 1H), 3.58 (s, 2H), 3.5 (m, 2H), 1.4 (m, 9H), 0.9 (m, 3H). $^{13}$C-nmr (CD$_3$OD): δ=175.4, 172.9, 166.7, 166.5, 163.5, 163.2, 141.8, 141.7, 113.9, 113.8, 113.7, 113.6, 103.9, 103.6, 103.2, 65.6, 53.2, 51.2, 43.3, 32.3, 29.7, 24.1, 18.7, 14.9. $C_{17}H_{24}F_2N_2O_3$ (MW=342.39); mass spectroscopy (MH$^+$) 343.

Example 229

Synthesis of N-[α-Hydroxy-α'-(4-hydroxyphenyl)isopropyl]-N'-(3,5-difluorophenylacetyl)-L-alaninamide Following General Procedure S and using N-[N-(3,5-difluorophenylacetyl)-L-alaninyl]-L-tyrosine methyl ester (from Example 15 above), the title compound was prepared as a solid (mp=179–183° C.). The reaction was monitored by tlc (Rf=0.42 in 10% MeOH/DCM) and the product was purified by recrystallization from MeOH/diethyl ether.

NMR data was as follows:

$^1$H-nmr (CDCl$_3$): δ=6.82 (d, J=8.3 Hz, 2H), 6.7 (m, 2H), 6.62 (t, J=9.1, 9.1 Hz, 1H), 6.47 (d, J=8.5 Hz, 2H), 4.1 (m, 1H), 3.7 (m, 1H), 3.34 (s, 2H), 3.2 (m, 2H), 2.5 (m, 2H), 1.08–0.94 (dd, J=7.1, 36.0, 7.1 Hz, 3H). $^{13}$C-nmr (CDCl$_3$): δ=175.0, 172.8, 157.4, 131.8, 131.8, 130.7, 116.6, 116.5, 113.9, 113.5, 64.1, 54.9, 51.1, 43.3, 37.4, 18.6. $C_{20}H_{22}F_2N_2O_4$ (MW=392); mass spectroscopy (MH$^+$)=393.

Example 230

Synthesis of N-2-Pyridylmethyl-N'-[N-(3,5-difluorophenylacetyl)-L-alaninyl]-L-phenylalaninamide Following General Procedure K and using N-[N-(3,5-difluorophenylacetyl)-L-alaninyl]-L-phenylalanine methyl ester (from Example 94 above) and 2-(aminomethyl)pyridine (Aldrich), the title compound was prepared.

NMR data was as follows:

$^1$H-nmr (CD$_3$OD): δ=8.45 (d, 1H), 7.75 (t, 1H), 7.2–7.4 (m, 6H), 7.1 (d, 1H), 6.8–7.0 (m, 3H) 4.63 (t, 1H) 4.45 (s, 2H), 4.2–4.35 (m, 1H), 3.6 (s, 2H), 3.0–3.25 (m, 2H), 1.30 (d, 3H). $^{13}$C-nmr (CD$_3$OD): δ=175.4, 174.0, 173.3, 166.6, 163.3, 163.2, 159.5, 150.0, 141.4, 139.4, 138.9, 130.9, 130.1, 128.4, 124.2, 123.2, 114.0, 113.9, 113.7, 113.6, 103.9, 103.2, 56.9, 51.4, 45.8, 43.1, 39.0, 18.2 $C_{26}H_{26}F_2N_4O_3$ (MW=480.52); mass spectroscopy (MH$^+$)=481.

Example 231

Synthesis of N-[α-Hydroxy-α'-pyrid-2-ylisopropyl]-N'-(3,5-difluorophenylacetyl)-L-alaninamide Following General Procedure S and using methyl N-[N-(3,5-difluorophenylacetyl)-L-alaninyl]-(S)-2-amino-3-(2-pyridyl)propionate (from Example 19 above), the title compound was prepared as a solid (mp=225–229° C.). The reaction was monitored by tlc (Rf=0.66 in 10% MeOH/DCM) and the product was purified by recrystallization from MeOH/diethyl ether.

NMR data was as follows:

$^1$H-nmr (CDCl$_3$): δ=8.21 (d, J=4.5 Hz, 1H), 7.46 (t, J=6.3, 7.6 Hz, 1H), 7.11 (d, J=7.6 Hz, 1H), 7.01 (t, J=5.5, 7.1 Hz, 1H), 6.70 (d, J=6.3 Hz, 2H), 6.62 (t, J=9.6, 9.0 Hz, 1H), 4.1 (m, 1H), 3.4 (m, 1H), 3.33 (s, 2H), 3.3 (m, 2H), 1.06 (d, J=7.0 Hz, 3H). $^{13}$C-nmr (CDCl$_3$): δ=172.754, 160.222, 150.134, 139.137, 126.198, 123.680, 113.936, 113.602, 103.578, 64.854, 53.689, 51.191, 43.304, 40.394, 18.769. C$_{19}$H$_{21}$F$_2$N$_3$O$_3$ (MW=377); mass spectroscopy (MH$^+$) 378.

Example 232

Synthesis of N-[α-Hydroxy-α'-pyrid-4-ylisopropyl]-N'-(3,5-difluorophenylacetyl)-L-alaninamide Following General Procedure S and using methyl N-[N-(3,5-difluorophenylacetyl)-L-alaninyl]-(S)-2-amino-3-(4-pyridyl)propionate (from Example 23 above), the title compound was prepared as a solid (mp=189–193° C.). The reaction was monitored by tlc (Rf=0.47 in 10% MeOH/DCM) and the product was purified by silica gel chromatography.

NMR data was as follows:

$^1$H-nmr (CDCl$_3$): δ=8.18 (d, J=5.6 Hz, 2H), 7.27 (d, J=5.6 Hz, 2H), 6.7 (m, 2H), 6.6 (m, 1H), 4.0 (m, 1H), 3.9 (m, 1H), 3.32 (s, 2H), 3.10 (s, 2H), 2.9 (m, 2H), 1.07 (d, J=7.2, 3H). $^{13}$C-nmr (CDCl$_3$): δ=175.8, 150.4, 150.2, 126.8, 113.9, 113.6, 103.6, 103.5, 72.0, 59.3, 55.2, 51.6, 42.9, 40.8, 38.3, 17.9. C$_{19}$H$_{21}$F$_2$N$_3$O$_3$ (MW=377); mass spectroscopy (MH$^+$) 378.

Example 233

Synthesis of N-[(S)-1-Hydroxy-4-methylpent-2-yl]-N'-(3,5-difluorophenylacetyl)-L-alaninamide Isomer A:

Following General Procedure B and using N-(3,5-difluorophenylacetyl)-L-alanine (from Example B2 above) and (S)-1-hydroxy-4-methylpent-2-ylamine (leucinol) (Bachem), the title compound was prepared as a solid (mp=141–151° C.). The reaction was monitored by tlc (Rf=0.5 in 5% MeOH/methylene chloride) and the product was purified by recrystallization from EtOAc/hexanes.

NMR data was as follows:

$^1$H-nmr (CD$_3$OD): δ=8.15 (s 1H), 7.5 (t, J=8 Hz, 1H), 6.80–6.55 (m, 3H), 4.15 (m, J=3.5 Hz, 1H), 3.7 (m 1H), 3.35 (s 2H), 3.22 (t, J=3 Hz, 2H), 1.4 (m, 1H), 1.1 (m, 5H), 0.7 (m, 6H). $^{13}$C-nmr (CD$_3$OD): δ=175.4, 175.3, 173.0, 113.9, 113.9, 113.6, 113.5, 103.9, 103.6, 103.2, 66.1, 51.6, 51.4, 51.3, 51.3, 43.4, 41.7, 41.6, 26.5, 26.3, 24.3, 22.8, 22.7, 19.0, 18.7, 18.6. C$_{17}$H$_{24}$N$_2$O$_3$F$_2$ (MW=342.19); mass spectroscopy (MH$^+$) 343.

Isomer B:

Following General Procedure B and using N-(3,5-difluorophenylacetyl)-L-alanine (from Example B2 above) and (S)-1-hydroxy-4-methylpent-2-ylamine (leucinol) (Aldrich), the title compound was prepared as a solid (mp=151–153° C.). The reaction was monitored by tlc (Rf=0.8 in 10% MeOH/DCM) and the product was purified by recrystallization, followed by flash column chromatography, followed by a preparative tlc using 10% MeOH/DCM as the eluent.

NMR data was as follows:

$^1$H-nmr (CD$_3$OD): δ=8.15 (s 1H), 7.5 (t, J=8 Hz, 1H), 6.80–6.55 (m, 3H), 4.15 (m, J=3.5 Hz, 1H), 3.7 (m, 1H), 3.35 (s, 2H), 3.22 (t, J=3 Hz, 2H), 1.4 (m, 1H), 1.1 (m, 5H), 0.7 (m, 6H). $^{13}$C-nmr (CD$_3$OD): δ=175.2, 172.9, 166.6, 166.5, 141.7, 113.9, 113.8, 113.6, 113.6, 103.9, 103.6, 103.2, 66.1, 51.2, 50.4, 50.1, 50.0, 49.8, 49.7, 49.6, 49.4, 49.38, 49.3, 49.0, 48.7, 43.4, 43.3, 41.7, 26.3, 24.3, 22.8, 18.7. C$_{17}$H$_{24}$N$_2$O$_3$F$_2$ (MW=342.19); mass spectroscopy (MH$^+$) 342.

Example 234

Synthesis of N-[1-Methoxyprop-2-yl]-N'-(3,5-difluorophenylacetyl)-L-alaninamide

Following General Procedure B and using N-(3,5-difluorophenylacetyl)-L-alanine (from Example B2 above) and 2-amino-1-methoxypropane (Aldrich), the title compound was prepared as a solid (mp=152° C.). The reaction was monitored by tlc (Rf=0.45 in 5% MeOH/DCM) and the product was purified by recrystallization from methanol/water.

NMR data was as follows:

$^1$H-nmr (CDCl$_3$): δ=6.9–6.7 (m, 3H), 6.6 (d, J=7 Hz, 1H), 6.3 (m, 1H), 4.5 (m, J=7 Hz, 1H), 4.1 (m, 1H), 3.5 (s, 2H), 3.3 (m, 5H), 1.4 (d, J=7 Hz, 3H), 1.15 (t, J=8 Hz, 3H). $^{13}$C-nmr (CDCl$_3$): δ=172.0, 113.0, 112.9, 112.62, 112.60, 103.7, 103.4, 78.0, 77.6, 77.2, 75.8, 75.7, 59.6, 59.58, 49.6, 49.5, 45.6, 45.6, 43.4, 19.4, 19.38, 18.9, 18.0. C$_{17}$H$_{20}$N$_2$O$_3$F$_2$ (MW=314.14); mass spectroscopy (MH$^+$) 315.

Example 235

Synthesis of N-[1-Hydroxy-3-methylbut-2-yl]-N'-(3,5-difluorophenylacetyl)-L-alaninamide Following General Procedure B and using N-(3,5-difluorophenylacetyl)-L-alanine (from Example B2 above) and valinol (Bachem), the title compound was prepared as a solid (mp=176–179° C.). The reaction was monitored by tlc (Rf=0.4 in 5% MeOH/DCM) and the product was purified by recrystallization from EtOAc/hexanes.

NMR data was as follows:

$^1$H-nmr (CD$_3$OD): δ=7.5 (d, J=9 Hz, 1H), 6.8–6.5 (m, 3H), 4.15 (m, 1H), 3.45 (m, 2H), 3.35 (m, 3H), 1.65 (m, J=7 Hz, 1H), 1.20 (d, J=5 Hz, 3H), 0.7 (m, 6H). $^{13}$C-nmr (acetone-d$_6$): δ=113.7, 113.4, 103.0, 63.3, 57.7, 57.69, 50.5, 50.4, 43.2, 31.1, 30.8, 30.6, 30.5, 30.3, 30.2, 30.1, 29.9, 29.9, 29.8, 29.7, 29.6, 20.5, 20.4, 19.5, 19.1, 19.0, 18.8. C$_{16}$H$_{22}$N$_2$O$_3$F$_2$ (MW=329.19); mass spectroscopy (MH$^+$) 329.

Example 236

Synthesis of Methyl N-[N-(3,5-Difluorophenylacetyl)-L-alaninyl]-2-amino-2-(6-aminopyrid-2-yl)acetate Following General Procedure C and using N-(3,5-difluorophenylacetyl)-L-alanine (from Example B2 above) and methyl 2-amino-2-(6-aminopyrid-2-yl)acetate (prepared from 2-(methoxyimino)-2-(6-aminopyrid-2-yl)acetic acid [CAS 71470-33-2] using General Procedures G and AC above), the title compound was prepared. The product was purified by LC 2000 preparative column chromatography using 1:1 EtOAc/hexanes as the eluent.

NMR data was as follows:

$^1$H-nmr (CDCl$_3$): δ=7.65–6.5 (m, 6H), 6.4 (d, J=8.19 Hz, 1H), 5.49–5.33 (m, 1H), 4.8–4.5 (m, 2H), 3.7 (s, 3H), 3.6 (s, 1H), 3.5 (s, 1H), 2.06 (bs, 2H), 1.44 (d, J=7.06 Hz, 1.5H), 1.35 (d, 7.06 Hz, 1.5H). C$_{19}$H$_{20}$4O$_4$F$_2$ (MW=406.39); mass spectroscopy (MH$^+$) 406.3.

Example 237

Synthesis of N-[1-Hydroxyprop-2-yl]-N'-(3,5-difluorophenylacetyl)-L-alaninamide

Following General Procedure B and using N-(3,5-difluorophenylacetyl)-L-alanine (from Example B2 above)

and alanol (Bachem), the title compound was prepared as a solid (mp=158–163° C.). The reaction was monitored by tlc (Rf=0.7 in 10% MeOH/DCM) and the product was purified by recrystallization from ethyl acetate, followed by flash column chromatography using 10% MeOH/DCM.

NMR data was as follows:

$^1$H-nmr (CD$_3$OD): δ=8.2 (m, 1H), 7.6 (m, 1H), 4.1 (m, J=7 Hz, 1H), 3.7 (m, J=5 Hz, 1H), 3.35 (s, 2H), 3.25 (m, 2H), 1.15 (d, J=7 Hz, 3H), 0.9 (d, J=7 Hz, 3H). $^{13}$C-nmr (CD$_3$OD): δ=175.1, 175.06, 172.9, 166.6, 166.5, 163.4, 163.2, 141.6, 113.9, 113.8, 113.7, 113.6, 103.9, 103.6, 103.2, 66.5, 51.4, 51.3, 51.3, 51.2, 50.4, 50.1, 49.8, 49.77, 49.6, 49.5, 49.3, 49.1, 49.0, 48.7, 43.3, 18.8, 17.5. C$_{14}$H$_{18}$N$_2$O$_3$F$_2$ (MW=300); mass spectroscopy (MH$^+$) 301.

Example 238

Synthesis of N-[(S)-2-Methoxy-1-phenyleth-1-yl]-N'-(3,5-difluorophenylacetyl)-L-alaninamide Following General Procedure C and using 3,5-difluorophenylacetic acid (Oakwood) and N-[(S)-2-methoxy-1-phenyleth-1-yl]-L-alaninamide (prepared from N-BOC-L-alanine (Sigma) and (S)-phenylglycinol methyl ether (from Example D15 above) using General Procedure C, followed by removal of the BOC-group using General Procedure P), the title compound was prepared as a solid (mp=180–182° C.). The reaction was monitored by tlc (Rf=0.4 in 10% MeOH/CHCl$_3$) and the product was purified by silica gel chromatography using 5% MeOH/CHCl$_3$ as the eluent, followed by recrystallization from 1-chlorobutane/acetonitrile.

NMR data was as follows:

$^1$H-nmr (DMSO-d$_6$): δ=1.22 (d, 3H), 3.23 (s, 3H). Optical Rotation: [α]$_{20}$=+12.3° @ 589 nm (c 1.04, DMSO). C$_{20}$H$_{22}$F$_2$N$_2$O$_3$ (MW=376.41); mass spectroscopy (MH$^+$) 377.

Example 239

Synthesis of N-[(S)-1-Methoxy-2-phenylprop-2-yl]-N'-(3,5-difluorophenylacetyl)-L-alaninamide Following General Procedure B and using N-(3,5-difluorophenylacetyl)-L-alanine (from Example B2 above) and L-phenylalaninol methyl ether hydrochloride (Fluka), the title compound was prepared as a fluffy solid. The product was purified by recrystallization from MeOH/EtOAc.

NMR data was as follows:

$^1$H-nmr (CDCl$_3$): δ=1.31 (d, J=7 Hz, 3H), 2.8 (d, J=7 Hz, 2H), 3.28 (d, J=3 Hz, 2H), 3.32 (s, 3H), 3.47 (s, 2H), 4.15–4.3 (m, 1H), 4.35–4.5 (m, 1H), 6.3–6.5 (m, 2H), 6.6–6.9 (m, 3H), 7.1–7.35 (m, 5H). $^{13}$C-nmr (CDCl$_3$): δ=19.1, 37.8, 43.4, 49.6, 51.0, 59.6, 72.7, 103.4, 112.6, 113.0, 127.1, 129.0, 129.9, 138.3, 169.8, 172.1.

Example 240

Synthesis of N-[(S)-1-Acetoxyhex-2-yl]-N'-(3,5-difluorophenylacetyl)-L-alaninamide Following General Procedure V and using N-[(S)-1-hydroxyhex-2-yl]-N'-(3,5-difluorophenylacetyl)-L-alaninamide (from Example 228 above), the title compound was prepared as a solid (mp=144–145° C.). The reaction was monitored by tlc (Rf=0.42 in 10% CH$_3$OH/CH$_2$Cl$_2$).

NMR data was as follows:

$^1$H-nmr (CD$_3$OD): δ=6.7 (m, 2H), 6.6 (m, 1H), 4.09 (q, 1H), 3.9–3.7 (m, 3H), 3.35 (s, 2H), 1.79 (s, 3H), 1.4–1.0 (m, 9H), 0.6 (m, 3H). $^{13}$C-nmr (CD$_3$OD): δ=175.5, 173.2, 172.8, 166.6, 166.5, 163.4, 163.2, 141.8, 141.7, 141.5, 113.9, 113.8, 113.7, 113.6, 103.9, 103.5, 103.2, 67.5, 51.2, 43.28, 43.26, 32.2, 29.6, 24.0, 21.3, 18.8, 14.8. C$_{19}$H$_{26}$F$_2$N$_2$O$_4$ (MW=384.43); mass spectroscopy (MH$^+$) 385.

Example 241

Synthesis of N-[(S)-1-(tert-Butylcarbonyloxy)-hex-2-yl]-N'-(3,5-difluorophenylacetyl)-L-alaninamide Following General Procedure W and using N-[(S)-1-hydroxyhex-2-yl]-N'-(3,5-difluorophenylacetyl)-L-alaninamide (from Example 228 above) and trimethylacetyl chloride (Aldrich), the title compound was prepared as a solid (mp=104–107.5° C.). The reaction was monitored by tlc (Rf=0.43 in 10% CH$_3$OH/CH$_2$Cl$_2$) and the product was purified by preparative thin layer chromatography using 10% CH$_3$OH/CH$_2$Cl$_2$ as the eluent.

NMR data was as follows:

$^1$H-nmr (CD$_3$OD): δ=7.67 (bd, 1H), 6.7 (m, 2H), 6.6 (m, 1H), 4.14 (q, 1H), 3.9–3.6 (m, 3H), 3.35 (s, 2H), 1.4–1.0 (m, 9H), 0.98 (s, 9H), 0.6 (m, 3H). $^{13}$C-nmr (CD$_3$OD): δ=180.3, 175.3, 175.2, 172.8, 166.6, 166.5, 163.4, 163.2, 141.8, 141.7, 141.5, 133.9, 113.8, 113.7, 113.6, 103.9, 103.6, 103.2, 67.6, 51.1, 51.0, 43.3, 40.4, 32.4, 32.3, 29.5, 28.2, 24.0, 19.0, 14.9. C$_{22}$H$_{32}$F$_2$N$_2$O$_4$ (MW=426.51); mass spectroscopy (MH$^+$) 427.5.

Example 242

Synthesis of N-[2-Hydroxy-1-(thien-2-yl)ethyl]-N'-(3,5-difluorophenylacetyl)-L-alaninamide Following General Procedure S and using methyl N-[N-(3,5-difluorophenylacetyl)-L-alaninyl]-(S)-2-amino-2-(2-thienyl)acetate (from Example 178 above), the title compound was prepared as a solid (mp=201–202° C.). The product was purified by trituration using 1:1 hexanes/EtOAc.

NMR data was as follows:

$^1$H-nmr (DMSO-d$_6$): δ=8.4–8.25 (m, 2H), 7.4–7.35 (m, 2H), 7.3–6.91 (m, 4H), 5.1–4.85 (m, 1H), 4.4–4.3 (m, 1H), 3.7–3.5 (m, 2H), 3.51 (s, 1H), 3.50 (s, 1H), 1.23–1.19 (overlaying doublets, 3H). C$_{21}$H$_{23}$F$_2$N$_2$O$_3$ (MW=368.4); mass spectroscopy (MH$^+$) 368.

Example 243

Synthesis of N-[(S)-2-hydroxy-2-methyl-1-phenylprop-1-yl]-N'-(3,5-difluorophenylacetyl)-L-alaninamide Following General Procedure C and using N-(3,5-difluorophenylacetyl)-L-alanine (from Example B2 above) and (S)-2-hydroxy-2-methyl-1-phenylprop-1-ylamine (from Example D 16 above), the title compound was prepared as a solid. The product was purified by recrystallization from methanol/ethyl acetate.

NMR data was as follows:

$^1$H-nmr (DMSO-d$_6$): δ=8.32 (d, 1H), 8.11 (d, 1H), 7.20–7.33 (m, 5H), 7.08 (m, 1H), 6.96 (m, 2H), 4.68 (d, 1H), 4.53 (s, 1H), 4.95 (m, 1H), 3.50 (d, 2H), 1.25 (d, 3H), 1.08 (s, 3H), 0.98 (s, 3H). Optical Rotation: [α]$_{23}$=−11° (C 1, MeOH). C$_{21}$H$_{24}$F$_2$N$_2$O$_3$ (MW=390.42); mass spectroscopy (MH$^+$) 391.

Example 244

Synthesis of N-[N-(3,5-Difluorophenylacetyl)-L-(thien-2-yl)glycinyl]-L-phenylalanine tert-Butyl Ester Following General Procedure E and using 3,5-difluorophenylacetic acid (Aldrich) and L-(2-thienyl)glycinyl-L-phenylglycine tert-butyl ester (prepared using N-(9-florenylmethoxycarbonyl)-L-(2-thienyl)glycine (prepared as described below) and L-phenylglycine tert-butyl ester hydrochloride using General Procedure AH, followed by deprotection using dicyclohexylamine in DMF and THF), the title compound was prepared as a solid (mp=176–177° C.). The product was purified by flash chromatography using EtOAc/dichloromethane as the eluent.

$C_{26}H_{26}N_2O_4F_2$ (MW=500.56); mass spectroscopy (MH$^+$) 500.

Preparation of N-(9-Fluorenylmethoxycarbonyl)-L-(2-Thienyl)glycine: A round bottom flask containing a magnetic stir bar under an atmosphere of nitrogen at room temperature was charged with water, dioxane, sodium carbonate (2.5 eq.) and L-α-(2-thienyl)glycine (1.0 eq.) (Sigma). Stirring was initiated and the slurry was cooled in an ice bath. 9-Flurenylmethyl chloroformate was added portionwise to the reaction and stirring was continued in an ice bath for 4 hours followed by 8 hours at room temperature. The reaction mixture was poured onto water and extracted with diethyl ether. The aqueous layer was cooled in an ice bath and acidified with vigorous stirring to a pH of 2. The resulting solid was isolated via vacuum filtration, washed with water (3×) and dried under reduced pressure.

Example 245

Synthesis of N-[N-(3,5-Difluorophenylacetyl)-L-phenylglycinyl]-L-phenylglycinol

Following General Procedure E and using 3,5-difluorophenylacetic acid (Aldrich) and L-phenylglycinyl-L-phenylglycinol (prepared from N-BOC-L-phenylgycine (Novabiochem) and L-phenylglycinol (Novabiochem) using General Procedure AH, followed by removal of the BOC-group using General Procedure P), the title compound was prepared as a solid (mp=231.4° C.). The product was purified by crystallization from ethyl acetate.

$C_{24}H_{22}N_2O_3F_2$ (MW=424.45); mass spectroscopy (MH$^+$) 424.9.

Example 246

Synthesis of N-[N-(Cyclopropaneacetyl)-L-phenylglycinyl]-L-phenylglycinol

Following General Procedure E and using cyclopropaneacetic acid (Aldrich) and L-phenylglycinyl-L-phenylglycinol (prepared from N-BOC-L-phenylgycine (Novabiochem) and L-phenylglycinol (Novabiochem) using General Procedure AH, followed by removal of the BOC-group using General Procedure P), the title compound was prepared as a solid (mp=202.5° C.). The product was purified by crystallization from ethyl acetate.

$C_{21}H_{24}N_2O_3$ (MW=352.43); mass spectroscopy (MH$^+$) 353.2.

Example 247

Synthesis of N-[N-(Cyclopentaneacetyl)-L-phenylglycinyl]-L-phenylglycinol

Following General Procedure E and using cyclopentaneacetic acid (Aldrich) and L-phenylglycinyl-L-phenylglycinol (prepared from N-BOC-L-phenylgycine (Novabiochem) and L-phenylglycinol (Novabiochem) using General Procedure AH, followed by removal of the BOC-group using General Procedure P), the title compound was prepared as a solid (mp=201.4° C.). The product was purified by flash chromatography using MeOH/CH$_2$CH$_2$ as the eluent.

$C_{23}H_{28}N_2O_3$ (MW=380.49); mass spectroscopy (MH$^+$) 381.4.

Example 248

Synthesis of N-[N-(3,5-Difluorophenylacetyl)-D,L-phenylglycinyl]-D,L-phenylglycinamide Following General Procedure AO and using N-[N-(3,5-difluorophenylacetyl)-D,L-phenylglycinyl]-D,L-phenylglycine methyl ester (from Example 99 above), the title compound was prepared as a solid (mp=285.5–288.5° C).

$C_{24}H_{21}N_3O_3F_2$ (MW=437.45); mass spectroscopy (MH$^+$) 437.1.

Example 249

Synthesis of N-[N-(3,5-Difluorophenylacetyl)-D,L-valinyl]-D,L-phenylglycinamide

Following General Procedure AO and using N-[N-(3,5-difluorophenylacetyl)-L-valinyl]-L-phenylglycine methyl ester (from Example 94 above), the title compound was prepared as a solid (mp=260.3–264.3° C.). The product was purified by recrystallization from ethyl acetate/methanol.

$C_{20}H_{23}N_3O_3F_2$ (MW=403.43); mass spectroscopy (MH$^+$) 404.

Example 250

Synthesis of N-[N-(2-Thienylacetyl)-L-alaninyl]-L-phenylglycinamide

Following the General Procedures described herein, the title compound was prepared.

Example 251

Synthesis of N-[N-(n-Caproyl)-L-alaninyl]-L-phenylglycinamide

Following the General Procedures described herein, the title compound was prepared.

Example 252

Synthesis of N-[N-(3,5-Difluorophenylacetyl)-L-norleucinyl]-L-phenylglycine Methyl Ester Following General Procedure E and using 3,5-difluorophenylacetic acid (Aldrich) and L-phenylglycinyl-L-phenylglycine methyl ester hydrochloride (prepared from N-BOC-L-norleucine (Lancaster) and L-phenylglycine methyl ester hydrochloride (Aldrich) using General Procedure E, followed by removal of the BOC-group using General Procedure P), the title compound was prepared as a solid (mp=188–189.5° C.). The product was purified by flash chromatography using ethyl acetate/hexanes as the eluent.

$C_{23}H_{26}N_2O_4F_2$ (MW=432.47); mass spectroscopy (MH$^+$) 432.

Example 253

Synthesis of N-[N-(3,5-Difluorophenylacetyl)-L-norvalinyl]-L-phenylglycine Methyl Ester Following General Procedure E and using 3,5-difluorophenylacetic acid (Aldrich) and L-norvalinyl-L- phenylglycine methyl ester hydrochloride (prepared from N-BOC-L-norvaline (Lancaster) and L-phenylglycine methyl ester hydrochloride (Aldrich) using General Procedure E, followed by removal of the BOC-group using General Procedure P), the title compound was prepared as a solid (mp=204–205° C.). The product was purified by flash chromatography using ethyl acetate/hexanes as the eluent.

$C_{22}H_{24}N_2O_4F_2$ (MW=418.44); mass spectroscopy (MH$^+$) 418.3.

Example 254

Synthesis of N-[N-(3,5-Difluorophenylacetyl)-L-tert-leucinyl]-L-phenylglycine Methyl Ester Following General Procedure E and using 3,5-difluorophenylacetic acid (Aldrich) and L-tert-leucinyl-L-phenylglycine methyl ester hydrochloride (prepared from N-BOC-L-tert-leucine (Bachem) and L-phenylglycine methyl ester hydrochloride (Aldrich) using General Procedure E, followed by removal of the BOC-group using General Procedure P), the title compound was prepared as a solid (mp=176.4° C.). The product was purified by flash chromatography using ethyl acetate/hexanes as the eluent.

$C_{23}H_{26}N_2O_4F_2$ (MW=432.47); mass spectroscopy (MH$^+$) 432.0.

Example 255

Synthesis of N-[N-(3,5-Difluorophenylacetyl)-L-isoleucinyl]-L-phenylglycine Methyl Ester Following General Procedure E and using 3,5-difluorophenylacetic acid (Aldrich) and L-isoleucinyl-L-phenylglycine methyl ester hydrochloride (prepared from N-BOC-L-isoleucine (Aldrich) and L-phenylglycine methyl ester hydrochloride (Aldrich) using General Procedure E, followed by removal of the BOC-group using General Procedure P), the title compound was prepared as a solid (mp=228.8° C.). The product was purified by flash chromatography using ethyl acetate/hexanes as the eluent.

$C_{23}H_{26}N_2O_4F_2$ (MW=432.46); mass spectroscopy (MH$^+$) 433.4.

Example 256

Synthesis of N-[N-(3,5-Difluorophenylacetyl)-L-cyclohexylalaninyl]-L-phenylglycine Methyl Ester Following General Procedure E and using 3,5-difluorophenylacetic acid (Aldrich) and L-cyclohexylalaninyl-L-phenylglycine methyl ester hydrochloride (prepared from N-BOC-L-cyclohexylalanine (Sigma) and L-phenylglycine methyl ester hydrochloride (Aldrich) using General Procedure E, followed by removal of the BOC-group using General Procedure P), the title compound was prepared as a solid (mp=174.8° C.). The product was purified by flash chromatography using ethyl acetate/hexanes as the eluent.

$C_{26}H_{30}N_2O_4F_2$ (MW=472.53); mass spectroscopy (MH$^+$) 473.2.

Example 257

Synthesis of N-[N-(3,5-Difluorophenylacetyl)-(S)-2-amino-2-(cyclopropyl)acetyl]-L-phenylglycine Methyl Ester Following General Procedure E and using 3,5-difluorophenylacetic acid (Aldrich) and (S)-2-amino-2-(cyclopropyl)acetyl-L-phenylglycine methyl ester hydrochloride (prepared from N-BOC-(S)-2-amino-2-cyclopropylacetic acid (prepared from cyclopropylacetic acid (Lancaster) and (4S)-4-benzyl-2-oxaxolidinone (Aldrich) using the procedures described in Evans et al., *J. Am. Chem. Soc.*, 1990, 112, 4011–4030 and references cited therein) and L-phenylglycine methyl ester hydrochloride (Aldrich) using General Procedure E, followed by removal of the BOC-group using General Procedure P), the title compound was prepared as a solid (mp=225–226.5° C.). The product was purified by flash chromatography using MeOH/CHCl$_3$ as the eluent.

$C_{22}H_{22}N_2O_4F_2$ (MW=416.42); mass spectroscopy (MH$^+$) 417.3.

Example 258

Synthesis of N-[N-(3,5-Difluorophenylacetyl)-(S)-2-amino-2-(thien-3-yl)acetyl]-L-phenylglycine Methyl Ester Following General Procedure E and using 3,5-difluorophenylacetic acid (Aldrich) and L-(S)-2-amino-2-(thien-3-yl)acetyl-L-phenylglycine methyl ester hydrochloride (prepared from N-BOC-L-thien-3-ylglycine (prepared from L-α-2-thienylglycine (Sigma) using General Procedure AJ) and L-phenylglycine methyl ester hydrochloride (Aldrich) using General Procedure E, followed by removal of the BOC-group using General Procedure P), the title compound was prepared as a solid (mp=229.3° C.). The product was purified by crystallization from ethyl acetate/hexanes.

$C_{23}H_{20}N_2O_4SF_2$ (MW=458.49); mass spectroscopy (MH$^+$) 458.

Example 259

Synthesis of N-[N-(3,5-Difluorophenylacetyl)-(S)-2-amino-2-(thien-2-yl)acetyl]-L-phenylglycine Methyl Ester Following General Procedure AH and using 3,5-difluorophenylacetic acid (Aldrich) and L-(S)-2-amino-2-(thien-2-yl)acetyl-L-phenylglycine methyl ester hydrochloride (prepared from N-BOC-L-thien-2-ylglycine (prepared from L-α-(thien-2-yl)glycine (Sigma) using General Procedure AI) and L-phenylglycine methyl ester hydrochloride (Aldrich) using General Procedure E, followed by removal of the BOC-group using General Procedure P), the title compound was prepared as a solid (mp=230.8° C.). The product was purified by flash chromatographyl using MeOH/CH$_2$CH$_2$ as the eluent.

$C_{23}H_{20}N_2O_4F_2S$ (MW=458.49); mass spectroscopy (MH$^+$) 458.

Example 260

Synthesis of N-[N-(3,5-Difluorophenylacetyl)-L-(4-fluorophenyl)glycinyl]-L-phenylglycine Methyl Ester Following General Procedure E and using 3,5-difluorophenylacetic acid (Aldrich) and L-(4-fluorophenyl)glycinyl-L-phenylglycine methyl ester hydrochloride (prepared from N-Cbz-(4-fluorophenyl)glycine (prepared from (4-fluorophenyl)glycine (prepared as described below) using General Procedure AK) and L-phenylglycine methyl ester hydrochloride (Aldrich) using General Procedure E, followed by silica gel chromatography using 5% ethyl acetate/toluene as the eluant and removal of the Cbz-group using General Procedure AJ), the title compound was prepared as a solid (mp=213.1° C.). The product was purified by flash chromatography using ethyl acetate/CHCl$_3$ as the eluent.

$C_{25}H_{212}O_4F_2$ (MW=470.44); mass spectroscopy (MH$^+$) 470.1.

Preparation of (4-Fluorophenyl)glycine:

(S)-(−)-4-Benzyl-2-oxazolidinone (15.0 g, 93 mmol) (Aldrich) was dissolved in THF (100 mL). The solution was cooled to −70° C. and reaction flask was purged twice with nitrogen. n-Butyl lithium (44.6 mL, 2.0 M, 89 mmol) was added to form a solid precipitate which broke up on stirring wo afford a slurry. 4-Fluorophenylacetyl chloride 16.1 g, 93 mmol) (Aldrich) was added to afford a light green solution and stirring was continued for 45 minutes. The reaction mixture was then stirred at room temperature for 1 hour. The reaction mixture was then treated with saturated sodium bisulfate (100 mL) and ethyl acetate (100 mL). The organic phase was washed with water, followed by brine. The organic phase was then dried over anhydrous sodium sulfate and concentrated under reduced pressure to afford an oil. The oil was crystallized to afford 24.4 g of 1-(4-fluorophenylacetyl)-(S)-(−)-4-Benzyl-2-oxazolidinone.

Potassium hexamethyldisilazane (140 mL, 0.5M, 70.0 mmol) was added to THF (80 mL). The solution was cooled to −50° C. under nitrogen and a cold solution (−60° C.) of 1-(4-fluorophenylacetyl)-(S)-(−)-4-benzyl-2-oxazolidinone (15.0 g, 46 mmol) in THF (100 mL). The resulting mixture was allowed to stir at −70° C. for 1 hour and to warm to about −20° C. The mixture was re-cooled to −70° C. and a cold solution (−65° C.) of trasylazide (21.6 g, 70.0 mmol) was added. The mixture was allowed to stir for about 15 min. while warming to −45° C. and then glacial acetic acid (18 mL) was added. The mixture was then stirred at about 30° C. for 3 hours. A precipitate formed and was removed by filtration. The filtrate was concentrated by 50 and then washed with water, saturated sodium bicarbonate solution and brine. The organic phase was dried over sodium sulfate, concentrated under reduced pressure to afford 37.7 g of crude 1-[2-(4-fluorophenyl)-2-azidoacetyl]-(S)-(−)-4-benzyl-2-oxazolidinone.

Crude 1-[2-(4-fluorophenyl)-2-azidoacetyl]-(S)-(−)-4-benzyl-2-oxazolidinone (10.0 g, 28.0 mmol) was dissolved in 100 mL of THF and 100 mL of methanol and trifluoroacetic acid (4.31 mL, 75.3 mmol) was added. Pallidium on carbon (10%, 2.0 g) was added and the mixture was hydrogenated on a Paar shaker at 50 psi overnight at room temperature. The reaction mixture was then filtered through a plug of Celite and the solid cake was rinsed with 100 mL of methanol. The filterate was concentrated to afford 1-[2-(4-fluorophenyl)-2-aminoacetyl]-(S)-(−)-4-benzyl-2-oxazolidinone trifluoroacetate salt as a yellowish oil.

To a mixture of THF and de-ionized water (50 mL/50 mL) was added 1-[2-(4-fluorophenyl)-2-aminoacetyl]-(S)-(−)-4-benzyl-2-oxazolidinone trifluoroacetate salt (4.14 g, 9.7 mmol) and lithium hydroxide monohydrate (1.22 g, 29 mmol). The homogenous solution was stirred for 2 hours at room temperature at which time Tlc indicated complete disappearance of starting material. The mixture was extracted with dichloromethane (3×100 mL) and the aqueous phase was acidified to pH 2–3 while cooling in an ice-bath. A precipitate formed. The mixture was then cooled in an ice-bath for 1.5 hours and then filtered. The solid was washed with water followed by pentane to afford 4-fluorophenylglycine hydrochloride.

Example 261

Synthesis of N-[N-(3,5-Difluorophenylacetyl)-D-(4-fluorophenyl)glycinyl]-L-phenylglycine Methyl Ester Following General Procedure E and using 3,5-difluorophenylacetic acid (Aldrich) and D-(4-fluorophenyl)glycinyl-L-phenylglycine methyl ester hydrochloride (prepared from N-Cbz-(4-fluorophenyl)glycine (prepared from (4-fluorophenyl)glycine (prepared as in Example 260) using General Procedure AK) and L-phenylglycine methyl ester hydrochloride (Aldrich) using General Procedure E, followed by silica gel chromatography using 5% ethyl acetate/toluene as the eluant and removal of the Cbz-group using General Procedure AJ), the title compound was prepared as a solid (mp=188.0° C.). The product was purified by flash chromatography using ethyl acetate/CHCl$_3$ as the eluent.

$C_{25}H_{21}N_2O_4F_3$ (MW=470.44); mass spectroscopy (MH$^+$) 470.1.

Example 262

Synthesis of N-[N-(3,5-Difluorophenylacetyl)-L-(4-methoxyphenyl)glycinyl]-L-phenylglycine Methyl Ester Following General Procedure E and using 3,5-difluorophenylacetic acid (Aldrich) and L-(4-methoxyphenyl)glycinyl-L-phenylglycine methyl ester hydrochloride (prepared from N-Cbz-L-(4-methoxyphenyl)glycine (prepared from (4-methoxyphenyl)glycine (prepared by the Bucherer modification of the Strecker procedure as described in Greenstein et al., "The Chemistry of Amino Acids", Vol. 1, p. 698, Wiley, New York (1961)) using General Procedure AK) and L-phenylglycine methyl ester hydrochloride (Aldrich) using General Procedure E, followed by removal of the Cbz-group using General Procedure AJ), the title compound was prepared as a solid (mp=224.6° C.). The product was purified by flash chromatography using MeOH/CHCl$_3$ as the eluent.

$C_{26}H_{24}N_2O_5F_2$ (MW=482.48); mass spectroscopy (MH$^+$) 482.1.

Example 263

Synthesis of N-[N-(3,5-Difluorophenylacetyl)-L-phenylglycinyl]-L-phenylglycine tert-Butyl Ester Following General Procedure E and using 3,5-difluorophenylacetic acid (Aldrich) and L-phenylglycinyl-L-phenylglycine tert-butyl ester (prepared from N-Cbz-L-phenylglycine (Novabiochem) and L-phenylglycine tert-butyl ester hydrochloride (Novabiochem) using General Procedure AH, followed by removal of the Cbz-group using General Procedure AJ), the title compound was prepared as a solid (mp=185.0° C.). The product was purified by flash chromatography using ethyl acetate/CH$_2$CH$_2$ as the eluant.

$C_{28}H_{28}N_2O_4F_2$ (MW=494.54); mass spectroscopy (MH$^+$, minus CO$_2$-t-Bu) 393.

Example 264

Synthesis of N-[N-(Cyclopropylacetyl)-L-phenylglycinyl]-L-phenylglycine tert-Butyl Ester Following General Procedure E and using cyclopropylacetic acid (Aldrich) and L-phenylglycinyl-L-phenylglycine tert-butyl ester hydrochloride (prepared from N-Cbz-L-phenylglycine (Novabiochem) and L-phenylglycine tert-butyl ester hydrochloride (Novabiochem) using General Procedure AH, followed by removal of the Cbz-group using General Procedure AJ), the title compound was prepared as a solid (mp=187.5° C.). The product was purified by crystallization from ethyl acetate.

$C_{25}H_{30}N_2O_4$ (MW=422.53); mass spectroscopy (MH$^+$) 423.4.

Example 265

Synthesis of N-[N-(Cyclopentylacetyl)-L-phenylglycinyl]-L-phenylglycine tert-Butyl Ester Following General Procedure E and using cyclopropylacetic acid (Aldrich) and L-phenylglycinyl-L-phenylglycine tert-butyl ester hydrochloride (prepared from N-Cbz-L-phenylglycine (Novabiochem) and L-phenylglycine tert-butyl ester hydrochloride (Novabiochem) using General Procedure AH, followed by removal of the Cbz-group using General Procedure AJ), the title compound was prepared as a solid (mp=190.8° C.). The product was purified by crystallization from ethyl acetate.

$C_{27}H_{34}N_2O_4$ (MW=450.58); mass spectroscopy (MH$^+$) 451.

Example 266

Synthesis of N-[N-(t-Butylacetyl)-L-alaninyl]-L-phenylglycinamide

Following the General Procedures described herein, the title compound was prepared.

Example 267

Synthesis of N-tert-Butyl-N'-[N-(3,5-Difluorophenylacetyl)-L-alaninyl]-L-(5-bromothien-2-yl)glycinamide Following General Procedure AB and using N-(3,5-difluorophenylacetyl)-L-alanine (from Example B2 above), 5-bromo-2-thiophenecarboxaldehyde (Aldrich), (S)-(−)-α-methylbenzylamine (Aldrich) and tert-butylisocyanide (Aldrich), the title compound was prepared as a solid (mp 227–228° C.). The product was purified by recrystallization from ethyl acetate/hexanes.

$C_{21}H_{24}N_3O_3BrS$ (MW 515); mass spectroscopy (MH$^+$) 515, 415.

Example 268

Synthesis of N-tert-Butyl-N'-[N-(3,5-Difluorophenylacetyl)-L-alaninyl]-D-(5-bromothien-2-yl)glycinamide Following General Procedure AB and using N-(3,5-difluorophenylacetyl)-L-alanine (from Example B2 above), 5-bromo-2-thiophenecarboxaldehyde (Aldrich), (S)-(−)-α-methylbenzylamine (Aldrich) and tert-butylisocyanide (Aldrich), the title compound was prepared as a solid (mp=216–217° C.). The product was purified by recrystallization from ethyl acetate/hexanes.

$C_{21}H_{24}N_3O_3BrS$ (MW=515); mass spectroscopy (MW) 515, 415.

Example 269

Synthesis of N-tert-Butyl-N'-[N-(3,5-Difluorophenylacetyl)-L-alaninyl]-L-(4-bromothien-2-yl)glycinamide Following General Procedure AB and using N-(3,5-difluorophenylacetyl)-L-alanine (from Example B2 above), 4-bromo-2-thiophenecarboxaldehyde (Aldrich), (S)-(−)-α-methylbenzylamine (Aldrich) and tert-butylisocyanide (Aldrich), the title compound was prepared as a solid (mp=246–247° C.). The product was purified by recrystallization from ethyl acetate/hexanes.

$C_{21}H_{24}N_3O_3BrS$ (MW=515); mass spectroscopy (MH$^+$) 515, 415.

Example 270

Synthesis of N-tert-Butyl-N'-[N-(3,5-Difluorophenylacetyl)-L-alaninyl]-L-(thien-2-yl)glycinamide Following General Procedure AB and using N-(3,5-difluorophenylacetyl)-L-alanine (from Example B2 above), 2-thiophenecarboxaldehyde (Aldrich), (S)-(−)-α-methylbenzylamine (Aldrich) and tert-butylisocyanide (Aldrich), the title compound was prepared as a solid (mp=241–242° C.). The product was purified by recrystallization from ethyl acetate/hexanes.

$C_{21}H_{25}N_3O_3F_2S$ (MW=438); mass spectroscopy (MH$^+$) 438, 338.

Example 271

Synthesis of N-tert-Butyl-N'-[N-(3,5-Difluorophenylacetyl)-L-alaninyl]-D-(thien-2-yl)glycinamide Following General Procedure AB and using N-(3,5-difluorophenylacetyl)-L-alanine (from Example B2 above), 2-thiophenecarboxaldehyde (Aldrich), (S)-(−)-α-methylbenzylamine (Aldrich) and tert-butylisocyanide (Aldrich), the title compound was prepared as a solid (mp=235–236° C.). The product was purified by recrystallization from ethyl acetate/hexanes.

$C_{21}H_{25}N_3O_3F_2S$ (MW=438); mass spectroscopy (MH$^+$) 438, 338.

Example 272

Synthesis of N-tert-Butyl-N'-[N-(3,5-Difluorophenylacetyl)-L-alaninyl]-L-(thien-3-yl)glycinamide Following General Procedure AB and using N-(3,5-difluorophenylacetyl)-L-alanine (from Example B2 above), 3-thiophenecarboxaldehyde (Aldrich), (S)-(−)-α-methylbenzylamine (Aldrich) and tert-butylisocyanide (Aldrich), the title compound was prepared as a solid (mp=240–241° C.). The product was purified by recrystallization from ethyl acetate/hexanes.

$C_{21}H_{25}N_3O_3F_2S$ (MW=438); mass spectroscopy (MH$^+$) 438, 338.

Example 273

Synthesis of N-tert-Butyl-N'-[N-(3,5-Difluorophenylacetyl)-L-alaninyl]-D-(thien-3-yl)glycinamide Following General Procedure AB and using N-(3,5-difluorophenylacetyl)-L-alanine (from Example B2 above), 3-thiophenecarboxaldehyde (Aldrich), (S)-(−)-α-methylbenzylamine (Aldrich) and tert-butylisocyanide (Aldrich), the title compound was prepared as a solid (mp=245–246° C.). The product was purified by recrystallization from ethyl acetate/hexanes.

$C_{21}H_{25}N_3O_3F_2S$ (MW=438); mass spectroscopy (MH$^+$) 438, 338.

Example 274

Synthesis of N-tert-Butyl-N'-[N-(3,5-Difluorophenylacetyl)-L-alaninyl]-D-phenylglycinamide Following General Procedure AB and using N-(3,5-difluorophenylacetyl)-L-alanine (from Example B2 above), benzaldehyde (Aldrich), (S)-(−)-α-methylbenzylamine (Aldrich) and tert-butylisocyanide (Aldrich), the title compound was prepared as a solid (mp=239–240° C.). The reaction was monitored by tlc (Rf=0.25 in 50% ethyl acetate/hexanes).

$C_{23}H_{27}N_3O_3F_2$ (MW=431.53); mass spectroscopy (MH$^+$) 432.

Example 275

Synthesis of N-tert-Butyl-N'-[N-(3,5-Difluorophenylacetyl)-L-alaninyl]-L-phenylglycinamide Following General Procedure AL and using N-(3,5-difluorophenylacetyl)-L-alanine (from Example B2 above), benzaldehyde (Aldrich), (S)-(−)-α-methylbenzylamine (Aldrich) and tert-butylisocyanide (Aldrich), the title compound was prepared as a solid (mp=240–241° C.).

$C_{23}H_{27}N_3O_3F_2$ (MW=431.53); mass spectroscopy (MH$^+$) 432. Anal. calc'd for $C_{23}H_{27}F_2N_3O_3$: C, 64.02; H, 6.31; N, 9.74. Found: C, 64.32; H, 6.30; N, 9.68.

Example 276

Synthesis of N-tert-Butyl-N'-[N-(3,5-Difluorophenylacetyl)-L-alaninyl]-D,L-(5-chlorothien-2-yl)glycinamide Following General Procedure AB and using N-(3,5-difluorophenylacetyl)-L-alanine (from Example B2 above), 5-chloro-2-thiophenecarboxaldehyde (from Example D17 above), (S)-(+)-α-methylbenzylamine (Aldrich) and tert-butylisocyanide (Aldrich), the title compound was prepared as a solid (mp=195–198° C.). The reaction was monitored by tlc (Rf=0.15 in 50% ethyl acetate/hexanes).

MS calcd for $C_{21}H_{25}N_3O_3F_2ClS$ (472.1276 (MH$^+$)); mass spectroscopy (MH$^+$) 472.1277.

Example 277

Synthesis of N-Cyclohexyl-N'-[N-(3,5-Difluorophenylacetyl)-L-alaninyl]-L-4-(phenyl)phenylglycinamide Following General Procedure AB and using N-(3,5-difluorophenylacetyl)-L-alanine (from Example B2 above), 4-biphenylcarboxaldehyde (Aldrich), (S)-(−)-α-methylbenzylamine (Aldrich) and cyclohexylisocyanide (Aldrich), the title compound was prepared as a solid (mp=300° C. (dec.)). The reaction was monitored by tlc (Rf=0.23 in 50% ethyl acetate/hexanes).

$C_{31}H_{33}N_3O_3F_2$ (MW=533.62); mass spectroscopy (MH$^+$, minus cyclohexylamide) 408.2.

Example 278

Synthesis of N-tert-Butyl-N'-[N-(3,5-Difluorophenylacetyl)-L-alaninyl]-L-3-(phenoxy)phenylglycinamide Following General Procedure AM and using N-(3,5-difluorophenylacetyl)-L-alanine (from Example B2 above), 3-phenoxybenzaldehyde (Aldrich), (S)-(+)-α-methylbenzylamine (Aldrich) and tert-butylisocyanide (Aldrich), the title compound was prepared. The reaction was monitored by tlc (Rf=0.29 in 50% ethyl acetate/hexanes).

MS calc'd for $C_{29}H_{32}N_3O_4F_2$ (MW=524.2361 (MH$^+$)); mass spectroscopy found (MH$^+$) 524.2355.

Example 279

Synthesis of N-(S)-α-Methylbenzyl-N'-[N-(3,5-Difluorophenylacetyl)-L-alaninyl]-D,L-phenylglycinamide Following General Procedure AB and using N-(3,5-difluorophenylacetyl)-L-alanine (from Example B2 above), benzaldehyde (Aldrich), (S)-α-methylbenzylamine (Aldrich) and (S)-(−)-α-methylbenzylisocyanide (from Example D18 above), the title compound was prepared.

MS calc'd for $C_{27}H_{28}N_3O_3F_2$ (MW=479.53); mass spectroscopy (MH$^+$) 480.21.

By following the procedures set forth above, N-(R)-(+)-α-Methylbenzyl-N'-[N-(3,5-Difluorophenylacetyl)-L-alaninyl]-D,L-phenylglycinamide was prepared merely by substitution of the appropriate isomer.

$C_{27}H_{28}N_3O_3F_2$ (MW=479.53 (MH$^+$)); mass spectroscopy (MH$^+$) 480.1. Anal. calc'd for $C_{27}H_{27}F_2N_3O_3$: C, 67.63; H, 5.68; N, 8.76. Found: C, 67.55; H, 5.48; N, 8.67.

Example 280

Synthesis of N-tert-Butyl-N'-[N-(3,5-Difluorophenylacetyl)-L-alaninyl]-L-3-(phenyl)phenylglycinamide Following General Procedure AM and using N-(3,5-difluorophenylacetyl)-L-alanine (from Example B2 above), 3-phenylbenzaldehyde (from Example D20 above), (S)-(+)-α-methylbenzylamine (Aldrich) and tert-butylisocyanide (Aldrich), the title compound was prepared. The reaction was monitored by tlc (Rf=0.25 in 50% ethyl acetate/hexanes).

$C_{29}H_{31}N_3O_3F_2$ (MW=507.63); mass spectroscopy (MH$^+$) 508.2. Anal. calc'd for $C_{29}H_{31}F_2N_3O_3$: C, 68.62; H, 6.16; N, 8.28. Found: C, 68.86; H, 6.00; N, 8.07.

Example 281

Synthesis of N-tert-Butyl-N'-[N-(3,5-Difluorophenylacetyl)-L-alaninyl]-L-4-(ethyl)phenylglycinamide Following General Procedure AM and using N-(3,5-difluorophenylacetyl)-L-alanine (from Example B2 above), 4-ethylbenzaldehyde (Aldrich), (S)-(−)-α-methylbenzylamine (Aldrich) and tert-butylisocyanide (Aldrich), the title compound was prepared. The reaction was monitored by tlc (Rf=0.20 in 50% ethyl acetate/hexanes).

$C_{25}H_{31}N_3O_3F_2$ (MW=459.59); mass spectroscopy (MH$^+$) 460.2. Anal. calc'd for $C_{25}H_{31}F_2N_3O_3$: C, 65.34; H, 6.80; N, 9.14. Found: C, 65.16; H, 6.69; N, 8.88.

Example 282

Synthesis of N-tert-Butyl-N'-[N-(3,5-Difluorophenylacetyl)-L-alaninyl]-L-2-(phenyl)phenylglycinamide Following General Procedure AM and using N-(3,5-difluorophenylacetyl)-L-alanine (from Example B2 above), 2-phenylbenzaldehyde (Aldrich), (S)-(−)-α-methylbenzylamine (Aldrich) and tert-butylisocyanide (Aldrich), the title compound was prepared. The reaction was monitored by tlc (Rf=0.15 in 50% ethyl acetate/hexanes).

$C_{29}H_{31}N_3O_3F_2$ (MW=507.63); mass spectroscopy (MH$^+$, minus tert-butylamide) 409.

Example 283

Synthesis of N-tert-Butyl-N'-[N-(3,5-Difluorophenylacetyl)-L-alaninyl]-L-2-(benzyl)phenylglycinamide Following General Procedure AM and using N-(3,5-difluorophenylacetyl)-L-alanine (from Example B2 above), 2-(benzyl)benzaldehyde (Aldrich), (S)-(−)-α-methylbenzylamine (Aldrich) and tert-butylisocyanide (Aldrich), the title compound was prepared. The reaction was monitored by tlc (Rf=0.19 in 50% ethyl acetate/hexanes).

$C_{30}H_{34}N_3O_3F_2$ (MW 522.2570 (MH$^+$)); mass spectroscopy (MH$^+$) 522.2574.

Example 284

Synthesis of N-tert-Butyl-N'-[N-(3,5-Difluorophenylacetyl)-L-alaninyl]-D,L-4-bromophenylglycinamide Following General Procedure AM and using N-(3,5-difluorophenylacetyl)-L-alanine (from Example B2 above), 4-bromobenzaldehyde (Aldrich), (S)-(−)-α-methylbenzylamine (Aldrich) and tert-butylisocyanide (Aldrich), the title compound was prepared. The reaction was monitored by tlc (Rf=0.06 in 50% ethyl acetate/hexanes).

$C_{23}H_{26}BrN_3O_3F_2$ (MW=510.42); mass spectroscopy (MH$^+$) 512.1. Anal. calc'd for $C_{23}H_{26}BrF_2N_3O_3$: C, 54.13; H, 5.13; N, 8.23. Found: C, 54.21; H, 5.25; N, 8.07.

Example 285

Synthesis of N-tert-Butyl-N'-[N-(3,5-Difluorophenylacetyl)-L-alaninyl]-L-4-(cyclohexyl)phenylglycinamide Following General Procedure AL and using N-(3,5-difluorophenylacetyl)-L-alanine (from Example B2 above), 4-(cyclohexyl)benzaldehyde (from Example D21 above), (S)-(−)-α-methylbenzylamine (Aldrich) and tert-butylisocyanide (Aldrich), the title compound was prepared as a solid (mp=232–235° C.).

$C_{29}H_{38}N_3O_3F_2$ (MW=514.2883 (MH$^+$)); mass spectroscopy (MH$^+$). 514.2888.

Example 286

Synthesis of N-tert-Butyl-N'-[N-(3,5-Difluorophenylacetyl)-L-alaninyl]-L-4-(4-ethylphenyl)phenylglycinamide Following General Procedure AL and using N-(3,5-difluorophenylacetyl)-L-alanine (from Example B2 above), 4,4'-ethylbiphenylcarboxaldehyde (Aldrich), (S)-(−)-α-methylbenzylamine (Aldrich) and tert-butylisocyanide (Aldrich), the title compound was prepared as a solid (mp=231–233° C.).

$C_{31}H_{36}N_3O_3F_2$ (MW=536.2727 (MH$^+$)); mass spectroscopy (MH$^+$) 536.2728.

Example 287

Synthesis of N-tert-Butyl-N'-[N-(3,5-Difluorophenylacetyl)-L-alaninyl]-D,L-4-(tert-butyl)phenylglycinamide Following General Procedure AL and using N-(3,5-difluorophenylacetyl)-L-alanine (from Example B2 above), 4-(tert-butyl)benzaldehyde (Aldrich), (S)-(−)-α-methylbenzylamine (Aldrich) and tert-butylisocyanide (Aldrich), the title compound was prepared as a solid (mp=280° C. (dec.)). The reaction was monitored by tlc (Rf=0.13 in 50% ethyl acetate/hexanes).

$C_{27}H_{36}N_3O_3F_2$ (MW=487.2727 (MH$^+$)); mass spectroscopy (MH$^+$) 488.2729.

Example 288

Synthesis of N-tert-Butyl-N'-[N-(3,5-Difluorophenylacetyl)-L-alaninyl]-D,L-3-(4-chlorophenoxy)phenylglycinamide Following General Procedure AL and using N-(3,5-difluorophenylacetyl)-L-alanine (from Example B2 above), 3-(4-chlorophenoxy)benzaldehyde (Aldrich), (S)-(−)-α-methylbenzylamine (Aldrich) and tert-butylisocyanide (Aldrich), the title compound was prepared as a solid (mp=192–195° C.).

$C_{29}H_{30}N_3O_4F_2Cl$ (MW=558.07); mass spectroscopy (MH$^+$) 558.20.

Example 289

Synthesis of N-Cyclohexyl-N'-[N-(3,5-Difluorophenylacetyl)-L-alaninyl]-D-4-(phenyl)phenylglycinamide Following General Procedure AB and using N-(3,5-difluorophenylacetyl)-L-alanine (from Example B2 above), 4-biphenylcarboxaldehyde (Aldrich), (S)-(+)-α-methylbenzylamine (Aldrich) and cyclohexylisocyanide (Aldrich), the title compound was prepared as a solid (mp=290–291 ° C.).

$C_{31}H_{33}N_3O_3F_2$ (MW=533.62); mass spectroscopy (MH$^+$) 534.3. Anal. calc'd for $C_{31}H_{33}F_2N_3O_3$: C, 69.78; H, 6.23; N, 7.87. Found: C, 69.94; H, 6.30; N, 7.73.

Example 290

Synthesis of N-[N-(3,5-Difluorophenyl-α-hydroxyacetyl)-L-alaninyl]-L-phenylglycine tert-Butyl Ester Following General Procedure C and using 3,5-difluoromandelic acid (Fluorochem) and N-(L-alaninyl)-L-phenylglycine tert-butyl ester (prepared using N-BOC-L-alanine (Sigma) and L-phenylglycine tert-butyl ester hydrochloride (Bachem) using General Procedure C, followed by removal of the BOC group using General Procedure P), the title compound was prepared.

$C_{23}H_{26}N_2O_5F_2$ (MW=479.53). Elemental analysis: Calc. (%) C, 61.60; H, 5.84; N, 6.25. Found (%) C, 61.32; H, 6.02; N, 6.17.

Example 291

Synthesis of N-tert-Butyl-N'-[N-(3,5-Difluorophenyl-α,α-difluoroacetyl)-L-alaninyl]-L-phenylglycinamide Following General Procedure G' and using 3,5-difluorophenyl-α,α-difluoroacetlc acid (from Example D23 above) and N-(L-alaninyl)-L-phenylglycine tert-butyl ester (prepared using N-BOC-L-alanine (Sigma) and L-phenylglycine tert-butyl ester hydrochloride (Bachem) using General Procedure C, followed by removal of the BOC group using General Procedure P), the title compound was prepared. The reaction was monitored by tlc (Rf=0.39 in 30% ethyl acetate/hexanes) and the product was purified by HPLC using 17% ethyl acetate/hexanes as the eluent.

$C_{23}H_{24}N_2O_4F_4$ (MW=468.49); mass spectroscopy (MH$^+$) 469.17.

Example 292

Synthesis of N-[N-(3,5-Difluorophenylacetyl)-L-alaninyl]-D-phenylglycine tert-Butyl Ester Following General Procedure C and using N-(3,5-difluorophenylacetyl)-L-alanine (from Example B2 above) and D-phenylglycine tert-butyl ester (prepared from D-phenylglycine (Sigma) using General Procedure J), the title compound was prepared. The reaction was monitored by tlc (Rf=0.1 in 10% MeOH/CHCl$_3$).

NMR data was as follows:

$^1$H-nmr (DMSO-d$_6$): δ=8.64 (d, 1H), 8.38 (d, 1H), 7.34 (m, 5H), 7.09 (m, 1H), 6.99 (m, 2H), 5.27 (d, 1H), 4.45 (m, 1H), 3.32 (s, 2H) 1.28 (s, 9H), 1.18 (d, 3H). Optical Rotation: [α]$_{20}$=−103.58 (c=1, MeOH). $C_{23}H_{26}N_2O_4F_2$ (MW=432.47); mass spectroscopy (MH$^+$) 433.

Example 293

Synthesis of N-[(S)-1-Oxo-1-phenylprop-2-yl]-N'-(3,5-difluorophenylacetyl)-L-alaninamide By oxidation of N-[(1R,2S)-1-hydroxy-1-phenylprop-2-yl]-N'-(3,5-difluorophenylacetyl)-L-alaninamide (from Example 226 above) using Jones reagent in acetone, the title compound was prepared. The reaction was monitored by tlc (Rf=0.7 in 9:1 CHCl$_3$/MeOH) and the product was purified by flash chromatography using 97:3 chloroform/methanol as the eluent.

NMR data was as follows:

$^1$H-nmr (CDCl$_3$): δ=7.98 (m, 2H), 7.26 (m, 1H), 7.50 (m, 2H), 6.84 (m, 2H), 6.72 (m, 1H), 6.25 (d, 1H), 5.49 (m, 3H), 4.54 (m, 3H), 3.54 (s, 2H), 1.41 (d, 3H), 1.38 (d, 3H). Optical Rotation: [α]$_{20}$=−106° @ 589 mn (c=1, MeOH). $C_{20}H_{20}F_2N_2O_3$ (MW=374.39); mass spectroscopy (MH$^+$) 374.

Example 294

Synthesis of N-[N-(3,5-Difluorophenylacetyl)-L-alaninyl]-D,L-(pyrid-3-yl)glycine tert-Butyl Ester Following General Procedure C and using N-(3,5-difluorophenylacetyl)-L-alanine (from Example B2 above) and tert-butyl 2-amino-2-(3-pyridyl)acetate (prepared as described in Kolar et al., *J. Heterocyclic Chem.*, 28, 171 (1991) and reference cited therein), the title compound was prepared. The reaction was monitored by tlc (Rf=0.2 in 5% MeOH/CHCl$_3$) and the product was purified by flash chromatography using 5% MeOH/CHCl$_3$ as the eluent.

NMR data was as follows:

$^1$H-nmr (CDCl$_3$): δ=8.63 (m, 1H), 8.54 (m, 1H), 7.62 (m, 1H), 7.45 (t, 1H), 7.26 (m, 1H), 6.82(m, 2H), 6.71 (m, 1H), 6.47 and 6.36 (d, 1H), 5.42 (d, 1H), 4.59 (m, 1H), 3.52 and 3.47 (two s, 2H), 1.38 and 1.36 (s, 9H), 1.34 and 1.28 (two d, 3H). $C_{22}H_{25}N_3O_4F_2$ (MW=433.46); mass spectroscopy (MH$^+$) 434.

Example 295

Synthesis of [N-[N-(3,5-Difluorophenylacetyl)-L-alaninyl]-D,L-phenylglycinyl]morpholine Following General Procedure C and using N-[N-(3,5-difluorophenylacetyl)-L-alaninyl]-D,L-phenylglycine (from Example D25 above) and morpholine (Aldrich), the title compound was prepared. The reaction was monitored by tlc (Rf=0.4 in 10% MeOH/CHCl$_3$) and the product was purified by flash chromatography using 5% MeOH/CHCl$_3$ as the eluent.

NMR data was as follows:

$^1$H-nmr (DMSO-d$_6$): δ=8.60 and 8.49 (two d's, 1H), 8.49 (m, 1H), 7.25 (m, 5H), 7.18 (m, 2H), 6.95 (m, 1H), 5.82 (m, 1H), 4.38 (m, 1H), 3.52 (m, 10H), 1.21 and 1.12 (two d's, 3H).

$C_{23}H_{25}N_3O_4F_2$ (MW=445.47); mass spectroscopy (MH$^+$) 446.

Example 296

Synthesis of N-[N-(3,5-Difluorophenylacetyl)-L-alaninyl]-D,L-(2-methoxy)phenylglycine Methyl Ester Following General Procedure C and using N-(3,5-difluorophenylacetyl)-L-alanine (from Example B2 above) and methyl 2-amino-2-(2-methoxy)acetate (prepared from 2-methoxybenzaldehyde (Aldrich) using the Bucherer modification of the Strecker procedure as described in J. P. Greenstein et al., "The Chemistry of Amino Acids", Wiley: New York, 1961, Vol. 1, p. 698), the title compound was prepared. The reaction was monitored by tlc (Rf=0.3 in 10% MeOH/CHCl$_3$) and the product was purified by flash chromatography using 10% MeOH/CHCl$_3$ as the eluent.

NMR data was as follows:

$^1$H-nmr (CDCl$_3$): δ=7.28 (m, 2H), 6.93 (d, 1H), 6.88 (m, 2H), 6.69 (m, 2H), 6.34 (m, 1H), 5.67 (m, 1H), 4.52 (m, 1H), 3.81 (two s, 3H), 3.68 (two s, 3H), 3.59 and 3.45 (two s, 3H) 1.41 and 1.28 (two d, 3H). $C_{21}H_{22}N_2O_5F_2$ (MW=420.42); mass spectroscopy (MH$^+$) 420.

Example 297

Synthesis of N-[N-(3,5-Difluorophenylacetyl)-L-alaninyl]-D,L-phenylglycine N-tert-Butoxycarbonyl (hydroxyl amine) Ester Following General Procedure C and using N-[N-(3,5-difluorophenylacetyl)-L-alaninyl]-D,L-phenylglycine (from Example D25 above) and N-BOC hydroxyl amine (Aldrich), the title compound was prepared. The reaction was monitored by tlc (Rf=0.35 in 10% MeOH/CHCl$_3$) and the product was purified by flash chromatography using 2% MeOH/CHCl$_3$ as the eluent.

NMR data was as follows:

$^1$H-nmr (CDCl$_3$): δ=7.79 (m, 1H), 7.41–7.28 (m, 5H), 6.78–6.59 (m, 3H), 5.52 (m, 1H), 4.69 (m, 1H), 3.38 (two s, 1H), 1.38 (d, 3H), 1.30 (s, 9H). $C_{24}H_{27}N_3O_6F_2$ (MW=491.49); mass spectroscopy (MH$^+$) 492.

Example 298

Synthesis of N-Neopentyl-N'-[N-(3,5-Difluorophenylacetyl)-L-alaninyl]-D,L-phenylglycinamide Following General Procedure M and using N-[N-(3,5-difluorophenylacetyl)-L-alaninyl]-D,L-phenyiglycine (from Example D25 above) and neopentylamine (Aldrich), the title compound was prepared. The reaction was monitored by tlc (Rf=0.4 in 10% MeOH/CHCl$_3$) and the product was purified by flash chromatography using 10% MeOH/CHCl$_3$ as the eluent.

NMR data was as follows:

$^1$H-nmr (DMSO-d$_6$): δ=8.44 (m, 1H), 7.41 (m, 2H), 7.31 (m, 3H), 7.12 (m, 1H), 6.99 (m, 2H), 5.50 (m, 1H), 4.47 (m, 1H), 3.52 (two s, 2H), 2.84 (m, 2H) 1.22 (m, 3H), 0.71 (s, 9H). C$_{24}$H$_{29}$N$_3$O$_3$F$_2$ (MW=460); mass spectroscopy (MH$^+$) 460.

Example 299

Synthesis of N-Tetrahydrofurfuryl-N'-[N-(3,5-Difluorophenylacetyl)-L-alaninyl]-D,L-phenylglycinamide Following General Procedure M and using N-[N-(3,5-difluorophenylacetyl)-L-alaninyl]-D,L-phenylglycine (from Example D25 above) and tetrahydrofurfurylamine (Aldrich), the title compound was prepared. The reaction was monitored by tlc (Rf=0.4 in 10% MeOH/CHCl$_3$) and the product was purified by flash chromatography using 10% MeOH/CHCl$_3$ as the eluent.

NMR data was as follows:

$^1$H-nmr (DMSO-d$_6$): δ=8.41 (m, 2H), 7.32 (m, 5H), 7.08 (m, 1H), 6.99 (m, 2H), 5.48 (m, 1H), 4.42 (m, 1H), 3.85–3.54 (m, 3H), 3.48 (two s, 2H), 3.14 (m, 2H), 1.76 (m, 4H), 1.21 (m, 3H). C$_{24}$H$_{27}$N$_3$O$_4$F$_2$ (MW=459.49); mass spectroscopy (MH$^+$) 460.

Example 300

Synthesis of N-Methoxy-N'-[N-(3,5-Difluorophenylacetyl)-L-alaninyl]-D,L-phenylglycinamide Following General Procedure M and using N-[N-(3,5-difluorophenylacetyl)-L-alaninyl]-D,L-phenylglycine (from Example D25 above) and methoxyamine hydrochloride (Aldrich), the title compound was prepared. The reaction was monitored by tlc (Rf=0.35 in 10% MeOH/CHCl$_3$) and the product was purified by flash chromatography using 10% MeOH/CHCl$_3$ as the eluent.

NMR data was as follows:

$^1$H-nmr (DMSO-d$_6$): δ=8.63 (m, 1H), 8.35 (m, 1H), 7.34 (m, 5H), 7.12 (m, 1H), 6.99 (m, 2H), 5.23 (d, 1H), 4.42 (m, 1H), 3.58 (s, 3H), 3.51 (two s, 2H), 1.22 (d, 3H). C$_{20}$H$_{21}$N$_3$O$_4$F$_2$ (MW=405); mass spectroscopy (MH$^+$) 405.

Example 301

Synthesis of [N-[N-(3,5-Difluorophenylacetyl)-L-alaninyl]-D,L-phenylglycinyl]azetidine Following General Procedure M and using N-[N-(3,5-difluorophenylacetyl)-L-alaninyl]-D,L-phenylglycine (from Example D25 above) and azetidine (Aldrich), the title compound was prepared. The reaction was monitored by tlc (Rf=0.6 in 10% MeOH/CHCl$_3$) and the product was purified by flash chromatography using 10% MeOH/CHCl$_3$ as the eluent.

NMR data was as follows:

$^1$H-nmr (DMSO-d$_6$): δ=8.61 and 8.46 (two d, 1H), 8.33 (m, 1H), 7.34 (m, 5H), 7.19 (m, 1H), 6.99 (m, 2H), 5.36 (two d, 1H), 4.42 (m, 1H), 4.31 (m, 1H), 3.88 (m, 3H), 3.5 (two s, 2H), 2.36 (m, 2H), 1.18 (two d, 3H). C$_{22}$H$_{23}$N$_3$O$_3$F$_2$ (MW=415.44); mass spectroscopy (MH$^+$) 416.

Example 302

Synthesis of N-Isobutyl-N'-[N-(3,5-Difluorophenylacetyl)-L-alaninyl]-D,L-phenylglycinamide Following General Procedure M and using N-[N-(3,5-difluorophenyl-acetyl)-L-alaninyl]-D,L-phenylglycine (from Example D25 above) and isobutylamine (Aldrich), the title compound was prepared. The reaction was monitored by tlc (Rf=0.65 in 10% MeOH/CHCl$_3$) and the product was purified by flash chromatography using 10% MeOH/CHCl$_3$ as the eluent.

NMR data was as follows:

$^1$H-nmr (DMSO-d$_6$): δ=8.41 (m, 1H), 8.22 (m, 1H), 7.38 (m, 2H), 7.09 (m, 1H), 6.98 (m, 2H), 5.52 (two d, 1H), 4.41 (m, 1H), 3.34 (two s, 2H), 2.85 (s, 2H), 1.61 (m, 1H), 1.20 (m, 3H), 0.92 (m, 6H). C$_{23}$H$_{27}$N$_3$O$_3$F$_2$ (MW=431.48); mass spectroscopy (MH$^+$) 432.

Example 303

Synthesis of N-Cyclopropanemethyl-N'-[N-(3,5-Difluorophenylacetyl)-L-alaninyl]-D,L-phenylglycinamide Following General Procedure M and using N-[N-(3,5-difluorophenylacetyl)-L-alaninyl]-D,L-phenylglycine (from Example D25 above) and (aminomethyl)cyclopropane (Aldrich), the title compound was prepared. The reaction was monitored by tlc (Rf=0.25 in 10% MeOH/CHCl$_3$) and the product was purified by flash chromatography using 10% MeOH/CHCl$_3$ as the eluent. C$_{23}$H$_{25}$N$_3$O$_3$F$_2$ (MW=429.47); mass spectroscopy (MH$^+$) 374.

Example 304

Synthesis of N-Methoxy-N-methyl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and N-methoxy-N-methylamine hydrochloride (Aldrich), the title compound was prepared. The reaction was monitored by tlc (Rf=0.3 in 10% MeOH/CHCl$_3$) and the product was purified by flash chromatography using 2% MeOH/CHCl$_3$ as the eluent.

NMR data was as follows:

$^1$H-nmr (DMSO-d$_6$): δ=8.65 and 8.53 (two d, 1H), 8.37 (m, 1H), 7.31 (m, 5H), 7.12 (m, 1H), 6.98 (m, 2H), 5.91 and 5.82 (two d, 1H), 4.49 (m, 1H), 3.60–3.42 (m, 5H), 3.08 (two s, 3H), 1.21 and 1.16 (two d, 3H). C$_{21}$H$_{23}$N$_3$O$_4$F$_2$ (MW= 419); mass spectroscopy (MH$^+$) 420.

Example 305

Synthesis of N-2-Methylprop-2-enyl-N'-[N-(3,5-Difluorophenylacetyl)-L-alaninyl]-D,L-phenylglycinamide Following General Procedure M and using N-[N-(3,5-difluorophenylacetyl)-L-alaninyl]-D,L-phenylglycine (from Example D25 above) and 1-amino-2-methylprop-2-ene (Aldrich), the title compound was prepared. The reaction was monitored by tlc (Rf=0.45 in 10% MeOH/CHCl$_3$) and the product was purified by flash chromatography using 3% MeOH/CHCl$_3$ as the eluent.

NMR data was as follows:

$^1$H-nmr (DMSO-d$_6$): δ=8.43 (m, 2H), 7.40 (m, 2H), 7.29 (m, 3H), 7.11 (m, 1H), 6.98 (m, 2H), 5.46 (d, 1H), 4.68 (m, 2H), 4.42 (m, 1H), 3.6 (m, 2H), 3.49 (s, 2H), 1.56 (s, 3H), 1.21 (d, 3H). C$_{23}$H$_{25}$N$_3$O$_3$F$_2$ (MW=429.47); mass spectroscopy (MH$^+$) 430.

Example 306

Synthesis of N-(Pyrid-3-yl)methyl-N'-[(N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and 3-(aminomethyl)pyridine (Aldrich), the title compound was prepared. The reaction was monitored by tlc (Rf=0.1 in 10% MeOH/CHCl$_3$) and the product was purified by flash chromatography using 3% MeOH/CHCl$_3$ as the eluent.

NMR data was as follows:

$^1$H-nmr (DMSO-d$_6$): δ=8.82 (m, 1H), 8.55 (m, 1H), 8.42 (m, 3H), 7.52 (m, 1H), 7.35 (m, 5H), 7.10 (m, 1H), 6.99 (m, 2H), 5.43 (d, 2H), 4.44 (m, 1H), 4.30 (bd, 2H) 3.52 (s, 2H) 1.26 (d, 3H). C$_{23}$H$_{24}$N$_4$O$_3$F$_2$ (MW=466.49); mass spectroscopy (MH$^+$) 467.

Example 307

Synthesis of N-(Pyrid-4-yl)methyl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and 4-(aminomethyl)pyridine (Aldrich), the title compound was prepared. The reaction was monitored by tlc (Rf=0.1 in 10% MeOH/CHCl$_3$) and the product was purified by flash chromatography using 3% MeOH/CHCl$_3$ as the eluent.

NMR data was as follows:

$^1$H-nmr (DMSO-d$_6$): δ=8.88 (m, 1H), 8.54 (d, 1H), 8.43 (m, 3H), 7.37 (m, 4H), 7.12 (m, 3H), 6.9(m, 1H), 5.44 (d, 1H), 4.45 (m, 1H), 4.31 (d, 2H), 3.51 (s, 2H), 1.25 (d, 3H). C$_{23}$H$_{24}$N$_4$O$_3$F$_2$ (MW=466.49); mass spectroscopy (MH$^+$) 467.

Example 308

Synthesis of N-Furfuryl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and furfurylamine (Aldrich), the title compound was prepared. The reaction was monitored by tlc (Rf=0.5 in 10% MeOH/CHCl$_3$) and the product was purified by flash chromatography using 3% MeOH/CHCl$_3$ as the eluent.

NMR data was as follows:

H-nmr (DMSO-d$_6$): δ=8.66 (m, 1H), 8.45 (d, 1H), 8.39 (m, 1H), 7.57 (s, 1H), 7.33 (m, 5H), 7.09 (m, 1H), 6.99 (m, 2H), 6.36 (m, 1H), 6.12 (s, 1H), 5.41 (d, 1H), 4.22 (m, 1H), 3.52 (s, 2H) 1.24 (d, 3H). C$_{24}$H$_{23}$N$_3$O$_4$F$_2$ (MW=455); mass spectroscopy (MH$^+$) 456.

Example 309

Synthesis of N-Cyclopentyl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and cyclopentylamine (Aldrich), the title compound was prepared. The product was purified by recrystallization from ethanol.

NMR data was as follows:

$^1$H-nmr (DMSO-d$_6$): δ=8.32 (m, 2H), 8.16 (m, 1H), 7.33–7.20 (m, 5H), 7.04 (m, 1H), 6.93 (m, 2H), 5.34 (d, 1H), 4.37 (m, 1H), 3.9 (m, 1H), 3.49 (s, 2H), 1.80–1.29 (m, 8H), 1.19 (d, 3H). C$_{24}$H$_{27}$N$_3$O$_3$F$_2$ (MW=443.49); mass spectroscopy (MH$^+$) 444.

Example 310

Synthesis of N-1-Benzylpiperidin-4-yl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and 4-amino-1-benzylpiperdine (Aldrich), the title compound was prepared. The reaction was monitored by tlc (Rf=0.2 in 10% MeOH/CHCl$_3$) and the product was purified by flash chromatography using 3% MeOH/CHCl$_3$ as the eluent.

NMR data was as follows:

$^1$H-nmr (DMSO-d$_6$): δ=8.39 (m, 2H), 8.21 (m, 1H), 7.30 (m, 5H), 7.11 (m, 1H), 6.98 (m, 2H), 5.39 (d, 1H), 4.21 (m, 1H), 3.54 (bm, 3H), 3.42 (bs, 2H), 2.70 (bm, 2H), 1.89 (bm, 2H), 1.71 (bm, 2H), 1.42 (3H), 1.22 (m, 3H). C$_{31}$H$_{34}$N$_4$O$_3$F$_2$ (MW=548.64); mass spectroscopy (MH$^+$) 548.

Example 311

Synthesis of N,N-Dimethyl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and dimethylamine (Aldrich), the title compound was prepared. The reaction was monitored by tlc (Rf=0.65 in 10% MeOH/CHCl$_3$) and the product was purified by flash chromatography using 5% MeOH/CHCl$_3$ as the eluent.

NMR data was as follows:

$^1$H-nmr (DMSO-d$_6$): δ=8.13 and 8.01 (two d, 1H), 7.32 (m, 5H), 6.78 (m, 2H), 6.63 (m, 1H), 5.88 (m, 1H), 4.72 (m, 1H), 3.45 (two s, 2H), 2.94 (two s, 6H), 1.32 and 1.17 (two d, 3H). C$_{21}$H$_{23}$N$_3$O$_3$F$_2$ (MW 403.43); mass spectroscopy (MH$^+$) 404.

Example 312

Synthesis of N-2,2,6,6-Tetramethylpiperidin-4-yl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and 4-amino-2,2,6,6,-tetramethylpiperdine (Aldrich), the title compound was prepared. The reaction was monitored by tlc (Rf=0.2 in 2% MeOH/CHCl$_3$) and the product was purified by flash chromatography using 2% MeOH/CHCl$_3$ as the eluent.

NMR data was as follows:

$^1$H-nmr (DMSO-d$_6$): δ=8.46 (d, 1H), 8.33 (d, 1H), 8.12 (bm, 1H), 7.33 (m, 5H), 7.13 (m, 1H), 6.99 (m, 2H), 5.37 (d, 1H), 4.41 (m, 1H), 3.98 (m, 1H), 3.52 (s, 2H), 1.67 (bm, 1H), 1.44 (bm, 1H), 1.22 (d, 3H), 1.01 (bm, 14H). C$_{28}$H$_{36}$N$_4$O$_3$F$_2$ (MW=514.62); mass spectroscopy (MH$^+$) 514.

Example 313

Synthesis of N-2-Methylcyclohexyl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and 2-methylcyclohexylamine (Aldrich), the title compound was prepared. The reaction was monitored by tlc (Rf=0.4 in 2% MeOH/CHCl$_3$).

NMR data was as follows:

$^1$H-nmr (DMSO-d$_6$): δ=8.41 (m, 2H), 8.0 (m, 1H), 7.33 (m, 5H), 7.11 (m, 1H), 6.99 (m, 2H), 5.35 (m, 1H), 4.41 (m, 1H), 3.52 (s, 2H), 3.18 (m, 1H), 1.78–0.82 (m 11H), 0.81 (m, 3H). C$_{26}$H$_{31}$N$_3$O$_3$F$_2$ (MW=472.5); mass spectroscopy (MH$^+$) 472.

Example 314

Synthesis of N-4-Methylcyclohexyl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and 4-methylcyclohexylamine (Aldrich), the title compound was prepared. The reaction was monitored by tlc (Rf=0.2 in 2% MeOH/CHCl$_3$) and the product was purified by flash chromatography using 2% MeOH/CHCl$_3$ as the eluent.

NMR data was as follows:

$^1$H-nmr (DMSO-d$_6$): δ=8.38 (m, 2H), 8.08 (m, 1H), 7.33 (m, 5H), 7.09 (m, 1H), 7.01 (m, 2H), 5.54 and 5.36 (two d, 1H), 4.43 (m, 2H), 3.76 (m, 1H), 3.52 (s, 2H), 1.79–1.17 (m, 11H), 0.84 (d, 3H). C$_{26}$H$_{31}$N$_3$O$_3$F$_2$ (MW=472.5); mass spectroscopy (MH$^+$) 472.

Example 315

Synthesis of N-1-Ethoxycarbonylpiperidin-4-yl-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and 4-amino-1-ethoxycarbonylpiperdine (Aldrich), the title compound was prepared. The reaction was monitored by tlc (Rf=0.2 in 2% MeOH/CHCl$_3$) and the product was purified by flash chromatography using 2% MeOH/CHCl$_3$ as the eluent.

NMR data was as follows:

$^1$H-nmr (DMSO-d$_6$): δ=8.42 (m, 2H), 8.23 (m, 1H), 7.33 (m, 5H), 7.09 (m, 1H), 6.98 (m, 2H), 5.38 (m, 1H), 4.41 (m, 1H), 4.01 (q, 2H), 3.9–3.64 (m, 3H), 3.49 (s, 2H), 2.88 (bm, 2H), 1.75 (m, 1H), 1.54 (m, 1H), 1.2 (m, 6H). C$_{27}$H$_{32}$N$_4$O$_5$F$_2$ (MW=530.57); mass spectroscopy (MH$^+$) 531.

Example 316

Synthesis of N-Methyl-N'-[N-(3,5-Difluorophenylacetyl)-L-alaninyl]-L-phenylglycinamide Following General Procedure C and using N-(3,5-difluorophenylacetyl)-L-alanine (from Example B2 above) and N-methyl-(S)-2-amino-2-phenylacetamide [CAS 129213-83-8], the title compound was prepared. The reaction was monitored by tlc (Rf=0.2 in 5% MeOH/CHCl$_3$) and the product was purified by flash chromatography using 5% MeOH/CHCl$_3$ as the eluent.

NMR data was as follows:

$^1$H-nmr (DMSO-d$_6$): δ=8.43 (m, 2H), 8.21 (m, 1H), 7.36 (m, 5H), 7.09 (m, 1H), 6.95 (m, 2H), 5.36 (m, 1H), 4.40 (m, 1H), 3.41 (s, 2H), 2.56 (d, 3H), 1.22 (d, 3H). Optical Rotation: [α]$_{20}$=−67 (c=1, MeOH). C$_{20}$H$_{21}$N$_3$O$_3$F$_2$.0.75H$_2$O (MW 403.43); mass spectroscopy (MH$^+$) 404.

Example 317

Synthesis of N-tert-Butoxy-N'-[N-(3,5-Difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and O-(tert-butoxy)hydroxylamine (Aldrich), the title compound was prepared. The reaction was monitored by tlc (Rf=0.65 in 10% MeOH/CHCl$_3$).

NMR data was as follows:

$^1$H-nmr (DMSO-d$_6$): δ=8.72 and 8.58 (two d, 1H), 8.39 (m, 1H), 7.37 (m, 5H), 7.10 (m, 1H), 6.99 (m, 2H), 5.41 (m, 1H), 4.46 (m, 1H), 3.51 (two s, 3H), 1.22 (m, 3H), 1.09 (s, 9H). C$_{23}$H$_{27}$N$_3$O$_4$F$_2$ (MW=447.48); mass spectroscopy (MH$^+$) 448.

Example 318

Synthesis of N-[N-(3,5-Difluorophenylacetyl)-L-alaninyl]-D,L-phenylglycine N-tert-Butyl (hydroxylamine) Ester Following General Procedure C and using N-[N-(3,5-difluorophenylacetyl)-L-alaninyl]-D,L-phenylglycine (from Example D25 above) and N-(tert-butoxy)hydroxylamine (Aldrich), the title compound was prepared. The reaction was monitored by tlc (Rf=0.65 in 10% MeOH/CHCl$_3$).

C$_{23}$H$_{27}$N$_3$O$_4$F$_2$.0.25H$_2$O (MW=447.48); mass spectroscopy (MH$^+$) 448.

Example 319

Synthesis of N-[N-(3,5-Difluorophenylacetyl)-L-alaninyl]-L-phenylglycine Hydrazide N-[N-(3,5-difluorophenylacetyl)-L-alaninyl]-L-phenylglycine methyl ester (2.0 g, 5.1 mmol) (from Example 111 above) was stirred in ethanol (40 mL) and anhydrous hydrazine (0.3 mL, 10 mmol) (Aldrich) was added. The solution was heated at reflux for 12 hours and then allowed to cool to ambient temperature with stirring. A title compound was collected as a white solid by filtration, washing with ethanol and dring in a vacuum oven (52% yield).

NMR data was as follows:

$^1$H-nmr (DMSO-d$_6$): δ=1.20 (t, 3H), 5.41 (m, 1H). C$_{19}$H$_{20}$N$_3$O$_4$F$_2$ (MW 390.39); mass spectroscopy (MH$^+$) 390.

Example 320

Synthesis of N-[N-(3,5-Difluorophenylacetyl)-L-alaninyl]-L-phenylglycine Acetohydrazonate N-[N-(3,5-Difluorophenylacetyl)-L-alaninyl]-L-phenylglycine hydrazide (0.5 g, 1.3 mmol) (from Example 319 above) was heated at reflux in triethylorthoacetate (40 mL). After 14 hours, the reaction mixture was concentrated under reduced pressure to afford the title compound as a white solid (84% yield). The reaction was monitored by tlc (Rf=0.65 in 10% MeOH/CHCl$_3$) and the product was purified by silica gel chromatography using 5% MeOH/CHCl$_3$ as the eluent.

NMR data was as follows:

$^1$H-nmr (DMSO-d$_6$): δ=4.03 (q, 2H), 5.54 (m, 1H). C$_{23}$H$_{26}$N$_4$O$_4$F$_2$ (MW=460.49); mass spectroscopy (MH$^+$) 460.

Example 321

Synthesis of N-[N-(Phenylacetyl)-L-alaninyl]-L-phenylglycine tert-Butyl Ester

Following General Procedure C and using phenylacetic acid (Aldrich) and L-alaninyl-L-phenylglycine tert-butyl ester (prepared using N-BOC-L-alanine (Sigma) and L-phenylglycine tert-butyl ester hydrochloride (Bachem) using General Procedure C, followed by removal of the BOC group using General Procedure P), the title compound was prepared. The reaction was monitored by tlc (Rf=0.25 in 3% MeOH/CHCl$_3$) and the product was purified by crystallization from chlorobutane/hexanes.

NMR data was as follows:

$^1$H-nmr (DMSO-d$_6$): δ=4.43 (m, 1H), 5.20 (d, 1H). C$_{23}$H$_{28}$N$_2$O$_4$ (MW=396.49); mass spectroscopy (MH$^+$) 397.

Example 322

Synthesis of N-4-(phenyl)butyl-N'-[N-(3,5-Difluorophenylacetyl)-L-alaninyl]-L-phenylglycinamide Following General Procedure C and using N-(3,5-difluorophenylacetyl)-L-alanine (from Example B2 above) and N-4-(phenyl)butyl-L-phenylglycinamide (prepared from N-BOC-L-phenylglycine (Advanced Chemtech) and 4-phenylbutylamine (Aldrich) using General Procedure C, followed by removal of the BOC-group using General Procedure P), the title compound was prepared. The reaction was monitored by tlc (Rf=0.45 in 5% MeOH/CHCl$_3$) and the product was purified by trituration in water, followed by trituration in acetonitrile.

NMR data was as follows:

$^1$H-nmr (DMSO-d$_6$): δ=4.42 (m, 1H), 5.37 (d, 1H). C$_{29}$H$_{31}$N$_3$O$_3$F$_2$ (MW=507.5); mass spectroscopy (MH$^+$) 507.

Example 323

Synthesis of N-3-(4-Iodophenyl)propyl-N'-[N-(3,5-Difluorophenylacetyl)-L-alaninyl]-L-phenylglycinamide Following General Procedure C and using N-(3,5-difluorophenylacetyl)-L-alanine (from Example B2 above) and N-3-(4-iodophenyl)propyl-L-phenylglycinamide (prepared from N-BOC-L-phenylglycine (Advanced Chemtech) and 3-(4-iodophenyl)propylamine (from Example D26 above) using General Procedure C, followed by removal of the BOC-group using General Procedure P), the title compound was prepared. The product was purified by trituration in water, followed by trituration in ethanol.

NMR data was as follows:

$^1$H-nmr (DMSO-d$_6$): δ=4.41 (q, 2H), 5.35 (m, 1H). C$_{28}$H$_{28}$N$_3$O$_4$F$_2$I (MW=635.45); mass spectroscopy (MH$^+$) 635.

Example 324

Synthesis of N-6-(Amino)hexyl-N'-[N-(3,5-difluorophenylacetyl)-L-alaninyl]-D,L-phenylglycinamide Hydrochloride Following General Procedure C and using N-[N-(3,5-difluorophenylacetyl)-L-alaninyl]-D,L-phenylglycine (from Example D25 above) and N-BOC-1,6-hexanediamine (Fluka), followed by removal of the BOC-group using General Procedure P, the title compound was prepared. The product was isolated as a white solid.

NMR data was as follows:

$^1$H-nmr (DMSO-d$_6$): δ=4.41 (m, 1H), 5.40 (t, 1H). C$_{25}$H$_{32}$N$_4$O$_3$F$_2$ (MW=474.56); mass spectroscopy (MH$^+$) 475.

Example 325

Synthesis of N-1-(Phthalimido)pent-2-yl-N'-(3,5-difluorophenylacetyl)-L-alaninamide Following General Procedure C and using N-(3,5-difluorophenylacetyl)-L-alanine (from Example B2 above) and 2-amino-1-phthalimidopentane hydrochloride (from Example D27 above), the title compound was prepared. The reaction was monitored by tlc (Rf=0.3 in 5% MeOH/CHCl$_3$) and the product was purified by silica gel chromatography using 5% MeOH/CHCl$_3$ as the eluent, followed by recrystallization from chlorobutane/acetonitrile.

NMR data was as follows:

$^1$H-nmr (DMSO-d$_6$): δ=4.1 (m, 2H), 7.83 (bs, 4H). C$_{24}$H$_{25}$N$_3$O$_4$F$_2$ (MW=457.48); mass spectroscopy (MH$^+$) 457.

Example 326

Synthesis of N-[N-(3,5-Difluorophenylacetyl)-L-(3,5-difluorophenyl)glycinyl]-L-(3,5-difluorophenyl) glycine Methyl Ester Following General Procedure AN and using N-(3,5-difluorophenylacetyl)-L-(3,5-difluorophenyl)glycine (from Example D30 above) and L-3,5-difluorophenylglycine methyl ester (from Example D29 above), the title compound was prepared. The product was purified by crystallization.

NMR data was as follows:

$^1$H-nmr (DMSO-d$_6$): δ=9.40 (m, 1H), 9.0 (m, 1H), 6.80–7.70 (m, 9H), 5.45 (d, 1H), 5.25 (m, 1H), 3.55–365 (m, 5H).

Example 327

Synthesis of N-[N-(3,5-Difluorophenylacetyl)-L-alaninyl]-L-norleucine

Following General Procedure AF and using THF/H$_2$O (1:1) on N-[N-(3,5-difluorophenylacetyl)-L-alaninyl]-L-norleucine methyl ester, the title compound was prepared as a solid (mp=158.5–160.5° C.). The reaction was monitored by tlc (Rf=0.29 in 10% MeOH/CH$_2$Cl$_2$).

NMR data was as follows:

$^1$H-nmr (CD$_3$OD): δ=8.46 (bd, J=6.71, 1H), 8.25 (bd, J=7.69, 1H), 7.00–6.79 (m, 3H), 4.50–4.35 (m, 2H), 3.61 (d, 2H), 1.94–1.79 (m, 1H), 1.78–1.60 (m, (includes d at 1.40, J=7.14, 3H), 0.92 (m, 3H). $^{13}$C-nmr (CD$_3$OD): δ=176.0, 175.5, 172.9, 166.6, 166.5, 163.4, 163.2, 141.7, 141.6, 141.5, 113.9, 113.8, 113.7, 113.6, 103.9, 103.6, 103.2, 54.1, 50.9, 43.3, 32.9, 29.4, 23.8, 18.6, 14.8. C$_{17}$H$_{22}$N$_2$O$_4$F$_2$ (MW=356.37); mass spectroscopy (MH$^+$) 357.

Example 328

Synthesis of N-[N-(Cyclopentaneacetyl)-L-alaninyl]-L-phenylglycine tert-Butyl Ester Following General Procedure D and using cyclopentylacetic acid (Aldrich) and L-alaninyl-L-phenylglycine tert-butyl ester (prepared from N-CBZ-L-alanine (Sigma) and L-phenylglycine tert-butyl ester hydrochloride (Bachem) using General Procedure C, followed by removal of the CBZ-group using General Procedure Y), the title compound was prepared as a solid (mp=133–138° C.). The reaction was monitored by tlc (Rf=0.48 in 50% EtOAc/hexanes) and the product was purified by flash chromatography using 25–50% EtOAc/hexanes as the eluent.

NMR data was as follows:

$^1$H-nmr (CDCl$_3$): δ=7/86 (bd, J=7.2 Hz, 1H), 7.30–7.15 (m, 5H), 6.81 (bd, J=7.82 Hz, 1H), 5.34 (d, J=7.20 Hz, 1H0, 4.72 (quint, J=7.2 Hz, 1H), 2.04 (m, 3H), 1.75–1.28 (m (includes s at 1.34, 9H) 18H), 1.1–0.9 (m, 2H). $^{13}$C-nmr (CDCl$_3$): δ=173.3, 172.8, 170.0, 137.1, 129.2, 128.6, 127.7, 82.7, 57.7, 48.9, 43.0, 37.6, 32.9, 28.3, 25.4, 19.3. C$_{22}$H$_{32}$N$_2$O$_4$ (MW=388.51); mass spectroscopy (MH$^+$) 389.5.

Example 329

Synthesis of N-[N-(2,5-Dichlorophenylmercaptoacetyl)-L-alaninyl]-L-phenylglycine Methyl Ester 2,5-Dichlorophenylmercaptoacetlc acid (TCI America, Portland, Oreg.) (237 mg) was converted to the acid chloride as described in the General Procedure A" and utilized to acylate methyl L-alaninyl-L-phenylglycinate as described in General Procedure B". The title compound (210 mg) was isolated as crystals from ethyl ether.

NMR data was as follows:

$^1$H-nmr (DMSO-d$_6$) δ=8.85 (d, 1H), 8.20 (d, 1H), 6.70–7.45 (m, 8H), 5.45 (d, 1H), 4.45–4.65 (m, 3H), 3.65 (s, 3H), 1.30 (d, 3H). C$_{20}$H$_{20}$Cl$_2$N$_2$O$_4$S (MW=455.363) mass spectroscopy (MH$^+$) 454.1. Anal. Calcd. for C$_{20}$H$_{20}$Cl$_2$N$_2$O$_4$S: C, 52.75 H, 4.42 N, 6.15; Found: C, 53.58 H, 5.01, N, 6.34.

Example 330

Synthesis of N-[N-(3,4-Dichlorophenylmercptoacetyl)-L-alaninyl]-L-phenylglycine Methyl Ester 3,4-Dichlorophenylmercaptoacetlc acid (J. Med. Chem., 15(9), 940–944 (1972)) (237 mg) was converted to the acid chloride as described in the General Procedure A" and utilized to acylate methyl L-alaninyl-L-phenylglycinate as described in General Procedure B". The title compound (182 mg) was isolated as cyrstals from ethyl ether.

NMR data was as follows:

$^1$H-nmr (DMSO-d$_6$) δ=8.8 (d, 1H), 8.40 (d, 1H), 7.25–7.65 (m, 8H), 5.40 (d, 1H), 4.45 (m, 1H), 3.80 (m, 2H), 3.65 (s, 3H), 1.25 (d, 3H). C$_{20}$H$_{20}$Cl$_2$N$_2$O$_4$S (MW=455.363); mass spectroscopy (MH$^+$) 454.1 Anal. Calcd. for C$_{20}$H$_{20}$Cl$_1$N$_2$O$_4$S: C, 52.75 H, 4.42 N, 6.15; Found: C, 53.05 H, 4.67 N, 6.26.

Example 331

Synthesis of N-[N-(3,5-Difluorophenoxyacetyl)-L-alaninyl]-L-phenylglycine Methyl Ester 3,5-Difluorophenoxyacetlc acid [prepared by refluxing an aqueous mixture of 3,5-difluorophenol (Aldrich), 2-chloroacetlc acid, and NaOH] (188 mg) was converted to the acid chloride as described in the General Procedure A" and utilized to acylate methyl L-alaninyl-L-phenylglycinate as described in General Procedure B". The title compound (210 mg) was isolated as crystals from ethyl ether.

NMR data was as follows:

$^1$H-nmr (DMSO-d$_6$) δ=8.85 (d, 1H), 8.20 (d, 1H), 6.70–7.45 (m, 8H), 5.45 (d, 1H), 4.45–4.65 (m, 3H), 3.65 (s, 3H), 1.30 (d, 3H). C$_{20}$H$_{20}$F$_2$N$_2$O$_5$ (MW=406.39); mass spectroscopy (MH$^+$) 406.3. Anal. Calcd. for C$_{20}$H$_{20}$F$_2$N$_2$O$_5$: C, 59.11 H, 4.96 N, 6.89; Found: C, 53.34 H, 4.80 N, 6.94.

Example 332

Synthesis of Methyl N-[N-(3,5-Difluorophenoxyacetyl)-L-alaninyl]-L-2,3-dihydroisoindole-1-carboxylate Following General Procedure AN, L-2,3-Dihydro-1H-isoindole-1-carboxylic acid methyl ester hydrochloride (Gazz. Chim. Ital., 106 (1–2) p. 65–75 (1976)) (417 mg) was coupled to N-(3,5-difluorophenylacetyl-L-alanine (from Example B2) to provide the title compound (150 mg).

NMR data was as follows:

$^1$H-nmr (DMSO-d$_6$) δ=8.55 (d, 1H), 6.85–7.45 (m, 7H), 5.50(m, 1H), 4.95(s, 1H), 4.55–4.90(m, 2+H), 3.65 (m, 3H), 1.30 (m, 3H). C$_{21}$H$_{20}$F$_2$N$_2$O$_4$ (MW=402.40); mass spectroscopy (MH$^+$) 402.3.

Example 333

Synthesis of N-[N-(3,5-Difluorophenylacetyl)-L-alaninyl]-1-amino-1,3-diphenylpropane-2-one To a solution of 200 mg of N-methoxy-N-methyl-N'-[N-(3,5-difluorophenylacetyl)-L-alaninyl]-D,L-phenylglycinamide (from Example 304 above) in THF was added 1.91 mL of a 2M solution of benzyl magnesium bromide in THF (Aldrich) at 0° C. The reaction mixture was stirred at ambient temperature for 72 hours, and was subsequently quenched by addition of water. The reaction mixture was partitioned between ethyl acetate and water and the organic phase was washed with 1N HCl solution. Following removal of solvent under reduced pressure, the crude ketone was purified by chromatography on silica gel, eluting with ethyl acetate, to afford 62 mg of the title compound as a 1:1 mixture of phenyl diastereomers.

NMR data was as follows:

$^1$H-Nmr (CDCl$_3$) (approx 1:1 mixture of diastereomers) δ=7.2–7.5 (m, 8H), 7.0–7.1 (m, 2H), 6.7–6.9 (m, 4H), 6.2 (m, 1H), 5.5(t, 1H), 3.5–3.6 (m, 2H), 1.28–1.45 (doublets in 1:1 ratio, 3H).

Example 334

Synthesis of N-[N-(3,5-Difluorophenylacetyl)-L-alaninyl]-D,L-phenylglycine Thiocarboxamide Step A—Preparation of t-Butoxycarbonyl-phenylglycine Thiocarboxamide:

To a suspension of 500 mg (2.00 mmol) t-butoxycarbonyl-L-phenylglycine carboxamide (prepared as in Example 141) in 50 mL of dry toluene was added 808 mg (2.00 mmol) Lawesson's reagent (Aldrich). The reaction mixture was heated to 95° C. for 5 min. Cooling to ambient temperature and dilution with 1:1 ethyl acetate/hexanes resulted in precipitation of insoluble material. Removal of the soluble phase, followed by additional washing of the solids and combination of the soluble phase, and removal of solvent afforded crude thiocarboxamide as a semisolid. Purification by chromatography on silica gel, eluting with ethyl acetate afforded 364 mg of thiocarboxamide.

Step B—Preparation of Phenylglycine Thiocarboxamide Hydrobromide:

A solution of 364 mg of t-butoxycarbonyl phenylglycine thiocarboxamide in 4 mL 30% HBr in acetIc acid was stirred for 1 hour. The volitile materials were removed under reduced pressure and the crude phenylglycine thiocarboxamide hydrobromide was obtained as a pale solid. The material was utilized without further purification.

To a stirred solution of 486 mg of (3,5-difluorophenylacetyl)-L-alanine (from B2) in 30 mL of dichoromethane was added 383 mg of EDCI, 270 mg of HOBT hydrate, followed by 350 µL of diisopropylethylamine. To this suspension was added phenylglycine thiocarboxamide hydrobromide in dichloromethane. The reaction mixture was stirred at ambient temperature for 72 hours. The reaction mixture was partioned between water and dichloromethane and the organic phase was washed with 1N HCl solution, followed by saturated aqueous sodium bicarbonate solution. Removal of solvent afforded the crude product, which was purified by chromatography on silica gel, eluting with ethyl acetate, to afford 271 mg of the title compound (approximately 3:2 mixture of phenylglycine diastereomers) as a pale solid.

NMR data was as follows:

$^1$H-Nmr (CDCl$_3$) (approx 3:2 mixture of diastereomers): δ=7.3–7.7 (m, 8H), 6.7–6.8 (m, 4H).

Example 335

Synthesis of N-[N-(3,5-Difluorophenyl-2-oxoacetyl)-L-alaninyl]-L-phenylglycine tert-Butyl Ester Following General Procedure C and using L-alaninyl-L-phenylglycine tert-butyl ester (prepared as described in Example 321) and 3,5-difluorophenylglyoxylate (prepared as described in *J. Org. Chem.*, 45(14), 28883 (1980)), the title compound was prepared as a solid. The product was purified by slurrying with EtOAc/hexanes.

Elemental Anal.: Calc.(%) C, 61.88, H, 5.42, N, 6.27; Found: C, 62.15, H, 5.51, N, 6.18.

Example 336

Synthesis of N-(2-Hydroxy-1-phenyleth-1-yl)-N'-[N-(3,5-Difluorophenylacetyl)-L-phenylglycinyl]-L-alaninamide Following General Procedure C and using N-(3,5-difluorophenylacetyl)-L-phenylglycinyl-L-alanine (prepared from N-(3,5-difluorophenylacetyl)-L-phenylglycinyl-L-alanine ethyl ester) and (S)-phenylglycinol (Aldrich), the title compound was prepared (m.p.=269–272° C.). The reaction was monitored by tlc (Rf=0.3 in 10% MeOH/CHCl$_3$) and the product was purified by chromatography using 10% MeOH/CHCl$_3$ as the eluent.

NMR data was as follows:

$^1$H-nmr (DMSO-d$_6$): δ=1.25 (d, 3H), 8.01 (d, 1H), 8.52 (d, 1H), 8.82 (d, 1H).

Optical Rotation: [α]$_{20}$=−62.7 @ 589 nm (c=1.02, DMSO). C$_{27}$H$_{27}$N$_3$O$_3$F$_2$ (MW=495.53); mass spectroscopy (MH$^+$) 496.

Example 337

Synthesis of N-(2-Hydroxyeth-1-yl)-N'-[N-(3,5-Difluorophenylacetyl)-L-alanyl]-L-phenylglycinamide Following General Procedure C and using N-(3,5-difluorophenylacetyl)-L-alanine (from Example B2 above) and L-phenylglycine (2-hydroxyethyl)amide hydrochloride (prepared from N-BOC-L-phenylglycine (Bachem) and 2-aminoethanol (Aldrich) using General Procedure C, followed by removal of the BOC group using General Procedure P), the title compound was prepared. The product was purified by chromatography using 10% MeOH/CHCl$_3$ as the eluent, followed by crystallization from EtOH.

NMR data was as follows:

$^1$H-nmr (DMSO-d$_6$): δ=1.22 (d, 3H), 5.42 (d, 1H). Optical Rotation: [α]$_{20}$=+8.77 @ 589 nm (c=1.03, DMSO). C$_{21}$H$_{23}$N$_3$O$_4$F$_2$ (MW=419.43); mass spectroscopy (MH$^+$) 420.

Example 338

Synthesis of N-(4-(4-Azido-2-hydroxybenzamido) but-1-yl)-N'-[N-(3,5-Difluorophenylacetyl)-L-alanyl]-L-phenylglycinamide Following General Procedure A and using N-(3,5-difluorophenylacetyl)-L-alanyl-L-phenylglycine (prepared as described herein) and 4-(4-azidosalicylamido)butylamine (Pierce Chemical), the title compound was prepared as a light sensitive solid. The reaction was conducted under low light conditions and the reaction vessel was protected from light. The reaction was monitered by tlc (Rf=0.2 in 2.5% MeOH/dichloromethane).

NMR data was as follows:

$^1$H-nmr (CD$_3$OH/CDCl$_3$): δ=7.72 (d, 2H), 7.30 (m, 5H), 6.84 (m, 2H), 6.73 (m, 1H), 6.54 (m, 2H), 5.34 (s, 1H), 4.39 (q, 1H), 3.56 (s, 2H), 3.31 (bs, 2H), 3.21 (bs, 2H), 1.57 (bs, 4H), 1.35 (d, 2H).

Example 339

Synthesis of N-(Methanesulfonyl)-N'-[N-(3,5-Difluorophenylacetyl)-L-alanyl]-L-phenylalanamide N-Cbz-L-Phenylalanine (Sigma) was coupled to N-hydroxysuccinimide (Aldrich) using DCC in dicloromethane. The resulting intermediate was reacted with methanesulfonamide in DMF with diisopropylethylamine to provide N-methanesulfonyl-N'-Cbz-L-phenylalanamide amide. The Cbz group was removed using General Procedure O and the resulting intermediate was coupled to N-(3,5-difluorophenylacetyl)-L-alanine (from Example B2 above) using General Procedure B to give the title compound, m.p.=203–205° C.

Examples 340–407

By following the procedures set forth above, the following additional compounds were prepared:

N-[N-(3,5-Difluorophenylacetyl)-L-alaninyl]-D-phenylglycine methyl ester (Ex 340)

N-[N-(3,5-Difluorophenylacetyl)-L-alaninyl]-L-(3-α-phenyl)proline methyl ester (Ex. 341)

N-[N-(3,5-Difluorophenylacetyl)-L-alaninyl]-L-azetidine methyl ester (Ex. 342)

methyl N-[N-(3,5-difluorophenylacetyl)-L-alaninyl]-2-amino-2-(5-chlorobenzothiophen-3-yl)acetate (Ex. 343)

t-butyl N-[N-(3,5-difluorophenylacetyl)-L-alaninyl]-(S)-2-amino-3-(thiazol-4-yl)propionate (Ex. 344)

t-butyl N-[N-(3,5-difluorophenylacetyl)-L-alaninyl]-L-phenylglycinamide (Ex. 345)

N-[N-(3,5-difluorophenylacetyl)-L-alaninyl]-D-(thien-2-yl)glycinamide (Ex. 346)

N-[N-(3,4-dichlorophenylacetyl)-L-alaninyl]-D-phenylglycinamide (Ex. 347)

N-[N-(3-chlorophenylacetyl)-L-alaninyl]-D-phenylglycinamide (Ex. 348)

N-[N-(3-bromophenylacetyl)-L-alaninyl]-D-phenylglycinamide (Ex. 349)

N-[N-(3-fluorophenylacetyl)-L-alaninyl]-D-phenylglycinamide (Ex. 350)

N-[N-(4-fluorophenylacetyl)-L-alaninyl]-D-phenylglycinamide (Ex. 351)

N-[N-(3-methylphenylacetyl)-L-alaninyl]-D-phenylglycinamide (Ex. 352)

N-[N-(4-methylphenylacetyl)-L-alaninyl]-D-phenylglycinamide (Ex. 353)

N-[N-(3-trifluoromethylphenylacetyl)-L-alaninyl]-D-phenylglycinamide (Ex. 354)

N-[N-(3-methoxyphenylacetyl)-L-alaninyl]-D-phenylglycinamide (Ex. 355)

N-[N-(2-chlorophenylacetyl)-L-alaninyl]-D-phenylglycinamide (Ex. 356)

N-[N-(1-naphthylacetyl)-L-alaninyl]-D-phenylglycinamide (Ex. 357)

N-[N-(2-naphthylacetyl)-L-alaninyl]-D-phenylglycinamide (Ex. 358)

N-[N-(phenylacetyl)-L-alaninyl]-D-phenylglycinamide (Ex. 359)

N-[N-(3,5-difluorophenylacetyl)-L-alaninyl]-D-phenylglycine (Ex. 360)

N'-[N-(3,5-difluorophenylacetyl)-L-alaninyl]-(S)-2-amino-2-(2-furanyl)acetamide (Ex. 361)

N'-[N-(3,4-difluorophenylacetyl)-D-alaninyl]-D-phenylglycinamide (Ex. 362)

N'-[N-(3,5-difluorophenylacetyl)-L-alaninyl]-L-phenylalanin-N-methylsulfonamide (Ex. 363)

N"-methyl-N"-phenyl-N'-[N-(3,5-difluorophenylacetyl)-L-alaninyl]-glycinamide (Ex. 364)

N"-methyl-N"-phenyl-N'-[N-(3,5-difluorophenylacetyl)-L-alaninyl]-L-alaninamide (Ex. 365)

N'-[N-(3,5-difluorophenylacetyl)-L-methioninyl]-L-phenylglycinamide (Ex. 366)

N"-methyl-N"-benzyl-N'-[N-(3,5-difluorophenylacetyl)-L-alaninyl]-glycinamide (Ex. 367)

N"-4-fluorobenzyl-N'-[N-(3,5-difluorophenylacetyl)-L-alaninyl]-L-phenylglycinamide (Ex. 368)

N'-[N-(3,5-difluorophenylacetyl)-L-alaninyl]-L-(4-fluoro)phenylglycineneopentyl ester (Ex. 369)

N-[N-(2,3,4,5,6-pentafluorophenylacetyl)-L-alaninyl]-L-(pyrid-3-yl)glycine methyl ester (Ex. 370)

N-[N-(3,5-difluorophenylacetyl)-L-(O-benzyl)serinyl]-L-phenylglycine methyl ester (Ex. 371)

N-[N-(3,5-difluorophenylacetyl)-L-(O-benzyl) threoninyl]-L-phenylglycine methyl ester (Ex. 372)

N-[N-(3,5-difluorophenylacetyl)-L-threoninyl]-L-phenylglycine methyl ester (Ex. 373)

N-[N-(3,5-difluorophenylacetyl)-L-serinyl]-L-phenylglycine methyl ester (Ex. 374)

N"-4-methylphenyl-N'-[N-(3,5-difluorophenylacetyl)-L-alaninyl]-L-phenylglycinamide (Ex. 375)

N"-tetrahydrofurfuryl-N'-[N-(3,5-difluorophenylacetyl)-L-alaninyl]-L-phenylglycinamide (Ex. 376)

N'-[N-(3,5-difluorophenylacetyl)-L-alaninyl]-L-4-fluorophenyl-glycinamide (Ex. 377)

N'-[N-(3,5-difluorophenylacetyl)-L-methionyl]-L-phenylglycinamide (Ex. 378)

N-[N-(3,5-difluorophenylacetyl)-2-aminobutanoyl]-L-phenylglycinamide (Ex. 379)

N'-[N-(3,5-difluorophenylacetyl)-L-phenylglycinyl]-L-phenylglycinamide (Ex. 380)

N-[N-(3,5-difluorophenylacetyl)-L-valinyl]-L-phenylglycinamide (Ex. 381)

N-[(R)-α-methylbenzyl]-N'-[N-(3,5-difluorophenylacetyl)-L-alaninyl]-L-phenylglycinamide (Ex. 382)

N-[1-phenyl-2-oxo-3-methylbutan-1-yl]-N'-(3,5-difluorophenylacetyl)-L-alaninamide (Ex. 383)

N-[1-phenyl-2-oxo-propan-1-yl]-N'-(3,5-difluorophenylacetyl)-L-alaninamide (Ex. 384)

N-[1-phenyl-2-oxo-pentan-1-yl]-N'-(3,5-difluorophenylacetyl)-L-alaninamide (Ex. 385)

N-[1-phenyl-2-oxo-2-phenyl-ethan-1-yl]-N'-(3,5-difluorophenyl-acetyl)-L-alaninamide (Ex. 386)

N-[1-phenyl-2-oxo-butan-1-yl]-N'-(3,5-difluorophenyl-acetyl)-L-alaninamide (Ex. 387)

N-[1-phenyl-2-oxo-4-methylpentan-1-yl]-N'-(3,5-difluorophenyl-acetyl)-L-alaninamide (Ex. 388)

N'-[N-(3,5-difluorophenylacetyl)-L-alaninyl]-L-α-hydroxyphenylalanine methyl ester (Ex. 389)

N"-[4-((2-hydroxy-4-azido)-phenyl)-NHC(O)-)butyl] N'-[N-(3,5-difluorophenylacetyl)-L-alaninyl]-L-phenylglycinamide (Ex. 390)

N'-[N-(3,5-difluorophenylacetyl)-L-alaninyl]-L-4-fluorophenylglycine t-butyl ester (Ex. 391)

N'-[N-(3,5-difluorophenylacetyl)-L-alaninyl]-L-4-phenylphenylglycine t-butyl ester (Ex. 392)

[N-(3,5-difluorophenylacetyl)-L-alaninyl]-L-(2,3-benzo[b]proline) methyl ester (Ex. 393)

N"-t-butyl-N'-[N-(3,5-difluorophenylacetyl)-L-alaninyl]-L-4-n-butylphenylglycinamide (Ex. 394)

N"-t-butyl-N'-[N-(3,5-difluorophenylacetyl)-L-alaninyl]-D,L-4-(phenylacetenyl)phenylglycinamide (Ex. 395)

N'-[N-(3,5-difluorophenylacetyl)-L-alaninyl]-D,L-phenylglycinthioamide (Ex. 396)

N-[1,3-diphenyl-2-oxo-propan-1-yl]-N'-(3,5-difluorophenylacetyl)-L-alaninamide (Ex. 397)

N-[1-phenyl-2-oxo-2-cyclopentylethan-1-yl]-N'-(3,5-difluorophenylacetyl)-L-alaninamide (Ex. 398)

N-[1-phenyl-2-oxo-hexan-1-yl]-N'-(3,5-difluorophenylacetyl)-L-alaninamide (Ex. 399)

N-[1-phenyl-2-oxo-3-methylpentan-1-yl]-N'-(3,5-difluorophenylacetyl)-L-alaninamide (Ex. 400)

N"-n-hexyl-6-biotinamidyl-N'-[N-(3,5-difluorophenylacetyl)-L-alaninyl]-D,L-phenylglycinthioamide (Ex. 401)

N'-[N-(3,5-difluorophenylacetyl)-L-methioninyl]-L-methionine (Ex. 402)

N'-[N-(2-t-BOC-amino)propionyl)-L-alaninyl]-L-phenylglycine methyl ester (Ex. 403)

N"-t-butyl N'-[N-(3,5-difluorophenylacetyl)-L-alaninyl]-L-2-fluorophenylglycinamide (Ex. 404)

N'-[N-(3,5-difluorophenylacetyl)-L-alaninyl]-D,L-2-phenylglycine methyl ester (Ex. 405)

N'-[N-(3,5-difluorophenylacetyl)-D,L-thien-3-ylglycinyl]-D,L-2-phenylglycine (Ex. 406)

N'-[N-(3,5-difluorophenylacetyl)-D,L-thien-3-ylglycinyl]-D,L-2-phenylglycine t-butyl ester (Ex. 407)

Example 408

Following the procedures set forth above, the following compounds of formula I were or could be prepared:

$R^1$ is 3,5-difluorophenyl; X' and X'' are hydrogen; $R^2$ is methyl; $R^4$ is p-fluorophenyl; $R^5$ is hydrogen; X is —C(O)OCH$_2$C(CH$_3$)$_3$; and n is 1;

$R^1$ is 3,5-difluorophenyl; X' and X'' are hydrogen; $R^2$ is methyl; $R^4$ is p-(phenyl)phenyl; $R^5$ is hydrogen; X is —C(O)NHC(CH$_3$)$_3$; and n is 1;

$R^1$ is cyclopentyl; X' and X'' are hydrogen; $R^2$ is methyl; $R^4$ is phenyl; $R^5$ is hydrogen; X is —C(O)OC(CH$_3$)$_3$; and n is 1;

$R^1$ is cyclopropyl; X' and X'' are hydrogen; $R^2$ is methyl; $R^4$ is phenyl; $R^5$ is hydrogen; X is —C(O)OC(CH$_3$)$_3$; and n is 1; and $R^1$ is 3,5-difluorophenyl; X' and X'' are hydrogen; $R^2$ is methyl; $R^4$ is phenyl; $R^5$ is hydrogen; X is —C(O)OCH$_2$C(CH$_3$)$_3$; and n is 1.

Example 409

Synthesis of N-Cyclohexyl-N-methyl-N'-[N-(3,5-difluorophenylacetyl)-L-alaninyl]-D,L-phenylglycinamide Following General Procedure C and using N-[N-(3,5-difluorophenylacetyl)-L-alaninyl]-D,L-phenylglycine (from Example D25 above) and N-cyclohexyl-N-methylamine (Aldrich), the title compound was prepared. The product was purified by flash chromatograph using CHCl$_3$/MeOH (97:3) as the eluent.

$C_{26}H_{31}F_2N_3O_3$ (MW=471.5); mass spectroscopy (MH$^+$) 471. Anal. Cald. for $C_{26}H_{31}F_2N_3O_3$; C, 66.23 H, 6.63 N, 8.91. Found: C, 65.99 H, 6.78, N, 8.98.

Example 410

Synthesis of N-Cyclohexyl-N-methyl-N'-[N-(3,5-difluorophenyl-α-hydroxyacetyl)-L-alaninyl]-D,L-phenylglycinamide Following General Procedure C and using 3,5-difluoromandelic acid (Aldrich) and N-cyclohexyl-N-methyl-(L-alaninyl)-D,L-phenylglycinamide hydrochloride, the title compound was prepared. The amine starting material was synthesized using the acid fluoride procedure of Carpino et al., J. Org. Chem. (1991), 56, 2611, utilizing Boc-phenylglycine (Aldrich) and N-cyclohexyl-N-methylamine followed by Boc-group removal using General Procedure P, coupling with Boc-L-alanine (Aldrich) using General Procedure C, and subsequent Boc-group removal using General Procedure P. The product was purified by flash chromatography using CHCl$_3$/MeOH (98:2) as the eluent.

$C_{26}H_{31}F_2N_3O_4$ (MW=487.5); mass spectroscopy (MH$^+$) 489. Anal. Cald for $C_{26}H_{31}F_2N_3O_4$; C, 64.05 H, 6.41 N, 8.62. Found; C, 64.01, H, 6.34 N, 8.04.

Example 411

Synthesis of N-Cyclohexyl-N-methyl-N'-[N-(2-hyroxy-3-methylbutyryl)-L-alaninyl]-D,L-phenylglycinamide Following General Procedure C and using 2-hydroxy-3-methylbutyric acid (Aldrich) and N-cyclohexyl-N-methyl-(L-alaninyl)-D,L-phenylglycinamide hydrochloride (prepared as described in Example 410), the title compound was prepared. The product was purified by flash chromatography using CHCl$_3$/MeOH (98:2) as eluent.

$C_{23}H_{35}N_3O_4$ (MW=417.5); mass spectroscopy (MH$^+$) 418. Anal. Cald for $C_{23}H_{35}N_3O_4$. 0.88 mol H$_2$O; C, 63.72 H, 8.55 N, 9.69. Found; C, 63.77 H, 8.71 N, 9.41.

Example 412

Synthesis of N-Cyclohexyl-N'-[N-3,5-difluorophenyl-α-hydroxyacetyl)-L-alaninyl]-D,L-phenylglycinamide Following General Procedure C and using 3,5-difluoromadelic acid (Oakwood) and N-cyclohexyl-(L-alaninyl)-D,L-phenylglycinamide hydorchloride (prepared as described in Example 410 using cyclohexylamine), the title compound was prepared. The product was purified by trituration from acetonitrile.

$C_{25}H_{29}F_2N_3O_4$ (MW=473.5); mass spectroscopy 474. Anal. Cald for $C_{25}H_{29}F_2N_3O_4$; C, 63.41 H, 6.17 N, 8.87. Found; C, 63.61 H, 5.93 N, 8.65.

Example 413

Synthesis of N-Cyclohexyl-N'-[N-(2-hydroxy-3-methylbutyryl)-L-alaninyl]-D,L-phenylglycinamide Following General Procedure C and using 2-hydroxy-3-methylbutyric acid (Aldrich) and N-cyclohexyl-(L-alaninyl)-D,L-phenylalycinamide hydrochloride (prepared as described in Example 412), the title compound was prepared. The product was purified by trituration from acetonitrile.

$C_{22}H_{33}N_3O_4$ (MW=403.5); mass spectroscopy 404. Anal. Cald for $C_{22}H_{33}N_3O_4$.0.5 mol H$_2$O; C, 64.05 H, 7.99 N, 10.18. Found; C, 64.29 H, 7.56 N, 10.14.

Example 414

Cellular Screen for the Detection of Inhibitors of β-Amyloid Production

Numerous compounds of formula I above were assayed for their ability to inhibit β-amyloid production in a cell line possessing the Swedish mutation. This screening assay employed cells (K293=human kidney cell line) which were stably transfected with the gene for amyloid precursor protein 751 (APP751) containing the double mutation Lys$_{651}$Met$_{652}$ to Asn$_{651}$Leu$_{652}$ (APP751 numbering) in the manner described in International Patent Application Publication No. 94/10569[8] and Citron et al.[12]. This mutation is commonly called the Swedish mutation and the cells, designated as "293 751 SWE", were plated in Coming 96-well plates at 1.5–2.5×10$^4$ cells per well in Dulbecco's minimal essential media plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media were removed and replaced with 200 μL of a compound of formula I (drug) containing media per well for a two hour pretreatment period and cells were incubated as above. Drug stocks were prepared in 100% dimethylsulfoxide such that at the final drug concentration used in the treatment, the concentration of dimethylsulfoxide did not exceed 0.5% and, in fact, usually equaled 0.1%.

At the end of the pretreatment period, the media were again removed and replaced with fresh drug containing media as above and cells were incubated for an additional two hours. After treatment, plates were centrifuged in a Beckman GPR at 1200 rpm for five minutes at room temperature to pellet cellular debris from the conditioned media. From each well, 100 μL of conditioned media or appropriate dilutions thereof were transferred into an ELISA plate precoated with antibody 266[14] against amino acids 13–28 of β-amyloid peptide as described in International Patent Application Publication No. 94/10569[8] and stored at 4° C. overnight. An ELISA assay employing labelled antibody 6C6[14] against amino acids 1–16 of β-amyloid peptide was run the next day to measure the amount of β-amyloid peptide produced.

Cytotoxic effects of the compounds were measured by a modification of the method of Hansen, et al.[13]. To the cells remaining in the tissue culture plate was added 25 μL of a 3,(4,5-dimethylthiazol-2-yl)2,5-diphenyltetrazolium bromide (MTT) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562\ nm}$ and the $OD_{650\ nm}$ was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a drug free control. All results are the mean and standard deviation of at least six replicate assays.

The test compounds were assayed for β-amyloid peptide production inhibition activity in cells using this assay. The results of this assay demonstrate that, each of the compounds within this invention tested reduced β-amyloid peptide production by at least 30% as compared to control.

Example 415

In Vivo Suppression of P-Amyloid Release and/or Synthesis

This example illustrates how the compounds of this invention could be tested for in vivo suppression of β-amyloid release and/or synthesis. For these experiments, 3 to 4 month old PDAPP mice are used [Games et al., (1995) Nature 373:523–527]. Depending upon which compound is being tested, the compound is usually formulated at either 5 or 10 mg/ml. Because of the low solubility factors of the compounds, they may be formulated with various vehicles, such as corn oil (Safeway, South San Francisco, Calif.); 10% EtOH in corn oil (Safeway); 2-hydroxypropyl-β-cyclodextrin (Research Biochemicals International, Natick Mass.); and carboxy-methyl-cellulose (Sigma Chemical Co., St. Louis Mo.). Specifically, for example 141 the vehicle was carboxy-methyl-cellulose (Sigma).

The mice are dosed subcutaneously with a 26 gauge needle and 3 hours later the animals are euthanized via $CO_2$ narcosis and blood is taken by cardiac puncture using a 1 cc 25G ⅝" tuberculin syringe/needle coated with solution of 0.5 M EDTA, pH 8.0. The blood is placed in a Becton-Dickinson vacutainer tube containing EDTA and spun down for 15 minutes at 1500×g at 5° C. The brains of the mice are then removed and the cortex and hippocampus are dissected out and placed on ice.

1. Brain Assay

To prepare hippocampal and cortical tissue for enzyme-linked immunosorbent assays (ELISAs) each brain region is homogenized in 10 volumes of ice cold guanidine buffer (5.0 M guanidine-HCl, 50 mM Tris-HCl, pH 8.0) using a Kontes motorized pestle (Fisher, Pittsburgh Pa.). The homogenates are gently rocked on a rotating platform for three to four hours at room temperature and stored at −20° C. prior to quantitation of β-amyloid.

The brain homogenates are diluted 1:10 with ice-cold casein buffer [0.25% casein, phosphate buffered saline (PBS), 0.05% sodium azide, 20 μg/ml aprotinin, 5 mM EDTA, pH 8.0, 10 μg/ml leupeptin], thereby reducing the final concentration of guanidine to 0.5 M, before centrifugation at 16,000×g for 20 minutes at 4° C. The β-amyloid standards (1–40 or 1–42 amino acids) were prepared such that the final composition equaled 0.5 M guanidine in the presence of 0.1% bovine serum albumin (BSA).

The total β-amyloid sandwich ELISA, quantitating both β-amyloid (aa 1-40) and β-amyloid (aa 1–42) consists of two monoclonal antibodies (mAb) to β-amyloid. The capture antibody, 266[14], is specific to amino acids 13–28 of β-amyloid. The antibody 3D6[15], which is specific to amino acids 1–5 of β-amyloid, is biotinylated and served as the reporter antibody in the assay. The 3D6 biotinylation procedure employs the manufacturer's (Pierce, Rockford Ill.) protocol for NHS-biotin labeling of immunoglobulins except that 100 mM sodium bicarbonate, pH 8.5 buffer is used. The 3D6 antibody does not recognize secreted β-amyloid precursor protein (APP) or full-length APP but detects only β-amyloid species with an amino terminal aspartlc acid. The assay has a lower limit of sensitivity of ~50 pg/ml (11 pM) and shows no cross-reactivity to the endogenous murine β-amyloid peptide at concentrations up to 1 ng/ml.

The configuration of the sandwich ELISA quantitating the level of β-amyloid (aa 1–42) employs the mAb 21F12[15] (which recognizes amino acids 33–42 of β-amyloid) as the capture antibody. Biotinylated 3D6 is also the reporter antibody in this assay which has a lower limit of sensitivity of ~125 pg/ml (28 pM).

The 266 and 21F12 capture mAbs are coated at 10 μg/ml into 96 well immunoassay plates (Costar, Cambidge Mass.) overnight at room temperature. The plates are then aspirated and blocked with 0.25% human serum albumin in PBS buffer for at least 1 hour at room temperature, then stored desiccated at 4° C. until use. The plates are rehydrated with wash buffer (Tris-buffered saline, 0.05% Tween 20) prior to use. The samples and standards are added to the plates and incubated overnight at 4° C. The plates are washed ≧3 times with wash buffer between each step of the assay. The biotinylated 3D6, diluted to 0.5 μg/ml in casein incubation buffer (0.25% casein, PBS, 0.05% Tween 20, pH 7.4) is incubated in the well for 1 hour at room temperature. Avidin-HRP (Vector, Burlingame Calif.) diluted 1:4000 in casein incubation buffer is added to the wells for 1 hour at room temperature. The colorimetric substrate, Slow TMB-ELISA (Pierce, Cambridge Mass.), is added and allowed to react for 15 minutes, after which the enzymatlc reaction is stopped with addition of 2 N $H_2SO_4$. Reaction product is quantified using a Molecular Devices Vmax (Molecular Devices, Menlo Park Calif.) measuring the difference in absorbance at 450 nm and 650 nm.

2. Blood Assay

The EDTA plasma is diluted 1:1 in specimen diluent (0.2 gm/l sodium phosphate.$H_2O$ (monobasic), 2.16 gm/l sodium phosphate.$7H_2O$ (dibasic), 0.5gm/l thimerosal, 8.5 gm/l sodium chloride, 0.5 ml TritonX-405, 6.0 g/l globulin-free bovine serum albumin; and water). The samples and standards in specimen diluent are assayed using the total β-amyloid assay (266 capture/3D6 reporter) described above for the brain assay except the specimen diluent was used instead of the casein diluents described.

From the foregoing description, various modifications and changes in the composition and method will occur to those skilled in the art. All such modifications coming within the scope of the appended claims are intended to be included therein.

What is claimed is:

1. A compound of the formula:

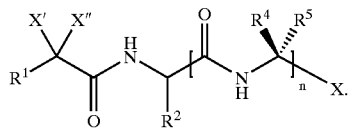

wherein $R^1$ is selected from the group consisting of:
(a) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl,
(b) a heteroaryl group substituted with 1 to 3 substituents selected from the group consisting hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl,
(c) cycloalkenyl,
(d) substituted alkyl provided that the substituent is not optionally substituted aryl and/or optionally substituted heteroaryl groups,
(e) substituted alkenyl provided that the substituent is not aralkenyl or heteroaralkenyl,
(f) substituted alkynyl provided that the substituent is not aralkynyl or heteroaralkynyl, and
(h) optionally substituted saturated heterocyclic;
$R^2$ is selected from the group consisting of alkyl, substituted alkyl, alkenyl, substituted alkenyl, alkynyl, substituted alkynyl, cycloalkyl, optionally substituted aryl, optionally substituted heteroaryl and optionally substituted heterocyclic;
each $R^4$ is independently selected from the group consisting of hydrogen, alkyl, alkenyl, alkynyl, optionally substituted aryl, cycloalkyl, cycloalkenyl, optionally substituted heteroaryl, optionally substituted heterocyclic, substituted alkyl, substituted alkenyl and substituted alkynyl;
each $R^5$ is selected from hydrogen and methyl or together with $R^4$ forms a cycloalkyl group of from 3 to 6 carbon atoms;

X is —C(O)Y or —C(S)Y where Y is selected from the group consisting of
(a) alkyl or cycloalkyl,
(b) substituted alkyl with the proviso that the substitution on said substituted alkyl do not include α-haloalkyl, α-diazoalkyl, α-OC(O)alkyl or α-OC(O)aryl groups,
(c) alkoxy or thioalkoxy,
(d) substituted alkoxy or substituted thioalkoxy,
(e) hydroxy,
(f) optionally substituted aryl,
(g) optionally substituted heteroaryl,
(h) optionally substituted heterocyclic,
(i) —NR'R" where R' and R" are independently selected from hydrogen, alkyl, substituted alkyl, alkenyl, substituted alkenyl, alkynyl, substituted alkynyl, cycloalkyl, optionally substituted aryl, optionally substituted heteroaryl, optionally substituted heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl, alkoxy or carboxyalkyl groups,
(j) —NHSO$_2$—R$^8$ where R$^8$ is selected from alkyl, substituted alkyl, alkenyl, substituted alkenyl, cycloalkyl, optionally substituted aryl, optionally substituted heteroaryl and optionally substituted heterocyclic,
(k) —NR$^9$NR$^{10}$R$^{10}$ where R$^9$ is hydrogen or alkyl, and each R$^{10}$ is independently selected from hydrogen, alkyl, substituted alkyl, alkenyl, substituted alkenyl, cycloalkyl, optionally substituted aryl, optionally substituted heteroaryl, optionally substituted heterocyclic, and
(l) —ONR$^9$[C(O)O]$_z$R$^{10}$ where z is zero or one, R$^9$ and R$^{10}$ are as defined above;
X can also be —CR$^6$R$^6$Y' where each R$^6$ is independently selected from the group consisting of hydrogen, alkyl, cycloalkyl, optionally substituted aryl, optionally substituted heteroaryl and optionally substituted heterocyclic and Y' is selected from the group consisting of hydroxyl, amino, thiol, alkoxy, substituted alkoxy, phthalimido, —OC(O)R$^7$, —SSR$^7$, —SSC(O)R$^7$ where R$^7$ is selected from the group consisting of alkyl, substituted alkyl, cycloalkyl, optionally substituted aryl, optionally substituted heteroaryl and optionally substituted heterocyclic,
X' is hydrogen, hydroxy or fluoro;
X" is hydrogen, hydroxy or fluoro, or X' and X" together form an oxo group, and
n is an integer equal to 1 or 2;
but, excluding the compounds:
(i) wherein $R^1$ is o-fluorophenyl, $R^2$ is 3,4-dichlorophenyl or ethyl, $R^4$ and $R^5$ are hydrogen, X' and X" are hydrogen, and X is —C(O)OCH$_3$;
(ii) wherein n is 1, $R^1$ is 5-fluoro-2-nitrophenyl, X' X" and $R^5$ are hydrogen, $R^4$ is 3-hydroxy-5-methoxyphenly or 3-isopropoxy-5-methoxyphenyl and $R^2$ is benzyl;
(iii) wherein n is 2, $R^1$ is —CH$_2$C(O)OCH$_3$, $R^2$ is —(CH$_2$)$_2$COOH, the first $R^4$ is isopropyl and the second $R^4$ is —(CH$_2$)$_4$NH$_2$, X', X" and each $R^5$ is hydrogen and X is —C(O)NHCH(C(O)CH$_2$Cl)CH$_2$phenyl, —C(O)NHCH(C(O)CH$_3$)CH$_2$phenyl or —C(O)NHCH(C(O)CF$_3$)CH$_2$phenyl;

213

(iv) wherein n is 2, $R^1$ is —$(CH_2)_6COOH$, $R^2$ is isopropyl, the first $R^4$ is —$(CH_2)_4NH_2$, the second $R^4$ is benzyl, X', X", and each $R^5$ is hydrogen and X is —$C(O)CH_2Cl$;

(v) wherein n is 2, $R^1$ is —$(CH)_3COOH$, $R^2$ is isopropyl, the first $R^4$ is —$(CH_2)_3NH_2$, the second $R^4$ is benzyl, X', X", and each $R^5$ is hydrogen and X is acetyl;

(vi) wherein n is 2, $R^1$ is —$CH_2C(O)OCH_3$, $R^2$ is —$(CH_2)_2COOH$, the first $R^4$ is isopropyl, the second $R^4$ is —$(CH_2)_3NH_2$, X', X" and each $R^5$ is hydrogen and X is —$C(O)NHCH(C(O)CF_3)CH_2phenyl$;

(vii) wherein n is 1, $R_1$ is —$CH(isopropyl)CH_2COOH$, Z is a bond, $R^2$ is —$(CH_2)_3NH_2$, $R^4$ is benzyl, X', X" and $R^5$ are hydrogen, and X is —$C(O)CH_2Cl$; and (viii) wherein $R_1$ is fluoro substituted aryl, n is 1, X' and X" are each hydrogen, $R^5$ is hydrogen or methyl, X is —C(O)Y where Y is haloalkyl, alkoxy, thioalkoxy, heterocyclic, —$CH_2$ heterocyclic, mono-substituted alkyl having its single substituent at the terminal position and wherein said substituent is diazo, —C(O)OR', —C(O) alkyl OR' or —C(O) NR', R" wherein R' and R" are independently hydrogen, alkyl, phenyl, benzyl or phenethyl, or Y is selected from the groups —$CH_2OR'$, —$CH_2SR'$, —$CH_2NR'R''$ or —NR'R" wherein R' and R" are independently hydrogen alkyl, phenyl, benzyl or phenethyl.

2. A compound of the formula:

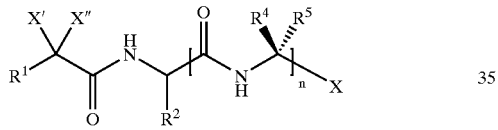

wherein $R^1$ is selected from the group consisting of alkyl, alkenyl, alkynyl, cycloalkyl, cycloalkenyl, substituted alkyl, substituted alkenyl, substituted alkynyl, optionally substituted aryl, optionally substituted heteroaryl and optionally substituted heterocyclic;

$R^2$ is selected from the group consisting of:
  (a) substituted alkyl provided that such substituted alkyl groups do not include optionally substituted aryl or optionally substituted heteroaryl substituted alkyl, or a side-chain of a naturally occurring amino acid,
  (b) substituted alkenyl provided that such substituted alkenyl groups do not include optionally substituted aryl or optionally substituted heteroaryl substituted alkenyl,
  (c) substituted alkynyl provided that such substituted alkynyl groups do not include optionally substituted aryl or optionally substituted heteroaryl substituted alkynyl,
  (d) optionally substituted saturated heterocyclic,
  (e) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl,

214 aminoacyl, alkaryl, optionally substituted aryloxy, carboxyl, carboxylalkyl, carboxylamido, and optionally substituted heteroaryl, and
  (f) a heteroaryl group substituted with 1 to 3 substituents selected from the group consisting of alkyl, alkoxy, optionally substituted aryl, alkaryl, optionally substituted aryloxy, halo, nitro, optionally substituted heteroaryl, thioalkoxy, thioaryloxy provided that if there is an alkyl substituent on the substituted optionally substituted heteroaryl group then there is at least one other substituent which is not alkyl;

each $R^4$ is independently selected from the group consisting of hydrogen, alkyl, alkenyl, alkynyl, optionally substituted aryl, cycloalkyl, cycloalkenyl, optionally substituted heteroaryl, optionally substituted heterocyclic, substituted alkyl, substituted alkenyl and substituted alkynyl;

each $R^5$ is selected from hydrogen and methyl or together with $R^4$ forms a cycloalkyl group of from 3 to 6 carbon atoms;

X is —C(O)Y or —C(S)Y where Y is selected from the group consisting of
  (a) alkyl or cycloalkyl,
  (b) substituted alkyl with the proviso that the substitution on said substituted alkyl do not include α-haloalkyl, α-diazoalkyl, α-OC(O)alkyl or α-OC(O)aryl groups,
  (c) alkoxy or thioalkoxy,
  (d) substituted alkoxy or substituted thioalkoxy,
  (e) hydroxy,
  (f) optionally substituted aryl,
  (g) optionally substituted heteroaryl,
  (h) optionally substituted heterocyclic,
  (i) —NR'R" where R' and R" are independently selected from hydrogen, alkyl, substituted alkyl, alkenyl, substituted alkenyl, alkynyl, substituted alkynyl, cycloalkyl, optionally substituted aryl, optionally substituted heteroaryl, optionally substituted heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl, alkoxy or carboxyalkyl groups,
  (j) —$NHSO_2$—$R^8$ where $R^8$ is selected from alkyl, substituted alkyl, alkenyl, substituted alkenyl, cycloalkyl, optionally substituted aryl, optionally substituted heteroaryl and optionally substituted heterocyclic,
  (k) —$NR^9NR^{10}R^{10}$ where $R^9$ is hydrogen or alkyl, and each $R^{10}$ is independently selected from hydrogen, alkyl, substituted alkyl, alkenyl, substituted alkenyl, cycloalkyl, optionally substituted aryl, optionally substituted heteroaryl, optionally substituted heterocyclic, and
  (l) —$ONR^9[C(O)O]_zR^{10}$ where z is zero or one, $R^9$ and $R^{10}$ are as defined above;

X can also be —$CR^6R^6Y'$ where each $R^6$ is independently selected from the group consisting of hydrogen, alkyl, alkoxy, substituted alkoxy, cycloalkyl, optionally substituted aryl, optionally substituted heteroaryl and optionally substituted heterocyclic and Y' is selected from the group consisting of hydroxyl, amino, thiol, alkoxy, phthalimido, —$OC(O)R^7$, —$SSR^7$, —$SSC(O)R^7$ where $R^7$ is selected from the group consisting of alkyl, substituted alkyl, cycloalkyl, optionally substituted aryl, optionally substituted heteroaryl and optionally substituted heterocyclic, X' is hydrogen, hydroxy or fluoro;

X" is hydrogen, hydroxy or fluoro, or X' and X" together form an oxo group, and n is an integer equal to 1 or 2, but excluding the following compounds:
(i) wherein n is 2, $R^1$ is n-$C_{17}H_{35}$, $R^2$ is —$CH_2OH$, the first $R^4$ is —$(CH_2)_2COOH$, the second $R^4$ is isopropyl, X', X" and each $R^5$ is hydrogen, and X is —C(O)NHCH(—$(CH_2)_4NH_2$)C(O)NHCH (benzyl) $CH_2Cl$;
(ii) wherein n is 2, R' is —$CH_2C(O)OCH_3$, $R^2$ is —$(CH_2)_2Cl$, the first $R^4$ is isopropyl, and the second $R^4$ is —$(CH_2)_4NH_2$, X', X" and each $R^5$ is hydrogen and X is —C(O)NHCH(C(O)$CH_2Cl$)$CH_2$phenyl, —C(O)NHCH(C(O)$CH_3$)$CH_2$phenyl or —C(O)NHCH(C(O)$CF_3$)$CH_2$phenyl;
(iii) wherein n is 2, R' is —$(CH_2)_6COOH$, $R^2$ is isopropyl, the first $R^4$ is —$(CH_2)_4NH_2$, the second $R^4$ is benzyl, X', X" and each $R^5$ is hydrogen and X is —C(O)$CH_2Cl$;
(iv) wherein n is 2, $R^1$ is —$(CH_2)_3COOH$, $R^2$ is isopropyl, the first $R^4$ is —$(CH_2)_3NH_2$, the second $R^4$ is benzyl, X', X" and each $R^5$ is hydrogen and X is acetyl;
(v) wherein n is 2, $R^1$ is —$CH_2C(O)OCH_3$, $R^2$ is —$(CH_2)_2COOH$, the first $R^4$ is isopropyl, the second $R^4$ is —$(CH_2)_3NH_2$, X', X" and each $R^5$ is hydrogen, and X is —C(O)NHCH(C(O)$CF_3$)$CH_2$phenyl; and
(vi) wherein n is 1, $R^1$ is —CH(isopropyl)$CH_2COOH$, Z is a bond, $R^2$ is —$(CH_2)_3NH_2$, $R^4$ is benzyl, X', X" and $R^5$ are hydrogen, and X is —C(O)$CH_2Cl$.

3. A compound of the formula:

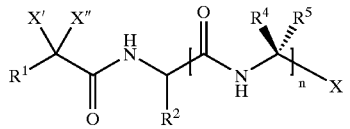

wherein $R^1$ is selected from the group consisting of alkyl, alkenyl, alkynyl, cycloalkyl, cycloalkenyl, substituted alkyl, substituted alkenyl, substituted alkynyl, optionally substituted aryl, optionally substituted heteroaryl and optionally substituted heterocyclic;

$R^2$ is selected from the group consisting of alkyl, substituted alkyl, alkenyl, substituted alkenyl, alkynyl, substituted alkynyl, cycloalkyl, optionally substituted aryl, optionally substituted heteroaryl and optionally substituted heterocyclic;

$R^4$ is selected from the group consisting of hydrogen, alkyl, alkenyl, alkynyl, optionally substituted aryl, cycloalkyl, cycloalkenyl, optionally substituted heteroaryl, optionally substituted heterocyclic, substituted alkyl, substituted alkenyl and substituted alkynyl provided that at least one $R^4$ is selected to be:
(a) substituted alkyl provided that such substituted alkyl groups do not include optionally substituted aryl or optionally substituted heteroaryl substituted alkyl, or a side-chain of a naturally occurring amino acid,
(b) substituted alkenyl provided that such substituted alkenyl groups do not include optionally substituted aryl or optionally substituted heteroaryl substituted alkenyl,
(c) substituted alkynyl provided that such substituted alkynyl groups do not include optionally substituted aryl or optionally substituted heteroaryl substituted alkynyl,
(d) optionally substituted saturated heterocyclic,
(e) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, and optionally substituted heteroaryl, and
(f) a heteroaryl group substituted with 1 to 3 substituents selected from the group consisting of alkyl, alkoxy, optionally substituted aryl, alkaryl, optionally substituted aryloxy, halo, nitro, optionally substituted heteroaryl, thioalkoxy, optionally substituted thioaryloxy provided that if there is an alkyl substituent on the substituted heteroaryl group then there is at least one other substituent which is not alkyl;

each $R^5$ is selected from hydrogen and methyl or together with $R^4$ forms a cycloalkyl group of from 3 to 6 carbon atoms;

X is —C(O)Y or —C(S)Y where Y is selected from the group consisting of
(a) alkyl or cycloalkyl,
(b) substituted alkyl with the proviso that the substitution on said substituted alkyl do not include α-haloalkyl, α-diazoalkyl, α-OC(O)alkyl or α-OC(O)aryl groups,
(c) alkoxy or thioalkoxy,
(d) substituted alkoxy or substituted thioalkoxy,
(e) hydroxy,
(f) optionally substituted aryl,
(g) optionally substituted heteroaryl,
(h) optionally substituted heterocyclic,
(i) —NR'R" where R' and R" are independently selected from hydrogen, alkyl, substituted alkyl, alkenyl, substituted alkenyl, alkynyl, substituted alkynyl, cycloalkyl, optionally substituted aryl, optionally substituted heteroaryl, optionally substituted heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl, alkoxy or carboxyalkyl groups,
(j) —$NHSO_2$—$R^8$ where $R^8$ is selected from alkyl, substituted alkyl, alkenyl, substituted alkenyl, cycloalkyl, optionally substituted aryl, optionally substituted heteroaryl and optionally substituted heterocyclic,
(k) —$NR^9NR^{10}R^{10}$ where $R^9$ is hydrogen or alkyl, and each $R^{10}$ is independently selected from hydrogen, alkyl, substituted alkyl, alkenyl, substituted alkenyl, cycloalkyl, optionally substituted aryl, optionally substituted heteroaryl, optionally substituted heterocyclic, and
(l) —$ONR^9[C(O)O]_zR^{10}$ where z is zero or one, $R^9$ and $R^{10}$ are as defined above;

X can also be —$CR^6R^6Y'$ where each $R^6$ is independently selected from the group consisting of hydrogen, alkyl, alkoxy, substituted alkoxy, cycloalkyl, optionally substituted aryl, optionally substituted heteroaryl and optionally substituted heterocyclic and Y' is selected from the group consisting of hydroxyl, amino, thiol, alkoxy, phthalimido, —OC(O)R$^7$, —SSR$^7$, —SSC(O) R$^7$ where R$^7$ is selected from the group consisting of alkyl, substituted alkyl, cycloalkyl, optionally substituted aryl, optionally substituted heteroaryl and optionally substituted heterocyclic, X' is hydrogen, hydroxy or fluoro;

X" is hydrogen, hydroxy or fluoro, or X' and X" together form an oxo group, and n is an integer equal to 1 or 2, but excluding the following compounds:
(i) wherein n is 1, R$^1$ is phenyl, X', X" and R$^5$ are each hydrogen, R$^2$ and R$^4$ are each methyl and X is —C(O)OCH$_3$;
(ii) wherein n is 2, R$^1$ is n-C$_{17}$H$_{35}$, R$^2$ is —CH$_2$OH, the first R$^4$ is —(CH$_2$)$_2$COOH, the second R$^4$ is isopropyl, X', X" and each R$^5$ is hydrogen and X is —C(O)NHCH(—(CH$_2$)$_4$NH$_2$)C(O)NHCH(benzyl)CH$_2$Cl;
(iii) wherein n is 2, R$^1$ is —CH$_2$C(O)OCH$_3$, R$^2$ is —(CH$_2$)$_2$COOH, the first R$^4$ is isopropyl and the second R$^4$ is —(CH$_2$)$_4$NH$_2$, X', X" and each R$^5$ is hydrogen and X is —C(O)NHCH(C(O)CH$_2$Cl)CH$_2$phenyl, or —C(O)NHCH(C(O)CH$_3$)CH$_2$phenyl, —C(O)NHCH(C(O)CF$_3$)CH$_2$phenyl;
(iv) wherein n is 2, R$^1$ is —(CH$_2$)$_6$COOH, R$^2$ is isopropyl, the first R$^4$ is —(CH$_2$)$_4$NH$_2$, the second R$^4$ is benzyl, X', X" and each R$^5$ is hydrogen and X is —C(O)CH$_2$Cl;
(v) wherein n is 2, R$^1$ is —(CH$_2$)$_3$COOH, R$^2$ is isopropyl, the first R$^4$ is —(CH$_2$)$_3$NH$_2$, the second R$^4$ is benzyl, X', X" and each R$^5$ is hydrogen and X is acetyl;
(vi) wherein n is 2, R$^1$ is —CH$_2$C(O)OCH$_3$, R$^2$ is —(CH$_2$)$_2$COOH, the first R$^4$ is isopropyl, the second R$^4$ is —(CH$_2$)$_3$NH$_2$, X', X" and each R$^4$ is hydrogen and X is —C(O)NHCH(C(O)CF$_3$)CH$_2$phenyl; and
(vii) wherein n is 1, R$^1$ is —CH(isopropyl)CH$_2$COOH, Z is a bond, R$^2$ is —(CH$_2$)$_3$NH$_2$, R$^4$ is benzyl, X', X" and R$^5$ are hydrogen, and X is —C(O)CH$_2$Cl.

4. A compound of the formula:

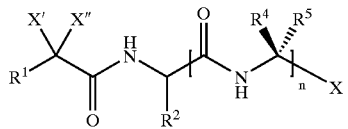

wherein R$^1$ is selected from the group consisting of alkyl, alkenyl, alkynyl, cycloalkyl, cycloalkenyl, substituted alkyl, substituted alkenyl, substituted alkynyl, optionally substituted aryl, optionally substituted heteroaryl and optionally substituted heterocyclic;

R$^2$ is selected from the group consisting of alkyl, substituted alkyl, alkenyl, substituted alkenyl, alkynyl, substituted alkynyl, cycloalkyl, optionally substituted aryl, optionally substituted heteroaryl and optionally substituted heterocyclic;

each R$^4$ is independently selected from the group consisting of hydrogen, alkyl, alkenyl, alkynyl, optionally substituted aryl, cycloalkyl, cycloalkenyl, optionally substituted heteroaryl, optionally substituted heterocyclic, substituted alkyl, substituted alkenyl and substituted alkynyl;

each R$^5$ is selected from hydrogen and methyl or together with R$^4$ forms a cycloalkyl group of from 3 to 6 carbon atoms;

X is selected from the group consisting of
(a) —C(O)-alkyl,
(b) —C(O)-substituted alkoxy or substituted thioalkoxy provided that the substituted alkoxy groups do not include benzyl and phenethyl,
(c) —C(O)-aryl wherein the aryl group is substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl,
(d) —C(O)-heteroaryl wherein the heteroaryl group is substituted with 1 to 3 substituents selected from the group consisting of alkyl, alkoxy, optionally substituted aryl, alkaryl, optionally substituted aryloxy, halo, nitro, optionally substituted heteroaryl, thioalkoxy and thioaryloxy
(e) —C(O)—NR'R" where R' and R" are independently selected from hydrogen, alkyl, substituted alkyl, cycloalkyl, optionally substituted aryl, optionally substituted heteroaryl, optionally substituted heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl or alkoxy groups, and X can also be —CR$^6$R$^6$Y' where each R$^6$ is independently selected from the group consisting of hydrogen, alkyl, cycloalkyl, optionally substituted aryl, optionally substituted heteroaryl and optionally substituted heterocyclic and Y' is selected from the group consisting of amino, thiol, alkoxy, phthalimido, —OC(O)R$^7$, —SSR$^7$, —SSC(O)R$^7$ where R$^7$ is selected from the group consisting of alkyl, substituted alkyl, cycloalkyl, optionally substituted aryl, optionally substituted heteroaryl and optionally substituted heterocyclic, provided that R' and R" are not both independently selected from hydrogen, alkyl, phenyl, benzyl and phenethyl;

X' is hydrogen, hydroxy or fluoro;

X" is hydrogen, hydroxy or fluoro, or X' and X" together form an oxo group, and n is an integer equal to 1 or 2;

but excluding the following compounds:
(i) wherein R$^1$ is iso-propyl, R$^2$ is phenyl, R$^4$ is methyl, R$^5$ is hydrogen, X' and X" are hydrogen, n is 2, the second R$^4$ at the carboxy terminus is methyl, and X is —C(O)NH-pNO$_2$-φ;
(ii) wherein n is 2, R$^1$ is n-C$_{17}$H$_{35}$, R$^2$ is —CH$_2$OH, the first R$^4$ is —(CH$_2$)$_2$COOH, the second R$^4$ is isopropyl, X', X" and each R$^5$ is hydrogen, and X is —C(O)NHCH(—(CH$_2$)$_4$NH$_2$)C(O)NHCH (benzyl)CH$_2$Cl;
(iii) wherein n is 2, R$^1$ is —CH$_2$C(O)OCH$_3$, R$^2$ is —(CH$_2$)$_2$Cl, the first R$^4$ is isopropyl and the second R$^4$ is —(CH$_2$)$_4$NH$_2$, X', X" and each R$^5$ is hydrogen and X is —C(O)NHCH(C(O)CH$_2$Cl)CH$_2$phenyl, —C(O)NHCH(C(O)CH$_3$)CH$_2$phenyl or —C(O)NHCH(C(O)CF$_3$)CH$_2$phenyl;

(iv) wherein n is 2, $R^1$ is —$(CH_2)_6COOH$, $R^2$ is isopropyl, the first $R^4$ is —$(CH_2)_4NH_2$, the second $R^4$ is benzyl, X', X" and each $R^5$ is hydrogen and X is —$C(O)CH_2Cl$, (v) wherein n is 2, $R^1$ is —$(CH_2)_3COOH$, $R^2$ is isopropyl, the first $R^4$ is —$(CH_2)_3NH_2$, the second $R^4$ is benzyl, X', X" and each $R^5$ is hydrogen and X is acetyl; and (vi) wherein n is 2, $R^1$ is —$CH_2C(O)OCH_3$, $R^2$ is —$(CH_2)_2COOH$, the first $R^4$ is isopropyl, the second $R^4$ is —$(CH_2)_3NH_2$, X', X" and each $R^5$ is hydrogen and X is —$C(O)NHCH(C(O)CF_3)CH_2phenyl$; and (vii) wherein n is 1, $R^1$ is —$CH(isopropyl)CH_2COOH$, Z is a bond, $R^2$ is —$(CH_2)_3NH_2$, $R^4$ is benzyl, X', X" and $R^5$ are hydrogen, and X is —$C(O)CH_2Cl$.

5. A compound of the formula:

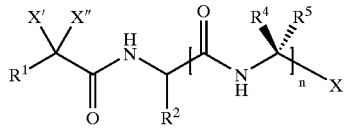

wherein $R^1$ is selected from the group consisting of:

(a) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl, (b) a heteroaryl group substituted with 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl, (c) cycloalkenyl, (d) substituted alkyl provided that the substituent is not optionally substituted aryl and/or optionally substituted heteroaryl groups, (e) substituted alkenyl provided that the substituent is not aralkenyl or heteroaralkenyl, (f) substituted alkynyl provided that the substituent is not aralkynyl or heteroaralkynyl, and (h) optionally substituted saturated heterocyclic;

$R^2$ is selected from the group consisting of (a) substituted alkyl provided that such substituted alkyl groups do not include optionally substituted aryl or optionally substituted heteroaryl substituted alkyl, or a side-chain of a naturally occurring amino acid, (b) substituted alkenyl provided that such substituted alkenyl groups do not include optionally substituted aryl or optionally substituted heteroaryl substituted alkenyl, (c) substituted alkynyl provided that such substituted alkynyl groups do not include optionally substituted aryl or optionally substituted heteroaryl substituted alkynyl, (d) optionally substituted saturated heterocyclic, (e) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, and optionally substituted heteroaryl, and (f) a optionally substituted heteroaryl group substituted with 1 to 3 substituents selected from the group consisting of alkyl, alkoxy, optionally substituted aryl, alkaryl, optionally substituted aryloxy, halo, nitro, optionally substituted heteroaryl, optionally substituted thioalkoxy, thioaryloxy provided that if there is an alkyl substituent on the substituted heteroaryl group then there is at least one other substituent which is not alkyl;

each $R^4$ is independently selected from the group consisting of hydrogen, alkyl, alkenyl, alkynyl, optionally substituted aryl, cycloalkyl, cycloalkenyl, optionally substituted heteroaryl, optionally substituted heterocyclic, substituted alkyl, substituted alkenyl and substituted alkynyl;

each $R^5$ is selected from hydrogen and methyl or together with $R^4$ forms a cycloalkyl group of from 3 to 6 carbon atoms;

X is —$C(O)Y$ or —$C(S)Y$ where Y is selected from the group consisting of (a) alkyl or cycloalkyl, (b) substituted alkyl with the proviso that the substitution on said substituted alkyl do not include α-haloalkyl, α-diazoalkyl, α-OC(O)alkyl or α-OC(O)aryl groups, (c) alkoxy or thioalkoxy, (d) substituted alkoxy or substituted thioalkoxy, (e) hydroxy, (f) optionally substituted aryl, (g) optionally substituted heteroaryl, (h) optionally substituted heterocyclic, (i) —NR'R" where R' and R" are independently selected from hydrogen, alkyl, substituted alkyl, alkenyl, substituted alkenyl, alkynyl, substituted alkynyl, cycloalkyl, optionally substituted aryl, optionally substituted heteroaryl, optionally substituted heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl, alkoxy or carboxyalkyl groups, (j) —$NHSO_2$—$R^8$ where $R^5$ is selected from alkyl, substituted alkyl, alkenyl, substituted alkenyl, cycloalkyl, optionally substituted aryl, optionally substituted heteroaryl and optionally substituted heterocyclic, (k) —$NR^9NR^{10}R^{10}$ where $R^9$ is hydrogen or alkyl, and each $R^{10}$ is independently selected from hydrogen, alkyl, substituted alkyl, alkenyl, substituted alkenyl, cycloalkyl, optionally substituted aryl, optionally substituted heteroaryl, optionally substituted heterocyclic, and (l) —ONR$^9$[C(O)O]$_z$R$^{10}$ where z is zero or one, R$^9$ and R$^{10}$ are as defined above;

X can also be —CR$^6$R$^6$Y' where each R$^6$ is independently selected from the group consisting of hydrogen, alkyl, cycloalkyl, optionally substituted aryl, optionally substituted heteroaryl and optionally substituted heterocyclic and Y' is selected from the group consisting of hydroxyl, amino, alkoxy, thiol, phthalimido, —OC(O)R$^7$, —SSR$^7$, —SSC(O)R$^7$ where R$^7$ is selected from the group consisting of alkyl, substituted alkyl, cycloalkyl, optionally substituted aryl, optionally substituted heteroaryl and optionally substituted heterocyclic, X' is hydrogen, hydroxy or fluoro;

X" is hydrogen, hydroxy or fluoro, or X and X" together form an oxo group, and n is an integer equal to 1 or 2;

but excluding the following compounds:

(i) wherein n is 2, R$^1$ is —CH$_2$C(O)OCH$_3$, R$^2$ is —(CH$_2$)$_2$COOH, the first R$^4$ is isopropyl and the second R$^4$ is —(CH$_2$)$_4$NH$_2$ X', X" and each R$^5$ is hydrogen and X is —C(O)NHCH(C(O)CH$_2$Cl)CH$_2$phenyl, —C(O)NHCH(C(O)CH$_3$)CH$_2$phenyl, or —C(O)NHCH(C(O)CF$_3$)CH$_2$phenyl;

(ii) wherein n is 2, R$^1$ is —(CH$_2$)$_6$COOH, R$^2$ is isopropyl, the first R$^4$ is —(CH$_2$)$_4$NH$_2$, the second R$^4$ is benzyl, X', X" and each R$^5$ is hydrogen and X is —C(O)CH$_2$Cl;

(iii) wherein n is 2, R$^1$ is —(CH$_2$)$_3$COOH, R$^2$ is isopropyl, the first R$^4$ is —(CH$_2$)$_3$NH$_2$, the second R$^4$ is benzyl, X', X" and each R$^5$ is hydrogen and X is acetyl;

(iv) wherein n is 2, R$^1$ is —CH$_2$C(O)OCH$_3$, R$^2$ is —(CH$_2$)$_2$COOH, the first R$^4$ is isopropyl, the second R$^4$ is —(CH$_2$)$_3$NH$_2$, X', X" and each R$^5$ is hydrogen and X is —C(O)NHCH(C(O)CF$_3$)CH$_2$phenyl;

(v) wherein n is 1, R$^1$ is —CH(isopropyl)CH$_2$COOH, Z is a bond, R$^2$ is —(CH$_2$)$_3$NH$_2$, R$^4$ is benzyl, X', X" and R$^5$ are hydrogen, and X is —C(O)CH$_2$Cl; and (vi) wherein R$^1$ is fluoro substituted aryl, n is 1, X' and X" are each hydrogen, R$^5$ is hydrogen or methyl, X is —C(O)Y where Y is haloalkyl, alkoxy, thioalkoxy, heterocyclic, —CH$_2$ heterocyclic, mono-substituted alkyl having its single substituent at the terminal position and wherein said substituent is diazo, —C(O)OR', —C(O)alkylOR' or —C(O)NR', R" wherein R' and R" are independently hydrogen, alkyl, phenyl, benzyl or phenethyl, or Y is selected from the groups —CH$_2$OR', —CH$_2$SR', —CH$_2$NR'R" or —NR'R" wherein R' and R" are independently hydrogen alkyl, phenyl, benzyl or phenethyl.

6. A compound of the formula:

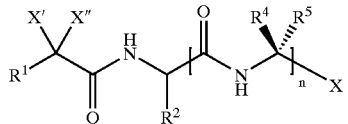

wherein R' is selected from the group consisting of:
(a) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl, (b) a heteroaryl group substituted with 1 to 3 substituents selected from the group consisting hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl, (c) cycloalkenyl, (d) substituted alkyl provided that the substituent is not optionally substituted aryl and/or optionally substituted heteroaryl groups, (e) substituted alkenyl provided that the substituent is not aralkenyl or heteroaralkenyl, (f) substituted alkynyl provided that the substituent is not aralkynyl or heteroaralkynyl, and (h) optionally substituted saturated heterocyclic;

R$^2$ is selected from the group consisting of alkyl, substituted alkyl, alkenyl, substituted alkenyl, alkynyl, substituted alkynyl, cycloalkyl, optionally substituted aryl, optionally substituted heteroaryl and optionally substituted heterocyclic;

R$^4$ is selected from the group consisting of hydrogen, alkyl, alkenyl, alkynyl, optionally substituted aryl, cycloalkyl, cycloalkenyl, optionally substituted heteroaryl, optionally substituted heterocyclic, substituted alkyl, substituted alkenyl and substituted alkynyl provided that at least one R$^4$ is selected to be:

(a) substituted alkyl provided that such substituted alkyl groups do not include optionally substituted aryl or optionally substituted heteroaryl substituted alkyl, or a side-chain of a naturally occurring amino acid, (b) substituted alkenyl provided that such substituted alkenyl groups do not include optionally substituted aryl or optionally substituted heteroaryl substituted alkenyl, (c) substituted alkynyl provided that such substituted alkynyl groups do not include optionally substituted aryl or optionally substituted heteroaryl substituted alkynyl, (d) optionally substituted saturated heterocyclic, (e) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, and optionally substituted heteroaryl, and (f) a heteroaryl group substituted with 1 to 3 substituents selected from the group consisting of alkyl, alkoxy, optionally substituted aryl, alkaryl, optionally substituted aryloxy, halo, nitro, optionally substituted heteroaryl, thioalkoxy, optionally substituted thioaryloxy provided that if there is an alkyl substituent on the substituted heteroaryl group then there is at least one other substituent which is not alkyl;

each $R^5$ is selected from hydrogen and methyl or together with $R^4$ forms a cycloalkyl group of from 3 to 6 carbon atoms;

X is —C(O)Y or —C(S)Y where Y is selected from the group consisting of
(a) alkyl or cycloalkyl,
(b) substituted alkyl with the proviso that the substitution on said substituted alkyl do not include α-haloalkyl, α-diazoalkyl, α-OC(O)alkyl or α-OC(O)aryl groups,
(c) alkoxy or thioalkoxy,
(d) substituted alkoxy or substituted thioalkoxy,
(e) hydroxy,
(f) optionally substituted aryl,
(g) optionally substituted heteroaryl,
(h) optionally substituted heterocyclic,
(i) —NR'R" where R' and R" are independently selected from hydrogen, alkyl, substituted alkyl, alkenyl, substituted alkenyl, alkynyl, substituted alkynyl, cycloalkyl, optionally substituted aryl, optionally substituted heteroaryl, optionally substituted heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl, alkoxy or carboxyalkyl groups,
(j) —NHSO$_2$—$R^8$ where $R^8$ is selected from alkyl, substituted alkyl, alkenyl, substituted alkenyl, cycloalkyl, optionally substituted aryl, optionally substituted heteroaryl and optionally substituted heterocyclic,
(k) —NR$^9$NR$^{10}$R$^{10}$ where $R^9$ is hydrogen or alkyl, and each $R^{10}$ is independently selected from hydrogen, alkyl, substituted alkyl, alkenyl, substituted alkenyl, cycloalkyl, optionally substituted aryl, optionally substituted heteroaryl, optionally substituted heterocyclic, and
(l) —ONR$^9$[C(O)O]$_z$R$^{10}$ where z is zero or one, $R^9$ and $R^{10}$ are as defined above;

X can also be —CR$^6$R$^6$Y' where each $R^6$ is independently selected from the group consisting of hydrogen, alkyl, cycloalkyl, optionally substituted aryl, optionally substituted heteroaryl and optionally substituted heterocyclic and Y' is selected from the group consisting of hydroxyl, amino, alkoxy, thiol, phthalimido, —OC(O)R$^7$, —SSR$^7$, —SSC(O)R$^7$ where $R^7$ is selected from the group consisting of alkyl, substituted alkyl, cycloalkyl, optionally substituted aryl, optionally substituted heteroaryl and optionally substituted heterocyclic, X' is hydrogen, hydroxy or fluoro;
X" is hydrogen, hydroxy or fluoro, or X' and X" together form an oxo group, and
n is an integer equal to 1 or 2;
but excluding the compounds:
(i) wherein n is 2, $R^1$ is —CH$_2$C(O)OCH$_3$, $R^2$ is —(CH$_2$)$_2$COOH, the first $R^4$ is isopropyl and the second $R^4$ is —(CH$_2$)$_4$NH$_2$, X', X" and each $R^5$ is hydrogen and X is —C(O)NHCH(C(O)CH$_2$Cl)CH$_2$phenyl, —C(O)NHCH(C(O)CH$_3$)CH$_2$phenyl, or —C(O)NHCH(C(O)CF$_3$)CH$_2$phenyl;
(ii) wherein n is 2, $R^1$ is —(CH$_2$)$_6$COOH, $R^2$ is isopropyl, the first $R^4$ is —(CH$_2$)$_4$NH$_2$, the second $R^4$ is benzyl, X', X" and each $R^5$ is hydrogen and X is —C(O)CH$_2$Cl
(iii) wherein n is 2, $R^1$ is —(CH$_2$)$_3$COOH, $R^2$ is isopropyl, the first $R^4$ is —(CH$_2$)$_3$NH$_2$, the second $R^4$ is benzyl, X', X" and each $R^5$ is hydrogen and X is acetyl;
(iv) wherein n is 2, $R^1$ is —CH$_2$C(O)OCH$_3$, $R^2$ is —(CH$_2$)$_2$COOH, the first $R^4$ is isopropyl, the second $R^4$ is —(CH$_2$)$_3$NH$_2$, X', X" and each $R^5$ is hydrogen and X is —C(O)NHCH(C(O)CF$_3$)CH$_2$phenyl; and
(v) wherein n is 1, $R^1$ is —CH(isopropyl)CH$_2$COOH, Z is a bond, $R^2$ is —(CH$_2$)$_3$NH$_2$, $R^4$ is benzyl, X', X" and $R^5$ are hydrogen, and X is —C(O)CH$_2$Cl.

7. A compound of the formula:

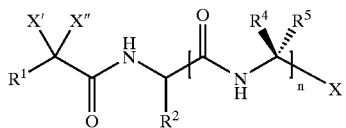

wherein $R^1$ is selected from the group consisting of:
(a) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl,
(b) a heteroaryl group substituted with 1 to 3 substituents selected from the group consisting hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl,
(c) cycloalkenyl,
(d) substituted alkyl provided that the substituent is not optionally substituted aryl and/or optionally substituted heteroaryl groups,
(e) substituted alkenyl provided that the substituent is not aralkenyl or heteroaralkenyl,
(f) substituted alkynyl provided that the substituent is not aralkynyl or heteroaralkynyl, and
(h) optionally substituted heterocyclic;

$R^2$ is selected from the group consisting of alkyl, substituted alkyl, alkenyl, substituted alkenyl, alkynyl, substituted alkynyl, cycloalkyl, optionally substituted aryl, optionally substituted heteroaryl and optionally substituted heterocyclic;

each $R^4$ is independently selected from the group consisting of hydrogen, alkyl, alkenyl, alkynyl, optionally substituted aryl, cycloalkyl, cycloalkenyl, optionally substituted heteroaryl, optionally substituted heterocyclic, substituted alkyl, substituted alkenyl and substituted alkynyl;

each $R^5$ is selected from hydrogen and methyl or together with $R^4$ forms a cycloalkyl group of from 3 to 6 carbon atoms;

X is selected from the group consisting of
  (a) —C(O)-alkyl,
  (b) —C(O)-substituted alkoxy or substituted thioalkoxy provided that the substituted alkoxy groups do not include benzyl and phenethyl,
  (c) —C(O)-aryl wherein the aryl group is substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl,
  (d) —C(O)-heteroaryl wherein the heteroaryl group is substituted with 1 to 3 substituents selected from the group consisting of alkyl, alkoxy, optionally substituted aryl, alkaryl, optionally substituted aryloxy, halo, nitro, optionally substituted heteroaryl, thioalkoxy and thioaryloxy
  (e) —C(O)—NR'R" where R' and R" are independently selected from hydrogen, alkyl, substituted alkyl, cycloalkyl, optionally substituted aryl, optionally substituted heteroaryl, optionally substituted heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl or alkoxy groups, and X can also be —CR⁶R⁶Y' where each $R^6$ is independently selected from the group consisting of hydrogen, alkyl, cycloalkyl, optionally substituted aryl, optionally substituted heteroaryl and optionally substituted heterocyclic and Y' is selected from the group consisting of amino, thiol, alkoxy, phthalimido, —OC(O)R⁷, —SSR⁷, —SSC(O)R⁷ where $R^7$ is selected from the group consisting of alkyl, substituted alkyl, cycloalkyl, optionally substituted aryl, optionally substituted heteroaryl and optionally substituted heterocyclic, provided that R' and R" are not both independently selected from hydrogen, alkyl, phenyl, benzyl and phenethyl;

X' is hydrogen, hydroxy or fluoro;

X" is hydrogen, hydroxy or fluoro, or X' and X" together form an oxo group, and n is an integer equal to 1 or 2;

but excluding the compounds:
  (i) wherein n is 2, $R^1$ is —CH₂C(O)OCH₃, $R^2$ is —(CH₂)₂COOH, the first $R^4$ is isopropyl and the second $R^4$ is —(CH₂)₄NH₂, X', X" and each $R^5$ is hydrogen and X is —C(O)NHCH(C(O)CH₂Cl)CH₂phenyl, —C(O)NHCH(C(O)CH₃)CH₂phenyl, or —C(O)NHCH(C(O)CF₃)CH₂phenyl;
  (ii) wherein n is 2, $R^1$ is —(CH₂)₆COOH, $R^2$ is isopropyl, the first $R^4$ is —(CH₂)₄NH₂, the second $R^4$ is benzyl, X', X" and each $R^5$ is hydrogen and X is —C(O)CH₂Cl
  (iii) wherein n is 2, $R^1$ is —(CH₂)₃COOH, $R^2$ is isopropyl, the first $R^4$ is —(CH₂)₃NH₂, the second $R^4$ is benzyl, X', X" and each $R^5$ is hydrogen and X is acetyl;
  (iv) wherein n is 2, $R^1$ is —CH₂C(O)OCH₃, $R^2$ is —(CH₂)₂COOH, the first $R^4$ is isopropyl, the second $R^4$ is —(CH₂)₃NH₂, X', X" and each $R^5$ is hydrogen and X is —C(O)NHCH(C(O)CF₃)CH₂phenyl; and
  (v) wherein n is 1, $R^1$ is —CH(isopropyl)CH₂COOH, Z is a bond, $R^2$ is —(CH₂)₃NH₂, $R^4$ is benzyl, X', X" and $R^5$ are hydrogen, and X is —C(O)CH₂Cl.

8. A compound of the formula:

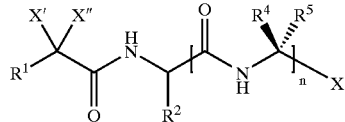

wherein $R^1$ is selected from the group consisting of:
  (a) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl,
  (b) a heteroaryl group substituted with 1 to 3 substituents selected from the group consisting hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl,
  (c) cycloalkenyl,
  (d) substituted alkyl provided that the substituent is not optionally substituted aryl and/or optionally substituted heteroaryl groups,
  (e) substituted alkenyl provided that the substituent is not aralkenyl or heteroaralkenyl,
  (f) substituted alkynyl provided that the substituent is not aralkynyl or heteroaralkynyl, and
  (h) optionally substituted heterocyclic;

$R^2$ is selected from the group consisting of
  (a) substituted alkyl provided that such substituted alkyl groups do not include optionally substituted aryl or optionally substituted heteroaryl substituted alkyl, or a side-chain of a naturally occurring amino acid,
  (b) substituted alkenyl provided that such substituted alkenyl groups do not include optionally substituted aryl or optionally substituted heteroaryl substituted alkenyl,
  (c) substituted alkynyl provided that such substituted alkynyl groups do not include optionally substituted aryl or optionally substituted heteroaryl substituted alkynyl,
  (d) optionally substituted saturated heterocyclic,
  (e) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, and optionally substituted heteroaryl, and (f) a heteroaryl group substituted with 1 to 3 substituents selected from the group consisting of alkyl, alkoxy, optionally substituted aryl, alkaryl, optionally substituted aryloxy, halo, nitro, optionally substituted heteroaryl, thioalkoxy, optionally substituted thioaryloxy provided that if there is an alkyl substituent on the substituted heteroaryl group then there is at least one other substituent which is not alkyl;

$R^4$ is selected from the group consisting of hydrogen, alkyl, alkenyl, alkynyl, optionally substituted aryl, cycloalkyl, cycloalkenyl, optionally substituted heteroaryl, optionally substituted heterocyclic, substituted alkyl, substituted alkenyl and substituted alkynyl provided that at least one $R^4$ is selected to be:

(a) substituted alkyl provided that such substituted alkyl groups do not include optionally substituted aryl or optionally substituted heteroaryl substituted alkyl, or a side-chain of a naturally occurring amino acid, (b) substituted alkenyl provided that such substituted alkenyl groups do not include optionally substituted aryl or optionally substituted heteroaryl substituted alkenyl, (c) substituted alkynyl provided that such substituted alkynyl groups do not include optionally substituted aryl or optionally substituted heteroaryl substituted alkynyl, (d) optionally substituted saturated heterocyclic, (e) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl, and (f) a heteroaryl group substituted with 1 to 3 substituents selected from the group consisting of alkyl, alkoxy, optionally substituted aryl, alkaryl, optionally substituted aryloxy, halo, nitro, optionally substituted heteroaryl, thioalkoxy, optionally substituted thioaryloxy provided that if there is an alkyl substituent on the substituted heteroaryl group then there is at least one other substituent which is not alkyl;

each $R^5$ is selected from hydrogen and methyl or together with $R^4$ forms a cycloalkyl group of from 3 to 6 carbon atoms;

X is selected from the group consisting of (a) —C(O)-alkyl, (b) —C(O)-substituted alkoxy or substituted thioalkoxy provided that the substituted alkoxy groups do not include benzyl and phenethyl, (c) —C(O)-aryl wherein the aryl group is substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl, (d) —C(O)-heteroaryl wherein the heteroaryl group is substituted with 1 to 3 substituents selected from the group consisting of alkyl, alkoxy, optionally substituted aryl, alkaryl, optionally substituted aryloxy, halo, nitro, optionally substituted heteroaryl, thioalkoxy and optionally substituted thioaryloxy (e) —C(O)—NR'R" where R' and R" are independently selected from hydrogen, alkyl, substituted alkyl, cycloalkyl, optionally substituted aryl, optionally substituted heteroaryl, optionally substituted heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl or alkoxy groups, and X can also be —$CR^6R^6Y'$ where each $R^6$ is independently selected from the group consisting of hydrogen, alkyl, cycloalkyl, optionally substituted aryl, optionally substituted heteroaryl and optionally substituted heterocyclic and Y' is selected from the group consisting of amino, thiol, alkoxy, phthalimido, —$OC(O)R^7$, —$SSR^7$, —$SSC(O)R^7$ where $R^7$ is selected from the group consisting of alkyl, substituted alkyl, cycloalkyl, optionally substituted aryl, optionally substituted heteroaryl and optionally substituted heterocyclic, provided that R' and R" are not both independently selected from hydrogen, alkyl, phenyl, benzyl and phenethyl;

X' is hydrogen, hydroxy or fluoro;

X" is hydrogen, hydroxy or fluoro, or X' and X" together form an oxo group, and n is an integer equal to 1 or 2;

but excluding the following compounds:

(i) wherein n is 2, $R^1$ is —$CH_2C(O)OCH_3$, $R^2$ is —$(CH_2)_2COOH$, the first $R^4$ is isopropyl and the second $R^4$ is —$(CH_2)_4NH_2$, X', X" and each $R^5$ is hydrogen and X is —$C(O)NHCH(C(O)CH_2Cl)CH_2$phenyl, —$C(O)NHCH(C(O)CH_3)CH_2$phenyl, or —$C(O)NHCH(C(O)CF_3)CH_2$phenyl;

(ii) wherein n is 2, $R^1$ is —$(CH_2)_6COOH$, $R^2$ is isopropyl, the first $R^4$ is —$(CH_2)_4NH_2$, the second $R^4$ is benzyl, X', X" and each $R^5$ is hydrogen and X is —$C(O)CH_2Cl$ (iii) wherein n is 2, $R^1$ is —$(CH_2)_3COOH$, $R^2$ is isopropyl, the first $R^4$ is —$(CH_2)_3NH_2$, the second $R^4$ is benzyl, X', X" and each $R^5$ is hydrogen and X is acetyl;

(iv) wherein n is 2, $R^1$ is —$CH_2C(O)OCH_3$, $R^2$ is —$(CH_2)_2COOH$, the first $R^4$ is isopropyl, the second $R^4$ is —$(CH_2)_3NH_2$, X', X" and each $R^5$ is hydrogen and X is —$C(O)NHCH(C(O)CF_3)CH_2$phenyl; and (v) wherein n is 1, $R^1$ is —$CH(isopropyl)CH_2COOH$, Z is a bond, $R^2$ is —$(CH_2)_3NH_2$, $R^4$ is benzyl, X', X" and $R^5$ are hydrogen, and X is —$C(O)CH_2Cl$.

9. A compound according to claims 1, 2, 3, 4, 5, 6, 7, or 8 wherein X" is hydrogen and X' is hydrogen or fluoro.

10. A compound according to claims 2, 3 or 4 wherein $R^1$ substituted aryl groups are selected from monosubstituted phenyls, disubstituted phenyls and trisubstituted phenyls.

11. The compound according to claim 10 wherein the substituted phenyl is selected from the group consisting of 4-fluorophenyl, 4-phenoxyphenyl, 4-(pyrid-2-yl)phenyl, 3-carboxyphenyl, 2-fluorophenyl, 3-fluorophenyl, 3-chloro-4-fluorophenyl, 3-fluoro-4-chlorophenyl, 3,5-difluorophenyl, 3-chloro-5-fluorophenyl, 2-chloro-4-fluorophenyl, and 2,5-difluorophenyl.

12. The compound according to claims 2, 3, or 4 wherein $R^1$ is a heteroaryl group.

13. The compound according to claim 12 wherein $R^1$ is selected from the group consisting of fluoropyridyls and 4-phenoxypyrid-2-yl.

14. The compound according to claim 1, 3, 4, 6 and 7 wherein $R^2$ is substituted alkyl or heterocyclic.

15. The compound according to claim 1, 2, 4, 5, or 7 wherein $R^4$ is selected from the group consisting of p-(CH$_3$)$_2$NCH$_2$CH$_2$CH$_2$O-benzyl, p-(CH$_3$)$_3$COC(O)CH$_2$O-benzyl, p-(HOOCCH$_2$O)-benzyl, 2-aminopyrid-6-yl, p-(N-morpholino-CH$_2$CH$_2$O)-benzyl, —CH$_2$—C(O)O-t-butyl, —CH[CH(CH$_3$)$_2$]COOCH$_3$, —CH$_2$CH$_2$N(CH$_3$)$_2$, —CH(O-t-butyl)CH$_3$, —CH$_2$OCH$_3$, —(CH$_2$)$_4$NH-Boc, —CH$_2$-(N-morpholino), p-(N-morpholino-CH$_2$CH$_2$O)-benzyl, 5-chlorobenzo[b]thiophen-2-yl, 5-chlorobenzo[b]thiophen-3-yl, and 6-methoxynaphth-2-yl.

16. A compound according to claim 1, 2, 3, 5, and 6 wherein X is —C(O)Y and Y is substituted alkoxy or —NR'R".

17. A compound according to claim 16 wherein Y is selected from the group consisting of 3-iodo-n-propoxy, 4-bromo-n-butoxy, N-morpholino, azetidino, N-thiomorpholino, N-piperidinyl, N-hexamethylene-imino, N-heptamethylene-imino, N-pyrrolidinyl, —NH-methallyl, —NHCH$_2$-(furan-2-yl), —NH(p-methylphenyl), —NHOCH$_3$, —NHCH$_2$(P-fluorophenyl), —NHCH$_2$CH$_2$OCH$_3$, —NHCH$_2$CH$_2$N(CH$_3$)$_2$, —NHCH$_2$-(pyrid-2-yl), —NHCH$_2$-(pyrid-3-yl), —NHCH$_2$-(pyrid-4-yl), N-thiazolindinyl, —NHOH, —NH(p-NO$_2$-φ), —NHCH$_2$(p-NO$_2$-φ), —NHCH$_2$(m-NO$_2$-φ), —N(CH$_3$)OCH$_3$, —NHCH$_2$-(3,5-di-fluorophenyl), —NHCH$_2$CH$_2$F, —NHCH$_2$(p-CH$_3$O-φ), —NHCH$_2$(m-CH$_3$O-φ), —NHCH$_2$(p-CF$_3$-φ), —NHCH$_2$CH$_2$OCH$_3$, —NHCH(CH$_3$)φ, —NHCH$_2$-(p-F-φ), —N(CH$_3$)CH$_2$CH$_2$N(CH$_3$)$_2$, and —NHCH$_2$-(tetrahydrofuran-2-yl).

18. A compound of the formula:

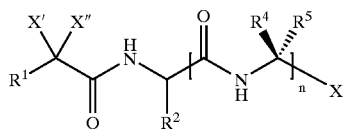

wherein R' is selected from the group consisting of:
(a) aryl group substituted with from 1 to 3 substituents selected from the group consisting of hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl,
(b) a heteroaryl group substituted with 1 to 3 substituents selected from the group consisting hydroxy, acyl, acyloxy, alkyl, alkoxy, alkenyl, alkynyl, amino, aminoacyl, alkaryl, optionally substituted aryl, optionally substituted aryloxy, carboxyl, carboxylalkyl, carboxylamido, cyano, halo, nitro, optionally substituted heteroaryl, and trihalomethyl provided that at least one of said substituents is selected from acyl, acyloxy, alkenyl, alkynyl, aminoacyl, alkaryl, optionally substituted aryloxy, carboxyl, carboxylalkyl, carboxylamido, fluoro and optionally substituted heteroaryl,
(c) cycloalkenyl,
(d) substituted alkyl provided that the substituent is not optionally substituted aryl and/or optionally substituted heteroaryl groups,
(e) substituted alkenyl provided that the substituent is not aralkenyl or heteroaralkenyl,
(f) substituted alkynyl provided that the substituent is not aralkynyl or heteroaralkynyl, and
(h) optionally substituted saturated heterocyclic;

$R^2$ is selected from the group consisting of alkyl, alkenyl, substituted alkenyl, alkynyl, substituted alkynyl, cycloalkyl, optionally substituted aryl, optionally substituted heteroaryl, optionally substituted heterocyclic and substituted alkyl which is an alkyl group of from 1 to 10 carbon atoms, having from 1 to 3 substituents selected from the group consisting of alkoxy, substituted alkoxy, optionally substituted aryloxy, optionally substituted heteroaryloxy, optionally substituted heterocyclyloxy, acyl, acylamino, amino, aminoacyl, aminocarboxy esters, cyano, cycloalkyl, halogen, hydroxyl, carboxyl, carboxylalkyl, oxyacyl, oxyacylamino, thiol, thioalkoxy, substituted thioalkoxy, optionally substituted heteroaryl, optionally substituted heterocyclic, nitro, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from alkyl, substituted alkyl, optionally substituted aryl, optionally substituted heteroaryl and optionally substituted heterocyclic;

each $R^4$ is independently selected from the group consisting of hydrogen, alkyl, alkenyl, alkynyl, optionally substituted aryl, cycloalkyl, cycloalkenyl, optionally substituted heteroaryl, optionally substituted heterocyclic, substituted alkyl, substituted alkenyl and substituted alkynyl;

each $R^5$ is selected from hydrogen and methyl or together with $R^4$ forms a cycloalkyl group of from 3 to 6 carbon atoms;

X is —C(O)Y or —C(S)Y where Y is selected from the group consisting of
(a) alkyl or cycloalkyl,
(b) substituted alkyl with the proviso that the substitution on said substituted alkyl do not include α-haloalkyl, α-diazoalkyl, α-OC(O)alkyl or α-OC(O)aryl groups,
(c) alkoxy or thioalkoxy,
(d) substituted alkoxy or substituted thioalkoxy,
(e) hydroxy,
(f) optionally substituted aryl,
(g) optionally substituted heteroaryl,
(h) optionally substituted heterocyclic,
(i) —NR'R" where R' and R" are independently selected from hydrogen, alkyl, substituted alkyl, alkenyl, substituted alkenyl, alkynyl, substituted alkynyl, cycloalkyl, optionally substituted aryl, optionally substituted heteroaryl, optionally substituted heterocyclic, where one of R' or R" is hydroxy or alkoxy, and where R' and R" are joined to form a cyclic group having from 2 to 8 carbon atoms optionally containing 1 to 2 additional heteroatoms selected from oxygen, sulfur and nitrogen and optionally substituted with one or more alkyl, alkoxy or carboxyalkyl groups, (j) —NHSO$_2$-R$^8$ where R$^8$ is selected from alkyl, substituted alkyl, alkenyl, substituted alkenyl, cycloalkyl, optionally substituted aryl, optionally substituted heteroaryl and optionally substituted heterocyclic, (k) —NR$^9$NR$^{10}$R$^{10}$ where R$^9$ is hydrogen or alkyl, and each R$^{10}$ is independently selected from hydrogen, alkyl, substituted alkyl, alkenyl, substituted alkenyl, cycloalkyl, optionally substituted aryl, optionally substituted heteroaryl, optionally substituted heterocyclic, and (l) —ONR$^9$[C(O)O]$_z$R$^{10}$ where z is zero or one, R$^9$ and R$^{10}$ are as defined above;

X can also be —CR$^6$R$^6$Y' where each R$^6$ is independently selected from the group consisting of hydrogen, alkyl, cycloalkyl, optionally substituted aryl, optionally substituted heteroaryl and optionally substituted heterocyclic and Y' is selected from the group consisting of hydroxyl, amino, thiol, alkoxy, substituted alkoxy, phthalimido, —OC(O)R$^7$, —SSR$^7$, —SSC(O)R$^7$ where R$^7$ is selected from the group consisting of alkyl, substituted alkyl, cycloalkyl, optionally substituted aryl, optionally substituted heteroaryl and optionally substituted heterocyclic, X' is hydrogen, hydroxy or fluoro;

X" is hydrogen, hydroxy or fluoro, or X' and X" together form an oxo group, and n is an integer equal to 1 or 2;

but excluding the compounds:

(i) wherein R$^1$ is o-fluorophenyl, R$^2$ is 3,4-dichlorophenyl or ethyl, R$^4$ and R$^5$ are hydrogen, X', and X" are hydrogen and X is —C(O)OCH$_3$;

(ii) wherein n is 2, R$^1$ is —CH$_2$C(O)OCH$_3$, R$^2$ is —(CH$_2$)$_2$COOH, the first R$^4$ is isopropyl and the second R$^4$ is —(CH$_2$)$_4$NH$_2$, X', X" and each R$^5$ is hydrogen and X is —C(O)NHCH(C(O)CH$_2$Cl)CH$_2$phenyl, —C(O)NHCH(C(O)CH$_3$)CH$_2$phenyl, or —C(O)NHCH(C(O)CF$_3$)CH$_2$phenyl;

(iii) wherein n is 2, R$^1$ is —(CH$_2$)$_6$COOH, R$^2$ is isopropyl, the first R$^4$ is —(CH$_2$)$_4$NH$_2$, the second R$^4$ is benzyl, X', X" and each R$^5$ is hydrogen and X is —C(O)CH$_2$Cl (iv) wherein n is 2, R$^1$ is —(CH$_2$)$_3$COOH, R$^2$ is isopropyl, the first R$^4$ is —(CH$_2$)$_3$NH$_2$, the second R$^4$ is benzyl, X', X" and each R$^5$ is hydrogen and X is acetyl;

(v) wherein n is 2, R$^1$ is —CH$_2$C(O)OCH$_3$, R$^2$ is —(CH$_2$)$_2$COOH, the first R$^4$ is isopropyl, the second R$^4$ is —(CH$_2$)$_3$NH$_2$, X', X" and each R$^5$ is hydrogen and X is —C(O)NHCH(C(O)CF$_3$)CH$_2$phenyl;

(vi) wherein n is 1, R$^1$ is —CH(isopropyl)CH$_2$COOH, Z is a bond, R$^2$ is —(CH$_2$)$_3$NH$_2$, R$^4$ is benzyl, X', X" and R$^5$ are hydrogen, and X is —C(O)CH$_2$Cl; and (vii) wherein R' is fluoro substituted aryl, n is 1, X' and X" are each hydrogen, R$^5$ is hydrogen or methyl, X is —C(O)Y where Y is haloalkyl, alkoxy, thioalkoxy, heterocyclic, —CH$_2$ heterocyclic, mono-substituted alkyl having its single substituent at the terminal position and wherein said substituent is diazo, —C(O)OR', —C(O) alkyl OR' or —C(O)NR', R" wherein R' and R" are independently hydrogen, alkyl, phenyl, benzyl or phenethyl, or Y is selected from the groups —CH$_2$OR', —CH$_2$SR', —CH$_2$NR'R" or —NR'R" wherein R' and R" are independently hydrogen alkyl, phenyl, benzyl or phenethyl.

19. A pharmaceutical composition comprising a pharmaceutically inert carrier and a pharmaceutically effective amount of a compound according to claim 18.

20. A pharmaceutical composition comprising a pharmaceutically acceptable carrier and a pharmaceutically effective amount of a compound according to claim 1.

21. A pharmaceutical composition comprising a pharmaceutically acceptable carrier and a pharmaceutically effective amount of a compound according to claim 2.

22. A pharmaceutical composition comprising a pharmaceutically acceptable carrier and a pharmaceutically effective amount of a compound according to claim 3.

23. A pharmaceutical composition comprising a pharmaceutically acceptable carrier and a pharmaceutically effective amount of a compound according to claim 4 and mixtures thereof.

24. A pharmaceutical composition comprising a pharmaceutically acceptable carrier and a pharmaceutically effective amount of a compound according to claim 5.

25. A pharmaceutical composition comprising a pharmaceutically acceptable carrier and a pharmaceutically effective amount of a compound according to claim 6.

26. A pharmaceutical composition comprising a pharmaceutically acceptable carrier and a pharmaceutically effective amount of a compound according to claim 7.

27. A pharmaceutical composition comprising a pharmaceutically acceptable carrier and a pharmaceutically effective amount of a compound according to claim 8.

28. A pharmaceutical composition according to claim 21 wherein n is 1.

* * * * *